United States Patent
Hibner et al.

(10) Patent No.: US 10,349,967 B2
(45) Date of Patent: Jul. 16, 2019

(54) ULTRASONIC SURGICAL INSTRUMENT WITH REMOVABLE HANDLE ASSEMBLY

(71) Applicant: Ethicon Endo-Surgery, Inc., Cincinnati, OH (US)

(72) Inventors: John A. Hibner, Mason, OH (US); Thomas B. Remm, Milford, OH (US)

(73) Assignee: Ethicon LLC, Guaynabo, PR (US)

( * ) Notice: Subject to any disclaimer, the term of this patent is extended or adjusted under 35 U.S.C. 154(b) by 562 days.

(21) Appl. No.: 14/868,574

(22) Filed: Sep. 29, 2015

(65) Prior Publication Data

US 2016/0015419 A1  Jan. 21, 2016

Related U.S. Application Data

(63) Continuation-in-part of application No. 14/623,812, filed on Feb. 17, 2015.
(Continued)

(51) Int. Cl.
*A61B 17/32* (2006.01)
*A61B 18/14* (2006.01)
(Continued)

(52) U.S. Cl.
CPC .. *A61B 17/320092* (2013.01); *A61B 18/1482* (2013.01); *A61B 2017/0046* (2013.01);
(Continued)

(58) Field of Classification Search
CPC ........ A61B 17/320092; A61B 18/1482; A61B 2017/0046; A61B 2018/1462;
(Continued)

(56) References Cited

U.S. PATENT DOCUMENTS 5,322,055 A  6/1994  Davison et al.
5,873,873 A  2/1999  Smith et al.
(Continued)

FOREIGN PATENT DOCUMENTS

CN  103027718 A  4/2013
CN  103584912 A  2/2014
(Continued)

OTHER PUBLICATIONS

International Search Report and Written Opinion dated May 18, 2015 re Application No. PCT/US2015/017178.
(Continued)

*Primary Examiner* — Phong Son H Dang
(74) *Attorney, Agent, or Firm* — Frost Brown Todd LLC

(57) ABSTRACT

An apparatus comprises a body and a shaft assembly. The shaft assembly is configured to couple with the body such that the shaft assembly extends distally relative to the body. The shaft assembly comprises a tubular member, an acoustic waveguide, and a guiding member. The acoustic waveguide is operable to selectively couple with an ultrasonic transducer assembly. The tubular member is configured to insertingly receive the acoustic waveguide. The acoustic waveguide comprises a guide feature. The guiding member is configured to engage the guide feature of the acoustic waveguide and thereby orient the acoustic waveguide in relation to the tubular member.

19 Claims, 138 Drawing Sheets

Related U.S. Application Data

(60) Provisional application No. 62/146,644, filed on Apr. 13, 2015, provisional application No. 61/946,168, filed on Feb. 28, 2014.

(51) Int. Cl.
*A61B 17/00* (2006.01)
*A61B 17/29* (2006.01)
*A61B 90/00* (2016.01)

(52) U.S. Cl.
CPC .............. *A61B 2017/00393* (2013.01); *A61B 2017/00455* (2013.01); *A61B 2017/00477* (2013.01); *A61B 2017/294* (2013.01); *A61B 2017/2929* (2013.01); *A61B 2017/2939* (2013.01); *A61B 2018/1462* (2013.01); *A61B 2090/0808* (2016.02); *A61B 2090/0813* (2016.02)

(58) Field of Classification Search
CPC .. A61B 2017/00455; A61B 2017/2939; A61B 2090/0808; A61B 2017/00393; A61B 2090/0813; A61B 2017/2929; A61B 2017/294; A61B 2017/00477
See application file for complete search history.

(56) References Cited

U.S. PATENT DOCUMENTS

| | | | |
|---|---|---|---|
| 5,897,523 A | 4/1999 | Wright et al. | |
| 5,980,510 A | 11/1999 | Tsonton et al. | |
| 5,989,264 A | 11/1999 | Wright et al. | |
| 6,063,098 A | 5/2000 | Houser et al. | |
| 6,090,120 A | 7/2000 | Wright et al. | |
| 6,325,811 B1 | 12/2001 | Messerly | |
| 6,454,782 B1 | 9/2002 | Schwemberger | |
| 6,589,200 B1 | 7/2003 | Schwemberger et al. | |
| 6,752,815 B2 | 6/2004 | Beaupre | |
| 6,773,444 B2 | 8/2004 | Messerly | |
| 6,783,524 B2 | 8/2004 | Anderson et al. | |
| 7,135,030 B2 | 11/2006 | Schwemberger et al. | |
| 7,621,930 B2 | 11/2009 | Houser | |
| 8,057,498 B2 | 11/2011 | Robertson | |
| 8,419,758 B2 | 4/2013 | Smith et al. | |
| 8,461,744 B2* | 6/2013 | Wiener .......... A61B 17/320092 310/323.01 | |
| 8,591,536 B2 | 11/2013 | Robertson | |
| 8,623,027 B2 | 1/2014 | Price et al. | |
| 8,986,302 B2 | 3/2015 | Aldridge et al. | |
| 9,023,071 B2 | 5/2015 | Miller et al. | |
| 9,044,261 B2 | 6/2015 | Houser | |
| 9,050,125 B2 | 6/2015 | Boudreaux et al. | |
| 9,095,367 B2 | 8/2015 | Olson et al. | |
| 9,301,772 B2 | 4/2016 | Kimball et al. | |
| 9,532,844 B2 | 1/2017 | Garvey et al. | |
| 9,539,020 B2 | 1/2017 | Conlon et al. | |
| 9,622,767 B2 | 4/2017 | Stoddard et al. | |
| 9,713,507 B2* | 7/2017 | Stulen ............ A61B 17/320092 | |
| 2002/0165538 A1* | 11/2002 | Schneiter ............... A61B 17/29 606/46 | |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2010/0331742 A1 | 12/2010 | Masuda | |
| 2011/0082486 A1* | 4/2011 | Messerly ....... A61B 17/320092 606/169 |
| 2011/0105845 A1* | 5/2011 | Gordon .............. A61B 1/00094 600/156 |
| 2012/0078139 A1* | 3/2012 | Aldridge ........ A61B 17/320092 601/2 |
| 2012/0112687 A1 | 5/2012 | Houser et al. |
| 2012/0116261 A1* | 5/2012 | Mumaw .......... A61B 17/00234 601/2 |
| 2012/0116265 A1 | 5/2012 | Houser et al. |
| 2012/0265196 A1* | 10/2012 | Turner ........... A61B 17/320092 606/34 |
| 2013/0008542 A1* | 1/2013 | Irwin ................... F16K 31/402 137/859 |
| 2013/0090577 A1* | 4/2013 | Boudreaux .... A61B 17/320092 601/2 |
| 2013/0253480 A1* | 9/2013 | Kimball .............. G06F 19/3481 606/1 |
| 2013/0253499 A1* | 9/2013 | Kimball ......... A61B 17/320092 606/33 |
| 2013/0324998 A1* | 12/2013 | Kimball ......... A61B 17/320068 606/41 |
| 2013/0345701 A1* | 12/2013 | Allen, IV ............. A61B 18/082 606/41 |
| 2014/0005701 A1* | 1/2014 | Olson .................. A61B 17/295 606/169 |
| 2014/0005702 A1 | 1/2014 | Timm et al. |
| 2014/0005703 A1 | 1/2014 | Stulen et al. |
| 2014/0190523 A1* | 7/2014 | Garvey ................. A61B 90/70 134/22.12 |
| 2014/0207124 A1 | 7/2014 | Aldridge et al. |
| 2015/0080924 A1* | 3/2015 | Stulen ............ A61B 17/320092 606/169 |
| 2015/0141981 A1* | 5/2015 | Price ................. A61B 18/1445 606/38 |
| 2015/0148835 A1* | 5/2015 | Faller ............ A61B 17/320068 606/169 |
| 2015/0182250 A1* | 7/2015 | Conlon .......... A61B 17/320092 606/169 |
| 2015/0245850 A1 | 9/2015 | Hibner et al. |

FOREIGN PATENT DOCUMENTS

| | | |
|---|---|---|
| EP | 0 897 696 A1 | 2/1999 |
| EP | 0908151 A1 | 4/1999 |
| EP | 2 692 297 A2 | 2/2014 |
| JP | 2010522034 A | 7/2010 |
| JP | 2012533346 A | 12/2012 |

OTHER PUBLICATIONS

U.S. Appl. No. 14/258,179, filed Apr. 22, 2014
U.S. Appl. No. 61/410,603, filed Nov. 5, 2010.
U.S. Appl. No. 61/946,168, filed Feb. 28, 2014.
U.S. Appl. No. 62/146,644, filed Apr. 13, 2015.
International Search Report and Written Opinion dated Jun. 1, 2016 for Application No. PCT/US2016/027112, 13 pgs.
Chinese Office Action, Notification of the First Office Action, and Search Report dated Aug. 27, 2018 for Application No. CN 201580023229.X, 13 pgs.
Japanese Office Action, Notification of Reasons for Refusal, dated Jan. 15, 2019 for Application No. JP 2016-554331, 5 pgs.

* cited by examiner

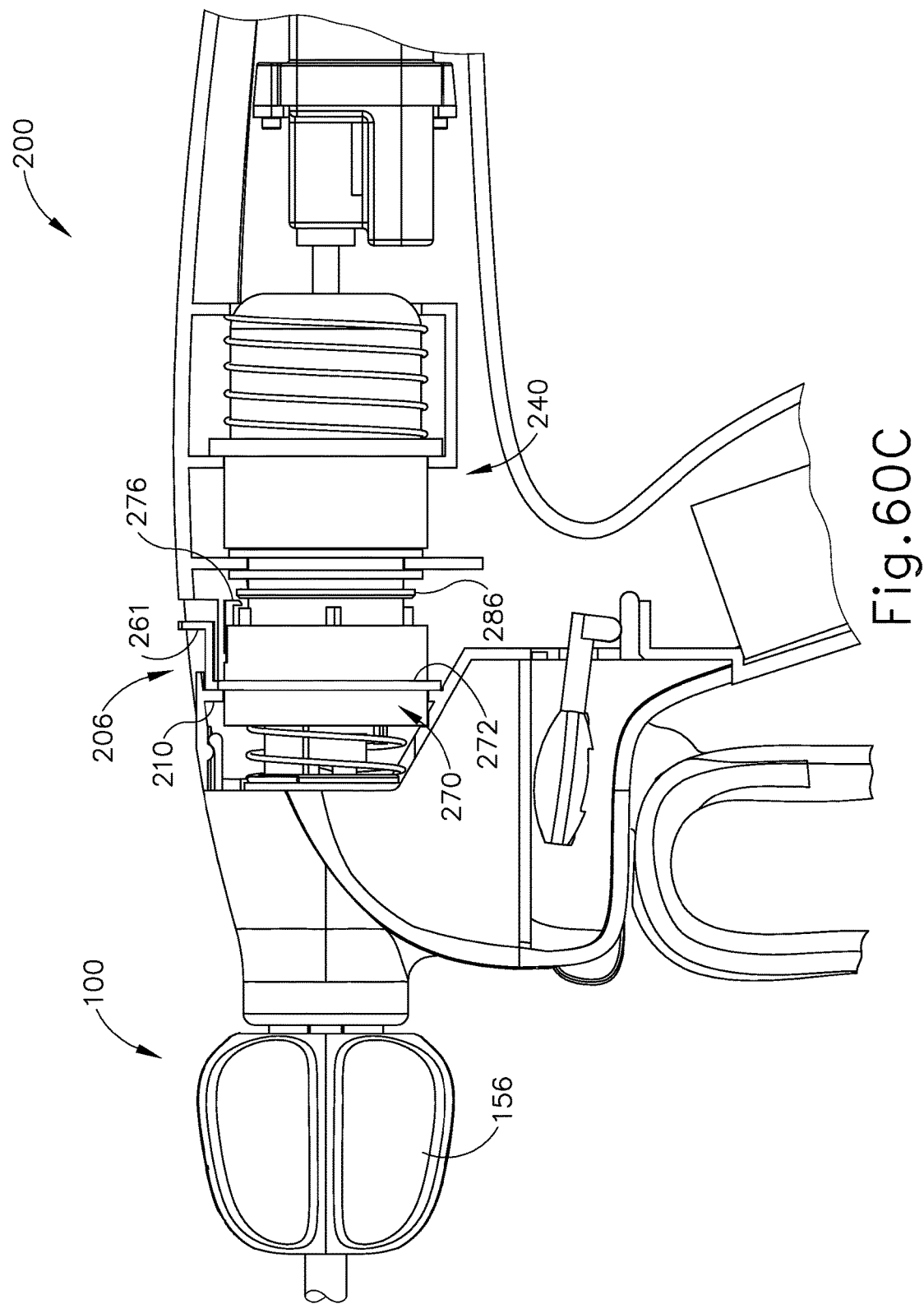

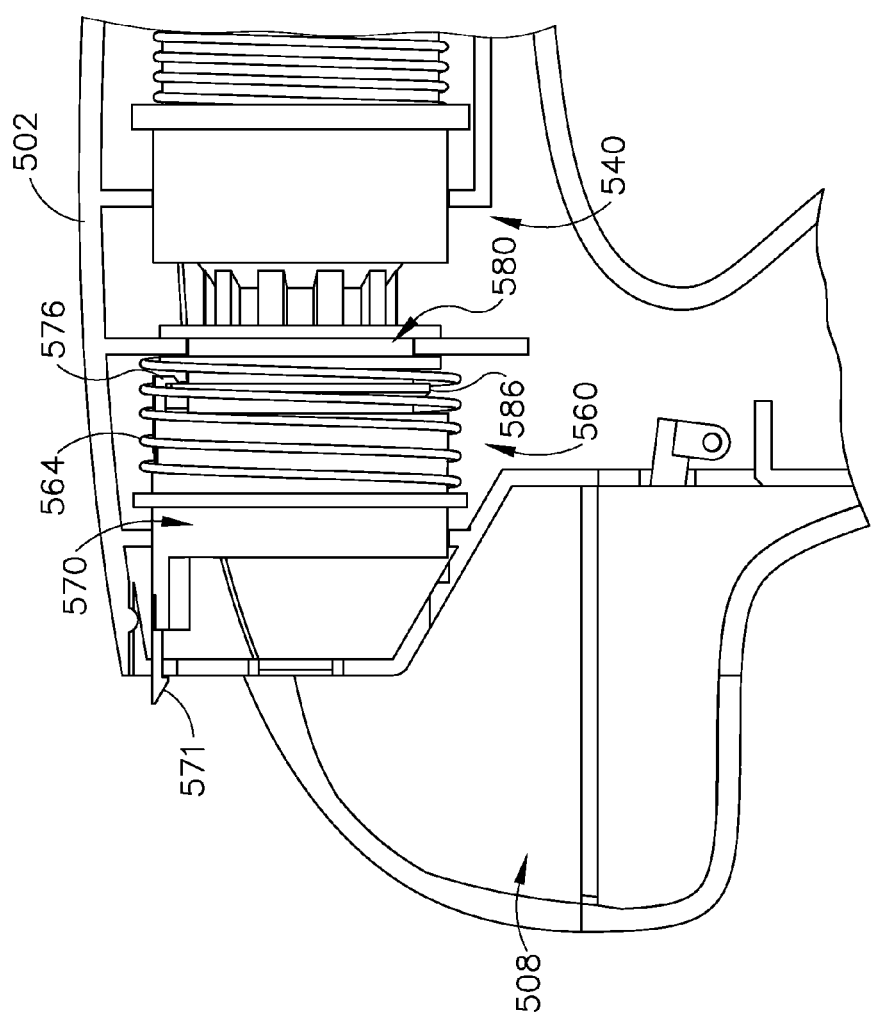

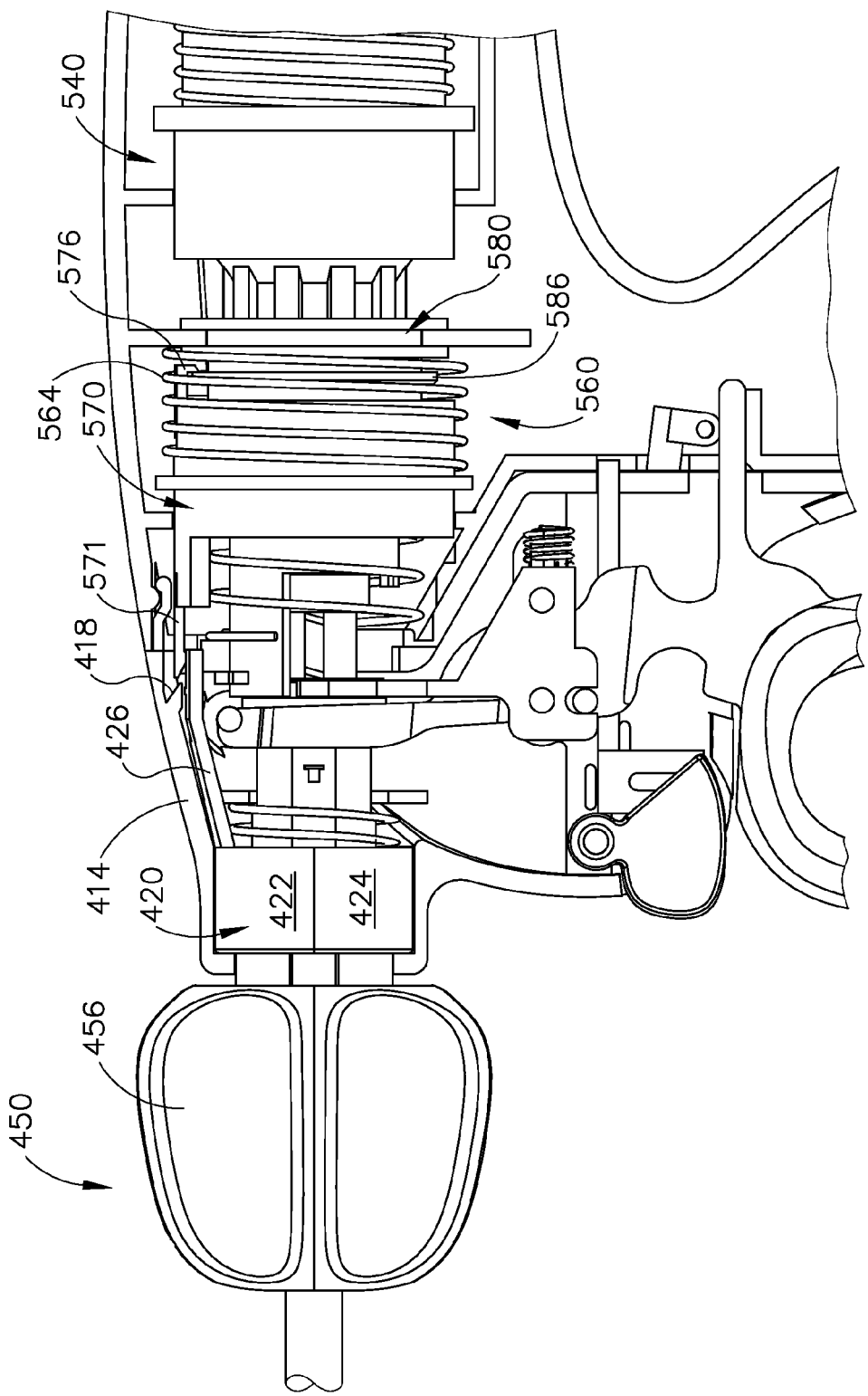

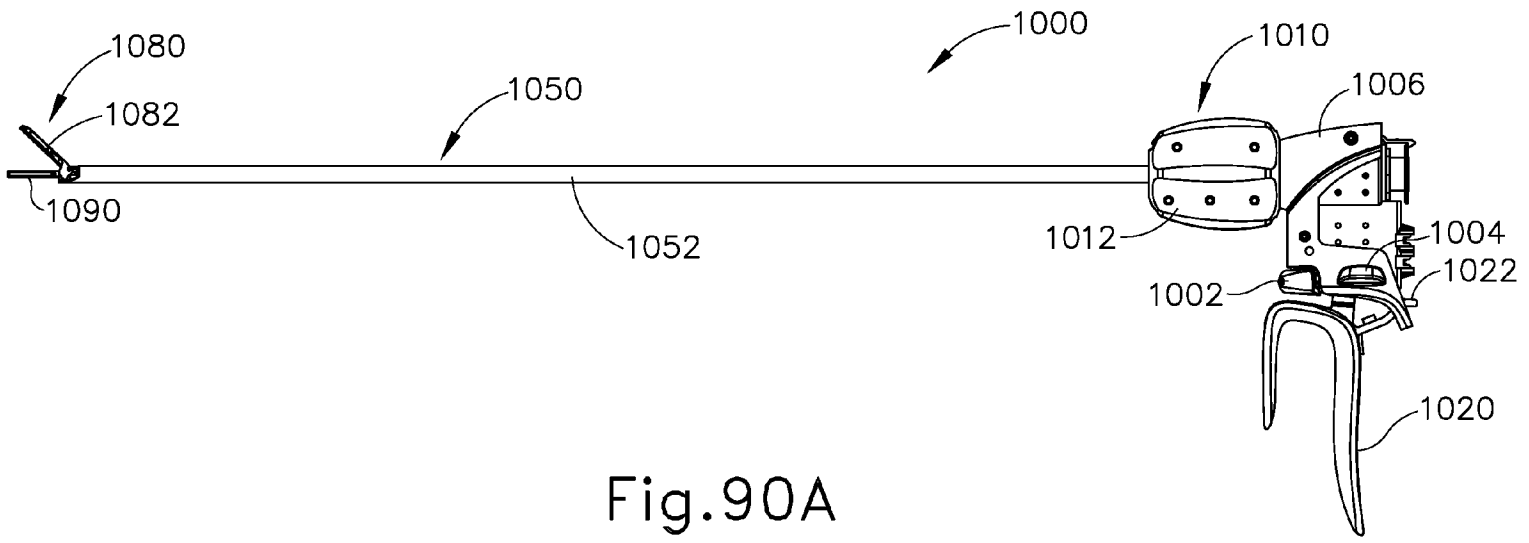
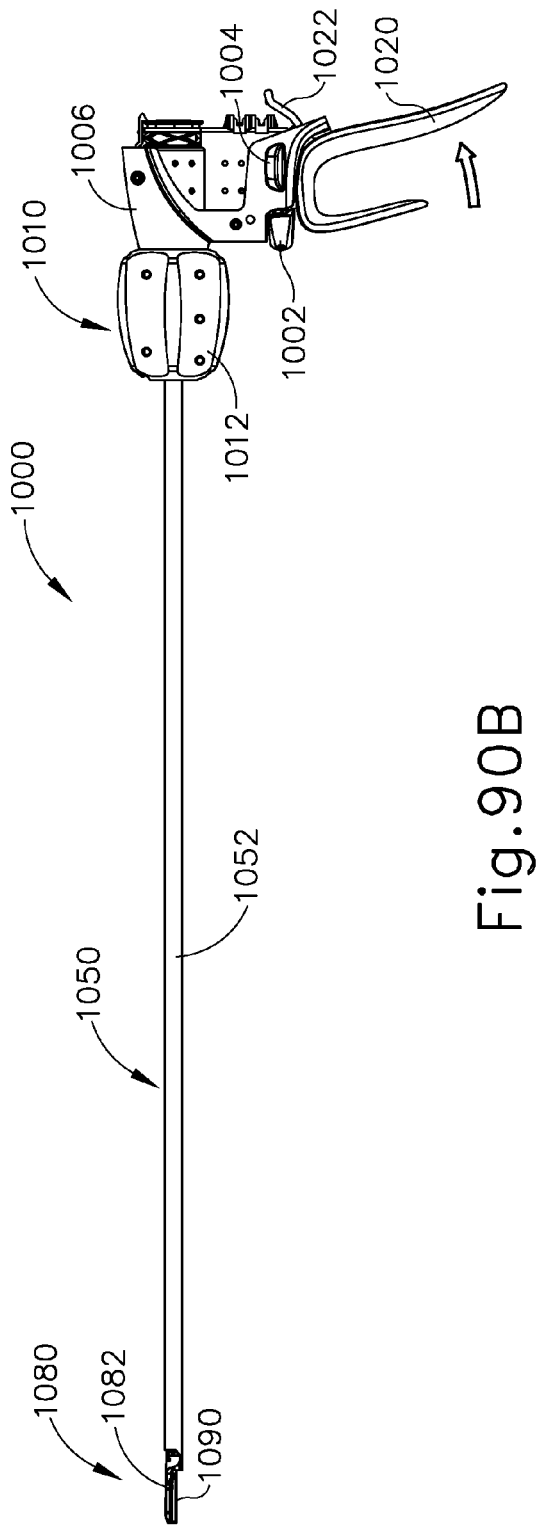
Fig. 90A
Fig. 90B

ULTRASONIC SURGICAL INSTRUMENT WITH REMOVABLE HANDLE ASSEMBLY

PRIORITY

This application claims priority to U.S. Provisional Pat. App. No. 62/146,644, entitled "Ultrasonic Surgical Instrument with Removable Handle Assembly," filed Apr. 13, 2015, the disclosure of which is incorporated by reference herein.

This application is also a continuation-in-part of U.S. patent application Ser. No. 14/623,812, entitled "Ultrasonic Surgical Instrument with Removable Handle Assembly," filed Feb. 17, 2015, issued as U.S. Pat. No. 10,010,340 on Jul. 3, 2018, the disclosure of which is incorporated by reference herein, and which claims priority to in U.S. Provisional Pat. App. No. 61/946,168, entitled "Ultrasonic Surgical Instrument with Removable Handle Assembly," filed Feb. 28, 2014, the disclosure of which is incorporated by reference herein.

BACKGROUND

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; and U.S. Pat. No. 8,623,027, entitled "Ergonomic Surgical Instruments," issued Jan. 7, 2014, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; and U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, entitled "Surgical Instruments with Articulating Shafts," issued as U.S. Pat. No. 9,393,037 on Jul. 19, 2016, the disclosure of which is incorporated by reference herein; U.S. Pub. No. 2014/0005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled "Ultrasonic Surgical Device with Articulating End Effector," filed Apr. 22, 2014, now U.S. Prov. App. No. 62/176,880 on Apr. 22, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 60C depicts a partial, side elevational view of the reusable portion of FIG. 45, with a housing half removed, with the disposable portion of FIG. 9 inserted into the recess of the reusable portion, and with the transducer assembly fully coupled with the waveguide;

FIG. 80A depicts a partial, side elevational view of the reusable portion of FIG. 65, with a housing half removed;

FIG. 80B depicts a partial, side elevational view of the reusable portion of FIG. 65, with a housing half removed, and with the disposable portion of FIG. 67 inserted into a recess of the reusable portion;

FIG. 90A depicts a side elevational view of the disposable portion of FIG. 89, with an end effector of the disposable portion in an open configuration;

FIG. 90B depicts a side elevational view of the disposable portion of FIG. 89, with the end effector in a closed configuration;

FIG. 92 depicts a perspective view of an actuation yoke of the disposable portion of FIG. 89;

FIG. 93A depicts a side elevational view of the proximal end of the disposable portion of FIG. 89, with a housing half and the actuation yoke removed, and with the trigger in the non-actuated position;

FIG. 93B depicts a side elevational view of the proximal end of the disposable portion of FIG. 89, with a housing half and the actuation yoke removed, and with the trigger in the actuated position;

FIG. 94 depicts a cross-sectional side view of the proximal end of shaft assembly components of the disposable portion of FIG. 89;

FIG. 95 depicts an exploded perspective view of the shaft assembly components of FIG. 94;

FIG. 96 depicts an exploded perspective view of a yoke actuated assembly of the shaft assembly components of FIG. 94;

FIG. 97 depicts a perspective view of a tube coupling member of the yoke actuated assembly of FIG. 96;

FIG. 98 depicts a cross-sectional perspective view of the coupling member of FIG. 97, taken along line 98-98 of FIG. 97;

FIG. 99 depicts a perspective view of the proximal end of an outer tube of the shaft assembly components of FIG. 94;

FIG. 100 depicts a cross-sectional perspective view of the proximal end of the outer tube of FIG. 99 with the coupling member of FIG. 97 separated from the outer tube;

FIG. 101 depicts a cross-sectional perspective view of the proximal end of the outer tube of FIG. 99 with the coupling member of FIG. 97 coupled with the outer tube;

FIG. 102 depicts a perspective view of an inner tube assembly of the shaft assembly components of FIG. 94;

Figure 89:
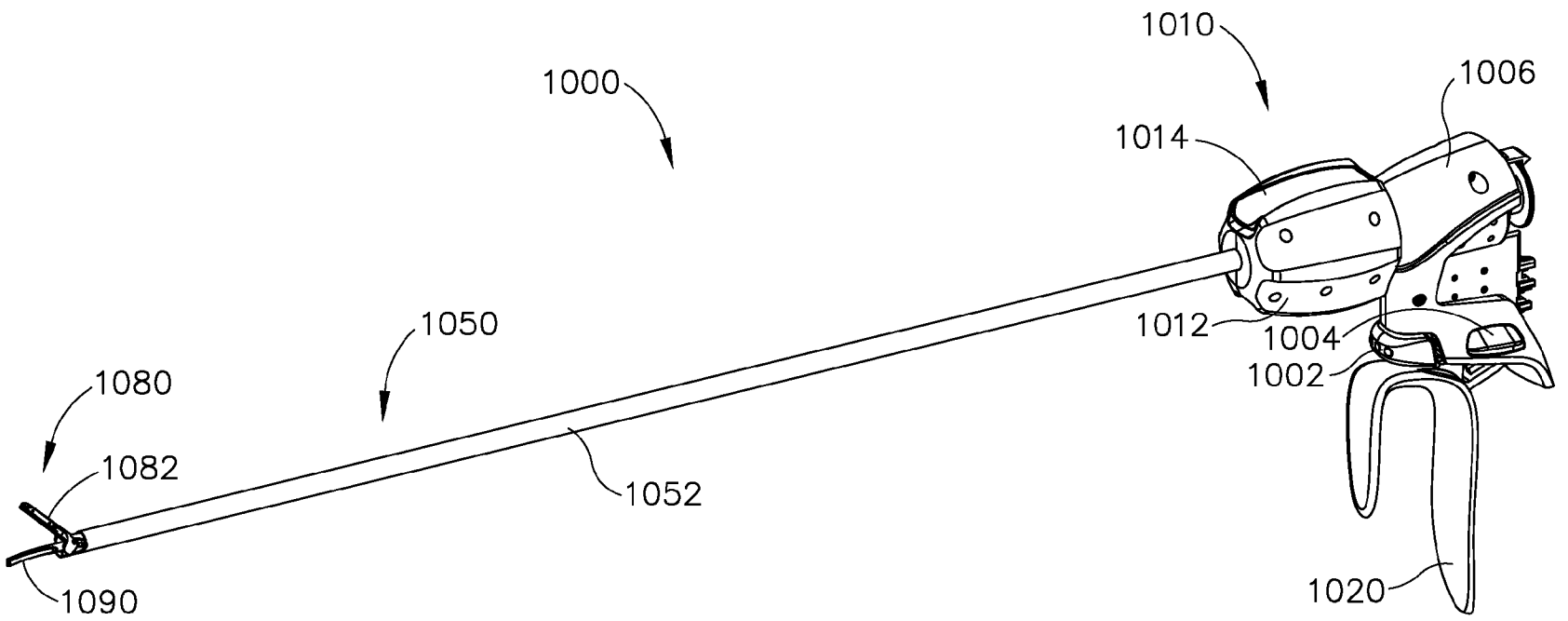
FIG. 89 depicts a perspective view of a disposable portion of the instrument of FIG. 83.
Figure 94:
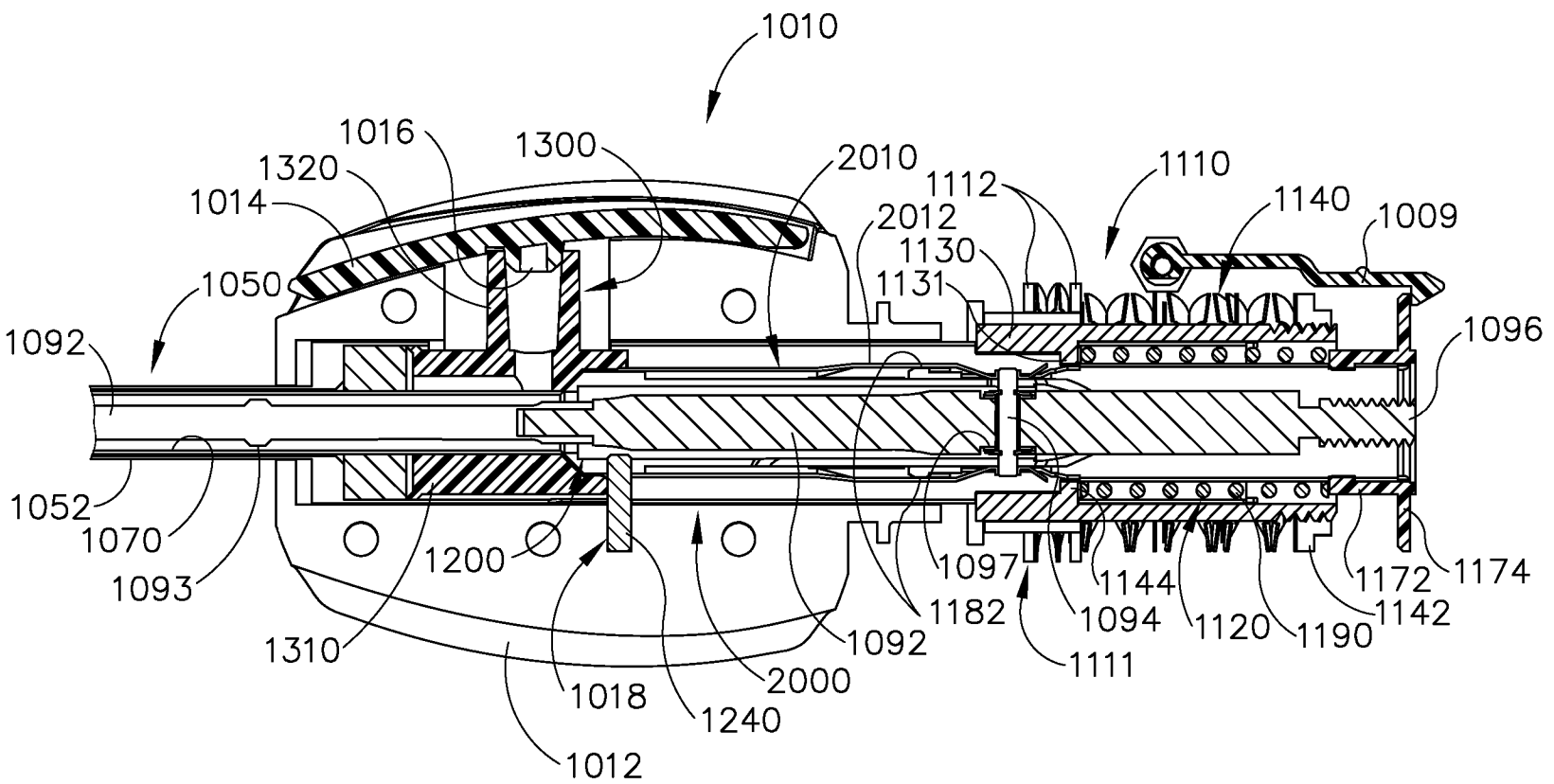
Figure 102:
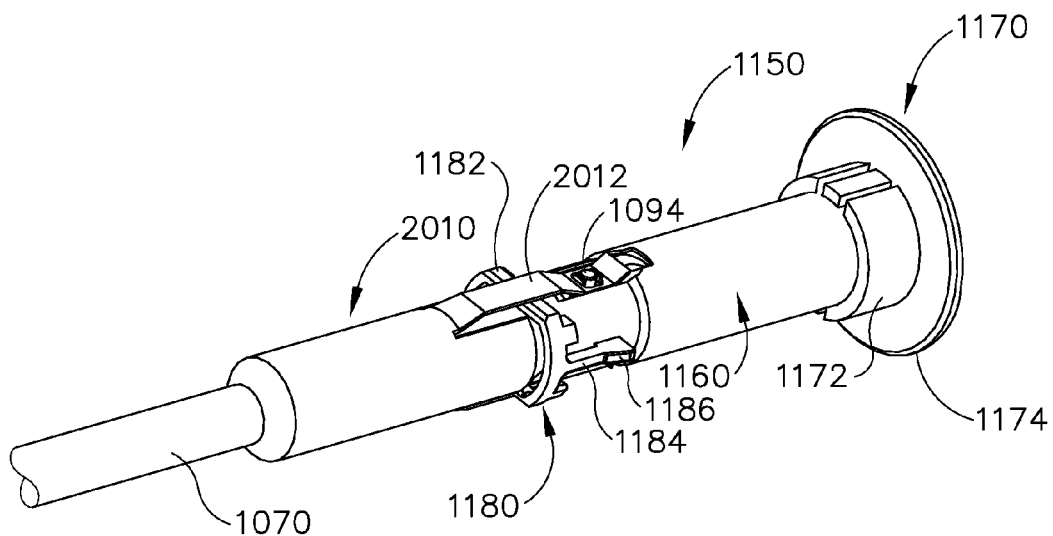
Figure 103:
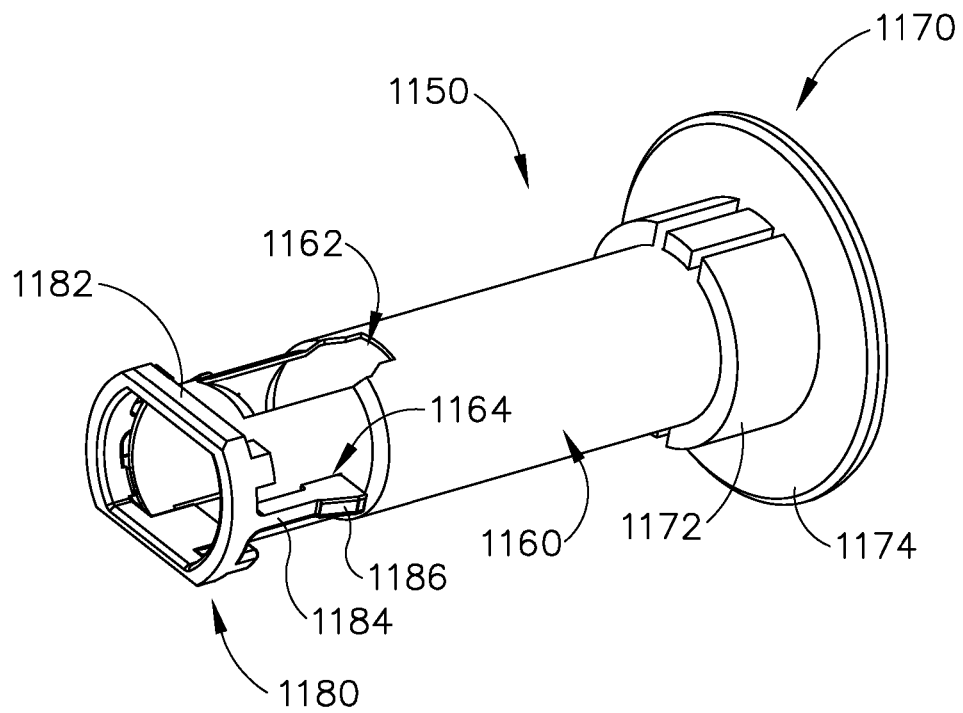
Figure 104:
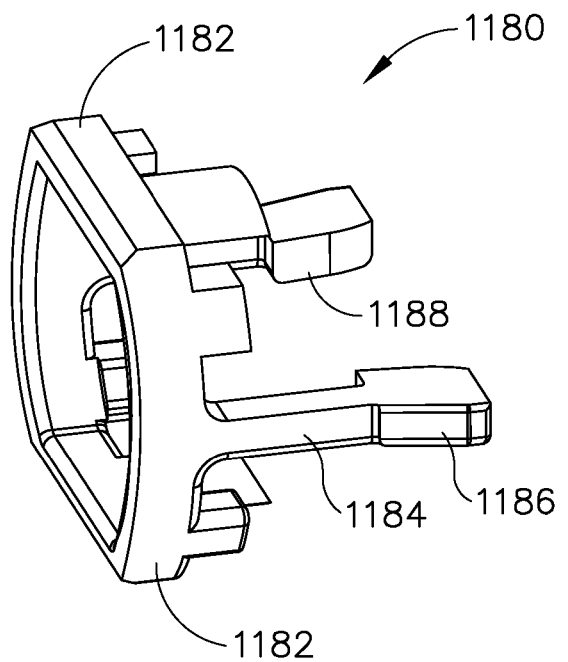
Figure 105:
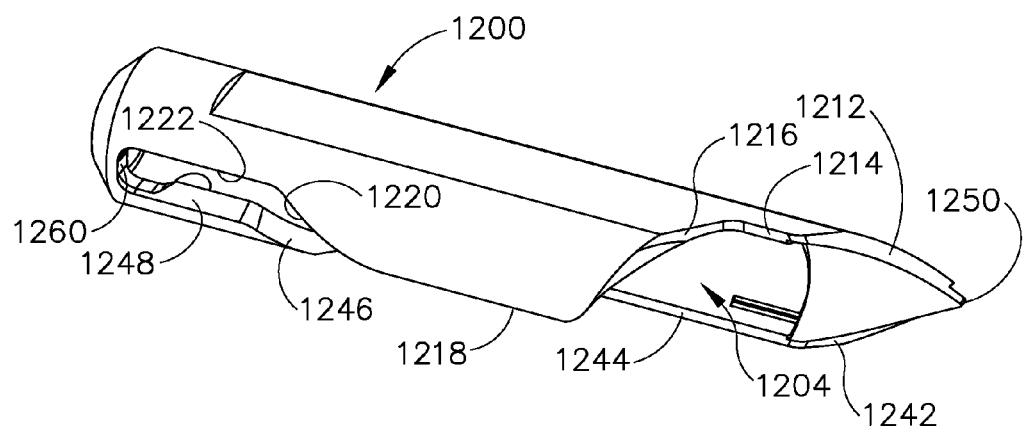
Figure 106:
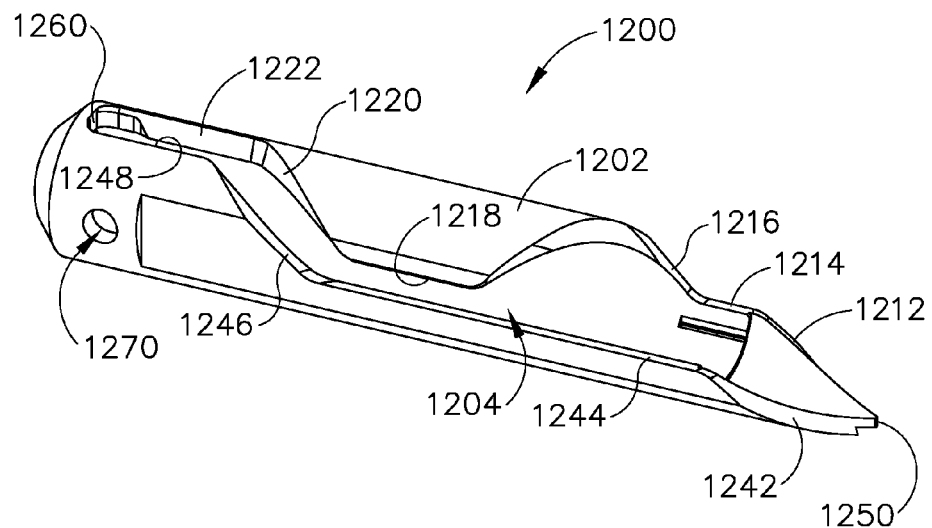
Figure 107:
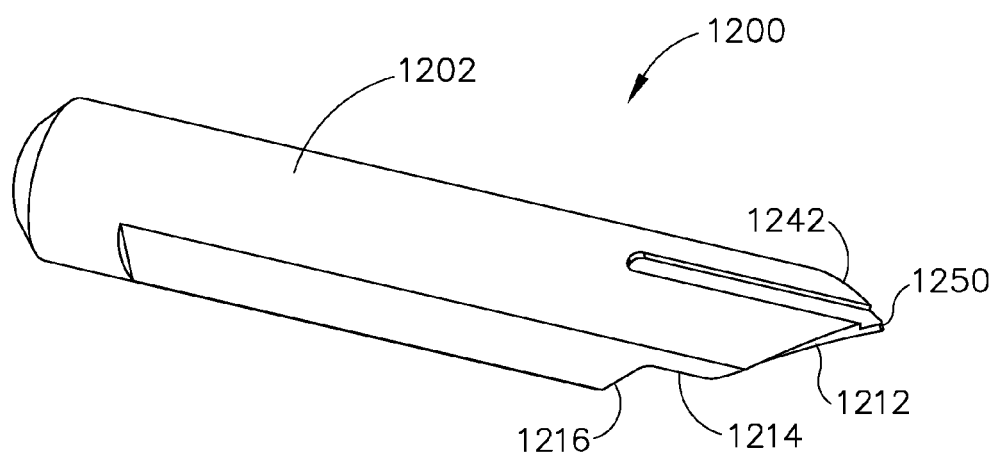
Figure 108:
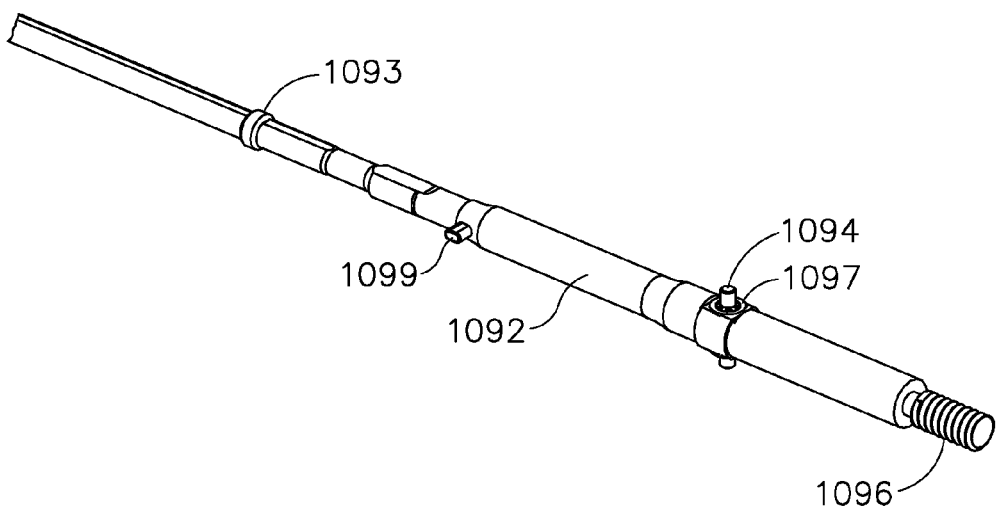
Figure 109:
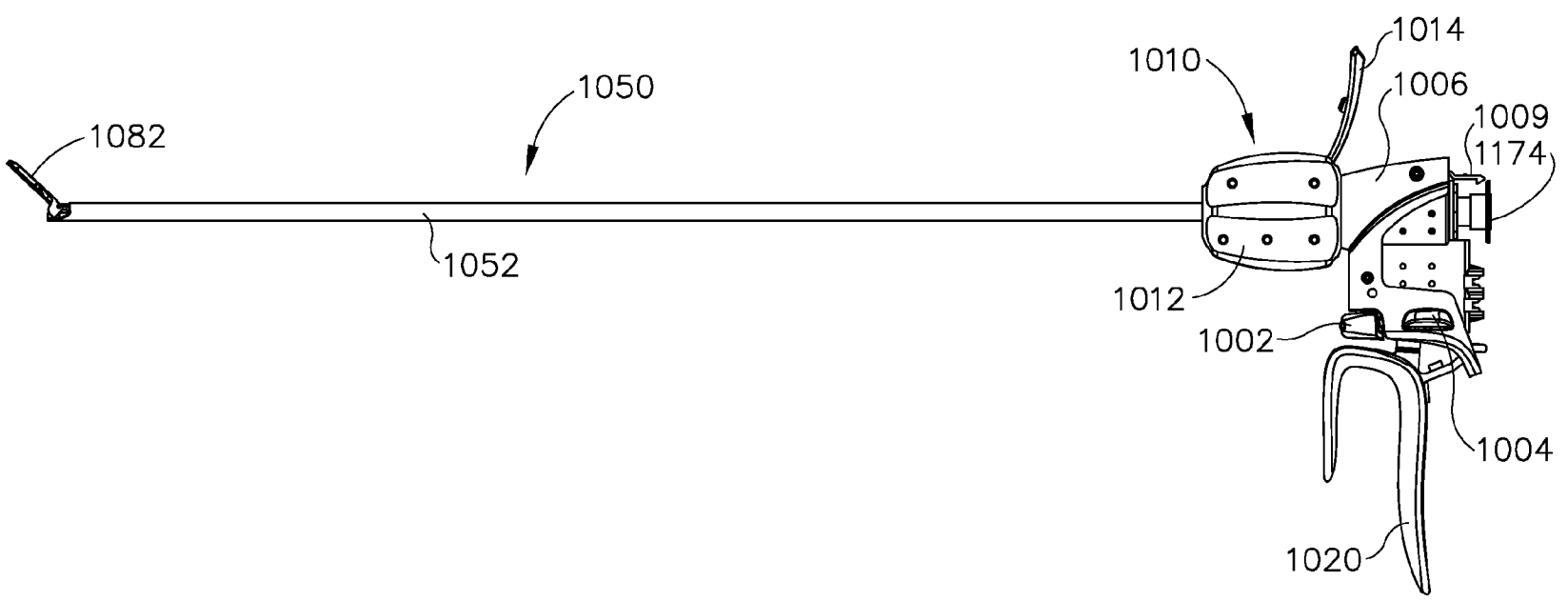
Figure 110:
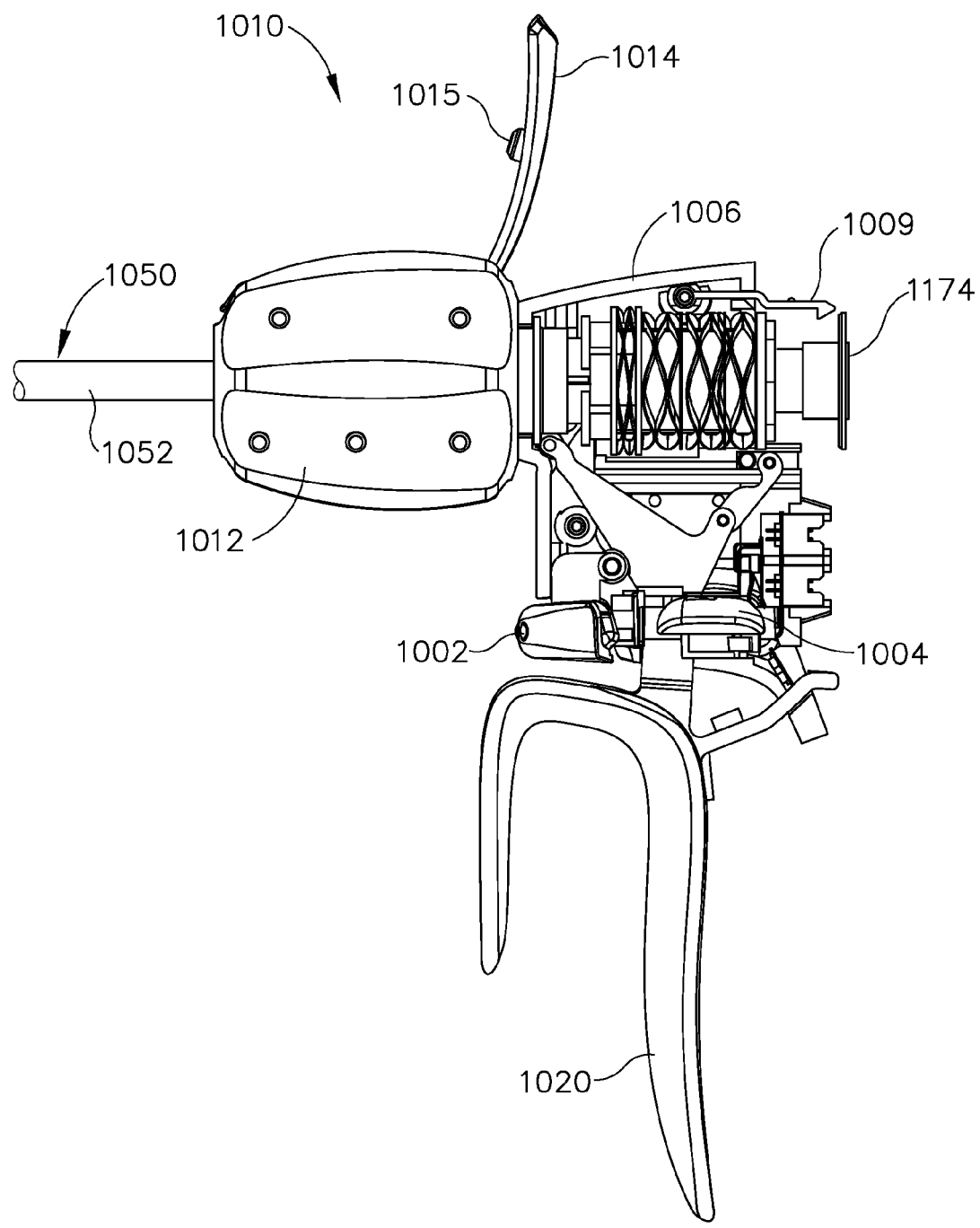
Figure 111:
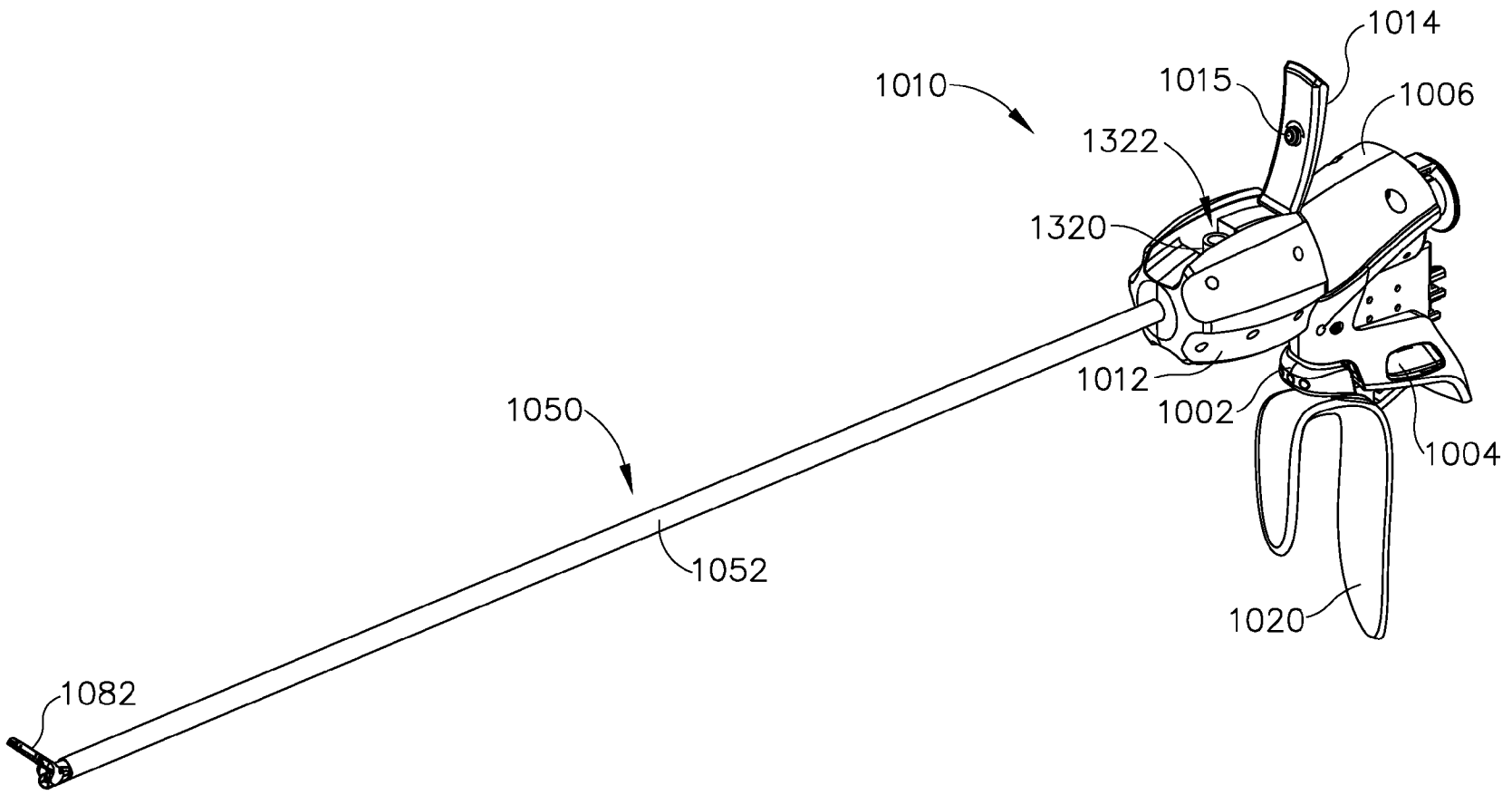
Figure 112:
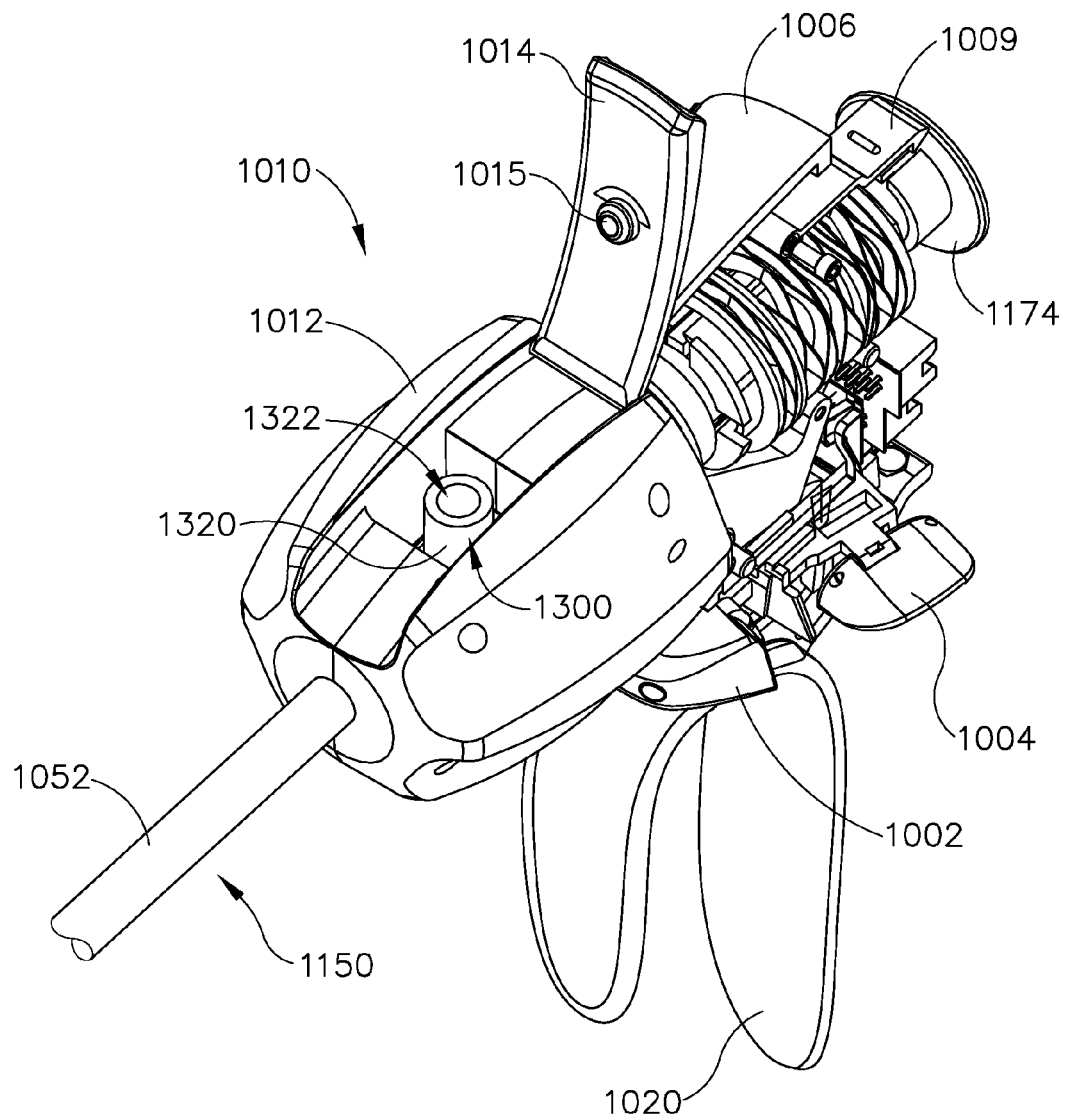
Figure 113:
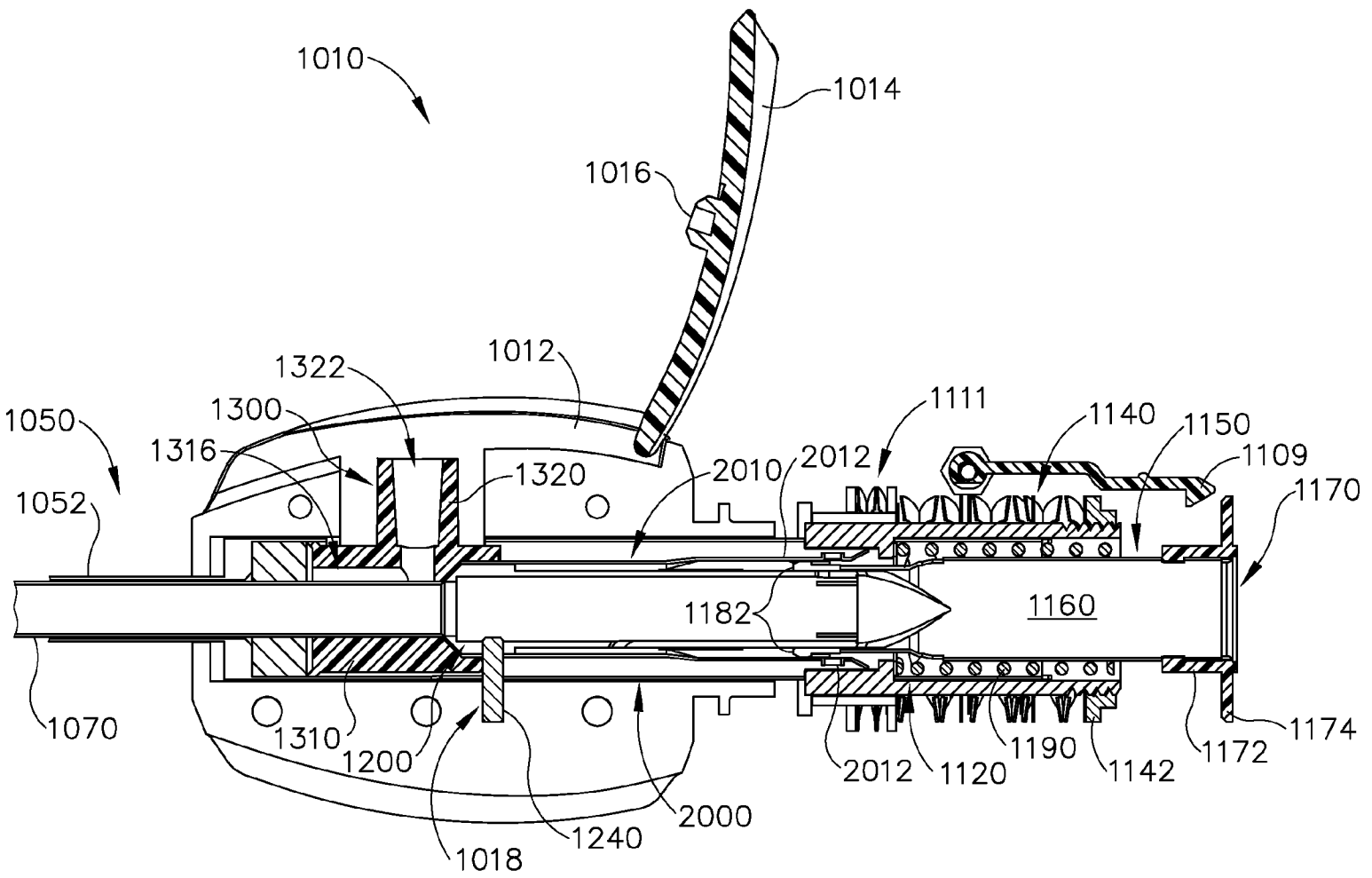
Figure 114:
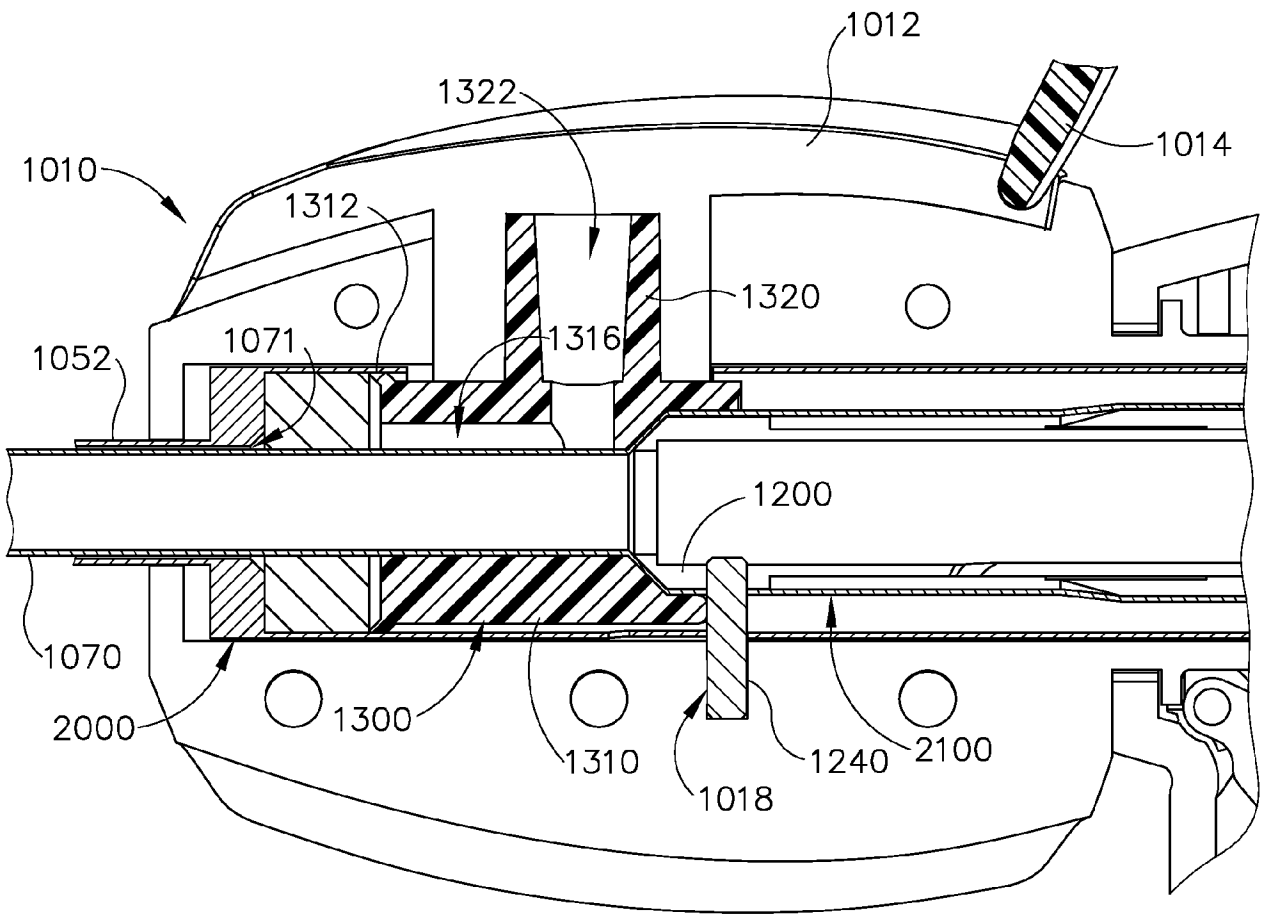
Figure 115:
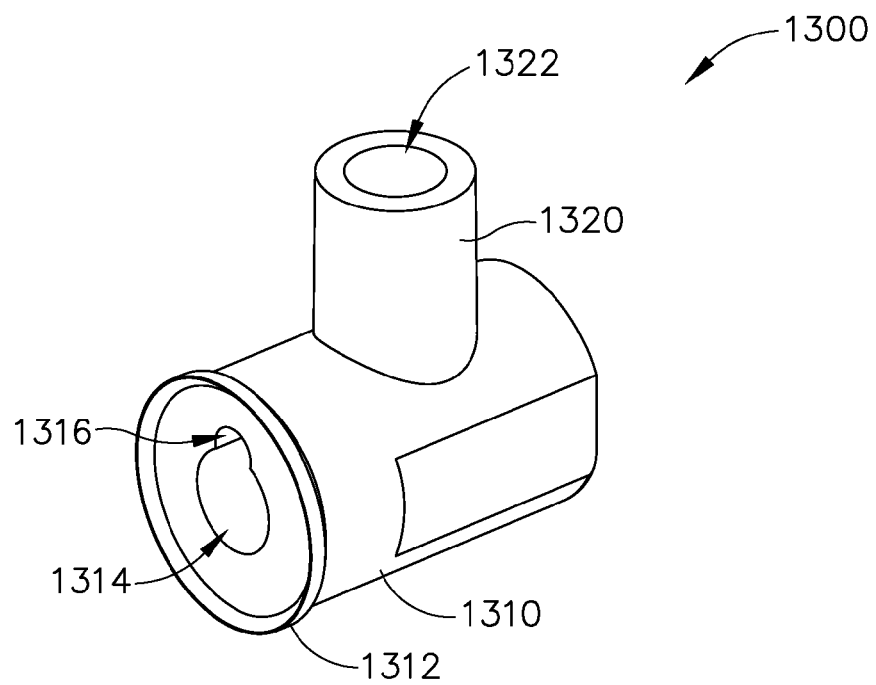
Figure 116:
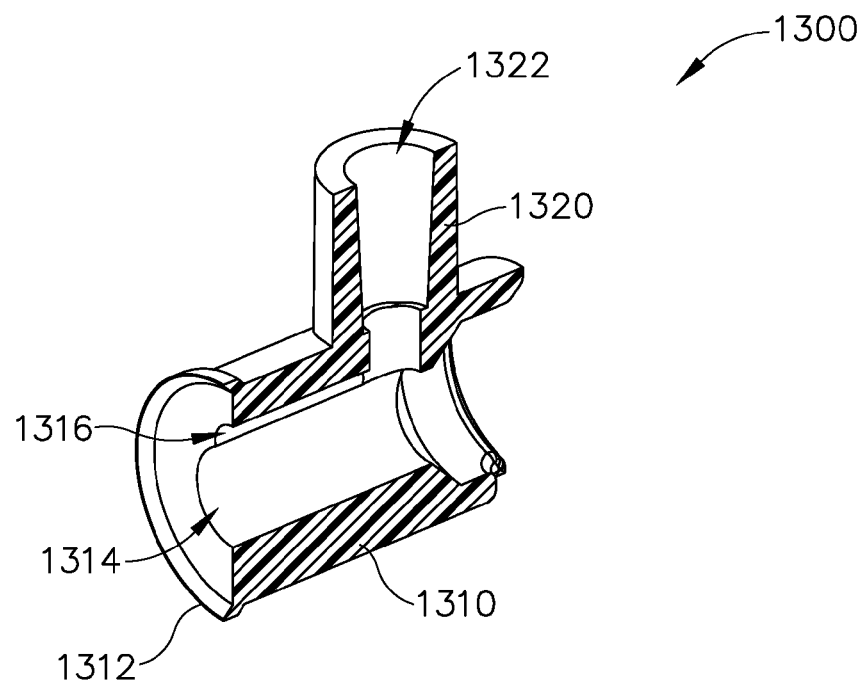
Figure 117A:
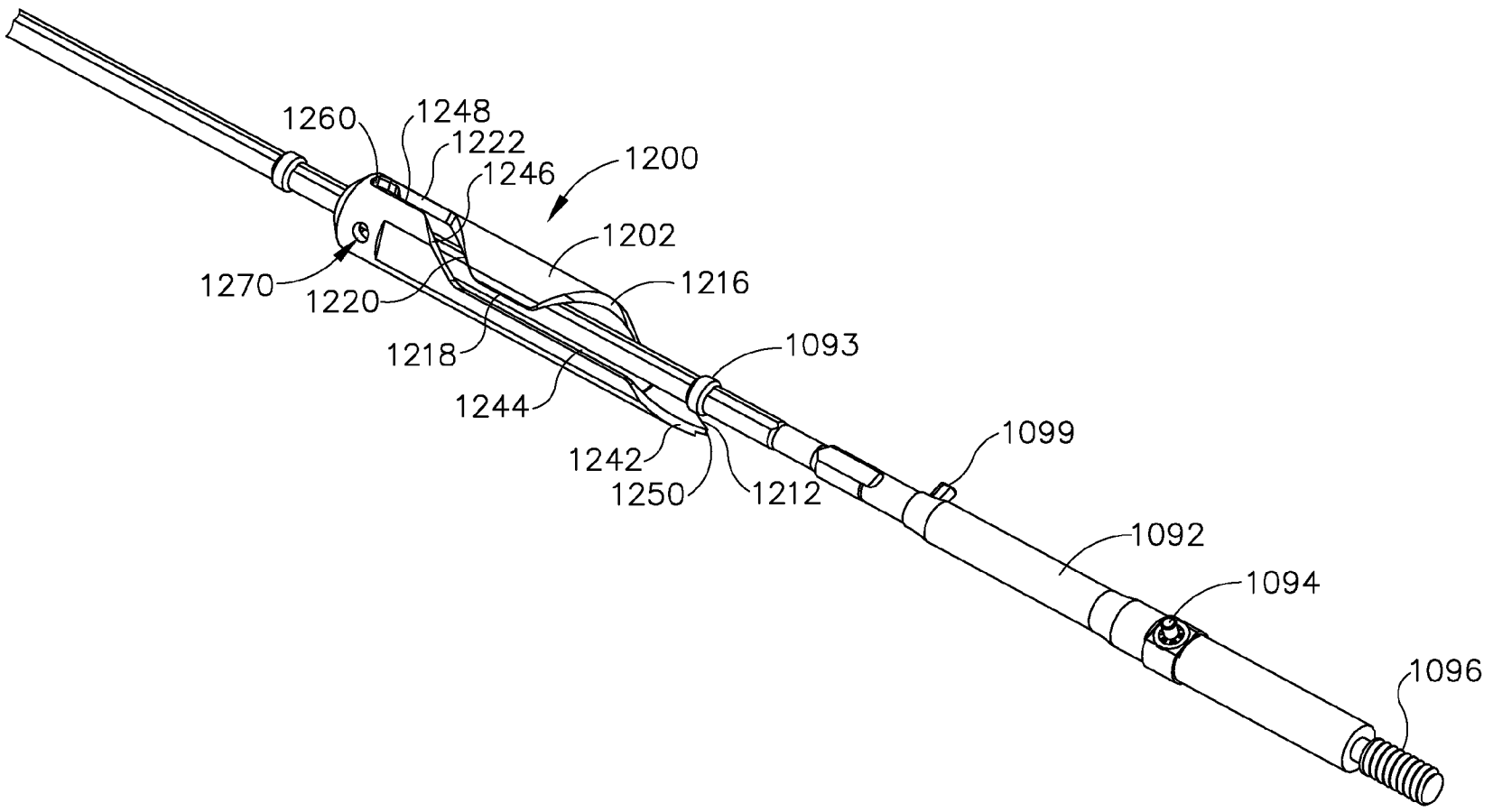
Figure 117B:
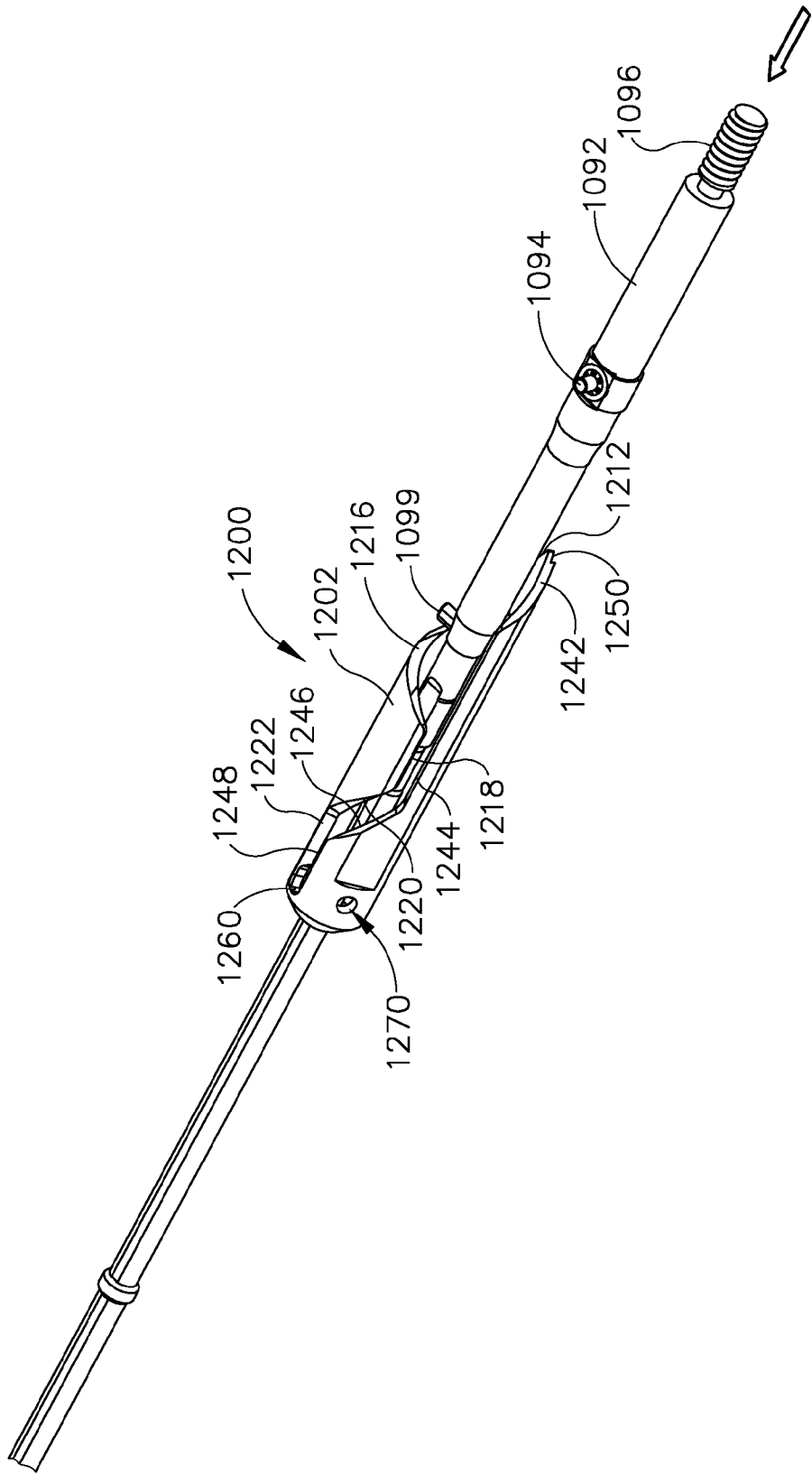
Figure 117C:
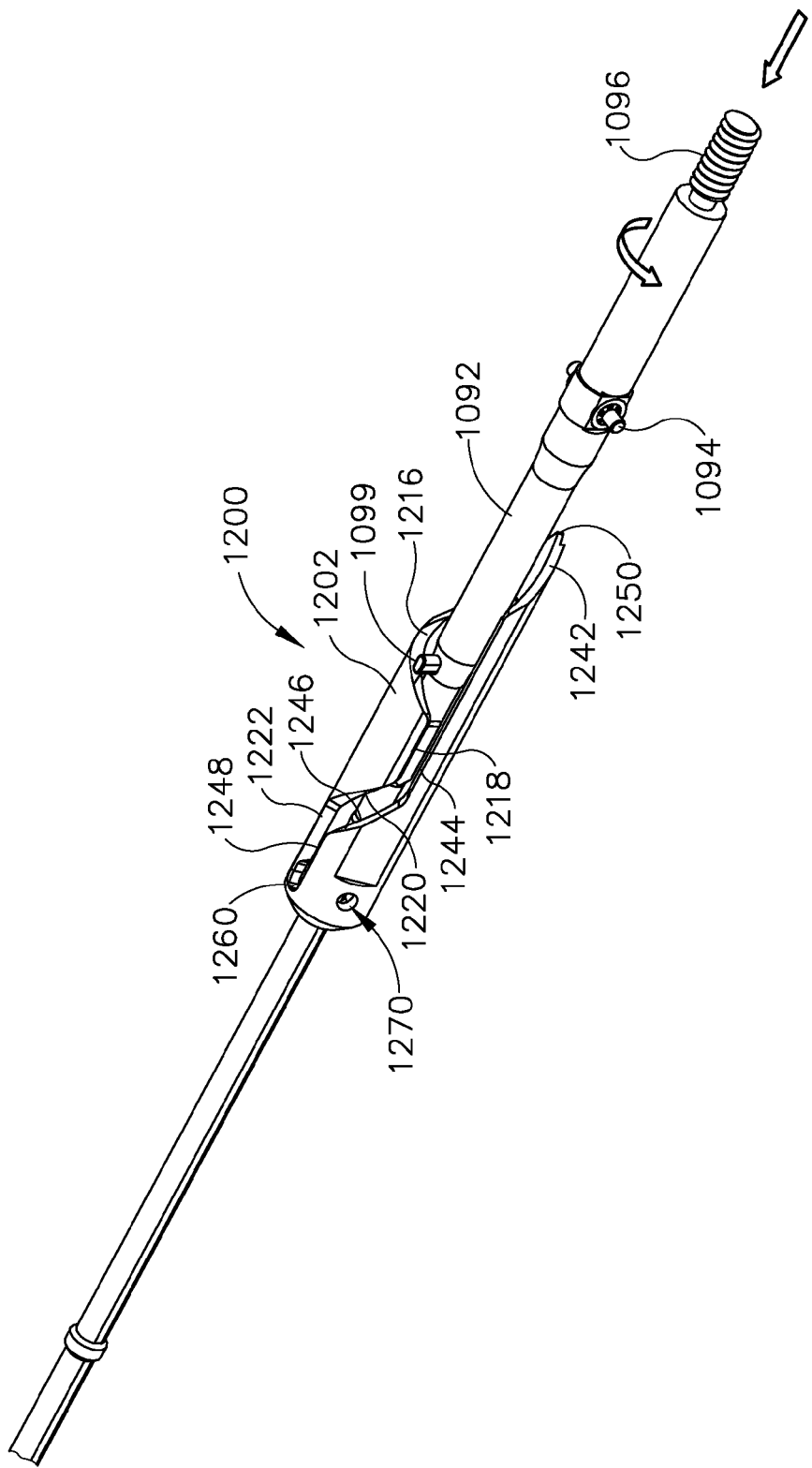
Figure 117D:
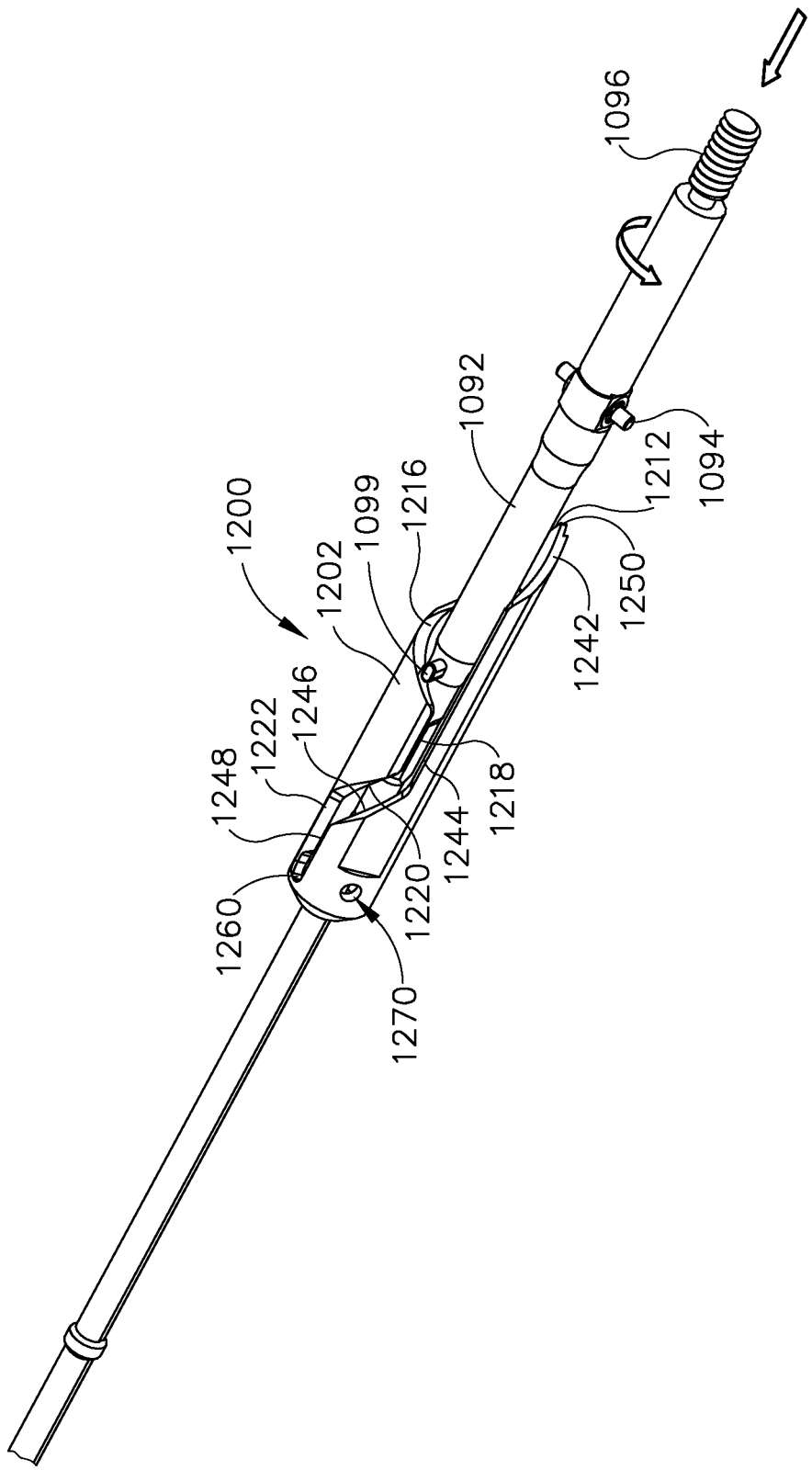
Figure 117E:
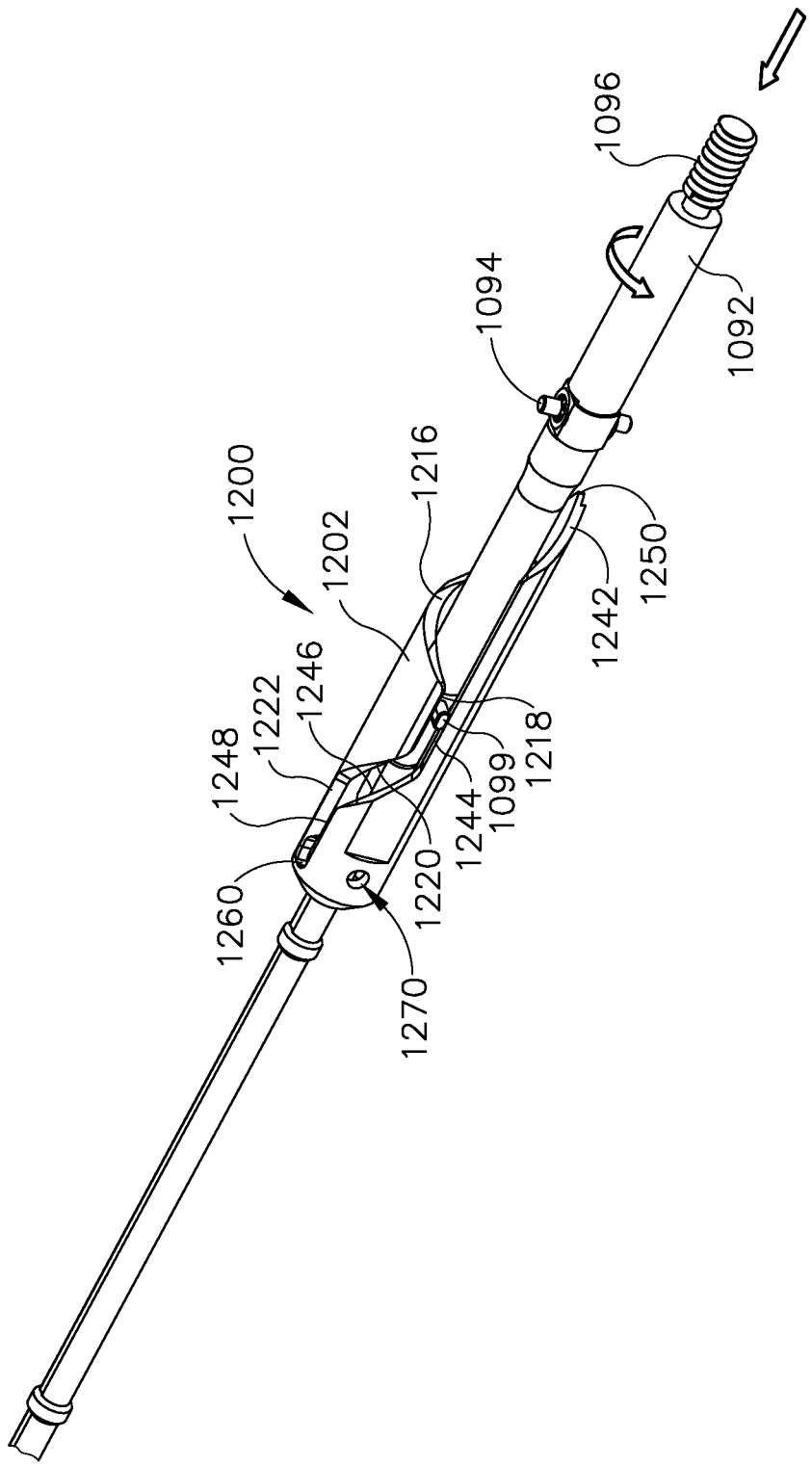
Figure 117F:
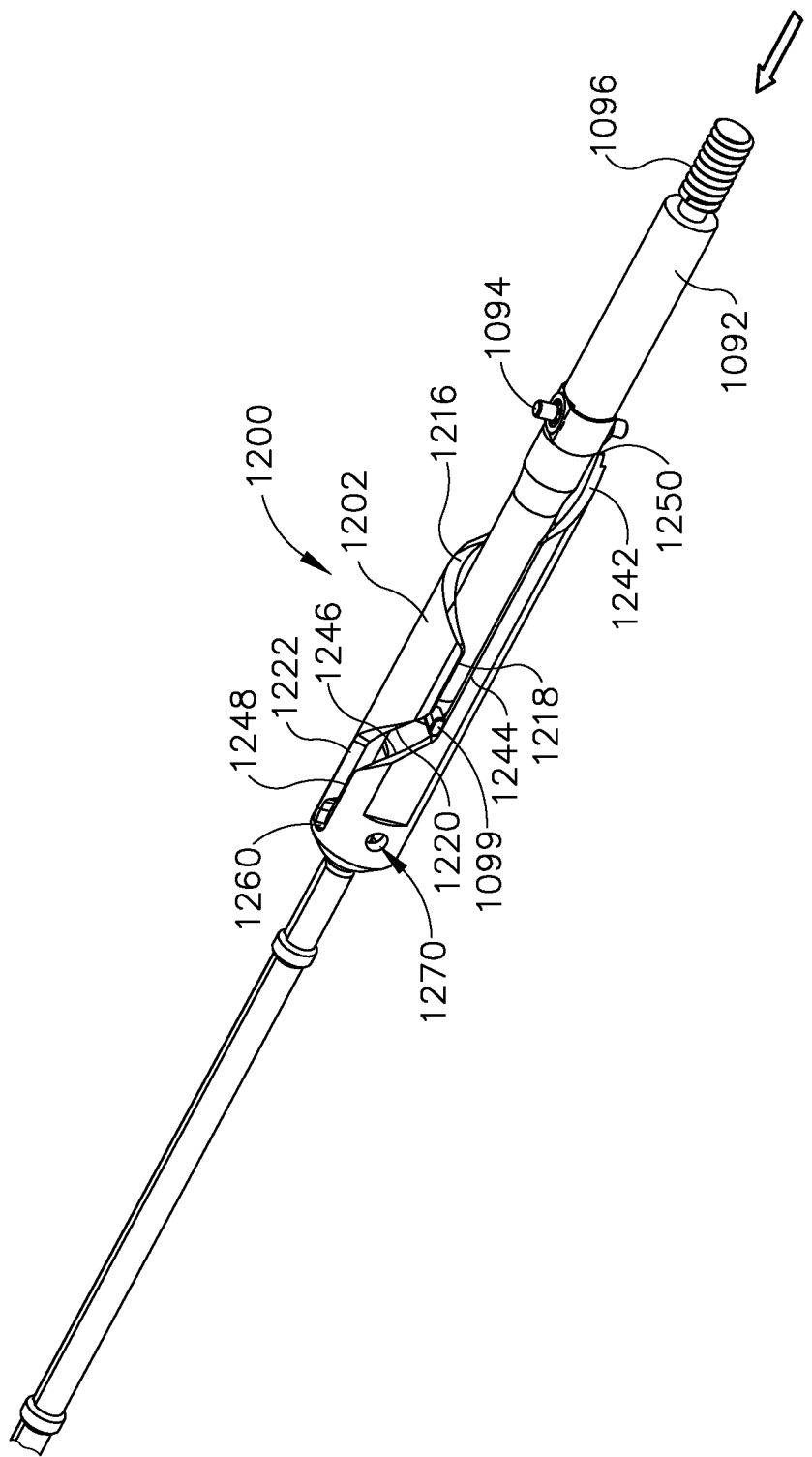
Figure 117G:
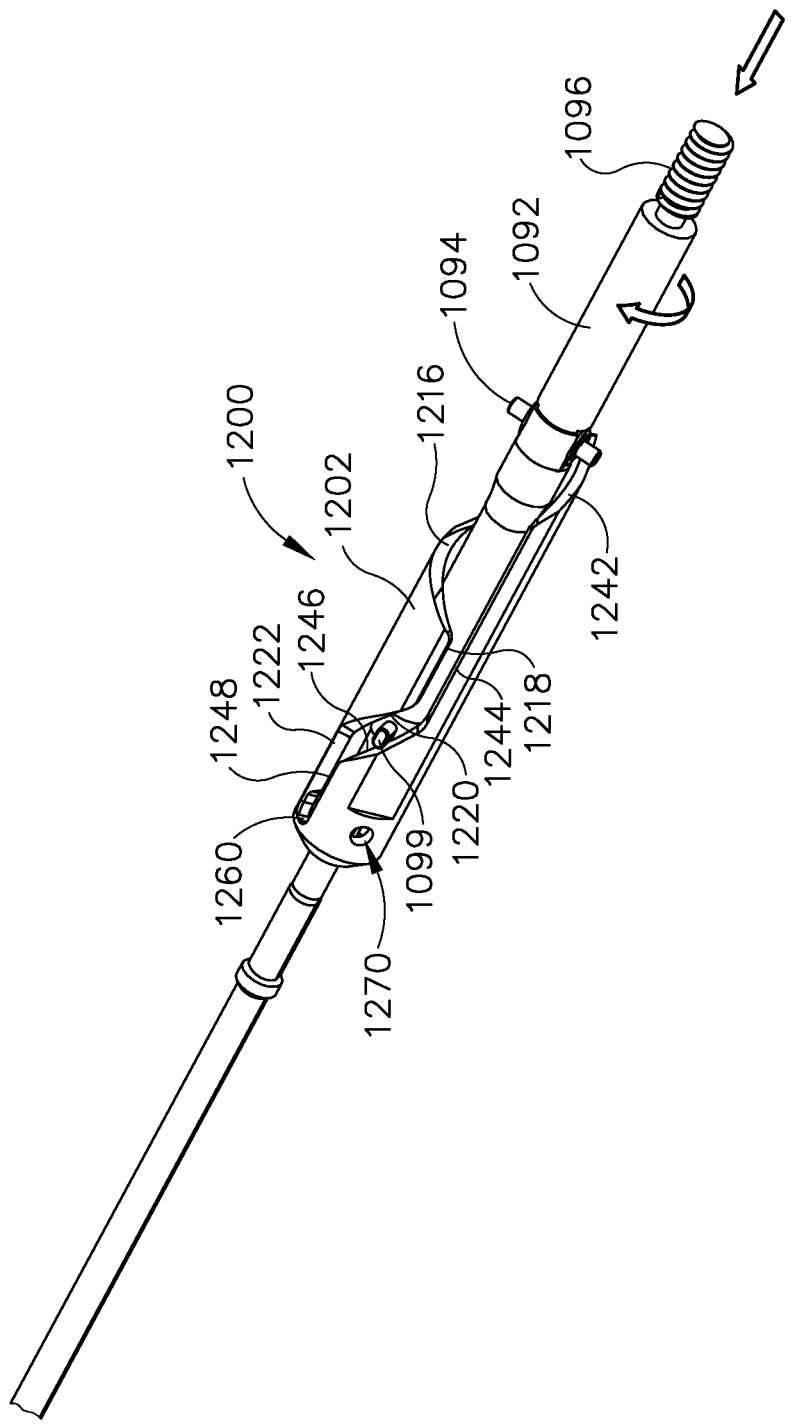
Figure 117H:
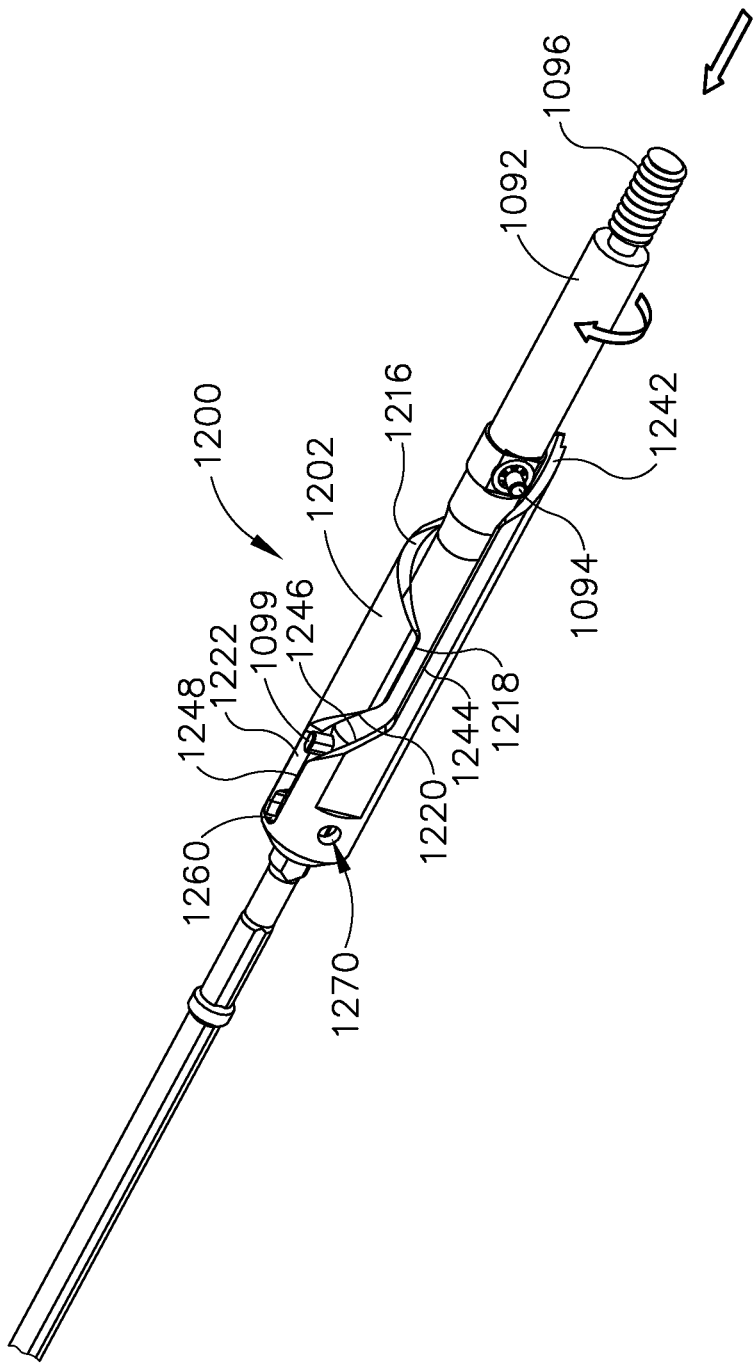
Figure 117I:
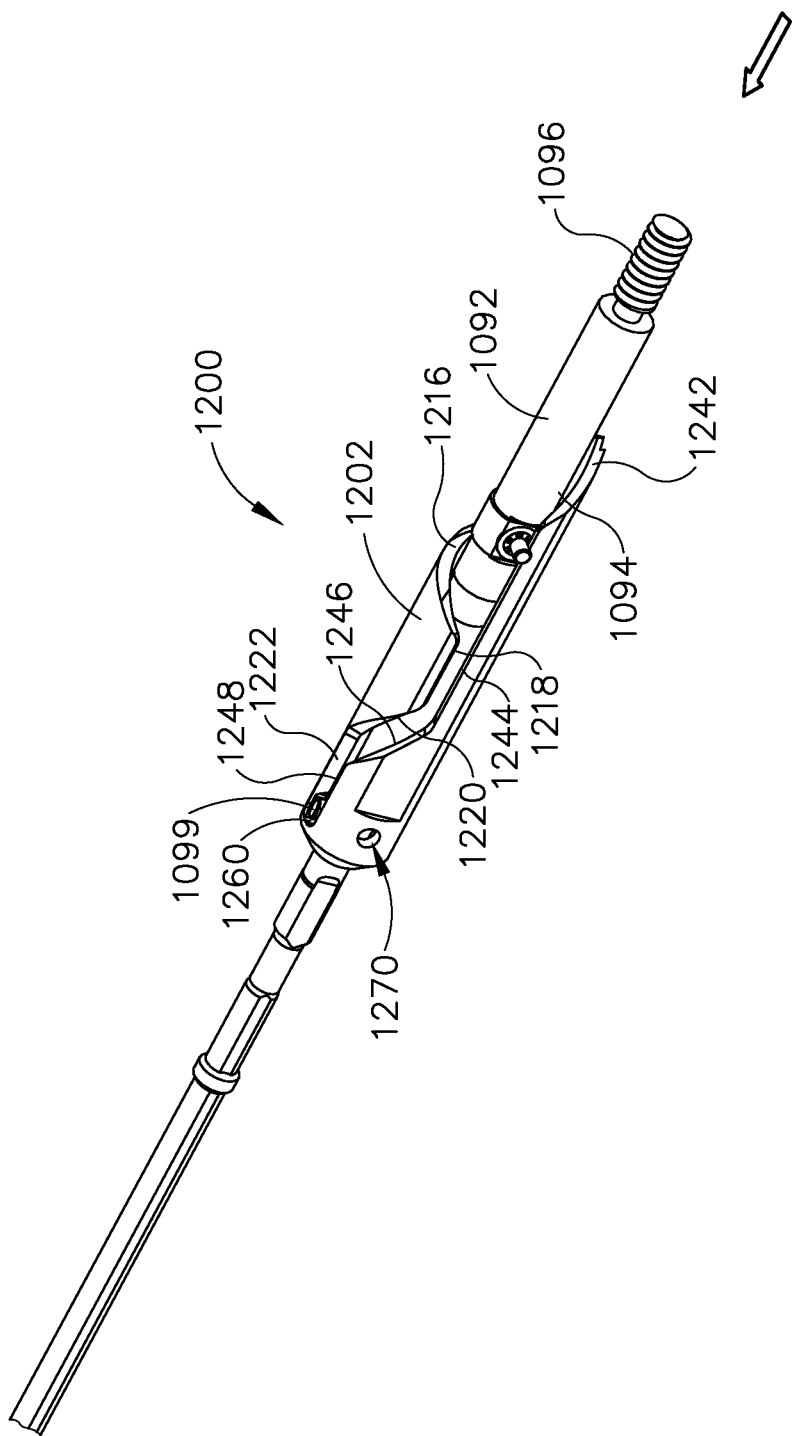
Figure 118A:
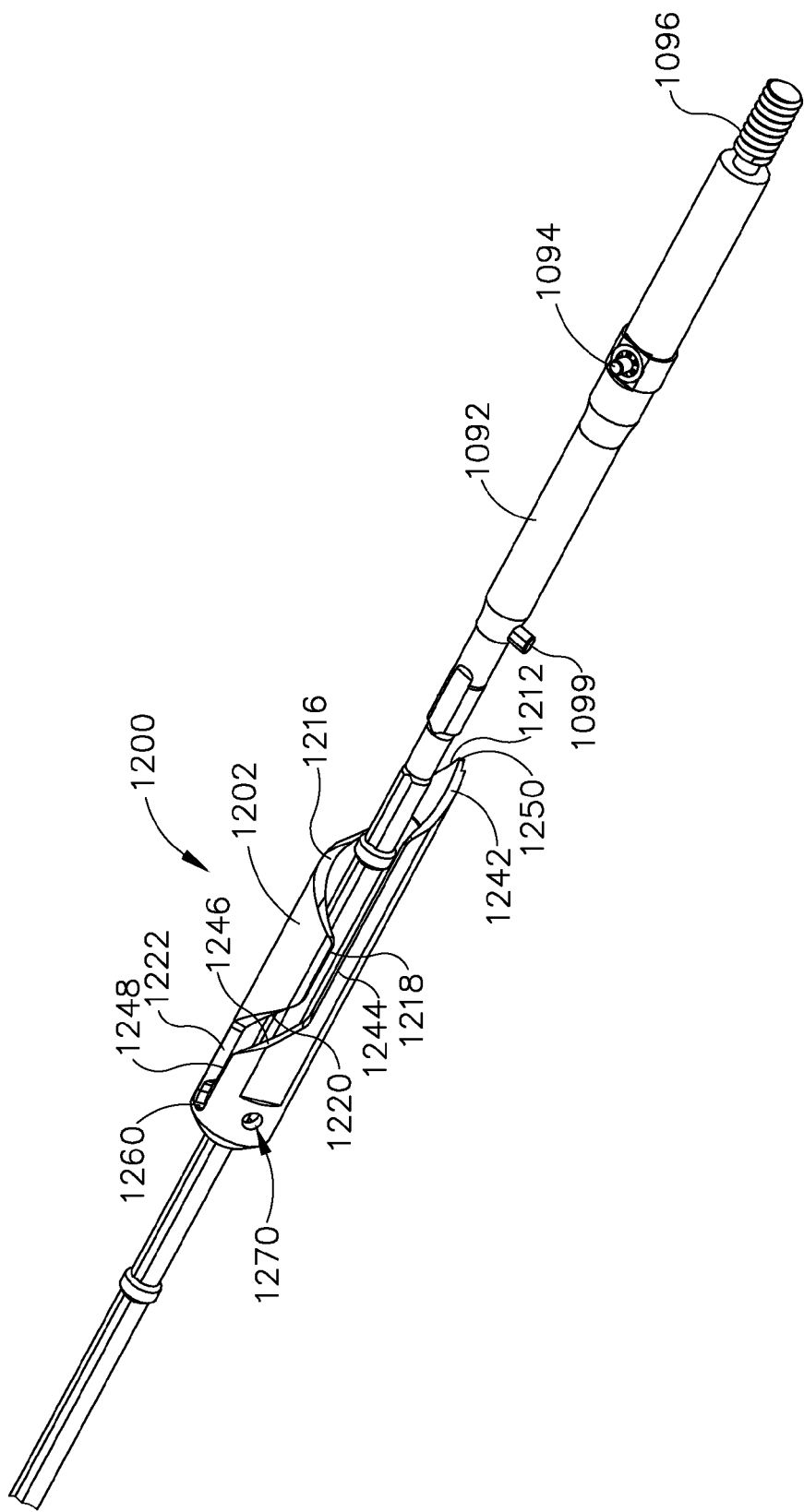
Figure 118B:
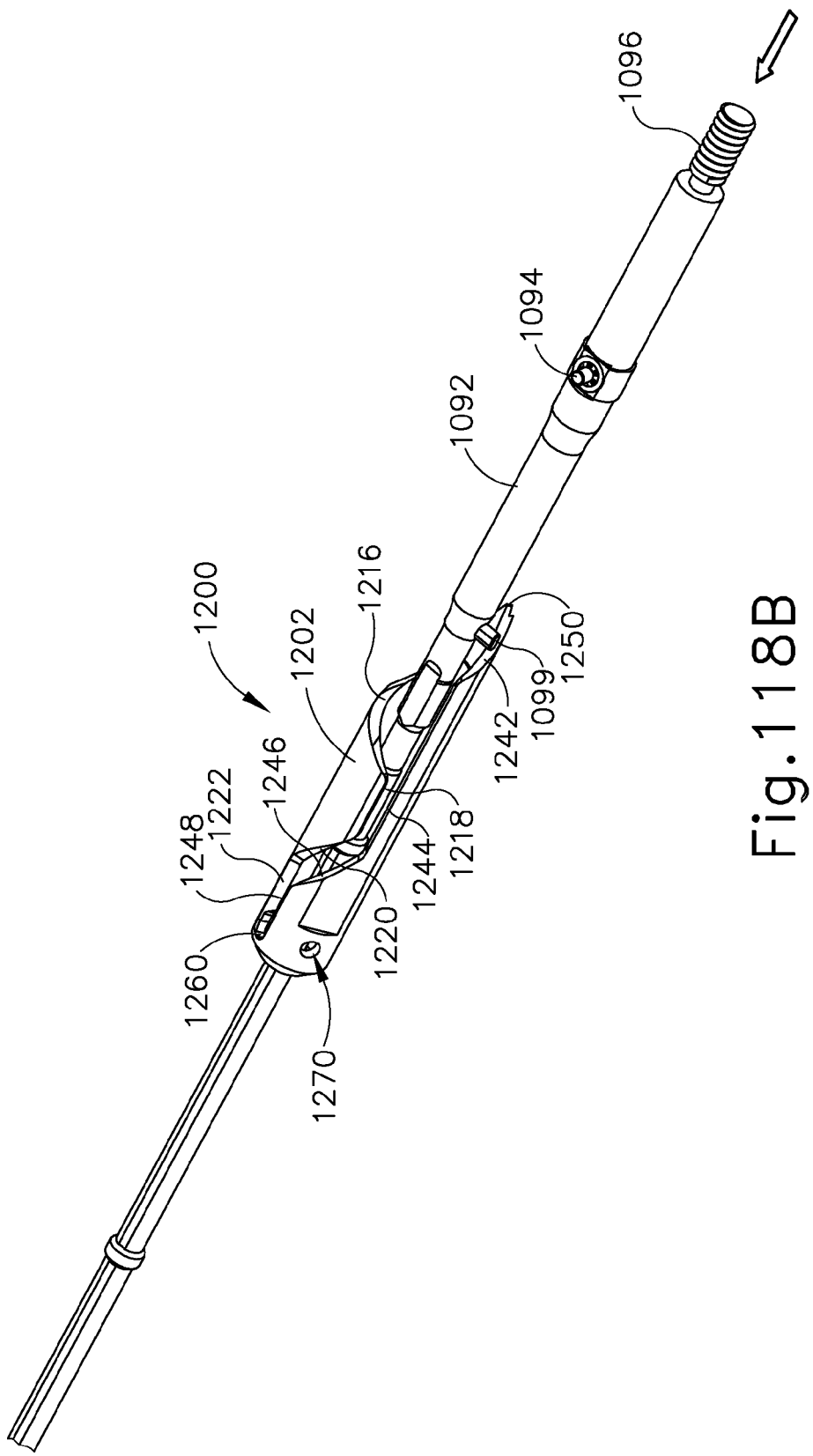
Figure 118C:
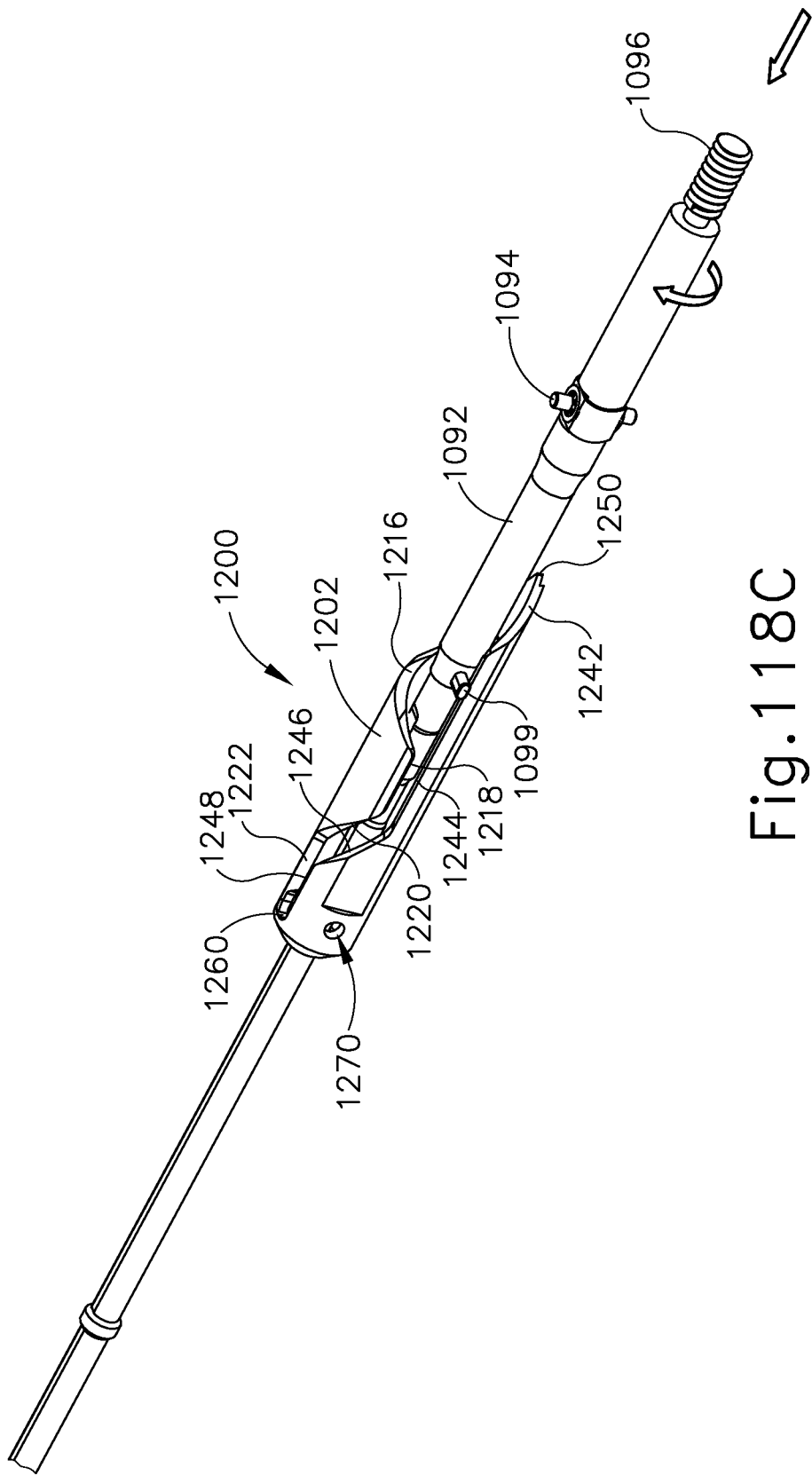
Figure 118D:
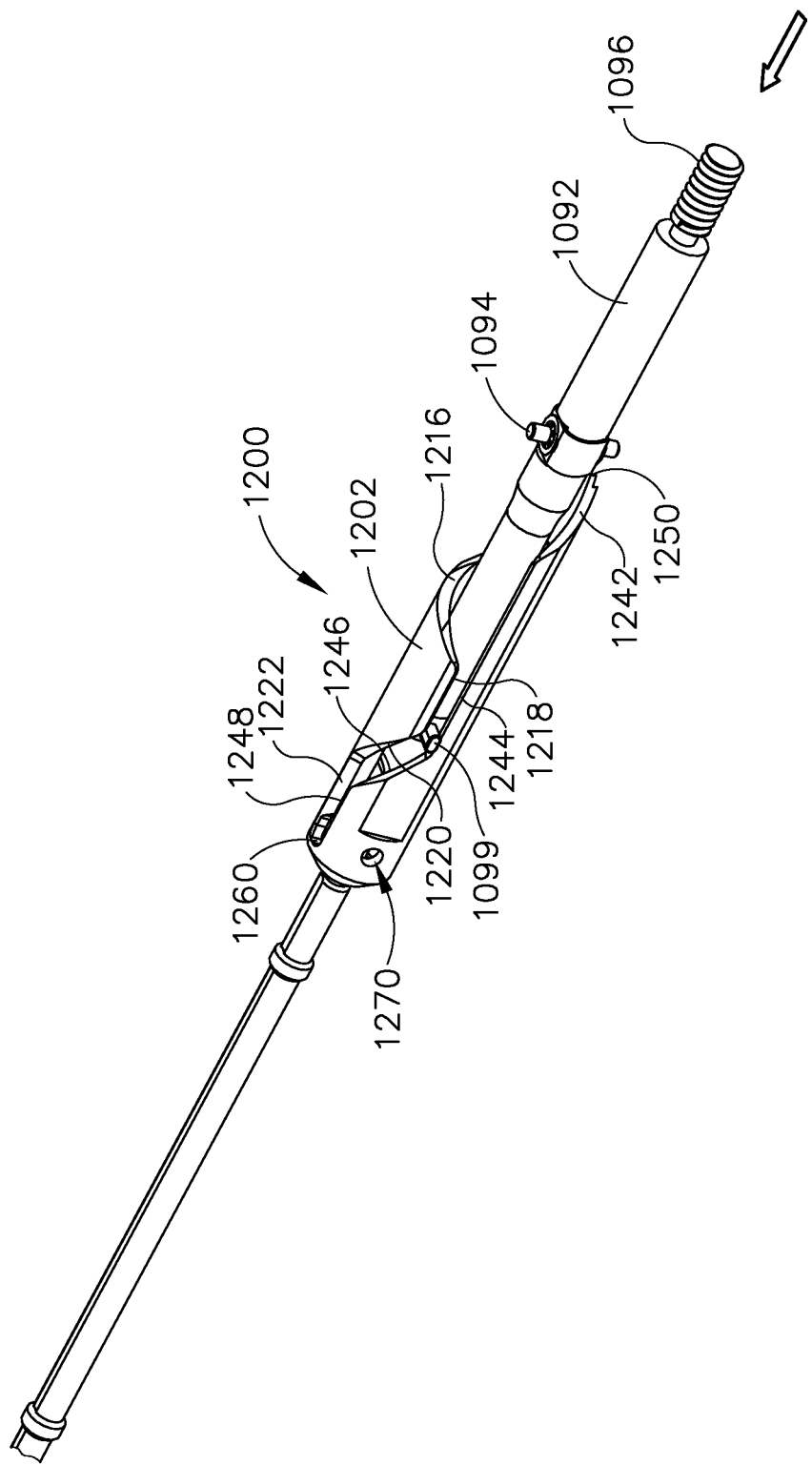
Figure 118E:
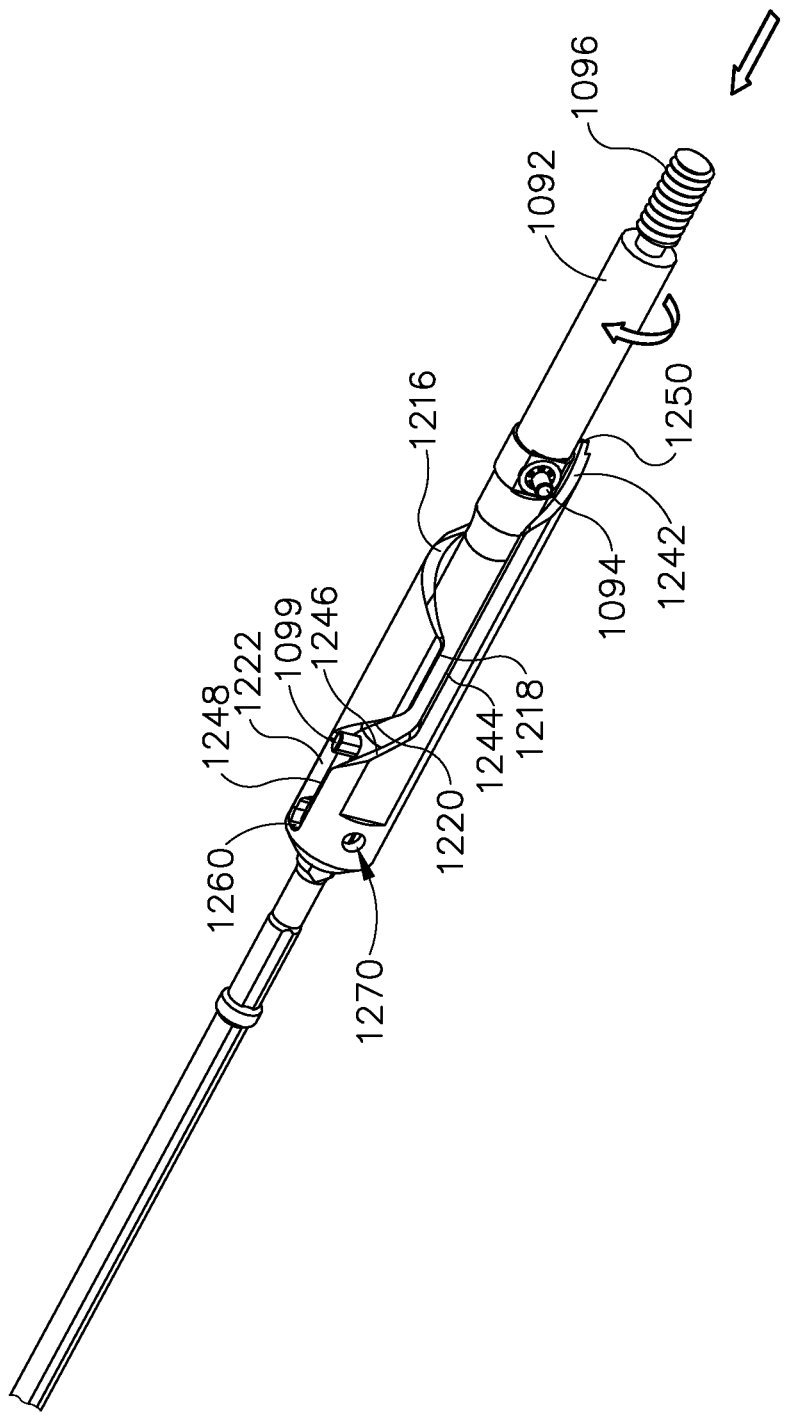
Figure 118F:
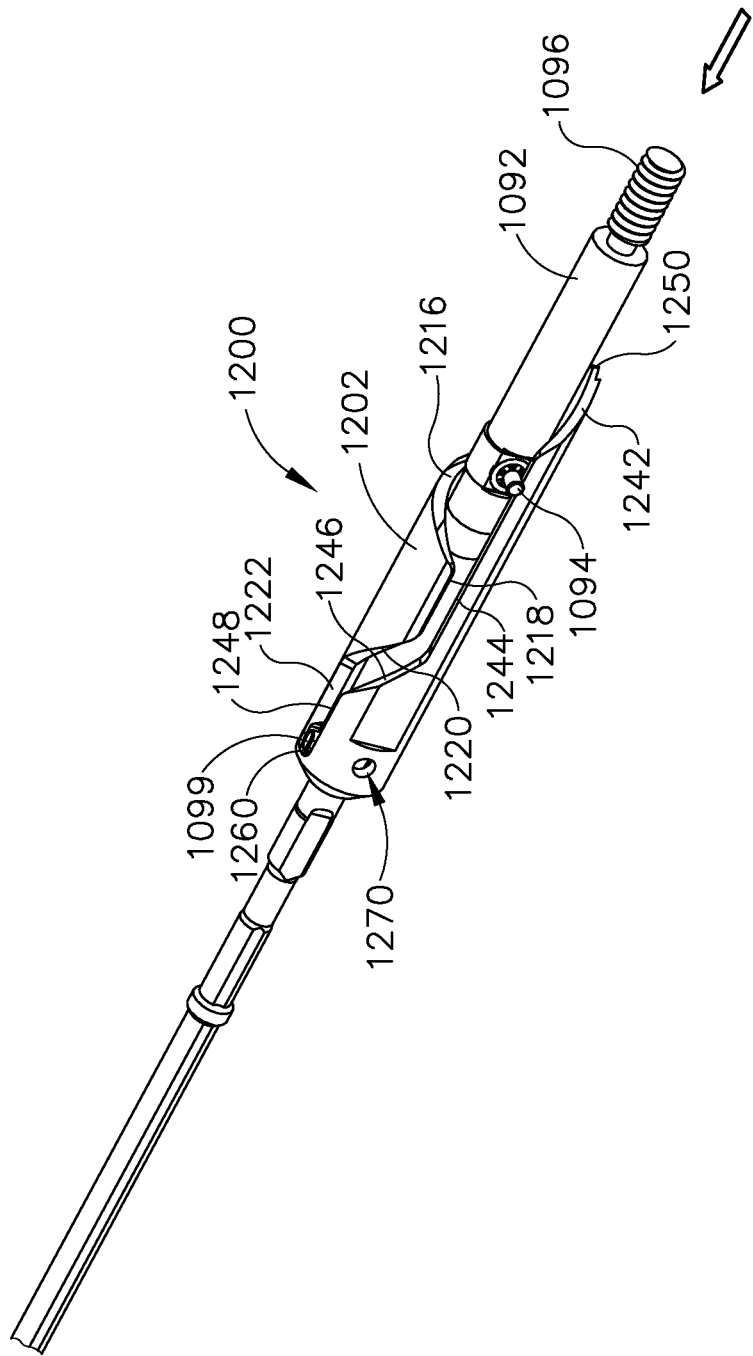

FIG. 103 depicts a perspective view of a coupling member assembly of the inner tube assembly of FIG. 102;

FIG. 104 depicts a perspective view of a deflector member of the coupling member assembly of FIG. 103;

FIG. 105 depicts a perspective view of a waveguide guiding member of the shaft assembly components of FIG. 94;

FIG. 106 depicts another perspective view of the waveguide guiding member of FIG. 105;

FIG. 107 depicts another perspective view of the waveguide guiding member of FIG. 105;

FIG. 108 depicts a perspective view of the proximal end of a waveguide of the shaft assembly components of FIG. 94;

FIG. 109 depicts a side elevational view of the disposable portion of FIG. 89 in a cleaning mode;

FIG. 110 depicts a side elevational view of the proximal end of the disposable portion of FIG. 89, with a housing half and the actuation yoke removed, and with the disposable portion in the cleaning mode of FIG. 109;

FIG. 111 depicts a perspective view of the disposable portion of FIG. 89 in the cleaning mode of FIG. 109;

FIG. 112 depicts another perspective view of the disposable portion of FIG. 89 in the cleaning mode of FIG. 109;

FIG. 113 depicts a cross-sectional side view of the proximal end of the shaft assembly components of FIG. 94, with the shaft assembly components in the cleaning mode of FIG. 109;

FIG. 114 depicts an enlarged cross-sectional side view of a knob assembly of the shaft assembly components of FIG. 94, with the shaft assembly components in the cleaning mode of FIG. 109;

FIG. 115 depicts a perspective view of a cleaning port body of the knob assembly of FIG. 114;

FIG. 116 depicts a cross-sectional perspective view of the cleaning port body of FIG. 115;

FIG. 117A depicts a perspective view of the waveguide of FIG. 108 at a first stage of insertion in the waveguide guiding member of FIG. 105, with the waveguide starting at a first angular orientation;

FIG. 117B depicts a perspective view of the waveguide of FIG. 108 at a second stage of insertion in the waveguide guiding member of FIG. 105, with the waveguide having started at the first angular orientation;

FIG. 117C depicts a perspective view of the waveguide of FIG. 108 at a third stage of insertion in the waveguide guiding member of FIG. 105, with the waveguide having started at the first angular orientation;

FIG. 117D depicts a perspective view of the waveguide of FIG. 108 at a fourth stage of insertion in the waveguide guiding member of FIG. 105, with the waveguide having started at the first angular orientation;

FIG. 117E depicts a perspective view of the waveguide of FIG. 108 at a fifth stage of insertion in the waveguide guiding member of FIG. 105, with the waveguide having started at the first angular orientation;

FIG. 117F depicts a perspective view of the waveguide of FIG. 108 at a sixth stage of insertion in the waveguide guiding member of FIG. 105, with the waveguide having started at the first angular orientation;

FIG. 117G depicts a perspective view of the waveguide of FIG. 108 at a seventh stage of insertion in the waveguide guiding member of FIG. 105, with the waveguide having started at the first angular orientation;

FIG. 117H depicts a perspective view of the waveguide of FIG. 108 at an eighth stage of insertion in the waveguide guiding member of FIG. 105, with the waveguide having started at the first angular orientation;

FIG. 117I depicts a perspective view of the waveguide of FIG. 108 fully inserted in the waveguide guiding member of FIG. 105, with the waveguide having started at the first angular orientation;

FIG. 118A depicts a perspective view of the waveguide of FIG. 108 at a first stage of insertion in the waveguide guiding member of FIG. 105, with the waveguide starting at a second angular orientation;

FIG. 118B depicts a perspective view of the waveguide of FIG. 108 at a second stage of insertion in the waveguide guiding member of FIG. 105, with the waveguide having started at the second angular orientation;

FIG. 118C depicts a perspective view of the waveguide of FIG. 108 at a third stage of insertion in the waveguide guiding member of FIG. 105, with the waveguide having started at the second angular orientation;

FIG. 118D depicts a perspective view of the waveguide of FIG. 108 at a fourth stage of insertion in the waveguide guiding member of FIG. 105, with the waveguide having started at the second angular orientation;

FIG. 118E depicts a perspective view of the waveguide of FIG. 108 at a fifth stage of insertion in the waveguide guiding member of FIG. 105, with the waveguide having started at the second angular orientation; and FIG. 118F depicts a perspective view of the waveguide of FIG. 108 fully inserted in the waveguide guiding member of FIG. 105, with the waveguide having started at the second angular orientation.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Overview of Exemplary Ultrasonic Surgical Instrument

Figure 1:
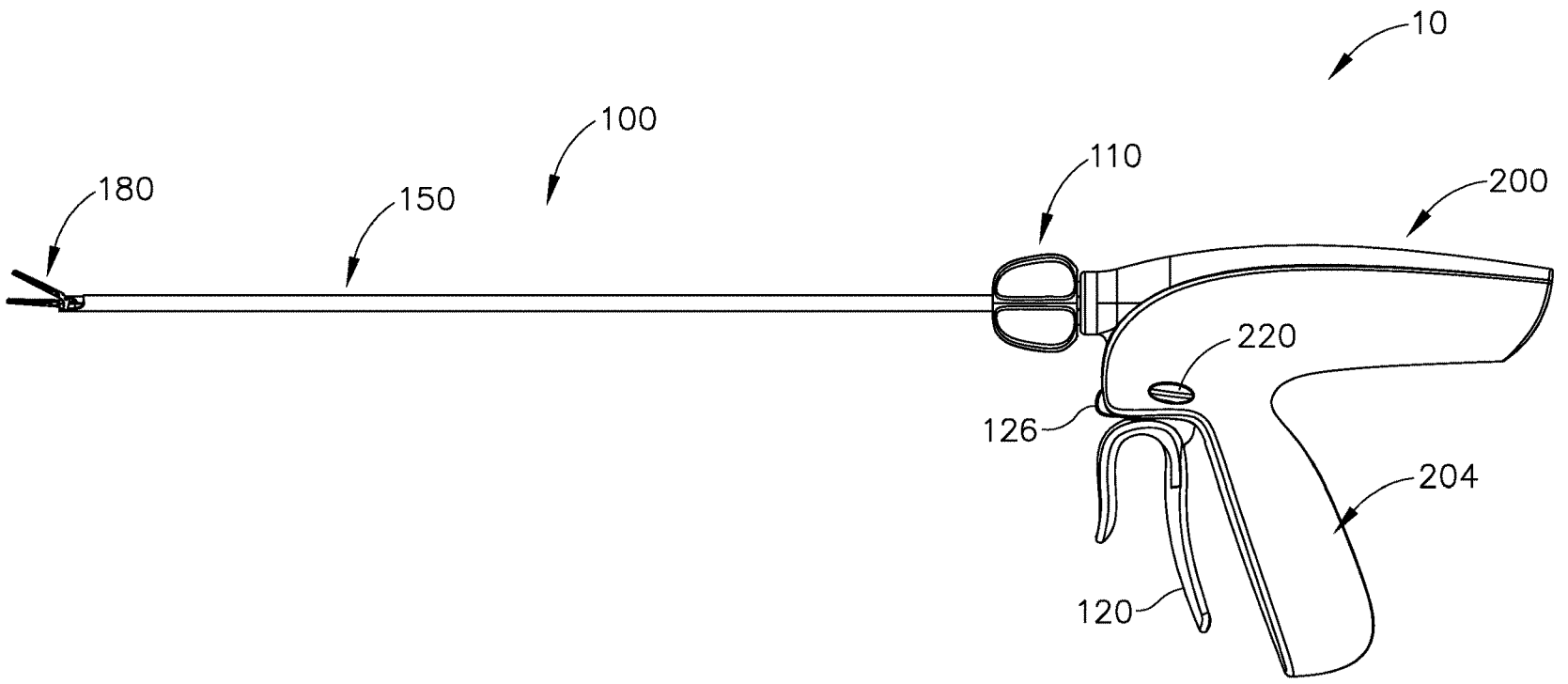
FIG. 1 depicts a side elevational view of an exemplary ultrasonic surgical instrument.
Figure 2:
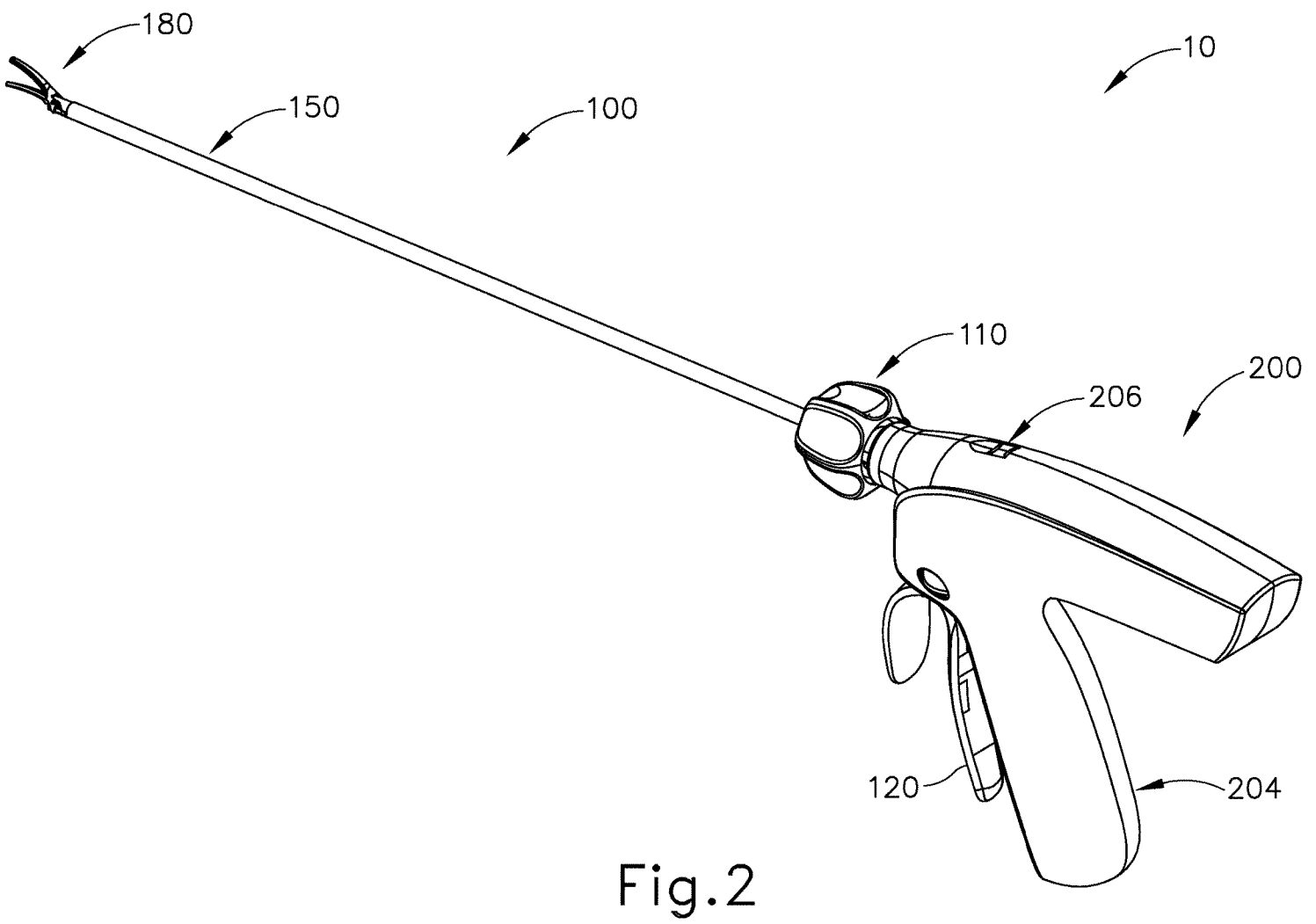
FIG. 2 depicts a perspective view of the instrument of FIG. 1.
Figure 3:

FIG. 3 depicts a perspective view of the instrument of FIG. 1, with a disposable portion separated from a reusable portion.
Figure 4:
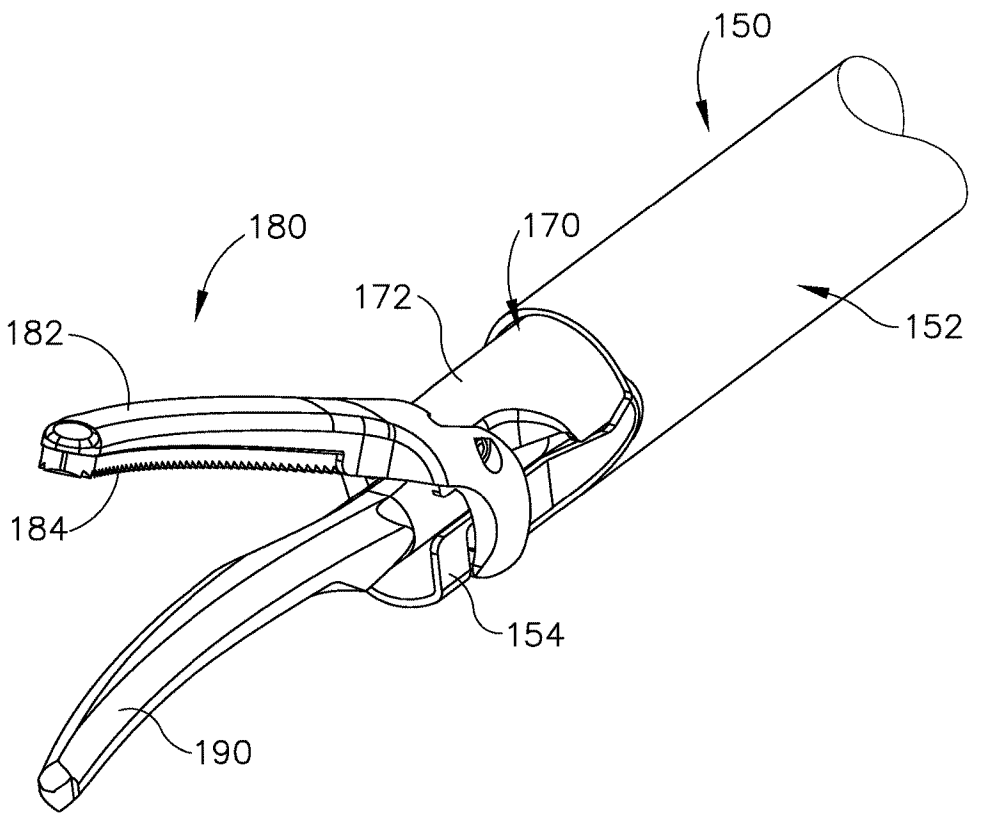
FIG. 4 depicts a perspective view of an end effector of the instrument of FIG. 1, in an open configuration.

FIGS. 1-3 show an exemplary ultrasonic surgical instrument (10) that is configured to be used in minimally invasive surgical procedures (e.g., via a trocar or other small diameter access port, etc.). As will be described in greater detail below, instrument (10) is operable to cut tissue and seal or weld tissue (e.g., a blood vessel, etc.) substantially simultaneously. Instrument (10) of this example comprises a disposable assembly (100) and a reusable assembly (200). The distal portion of reusable assembly (200) is configured to removably receive the proximal portion of disposable assembly (100), as seen in FIGS. 2-3, to form instrument (10).

In an exemplary use, assemblies (100, 200) are coupled together to form instrument (10) before a surgical procedure, the assembled instrument (10) is used to perform the surgical procedure, and then assemblies (100, 200) are decoupled from each other for further processing. In some instances, after the surgical procedure is complete, disposable assembly (100) is immediately disposed of while reusable assembly (200) is sterilized and otherwise processed for re-use. By way of example only, reusable assembly (200) may be sterilized in a conventional relatively low temperature, relatively low pressure, hydrogen peroxide sterilization process. Alternatively, reusable assembly (200) may be sterilized using any other suitable systems and techniques (e.g., autoclave, etc.). In some versions, reusable assembly (200) may be sterilized and reused approximately 100 times. Alternatively, reusable assembly (200) may be subject to any other suitable life cycle. For instance, reusable assembly (200) may be disposed of after a single use, if desired. While disposable assembly (100) is referred to herein as being "disposable," it should be understood that, in some instances, disposable assembly (100) may also be sterilized and otherwise processed for re-use. By way of example only, disposable assembly (100) may be sterilized and reused approximately 2-30 times, using any suitable systems and techniques. Alternatively, disposable assembly (100) may be subject to any other suitable life cycle.

In some versions, disposable assembly (100) and/or reusable assembly (200) includes one or more features that are operable to track usage of the corresponding assembly (100, 200), and selectively restrict operability of the corresponding assembly (100, 200) based on use. For instance, disposable assembly (100) and/or reusable assembly (200) may include one or more counting sensors and a control logic (e.g., microprocessor, etc.) that is in communication with the counting sensor(s). The counting sensor(s) may be able to detect the number of times the ultrasonic transducer of instrument (10) is activated, the number of surgical procedures the corresponding assembly (100, 200) is used in, the number of trigger closures, and/or any other suitable conditions associated with use. The control logic may track data from the counting sensor(s) and compare the data to one or more threshold values. When the control logic determines that one or more threshold values have been exceeded, the control logic may execute a control algorithm to disable operability of one or more components in the corresponding assembly (100, 200). In instances where the control logic stores two or more threshold values (e.g., a first threshold for number of activations and a second threshold for number of surgical procedures, etc.), the control logic may disable operability of one or more components in the corresponding assembly (100, 200) the first time one of those thresholds is exceeded, or on some other basis.

In versions where a control logic is operable to disable instrument (10) based on the amount of use, the control logic may also determine whether instrument (10) is currently being used in a surgical procedure, and refrain from disabling instrument (10) until that particular surgical procedure is complete. In other words, the control logic may allow the operator to complete the current surgical procedure but prevent instrument (10) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (10) will be apparent to those of ordinary skill in the art in view of the teachings herein. Of course, some versions of instrument (10) may simply omit features that track and/or restrict the amount of usage of instrument (10).

Figure 5:
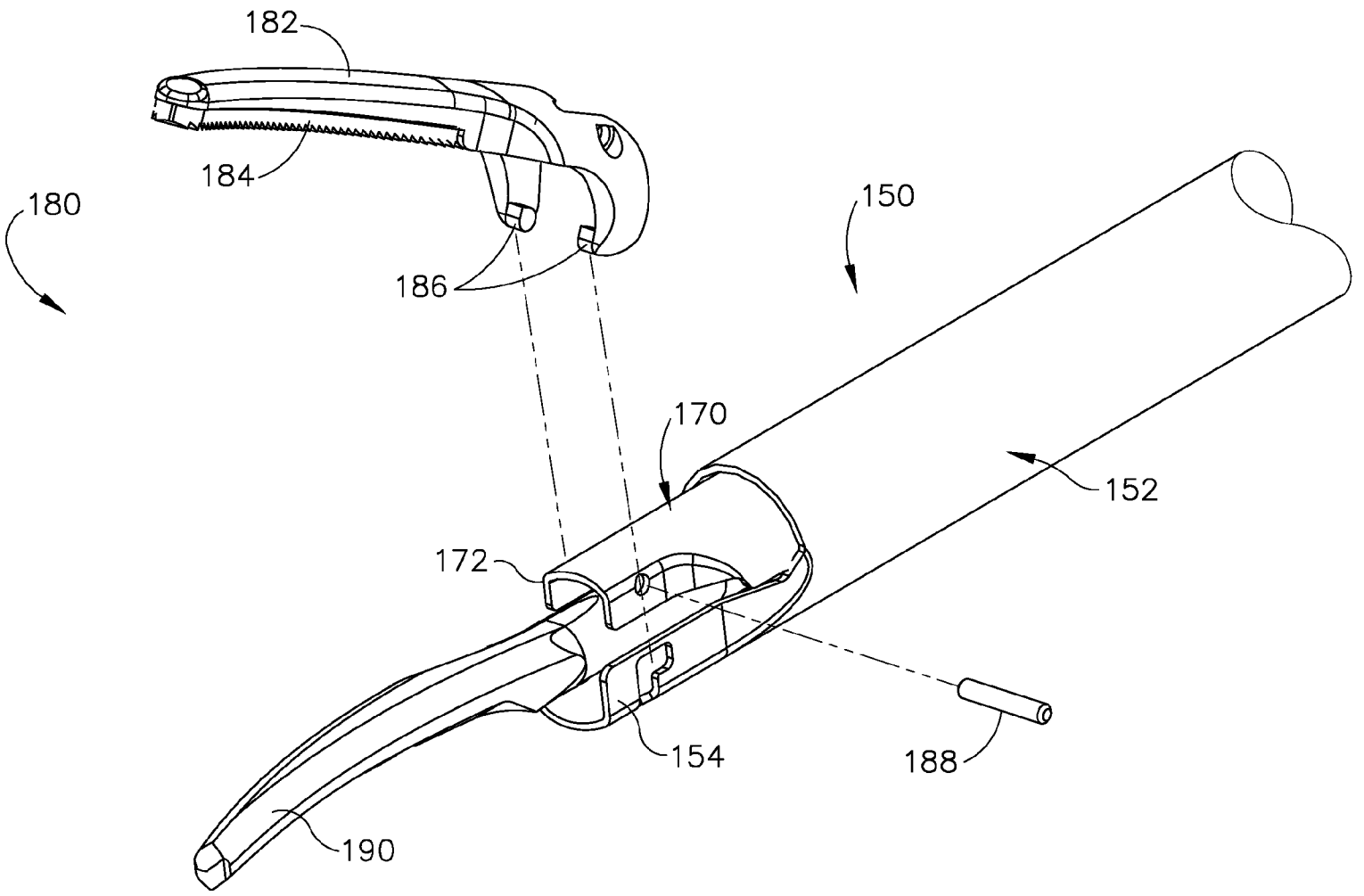
FIG. 5 depicts a partially exploded view of the end effector of FIG. 4.
Figure 6A:
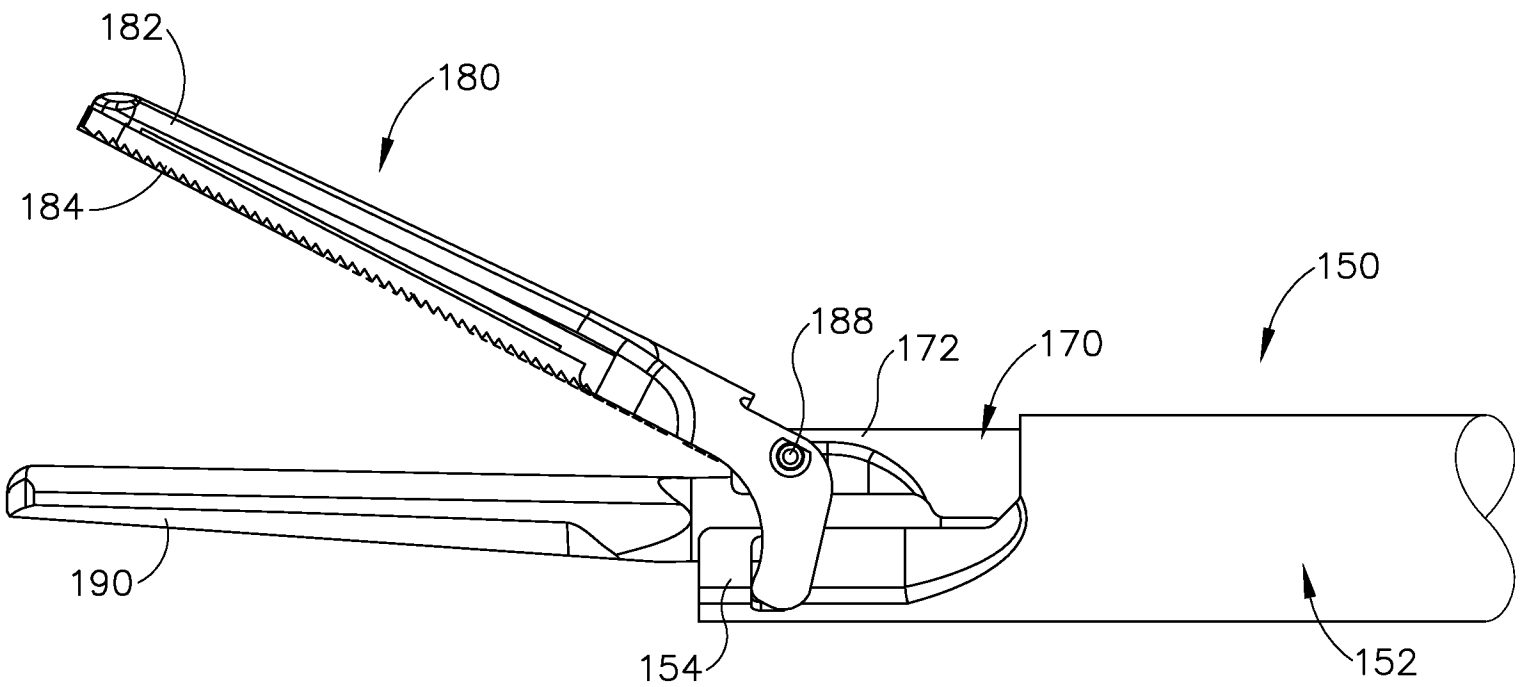
FIG. 6A depicts a side elevational view of the end effector of FIG. 4, in the open configuration.
Figure 6B:
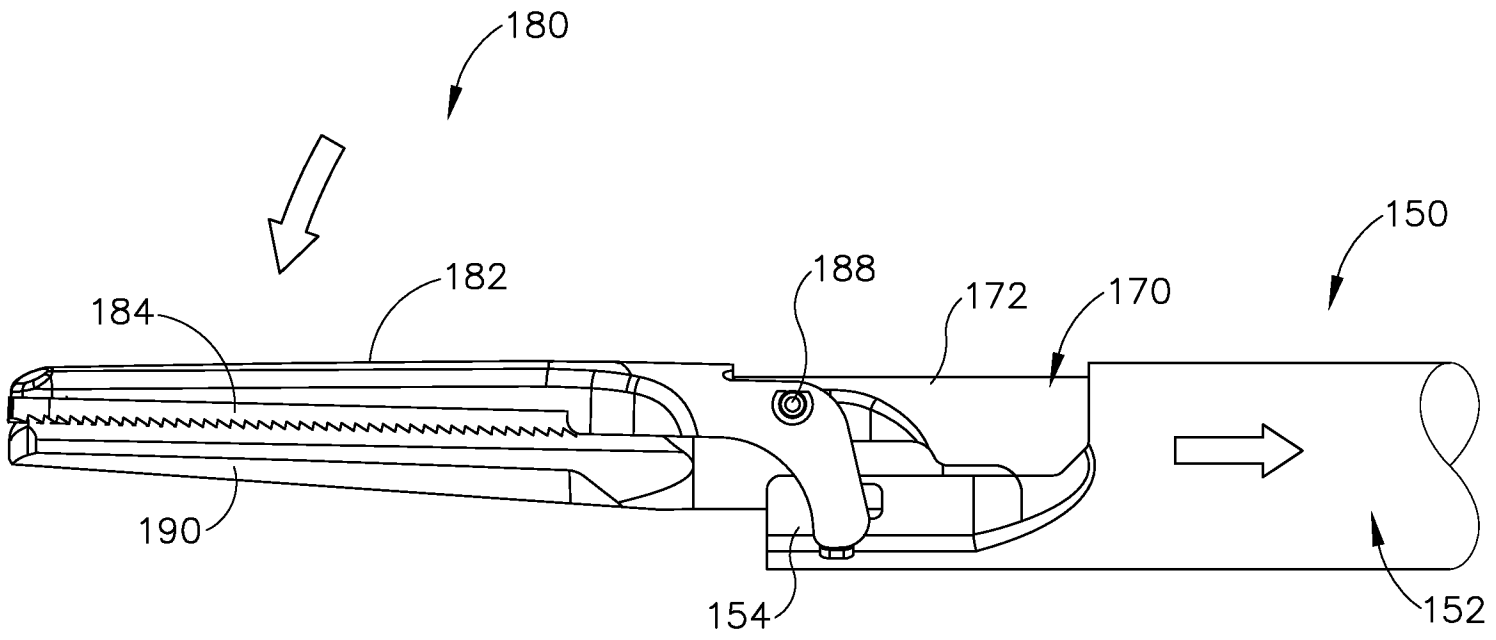
FIG. 6B depicts a side elevational view of the end effector of FIG. 4, in a closed configuration.
Figure 7:
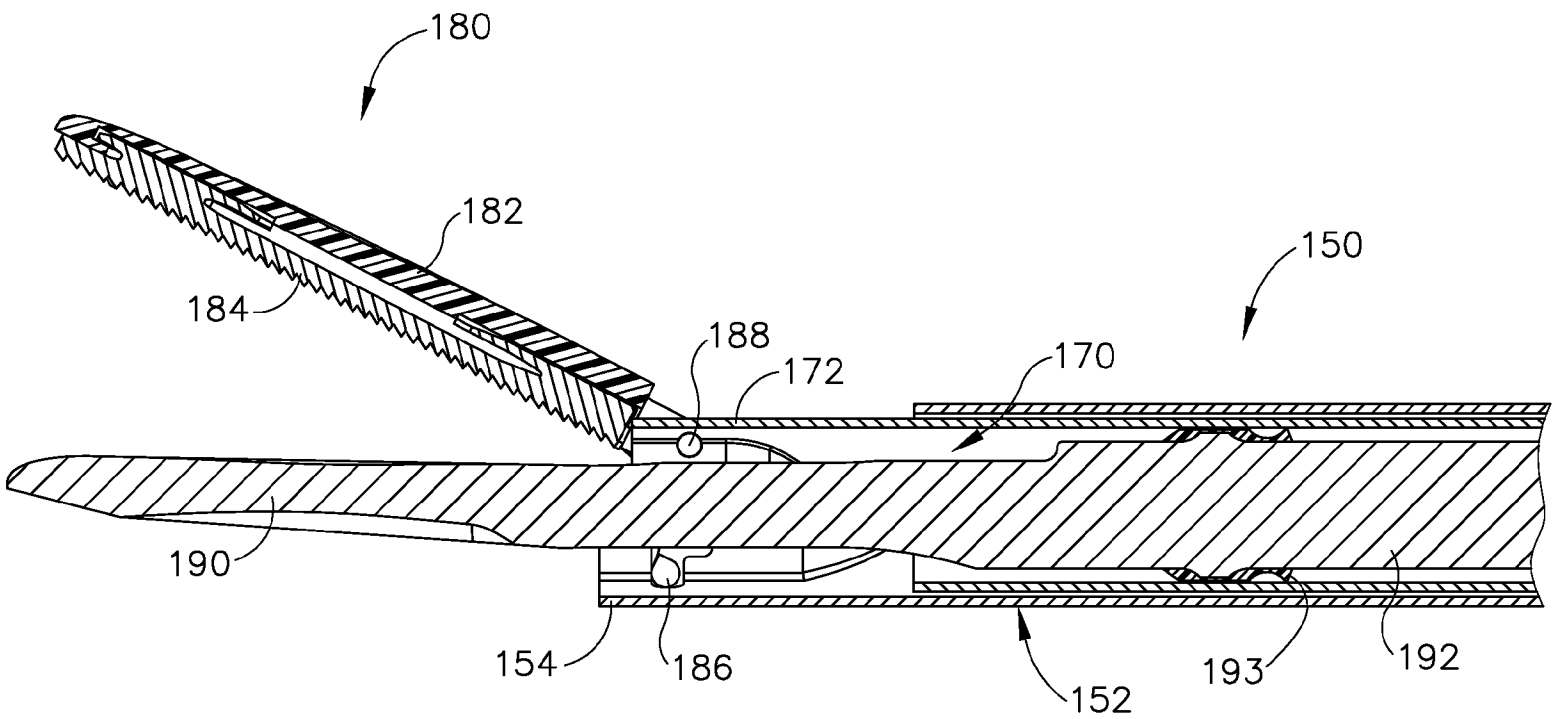
FIG. 7 depicts a side cross-sectional view of the end effector of FIG. 4, in the open configuration.

Disposable assembly (100) of the present example comprises a body portion (110), a shaft assembly (150) extending distally from body portion (110), and an end effector (180) located at the distal end of shaft assembly (150). As best seen in FIGS. 4-7, end effector (180) of this example comprises a clamp arm (182) and an ultrasonic blade (190). Clamp arm (182) includes a clamp pad (184), which faces blade (190). As shown in FIGS. 6A-6B and as will be described in greater detail below, clamp arm (182) is pivotable toward and away from blade (190) to selectively compress tissue between clamp pad (184) and blade (190). As seen in FIG. 7, blade (190) is an integral feature of the distal end of an acoustic waveguide (192), which extends coaxially through tubes (152, 170), and which is configured to communicate ultrasonic vibrations to blade (190) as will be described in greater detail below.

Shaft assembly (150) comprises an outer tube (152) and an inner tube (170). Outer tube (152) is operable to translate longitudinally relative to inner tube (170) to selectively pivot clamp arm (182) toward and away from blade (190). To accomplish this, and as best seen in FIGS. 5 and 7, integral pin features (186) of clamp arm (182) pivotally secure a first portion of clamp arm (182) to a distally projecting tongue (154) of outer tube (152); while an inserted pin (188) pivotally secures a second portion of clamp arm (182) to a distally projecting tongue (172) of inner tube (170). Thus, as can be seen in the transition from FIG. 6A to FIG. 6B, tubes (152, 170) cooperate to pivot clamp arm (182) toward blade (190) when outer tube (152) is retracted proximally relative to inner tube (170). It should be understood that clamp arm (182) may be pivoted back away from blade (190) (e.g., from the position shown in FIG. 6B to the position shown in FIG. 6A) by translating outer tube (152) distally relative to inner tube (170), in reverse of the operation shown in FIGS. 6A-6B. In an exemplary use, clamp arm (182) may be pivoted toward blade (190) to grasp, compress, seal, and sever tissue captured between clamp pad (184) and blade (190). Clamp arm (182) may be pivoted away from blade (190) to release tissue from between clamp pad (184) and blade (190); and/or to perform blunt dissection of tissue engaging opposing outer surfaces of clamp arm (182) and blade (190).

Figure 8:
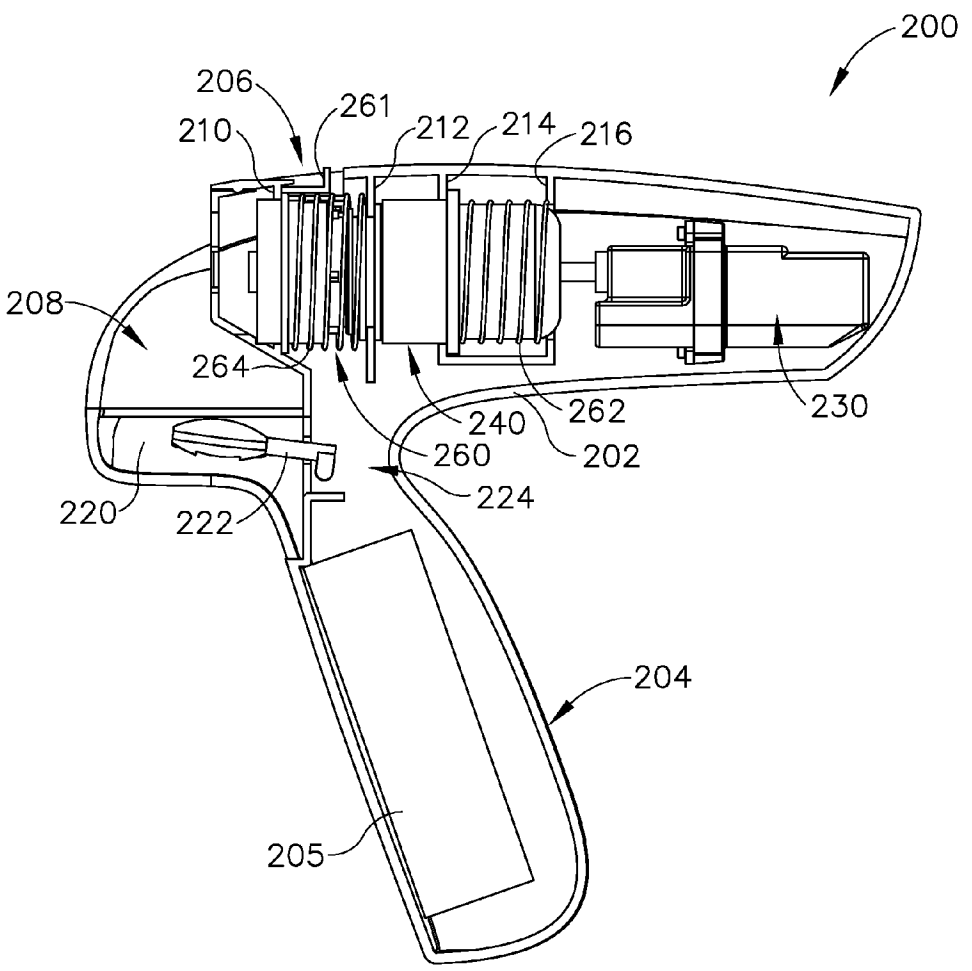
FIG. 8 depicts a side elevational view of the reusable portion of the instrument of FIG. 1, with a housing half removed.

As seen in FIG. 8, reusable assembly (200) comprises a handle housing (202). While FIG. 8 only shows one housing (202), FIGS. 2-3 show how a pair of complementary housings (202) are joined together. Housing (202) defines a pistol grip (204), an upper window (206), and a distal recess (208). While reusable assembly (200) includes a pistol grip (204) in this example, it should be understood that any other suitable kind of grip may be used. Housing (202) of the present example also includes several integral bosses (210, 212, 214, 216) that provide support for additional components as will be described in greater detail below, such that housing (202) serves as a chassis for components contained within housing (202). As also shown in FIG. 8, reusable assembly (200) includes a battery (205), a generator (230), an ultrasonic transducer assembly (240), and a torque wrench assembly (260). As will be described in greater detail below, battery (205) is operable to provide electrical power to generator (230); generator (230) is operable to provide electrical power to ultrasonic transducer assembly (240); ultrasonic transducer assembly is operable to convert electrical power into ultrasonic vibrations; and torque wrench assembly (260) is operable to mechanically and acoustically couple waveguide (192) with ultrasonic transducer assembly (240).

When waveguide (192) is sufficiently coupled with transducer assembly (240), ultrasonic vibrations that are generated by transducer assembly (240) are communicated along waveguide (192) to reach blade (190). In the present example, the distal end of blade (190) is located at a position corresponding to an anti-node associated with resonant ultrasonic vibrations communicated through waveguide (192), in order to tune the acoustic assembly to a preferred resonant frequency $f_o$ when the acoustic assembly is not loaded by tissue. When transducer assembly (240) is energized, the distal end of blade (190) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (240) of the present example is activated, these mechanical oscillations are transmitted through waveguide (192) to reach blade (190), thereby providing oscillation of blade (190) at the resonant ultrasonic frequency. Thus, when tissue is secured between blade (190) and clamp pad (184), the ultrasonic oscillation of blade (190) may simultaneously sever the tissue and denature the proteins in adjacent tissue cells, thereby providing a coagulative effect with relatively little thermal spread. In some versions, an electrical current may also be provided through blade (190) and/or clamp pad (184) to also seal the tissue.

Further exemplary features and operabilities for disposable assembly (100) and reusable assembly (200) will be described in greater detail below, while other variations will be apparent to those of ordinary skill in the art in view of the teachings herein.

II. Disposable Assembly of Exemplary Ultrasonic Surgical Instrument

Figure 9:
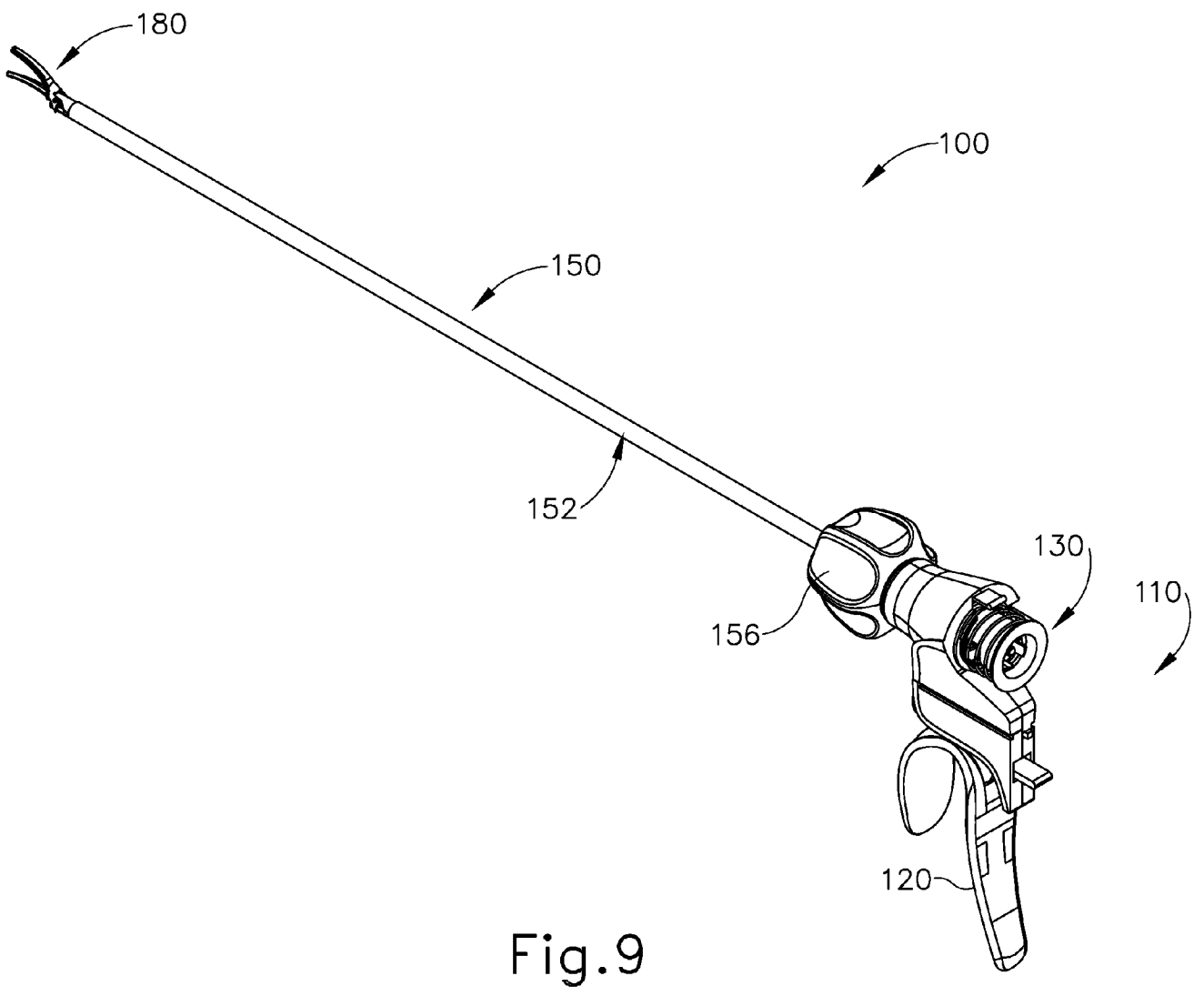
FIG. 9 depicts a perspective view of the disposable portion of the instrument of FIG. 1.
Figure 10:
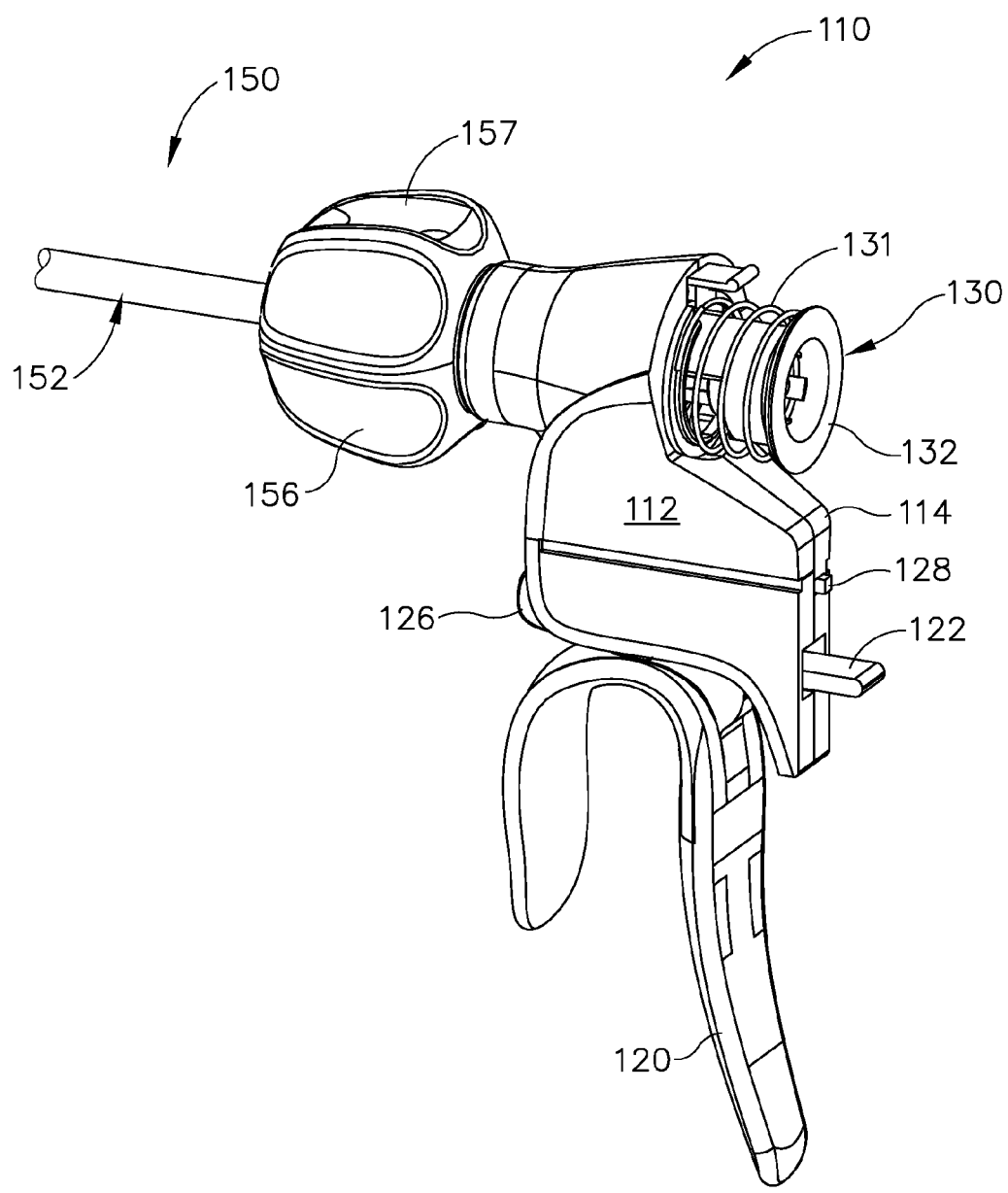
FIG. 10 depicts a perspective view of the proximal end of the disposable portion of FIG. 9.

FIGS. 9-10 show disposable assembly (100) in greater detail. As noted above, disposable assembly (100) of the present example comprises body portion (110), shaft assembly (150), and end effector (180). As shown in FIG. 10, body portion (110) comprises a pair of housing halves (112, 114), a trigger (120), and a button (126). Trigger (120) includes an integral tab (122) that protrudes proximally from housing halves (112, 114), as will be described in greater detail below. Similarly, the proximal end of an arm (128) associated with button (126) protrudes proximally from housing halves (112, 114), as will also be described in greater detail below. As also shown in FIGS. 9-10. Further exemplary features and operabilities for disposable assembly (100) will be described in greater detail below, while other variations will be apparent to those of ordinary skill in the art in view of the teachings herein.

A. Shaft Assembly of Disposable Assembly

Figure 11:
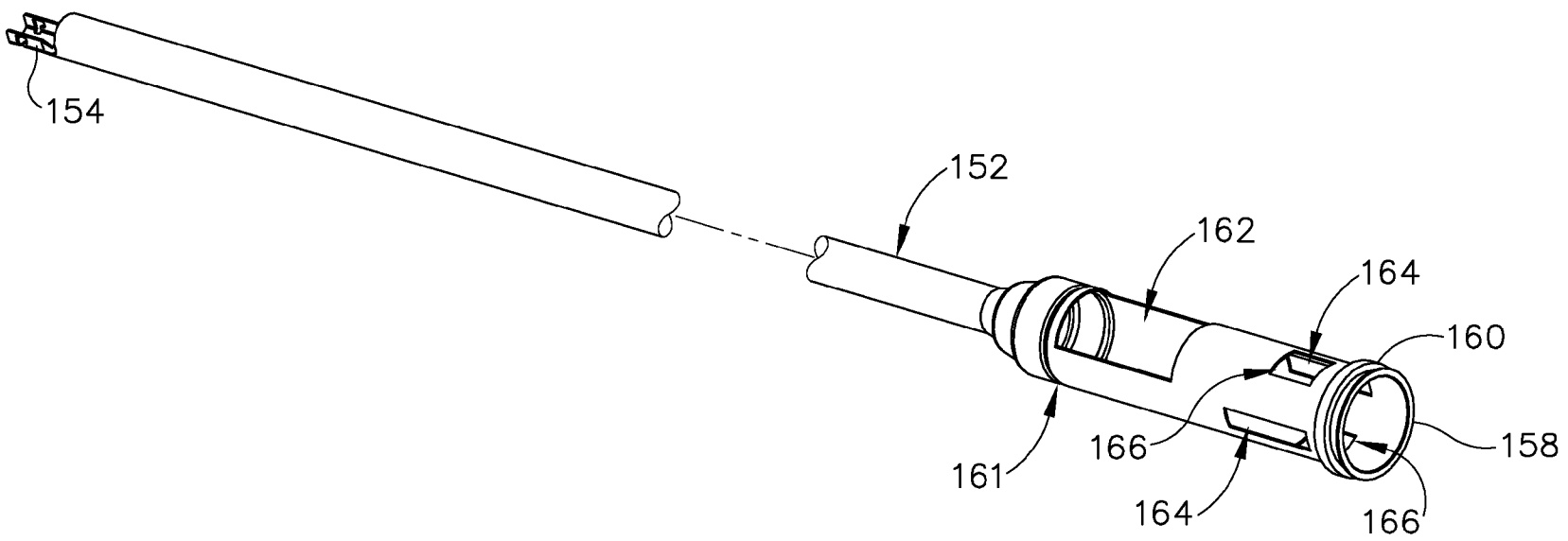
FIG. 11 depicts a perspective view of an outer tube from a shaft assembly of the disposable portion of FIG. 9.
Figure 12:
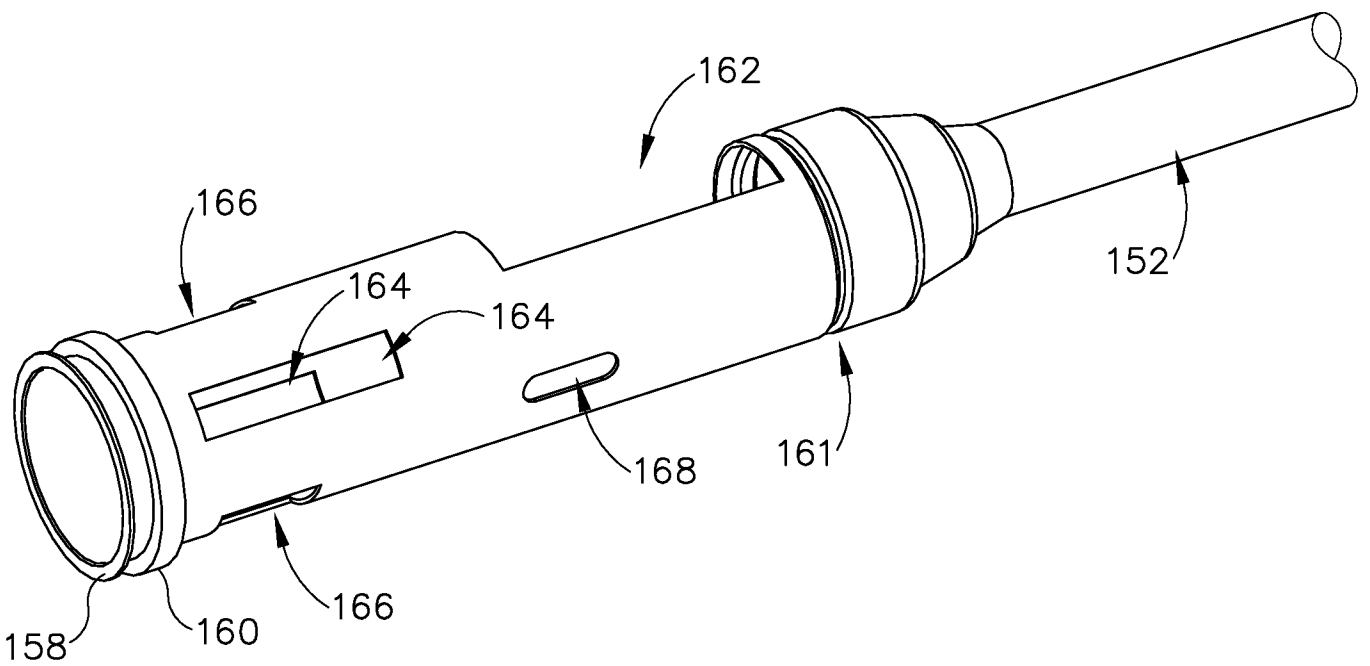
FIG. 12 depicts a perspective view of the proximal portion of the outer tube of FIG. 11.

FIGS. 11-30 show various components of shaft assembly (150) in greater detail. As noted above, shaft assembly (150) of the present example comprises outer tube (152), inner tube (170), and waveguide (192). Referring back to FIGS. 9-10, a knob (156) is secured to outer tube (152) and is thereby operable to rotate the entire shaft assembly (150) relative to body (110) as will be described in greater detail below. As shown in FIGS. 11-12, the proximal end of outer tube (152) includes an integral flange (158) and a ring (160) that is spaced distally from flange (158). Ring (160) is fixedly secured to outer tube (152). The proximal end of outer tube (152) also includes an annular indentation (161), a distal side opening (162), a pair of lateral side openings (164), upper and lower side openings (166), and a pin side opening (168).

Figure 13:
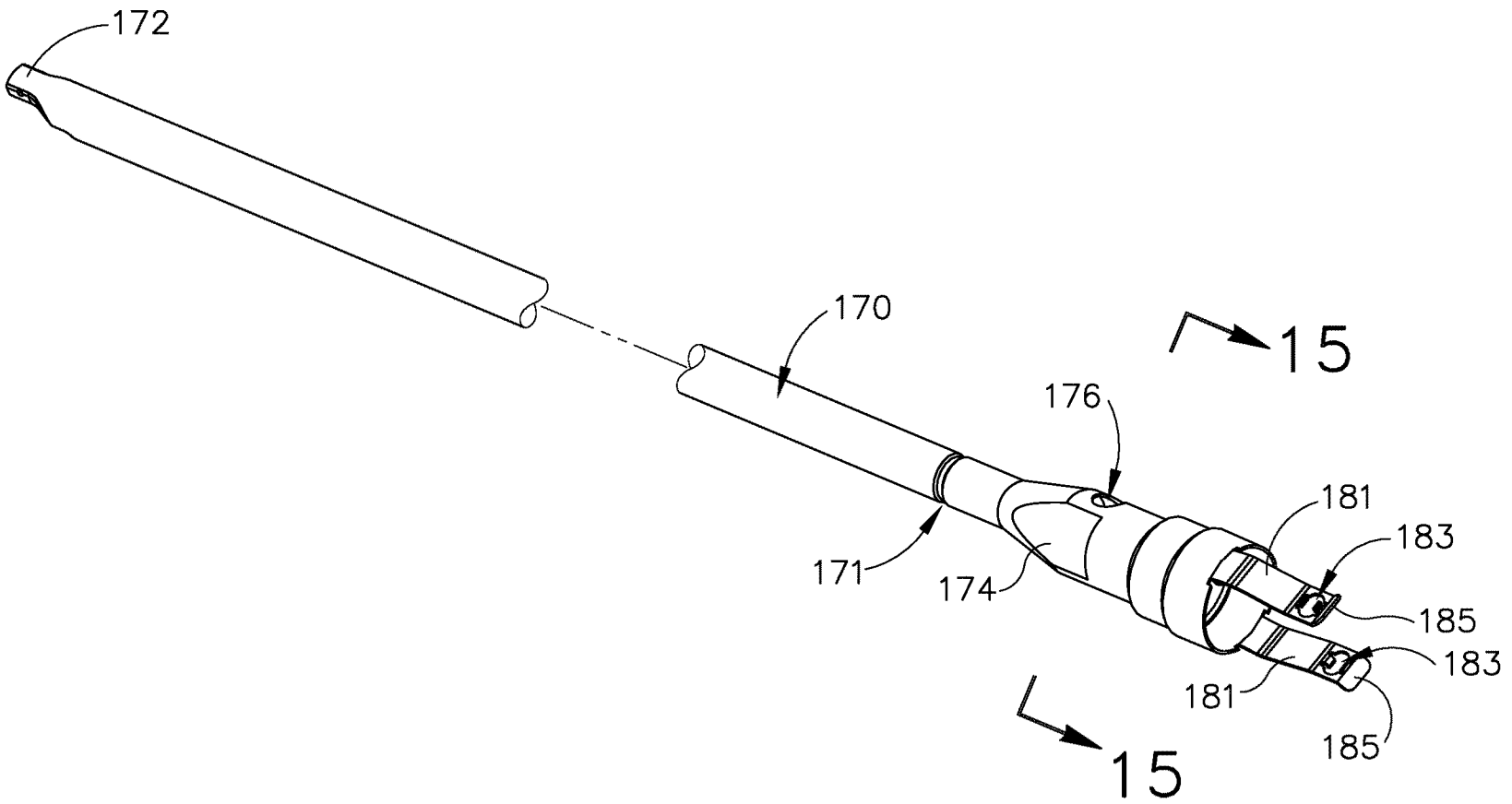
FIG. 13 depicts a perspective view of an inner tube from the shaft assembly of the disposable portion of FIG. 9.
Figure 14:
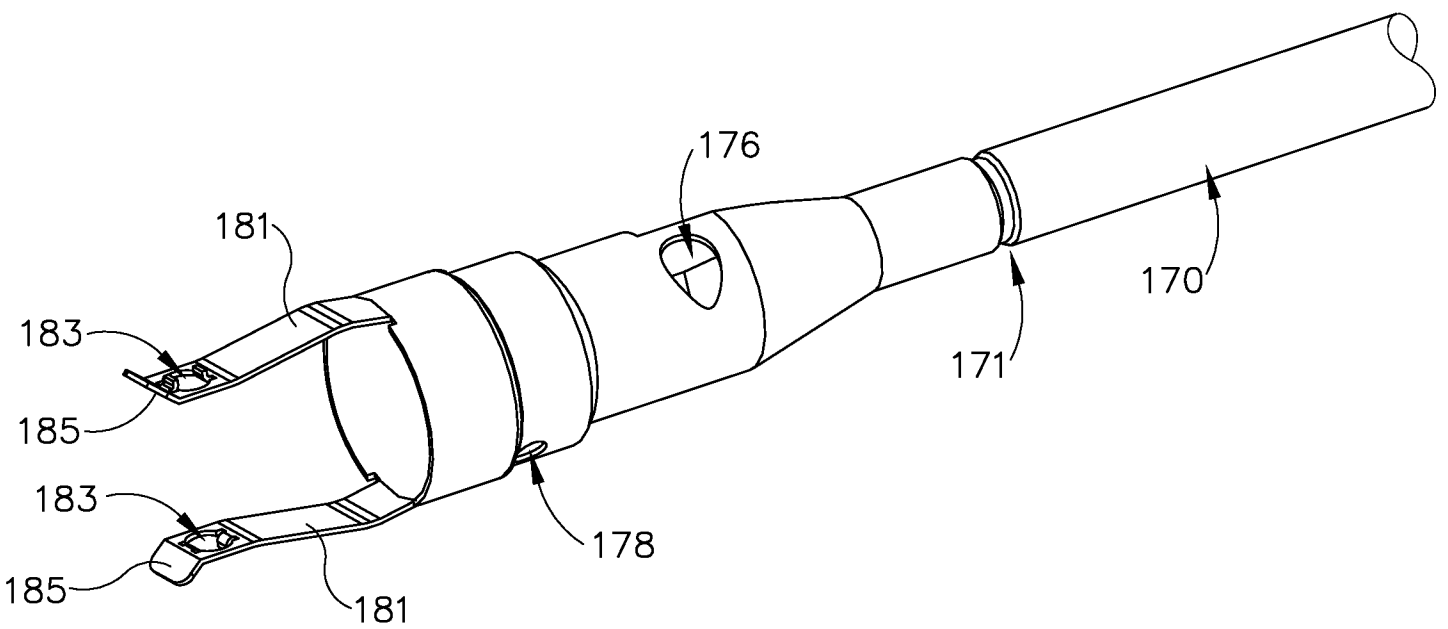
FIG. 14 depicts a perspective view of the proximal portion of the inner tube of FIG. 13.
Figure 15:
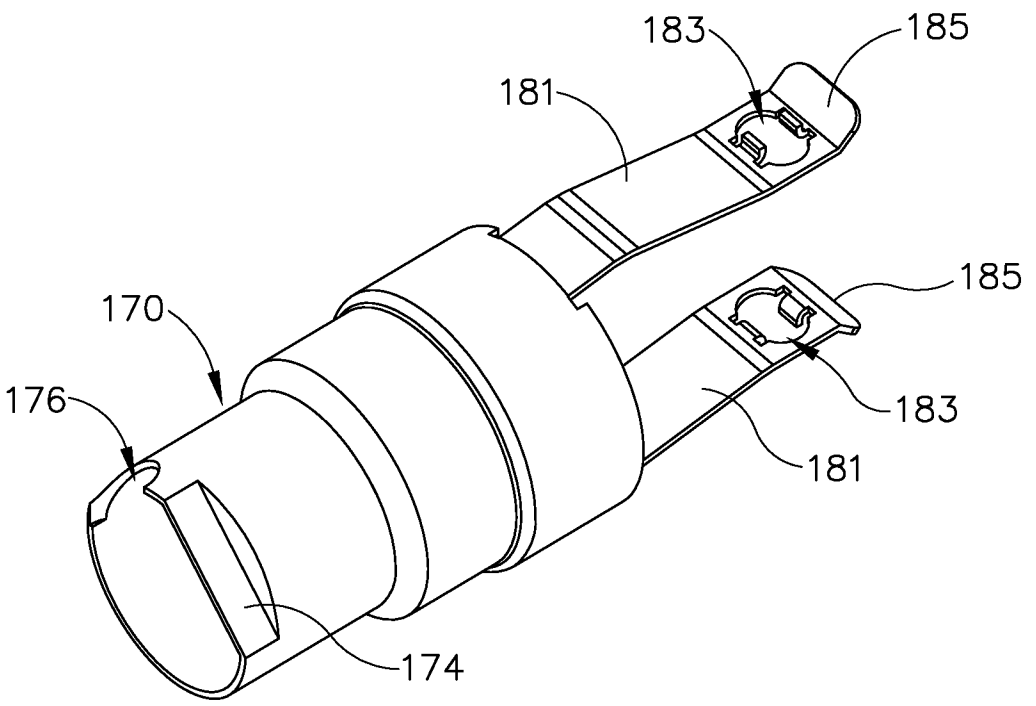
FIG. 15 depicts a cross-sectional perspective view of the inner tube of FIG. 13, taken along line 15-15 of FIG. 13.

As shown in FIGS. 13-15, inner tube (170) includes an oblique flat (174), a flush side opening (176), and a pin side opening (178) Inner tube (170) further includes a pair of proximally projecting resilient arms (181). Each arm (181) defines a respective pin opening (183). The free end (185) of each arm (181) is flared outwardly. Arms (181) are resiliently biased to assume the positions shown in FIGS. 13-15, yet arms (181) are configured to flex outwardly as will be described in greater detail below. As best seen in FIG. 14, inner tube (170) also includes an annular indentation (171).

Figure 16:
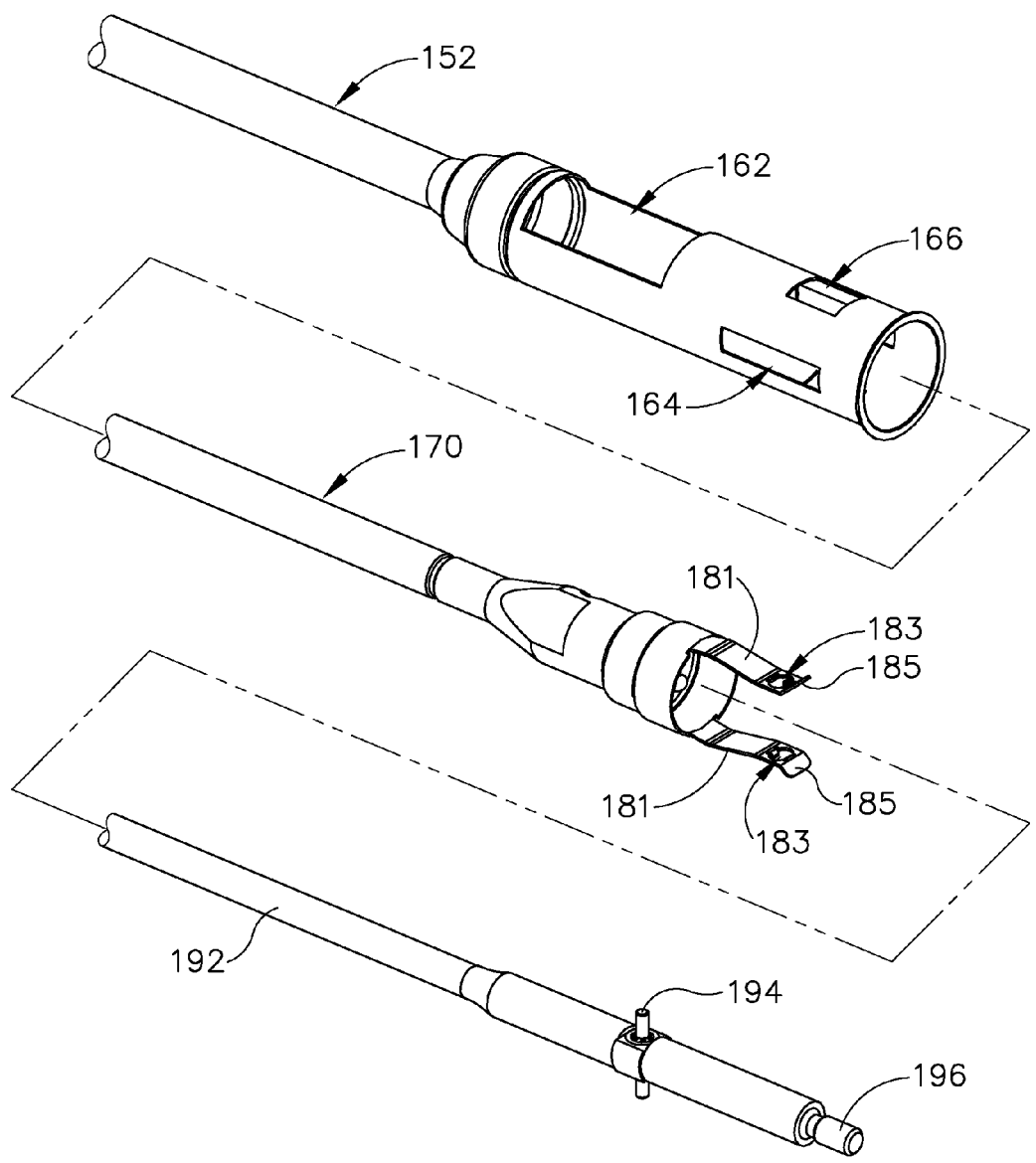
FIG. 16 depicts an exploded view of the proximal portion of the outer tube of FIG. 11, the proximal portion of the inner tube of FIG. 13, and the proximal portion of an acoustic waveguide from the shaft assembly of the disposable portion of FIG. 9.

As shown in FIG. 16, the proximal end of waveguide (192) includes a pin (194) disposed transversely through waveguide (192). Pin (194) is located at a longitudinal position corresponding to a node associated with ultrasonic vibrations that are communicated through waveguide (192) when ultrasonic transducer assembly (240) is activated. As best seen in FIGS. 41A-41D, pin is secured in waveguide (192) via a pair of e-clips (197). E-clips (197) are configured to ensure that pin (194) is centered within the corresponding transverse bore formed through waveguide (192), to secure and support pin (194) in that bore, and to provide acoustic isolation between waveguide (192) and pin (194). Of course, any other suitable structures or features may be used in addition to or in lieu of e-clips (197). A threaded stud (196) extends proximally and unitarily from waveguide (192). As will be described in greater detail below, stud (196) is configured to provide a mechanical and acoustic coupling between waveguide (192) and ultrasonic transducer assembly (240).

Figure 17:
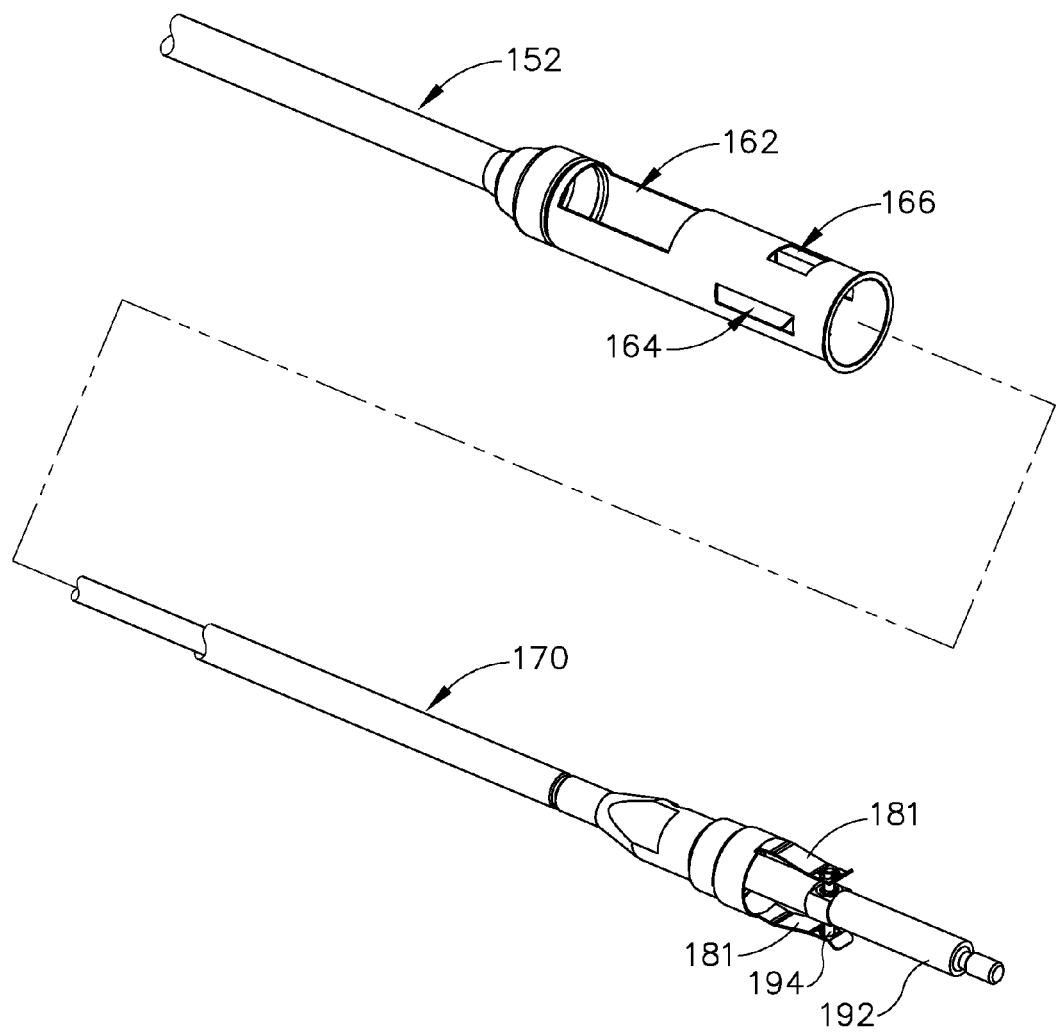
FIG. 17 depicts a partially exploded view of the components of FIG. 16, with the waveguide inserted in the inner tube.
Figure 18:
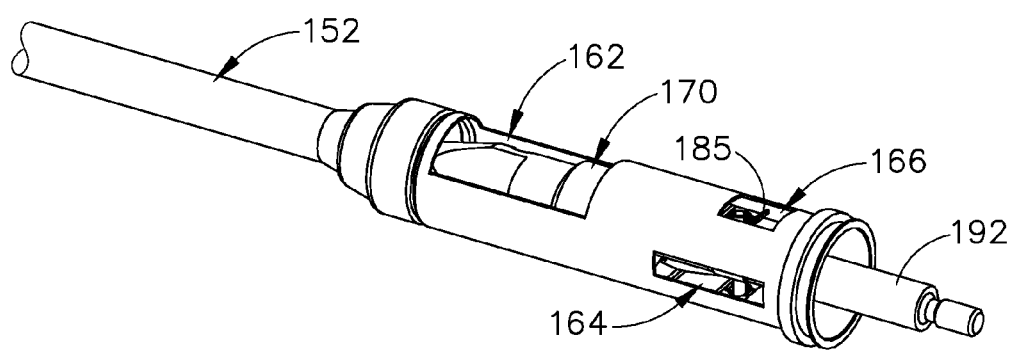
FIG. 18 depicts a perspective view of the components of FIG. 16 assembled together.

FIGS. 16-18 depict the coaxial arrangement of outer tube (152), inner tube (170), and waveguide (192). As shown in FIG. 17, pin (194) is received in pin openings (183) of resilient arms (181). Pin (194) thus mechanically couples waveguide (192) with inner tube (170), such that inner tube (170) and waveguide (192) rotate unitarily with each other, and such that inner tube (170) and waveguide (192) do not translate relative to each other, when pin (194) is disposed in pin openings (183). While waveguide (192) is mechanically coupled with inner tube (170), waveguide (192) is not acoustically coupled with inner tube (170) in this example. In particular, as noted above, pin (194) is located at a longitudinal position corresponding to a node associated with ultrasonic vibrations that are communicated through waveguide (192). Moreover, resilient arms (181) are configured such that resilient arms (181) do not contact waveguide (192), even when pin (194) is disposed in pin openings (183). In some versions, a plurality of annular sealing members (e.g., o-rings, etc.) are positioned at other nodal positions along the length of waveguide (192). Such annular sealing members may provide additional points of contact between waveguide (192) and inner tube (170), yet such annular sealing members would not transmit acoustic vibrations from waveguide (192) to inner tube (170) since such annular sealing members would be located at longitudinal positions corresponding to nodes associated with ultrasonic vibrations that are communicated through waveguide (192). Other suitable structures and relationships between waveguide (192) and inner tube (170) will be apparent to those of ordinary skill in the art in view of the teachings herein.

As shown in FIG. 18, when waveguide (192) and inner tube (170) are fully inserted in outer tube (152), resilient arms (181) are positioned to correspond with upper and lower side openings (166). As will be described in greater detail below with reference to FIGS. 41A-41D, upper and lower side openings (166) provide clearance for resilient arms (181) to flex outwardly to release pin (194) when shaft assembly (150) is transitioned to a cleaning mode. Also in the present example, pin side opening (178) of inner tube (170) aligns with pin side opening (168) of outer tube (152)

when inner tube (170) is fully inserted in outer tube (152). This allows inner tube (170) to be coupled with outer tube (152) via a pin (not shown). Due to this coupling, inner tube (170) and outer tube (152) rotate together unitarily. As noted above, inner tube (170) also rotates unitarily with waveguide (192) due to the coupling provided by pin (194). It should therefore be understood that outer tube (152), inner tube (170) and waveguide (192) all rotate together unitarily. It should also be noted that pin side opening (168) of outer tube (152) is elongate, extending longitudinally. This elongate, longitudinal configuration allows outer tube (152) to translate longitudinally relative to inner tube (170), even with a pin disposed in openings (168, 178).

Figure 19:
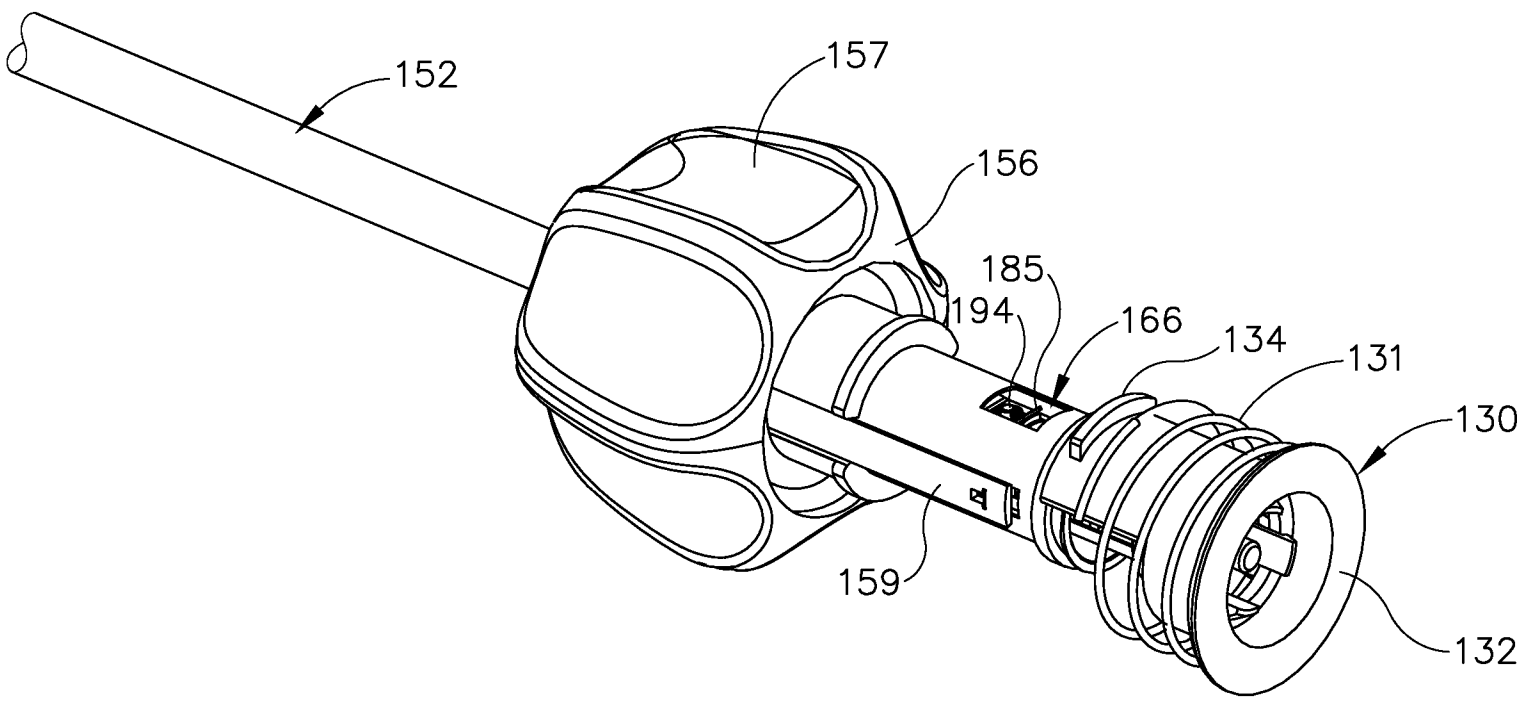
FIG. 19 depicts a proximal end of the shaft assembly of the disposable portion of FIG. 9.
Figure 20:
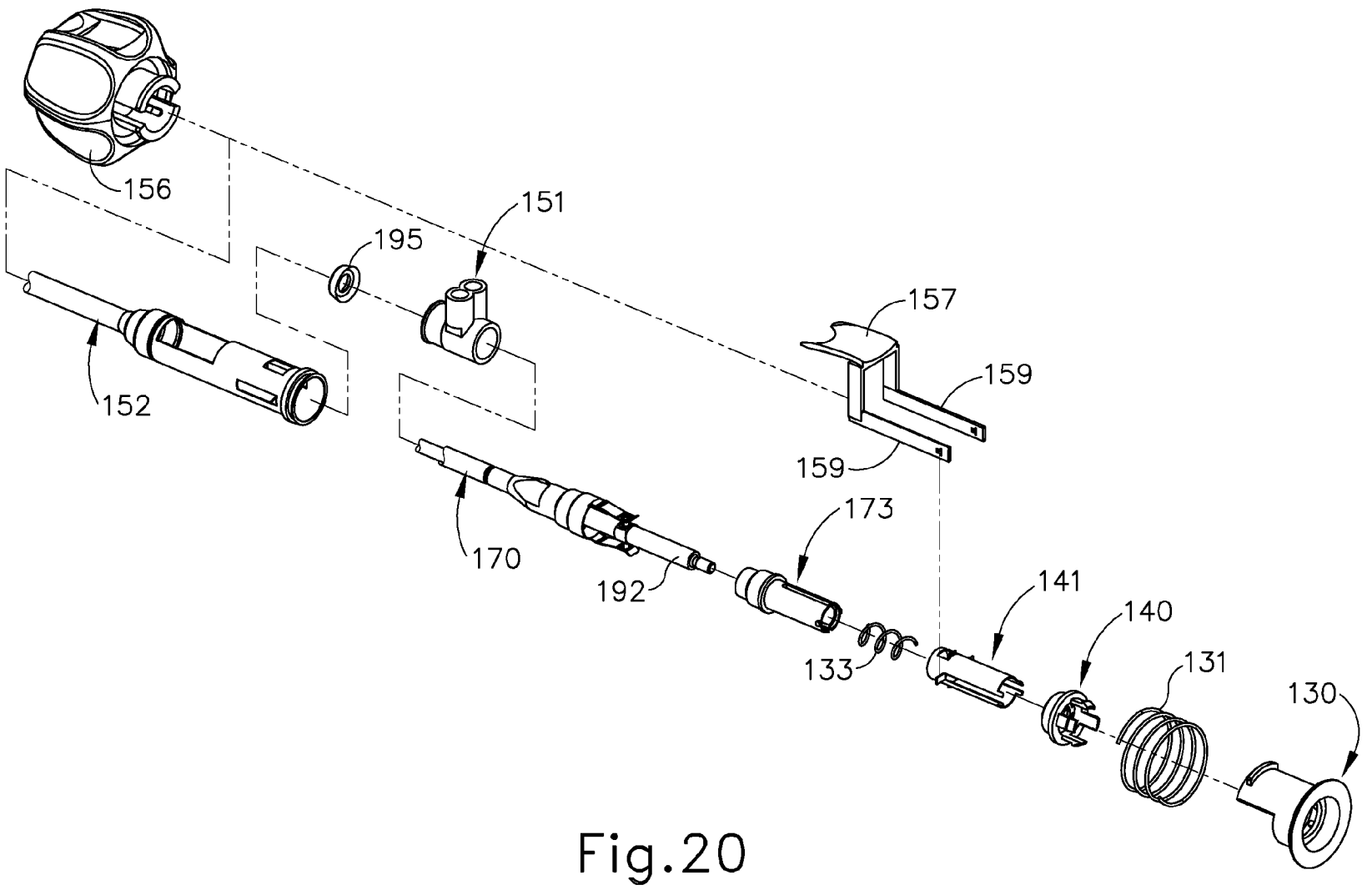
FIG. 20 depicts a partially exploded view of the shaft assembly of FIG. 19.
Figure 21:
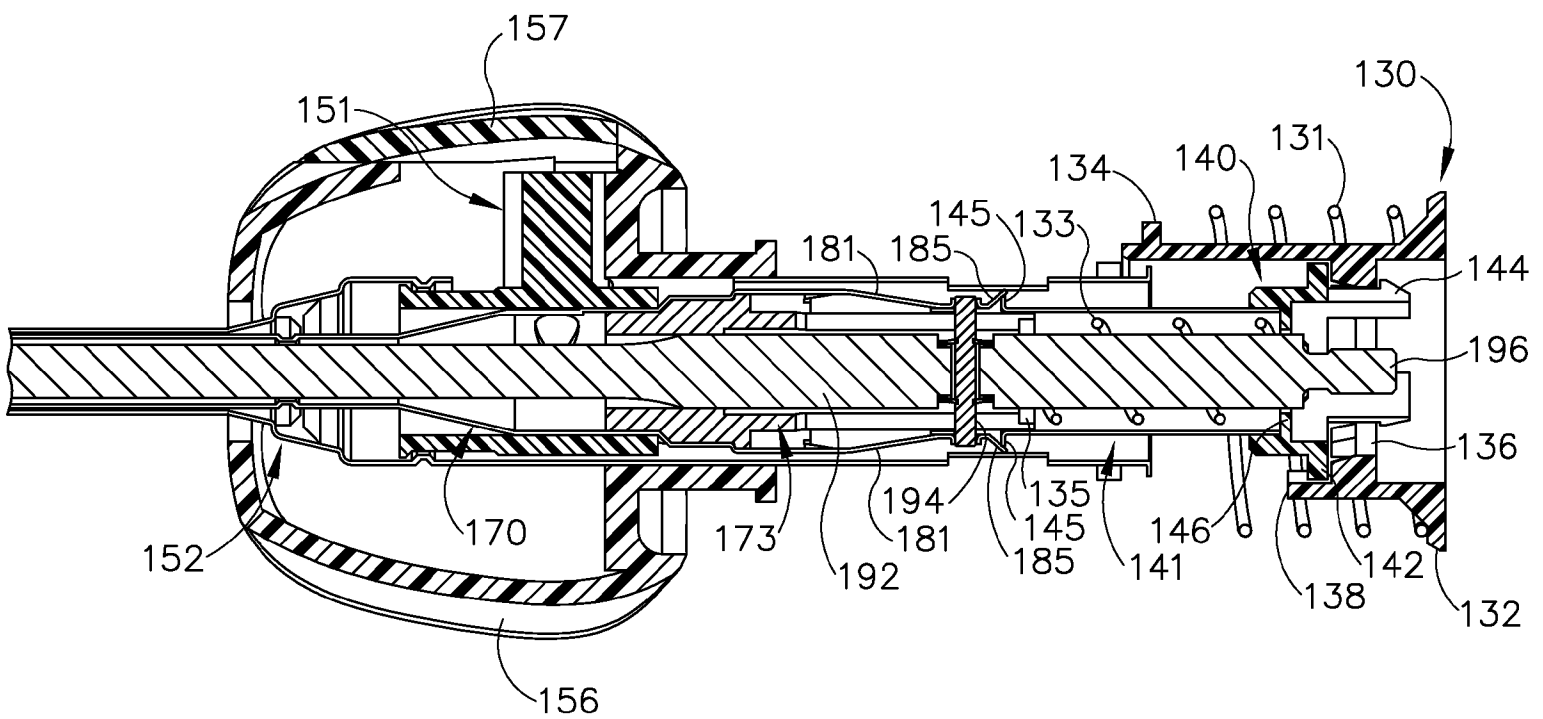
FIG. 21 depicts a side cross-sectional view of the shaft assembly of FIG. 19.
Figure 22:
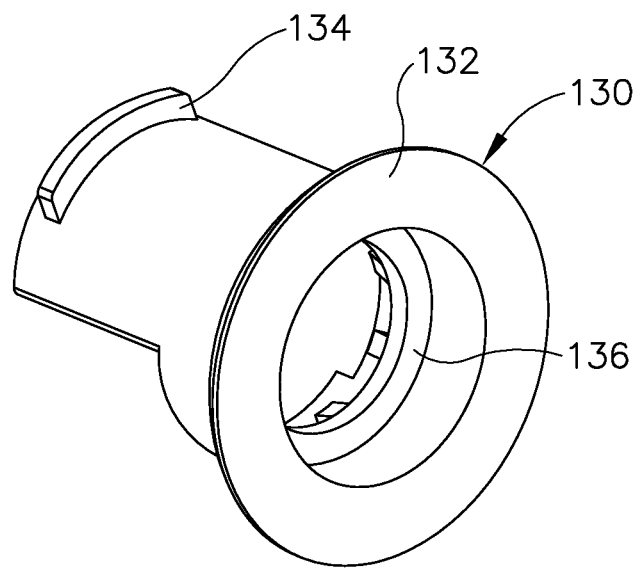
FIG. 22 depicts a perspective view of a mode selection knob of the shaft assembly of FIG. 19.
Figure 23:
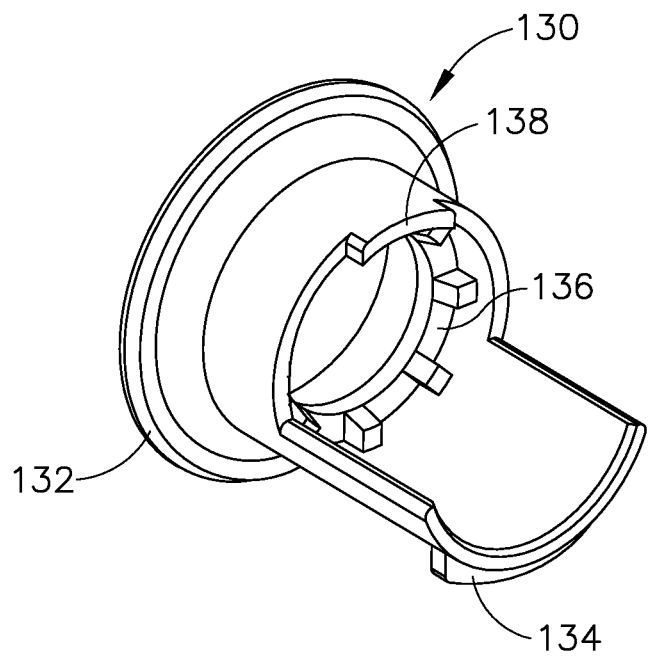
FIG. 23 depicts another perspective view of the knob of FIG. 22.

As shown in FIGS. 19-21, a mode selection knob (130) is positioned at the proximal end of shaft assembly (150). As best seen in FIGS. 22-23, mode selection knob (130) includes a proximal flange (132), a distal flange (134), an inner shoulder (136), and a distal edge (138). Referring back to FIGS. 19-21, a coil spring (131) is coaxially positioned about mode selection knob (130). Coil spring (131) is longitudinally interposed between housing halves (112, 114) and proximal flange (132). Coil spring (131) thereby biases mode selection knob (130) proximally. Distal flange (134) is captured within assembled housing halves (112, 114) and thereby provides retention preventing mode selection knob (130) from disengaging housing halves (112, 114) under the resilient bias of coil spring (131).

Figure 24:
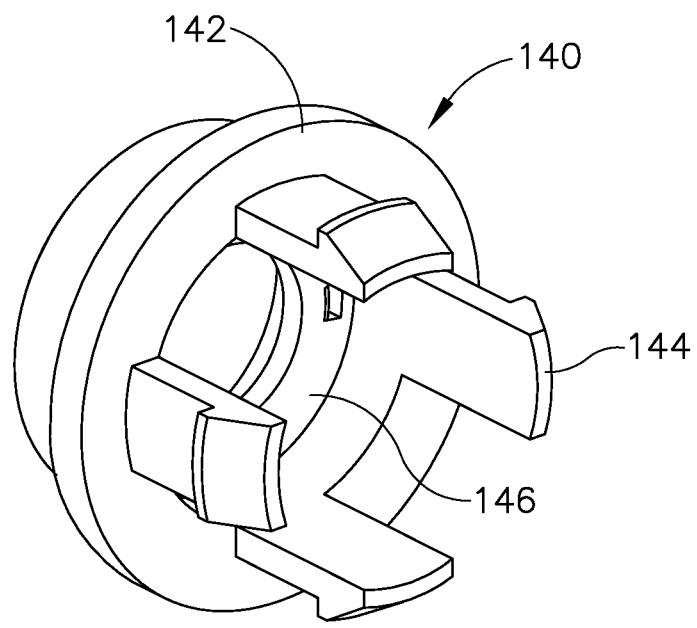
FIG. 24 depicts a perspective view of a coupling member of the shaft assembly of FIG. 19.
Figure 25:
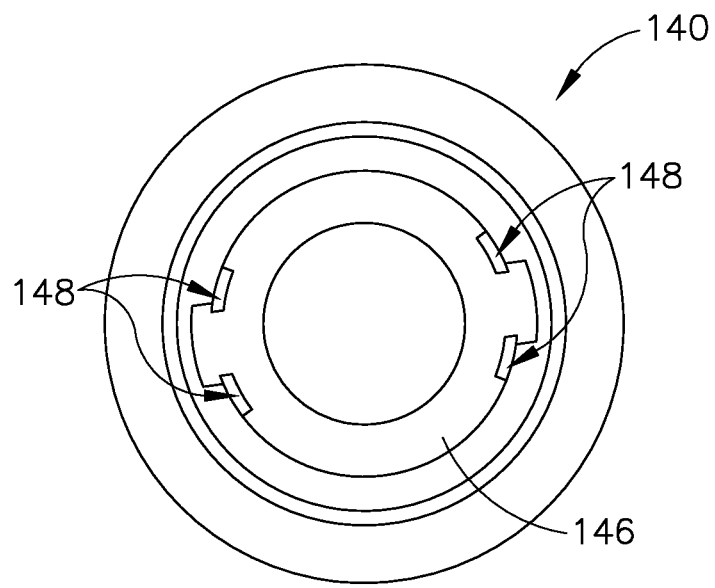
FIG. 25 depicts an elevational view of the distal end of the coupling member of FIG. 24.

As also shown in FIGS. 20-21, a coupling member (140) is coupled with mode selection knob (130). As best seen in FIGS. 24-25, coupling member (140) includes an outer flange (142), a set of longitudinally extending snapping arms (144), an inner flange (146), and a set of openings (148) formed through inner flange (146). Referring back to FIGS. 20-21, coupling member (140) is coupled with mode selection knob (130) such that inner shoulder (136) of mode selection knob (130) is captured between outer flange (142) and snapping arms (144). Coupling member (140) is thus secured to mode selection knob (130) in a snap fitting.

Figure 26:
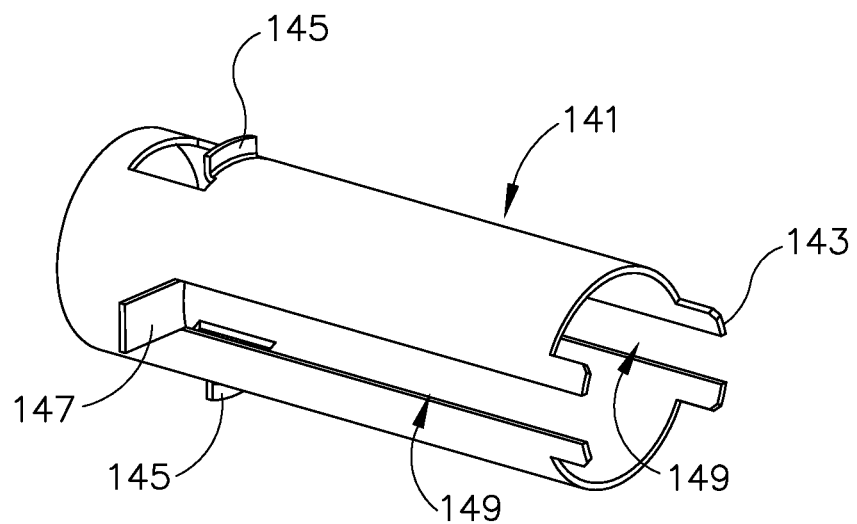
FIG. 26 depicts a perspective view of a mode drive member of the shaft assembly of FIG. 19.
Figure 27:
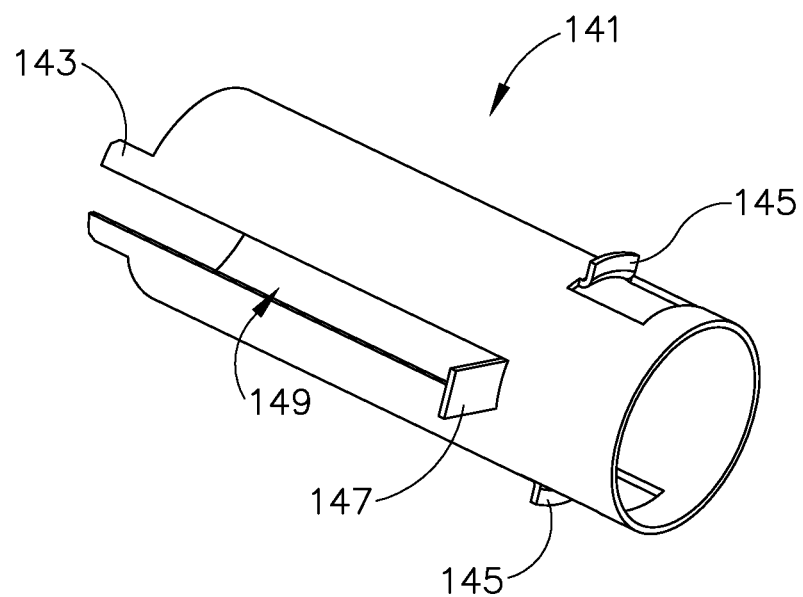
FIG. 27 depicts another perspective view of the mode drive member of FIG. 26.

As also shown in FIGS. 20-21, a mode drive member (141) is coupled with coupling member (140). As best seen in FIGS. 26-27, mode drive member (141) comprises a set of proximally extending fingers (143), a pair of outwardly extending upper and lower tabs (145), a pair of outwardly extending lateral tabs (147), and a pair of elongate longitudinal slots (149) proximal to lateral tabs (147). Fingers (143) are disposed within openings (148) of inner flange (146) in coupling member (140), with the proximal end of mode drive member (141) contacting the distal face of inner flange (146). In some versions, fingers (143) are secured within openings (148) through an interference fitting. Upper and lower tabs (145) are positioned to correspond with resilient arms (181) as will be described in greater detail below. Lateral tabs (147) are positioned to extend through lateral side openings (164) of outer tube (152). Referring back to FIGS. 11-12, lateral side openings (164) are both elongate, extending longitudinally. This elongate, longitudinal configuration allows mode drive member (141) to translate longitudinally relative to outer tube (152), even with lateral tabs (147) disposed in lateral side openings (164). The positioning of lateral tabs (147) in lateral side openings (164) nevertheless provides unitary rotation of mode drive member (141) with outer tube (152).

Figure 28:
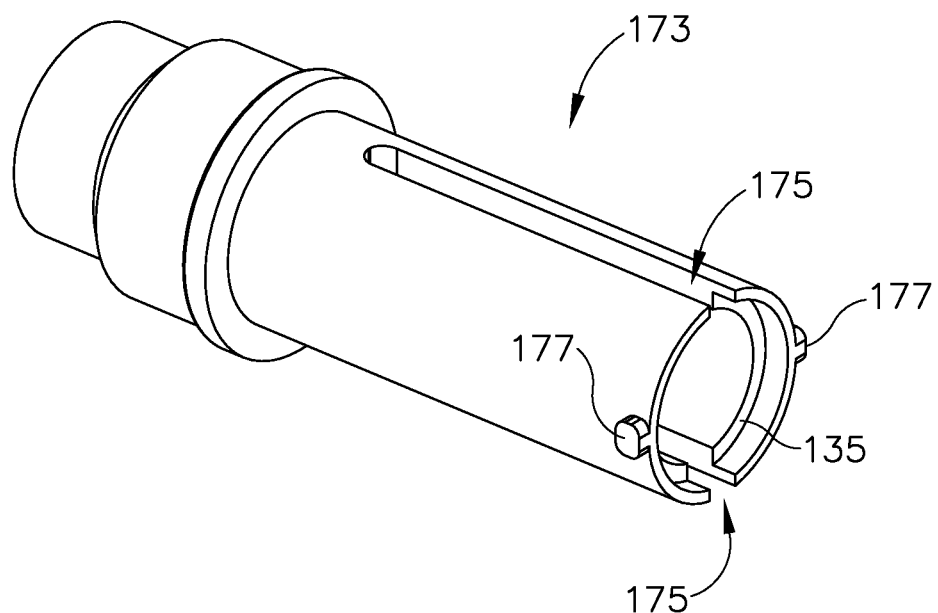
FIG. 28 depicts a perspective view of an inner tube grounding member of the shaft assembly of FIG. 19.
Figure 29:
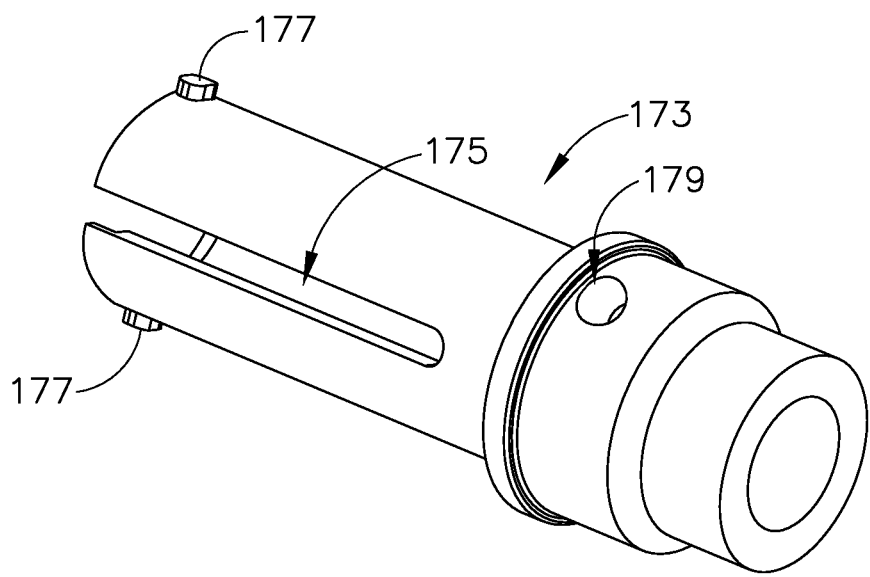
FIG. 29 depicts another perspective view of the grounding member of FIG. 28.
Figure 30:
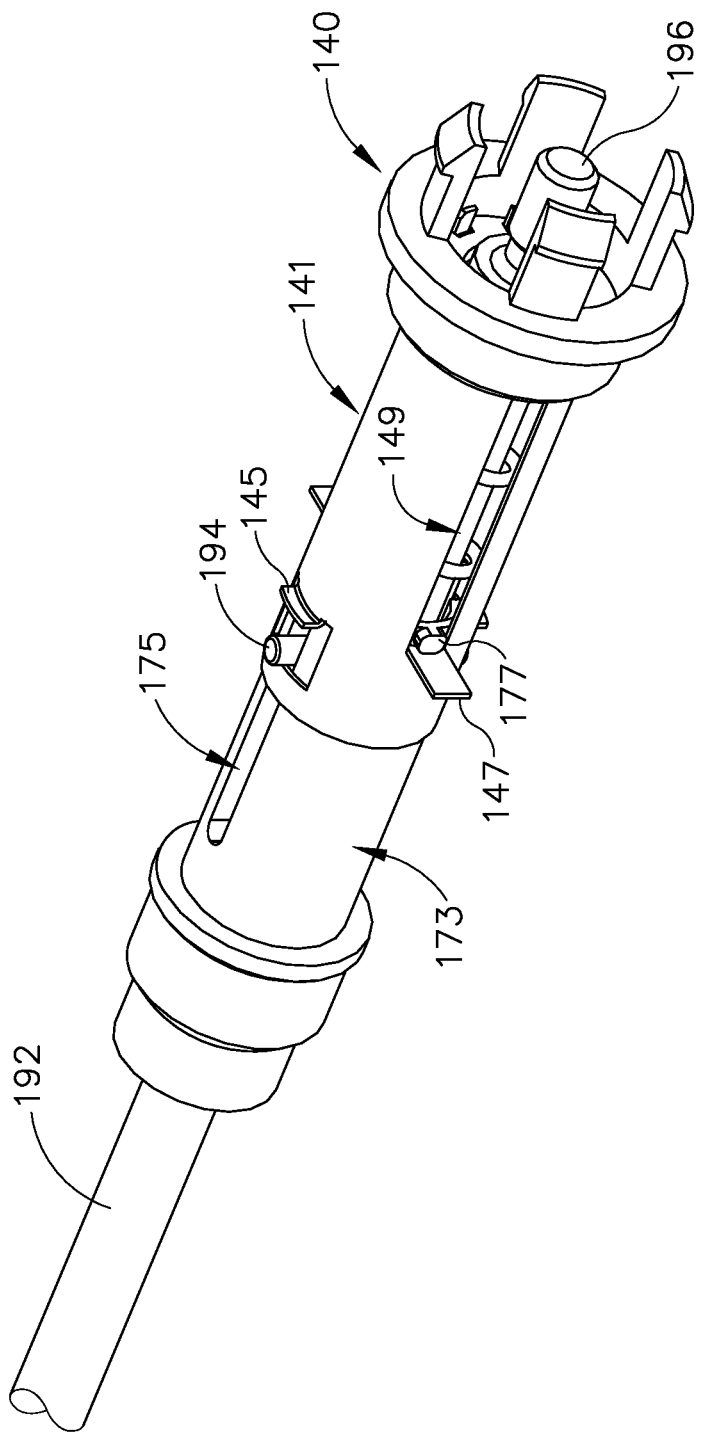
FIG. 30 depicts a perspective view of a portion of the shaft assembly of FIG. 19, showing the coupling member of FIG. 24, the mode drive member of FIG. 26, the grounding member of FIG. 28, and the waveguide.
Figure 31:
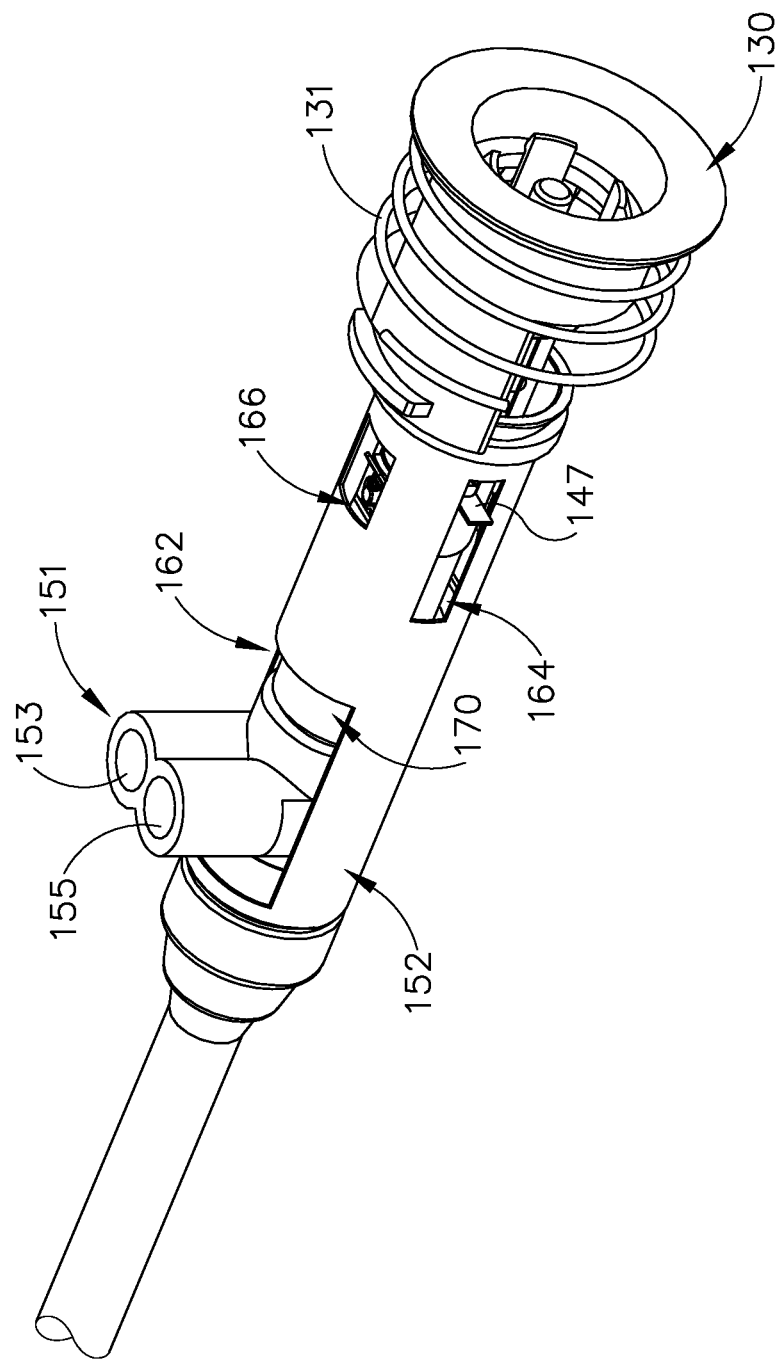
FIG. 31 depicts a perspective view of the components of FIG. 30, along with the knob of FIG. 22, a return spring, the outer tube of FIG. 11, and a flush port member.
Figure 32:
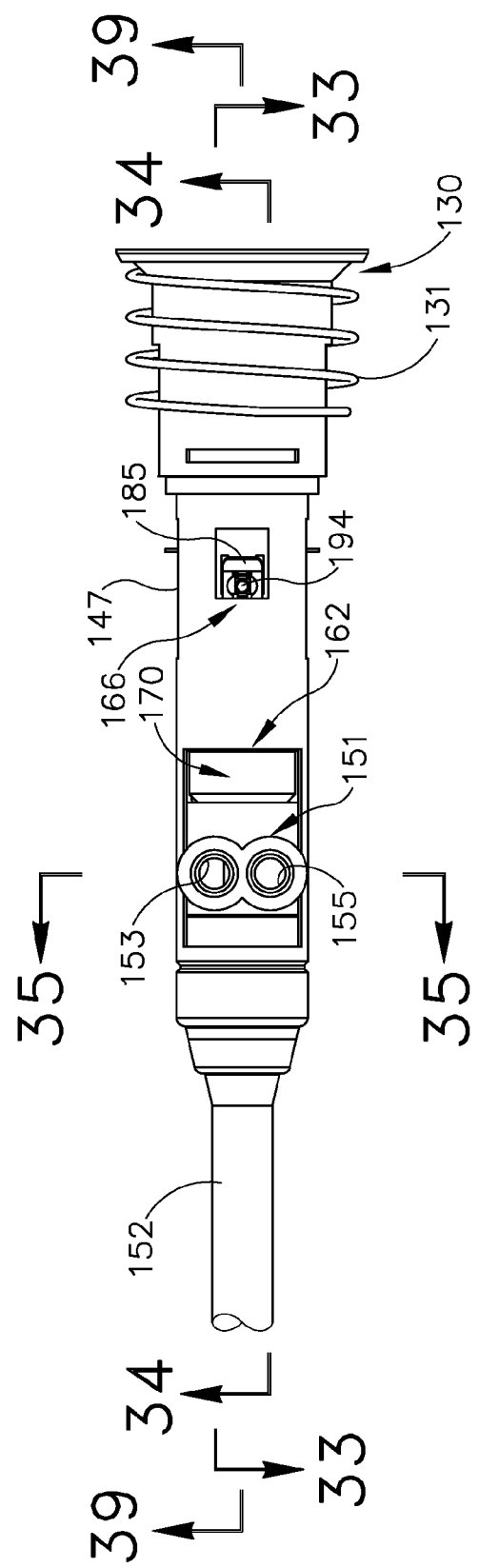
FIG. 32 depicts a top plan view of the components of FIG. 31.

As also shown in FIGS. 20-21, an inner tube grounding member (173) is disposed within inner tube (170). As best seen in FIGS. 28-29, grounding member (173) includes a pair of longitudinally extending slots (175), a pair of outwardly extending lateral tabs (177), and a pin side opening (179). As best seen in FIG. 30, slots (175) are configured to receive pin (194) of waveguide (192). The elongate, longitudinal configuration of slots (175) allows pin (194) and, hence, waveguide (192), to translate longitudinally relative to grounding member (173) and inner tube (170); yet also provides unitary rotation of pin (194) and waveguide (192) with grounding member (173) and inner tube (170). As also best seen in FIG. 30, lateral tabs (177) of grounding member (173) are slidably disposed in elongate longitudinal slots (149) of mode drive member (141). The longitudinal configuration of slots (149) allows lateral grounding member (173) and inner tube (170) to translate longitudinally relative to mode drive member (141); yet also provides unitary rotation of lateral grounding member (173) with mode drive member (141). Pin side opening (179) of grounding member (173) is positioned to align with pin side opening (178) of inner tube (170) when grounding member (173) is fully inserted within inner tube (170). As noted above, a pin (not shown) is disposed in pin side opening (178), coupling inner tube (170) with outer tube (152). This same pin is further disposed in pin side opening (179) of grounding member (173). This pin thereby provides unitary fixation of inner tube (170) with grounding member (173); and unitary rotation of grounding member (173) with inner tube (170).

As best seen in FIG. 21, coil spring (133) is coaxially disposed about the proximal end of waveguide (192). Coil spring (133) is positioned between a proximally facing shoulder (135) formed in the proximal end of grounding member (173) and the distal face of the inner flange (146) of coupling member (140). Coil spring (133) thus biases coupling member (140) and mode drive member (141) proximally relative to grounding member (173). It should be understood that coil spring (133) may provide assistance to coil spring (131) described above. In addition, coil spring (133) allows coupling member (140) to float axially (i.e., such that coil spring (133) does not have an axial force bias. This may in turn decrease the torque required by the operator to rotate shaft assembly (150) during a surgical procedure.

Various exemplary functions and operabilities that may be provided by the components of shaft assembly (150) described above will be described in greater detail below. Other functions and operabilities that may be provided by the components of shaft assembly (150) described above will be apparent to those of ordinary skill in the art in view of the teachings herein. Similarly, other features, components, and configurations that may be incorporated into shaft assembly (150) will be apparent to those of ordinary skill in the art in view of the teachings herein.

B. Cleaning Features of Disposable Assembly

Those of ordinary skill in the art will appreciate that one or more components of shaft assembly (150) may experience a buildup of surgical debris when instrument (10) is used in a surgical procedure. By way of example only, one or more components of shaft assembly (150) may experience a buildup of coagulated blood, tissue particles, and/or other kinds of surgical debris. Thus, in some instances, it may be desirable to clean one or more components of shaft assembly (150). By way of example only, after instrument (10) has been used in a surgical procedure, it may be desirable to clean one or more components of shaft assembly (150) before shaft assembly (150) is used in another surgical procedure. In addition or in the alternative, it may be desirable to clean one or more components of shaft assembly (150) in the middle of a surgical procedure. For instance, instrument (10) may be used during a first portion of a surgical procedure, then one or more components of shaft assembly (150) may be cleaned during a pause in the surgical procedure, and then instrument (10) may again be used in a second portion of the same surgical procedure (e.g., on the same day as the first portion of the same surgical procedure and immediately subsequent to the first portion of the same surgical procedure). The below description relates to various features and techniques that may be employed to clean one or more components of shaft assembly (150) at the completion of or during a surgical procedure.

Figure 33:
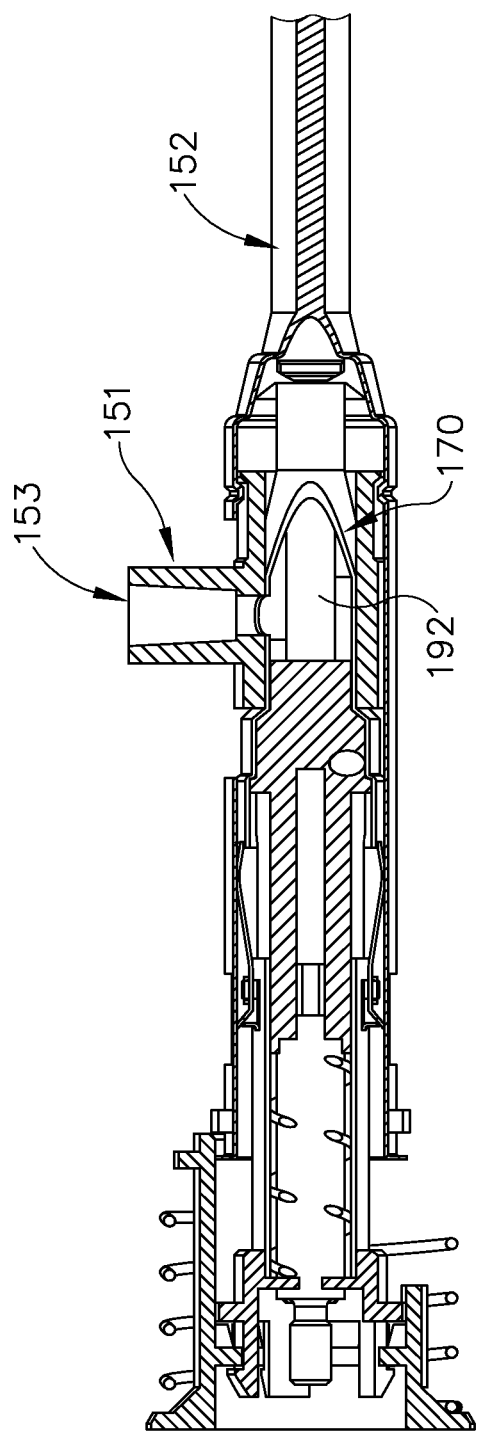
FIG. 33 depicts a cross-sectional view of the components of FIG. 31, taken along line 33-33 of FIG. 32.
Figure 34:
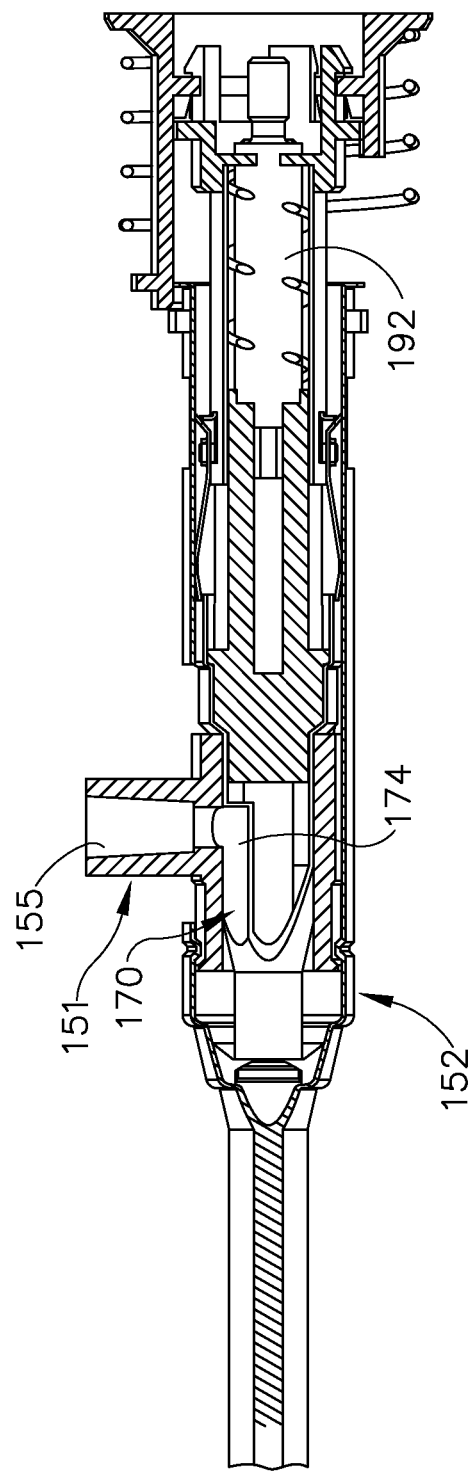
FIG. 34 depicts a cross-sectional view of the components of FIG. 31, taken along line 34-34 of FIG. 32.
Figure 35:
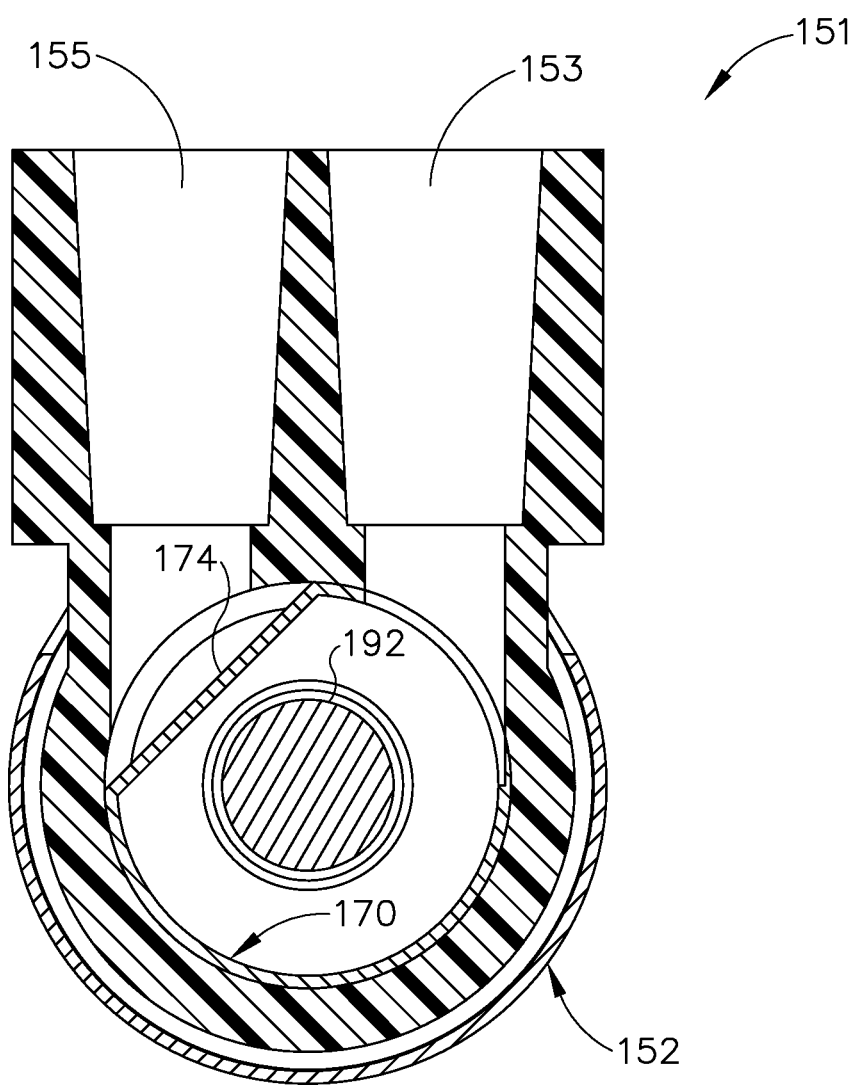
FIG. 35 depicts a cross-sectional view of the components of FIG. 31, taken along line 35-35 of FIG. 32.

As best seen in FIGS. 31-35, a cleaning port body (151) is disposed about the exterior of inner tube (170). Cleaning port body (151) includes a first port (153) and a second port (155), both of which extend transversely relative to inner tube (170), through distal side opening of outer tube (152). As best seen in FIGS. 33 and 35, first port (153) is in fluid communication with the gap between the inner diameter of inner tube (170) and the outer diameter of waveguide (192). As best seen in FIGS. 34-35, second port (155) is in fluid communication with the gap between the inner diameter of outer tube (152) and the outer diameter of inner tube (170). As also seen in FIGS. 34-35, oblique flat (174) of inner tube (170) directs fluid from second port to the gap between the inner diameter of outer tube (152) and the outer diameter of inner tube (170). It should be understood that ports (153, 155) are in fluid isolation relative to each other, such that second port (155) does not have a path for fluid communication with the gap between the inner diameter of inner tube (170) and the outer diameter of waveguide (192); and such that first port (153) does not have a path for fluid communication with the gap between the inner diameter of outer tube (152) and the outer diameter of inner tube (170).

Each port (153, 155) is configured to couple with a corresponding source of cleaning fluid. For instance, each port (153, 155) may receive a respective flexible tube to provide a fluid path between port (153, 155) and the corresponding source of cleaning fluid. In addition or in the alternative, each port (153, 155) may receive a nipple, fitting associated with syringes, or other feature of a cleaning fluid injecting device. Other suitable ways in which ports (153, 155) may be coupled with respective sources of cleaning fluid will be apparent to those of ordinary skill in the art in view of the teachings herein.

Referring back to FIGS. 19-21, knob (156) of the present example includes a sliding shield (157) that is operable to selectively cover and uncover ports (153, 155) as will be described in greater detail below. Shield (157) includes a pair of integral, proximally extending arms (159). The proximal ends of arms (159) are secured to lateral tabs (147) of mode drive member (141). Thus, when mode drive member (141) translates longitudinally relative to other portions of shaft assembly, arms (159) and shield (157) translate with mode drive member (141).

As shown in FIGS. 36A-41D, disposable assembly (100) is configured to transition between an operational mode (FIGS. 36A, 38A, 39A, 40A, and 41A) and a cleaning mode (FIGS. 36B, 37, 38B, 39B, 40B, and 41D). This is accomplished by driving mode selection knob (130) distally relative to housing halves (112, 114). It should therefore be understood that, in the present example, disposable assembly (100) will only transition from the operational mode to the cleaning mode when disposable assembly (100) is decoupled from reusable assembly (200). In some other versions, disposable assembly (100) may transition from an operational mode to a cleaning mode when disposable assembly (100) is coupled with reusable assembly (200). As seen in FIGS. 36B, 37, 38B, 39B, 40B, and 41D, clamp arm (182) pivots to a hyperextended position and blade (190) advances to a distal position when disposable assembly (100) is placed in the cleaning mode. In addition, shield (157) slides distally to reveal ports (153, 155) when disposable assembly (100) is placed in the cleaning mode.

Figure 38A:
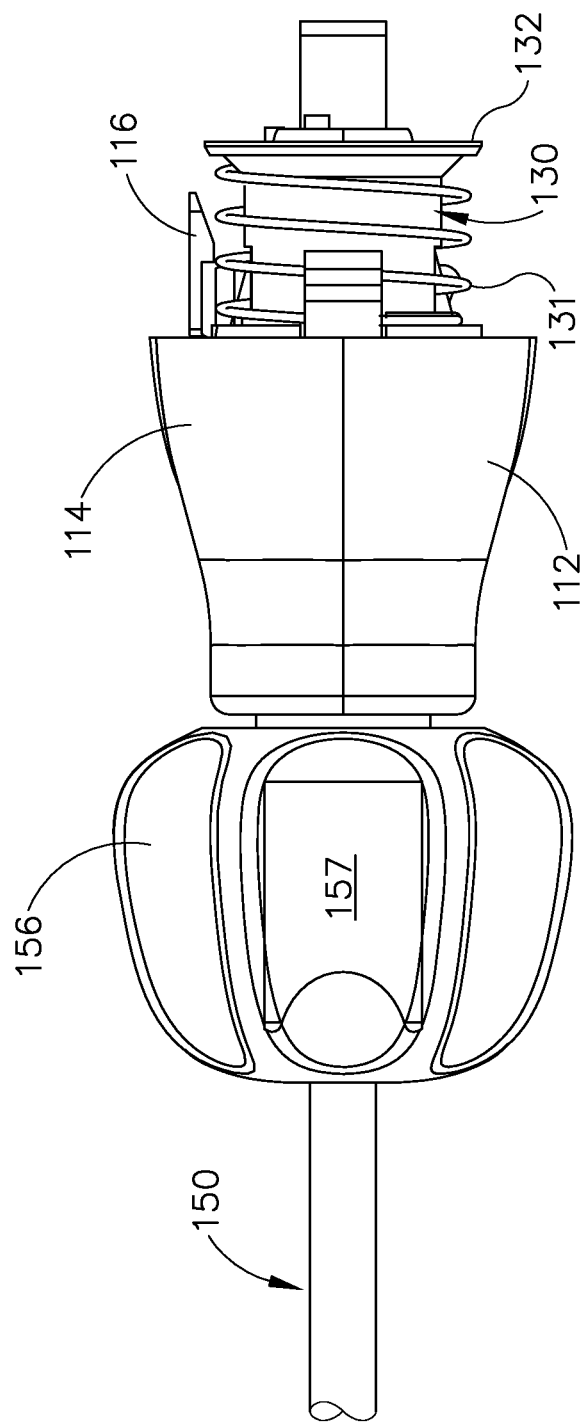
FIG. 38A depicts a top plan view of the proximal portion of the disposable portion of FIG. 9, with the mode selection knob in the non-actuated position.
Figure 38B:
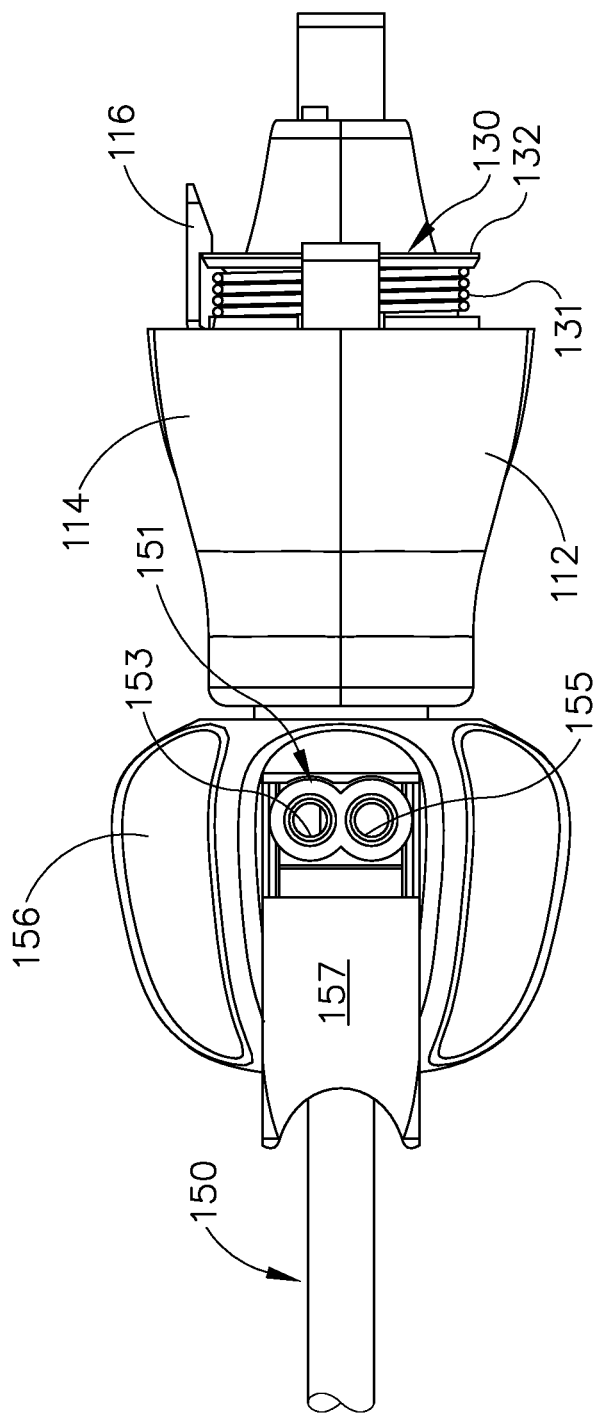
FIG. 38B depicts a top plan view of the proximal portion of the disposable portion of FIG. 9, with the mode selection knob in the actuated position.
Figure 39A:
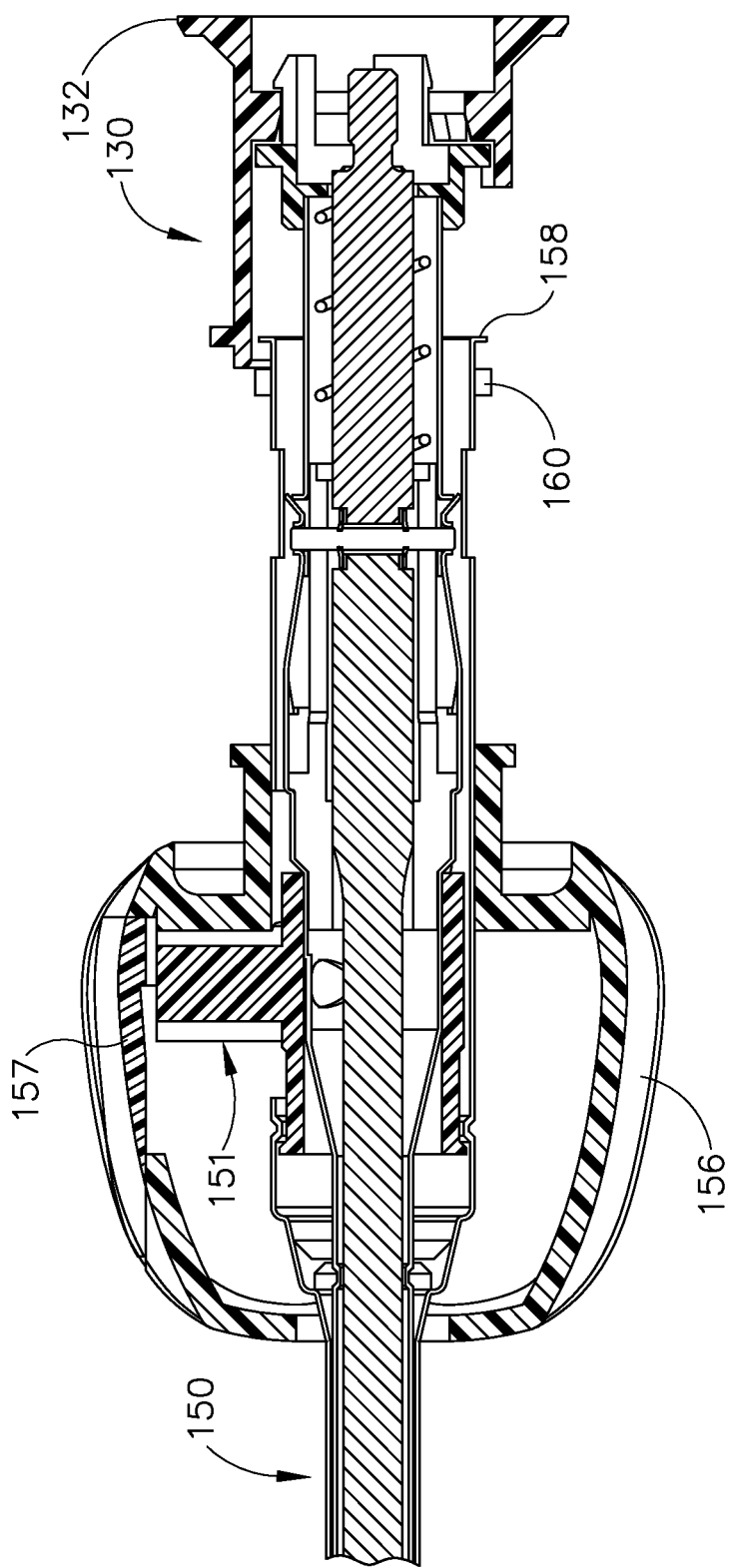
FIG. 39A depicts a side cross-sectional view of the proximal portion of the disposable portion of FIG. 9, taken along line 39-39 of FIG. 32, with the mode selection knob in the non-actuated position.
Figure 39B:
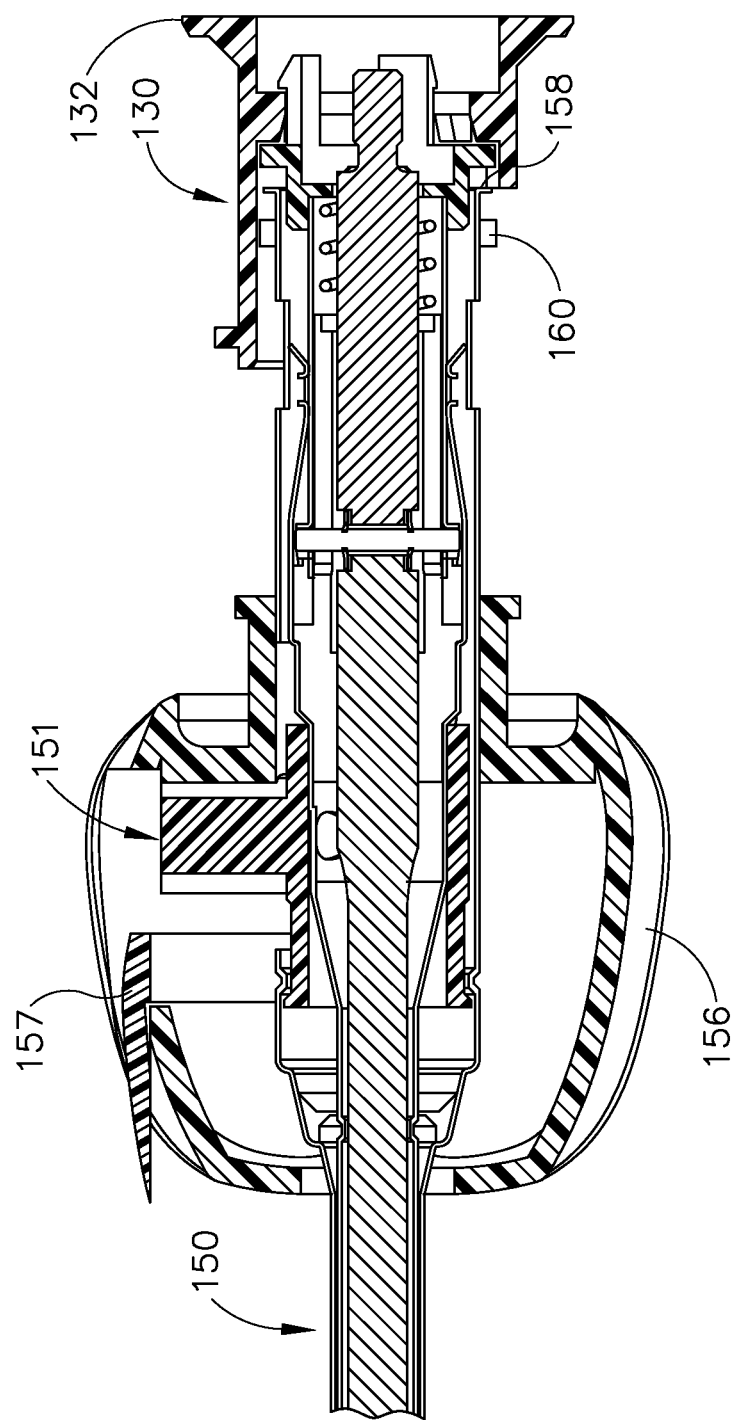
FIG. 39B depicts a side cross-sectional view of the proximal portion of the disposable portion of FIG. 9, taken along line 39-39 of FIG. 32, with the mode selection knob in the actuated position.

As best seen in FIGS. 38A-38B, when mode selection knob (130) is driven distally to place disposable assembly (100) in the cleaning mode, a latch (116) of housing half (114) engages proximal flange (132) of mode selection knob (130), thereby holding mode selection knob (130) in the distal, cleaning mode position. Latch (116) is resiliently biased to assume the position shown in FIGS. 38A-38B. In the present example, reusable assembly (200) includes a feature that drives latch (116) laterally outwardly when disposable assembly (100) is inserted in distal recess (208) of reusable portion (200). This laterally outward deflection of latch (116) causes latch (116) to release proximal flange (132) of mode selection knob (130). When this occurs, coil spring (131) drives mode selection knob (130) and associated components proximally, thereby transitioning disposable assembly (100) back to the operational mode. Thus, the act of coupling disposable assembly (100) with reusable assembly (200) may automatically transition disposable assembly (100) from the cleaning mode to the operational mode. Alternatively, the operator may manually deflect latch (116) laterally outwardly to release proximal flange (132) of mode selection knob (130), thereby transitioning disposable assembly (100) from the cleaning mode to the operational mode.

Figure 37:
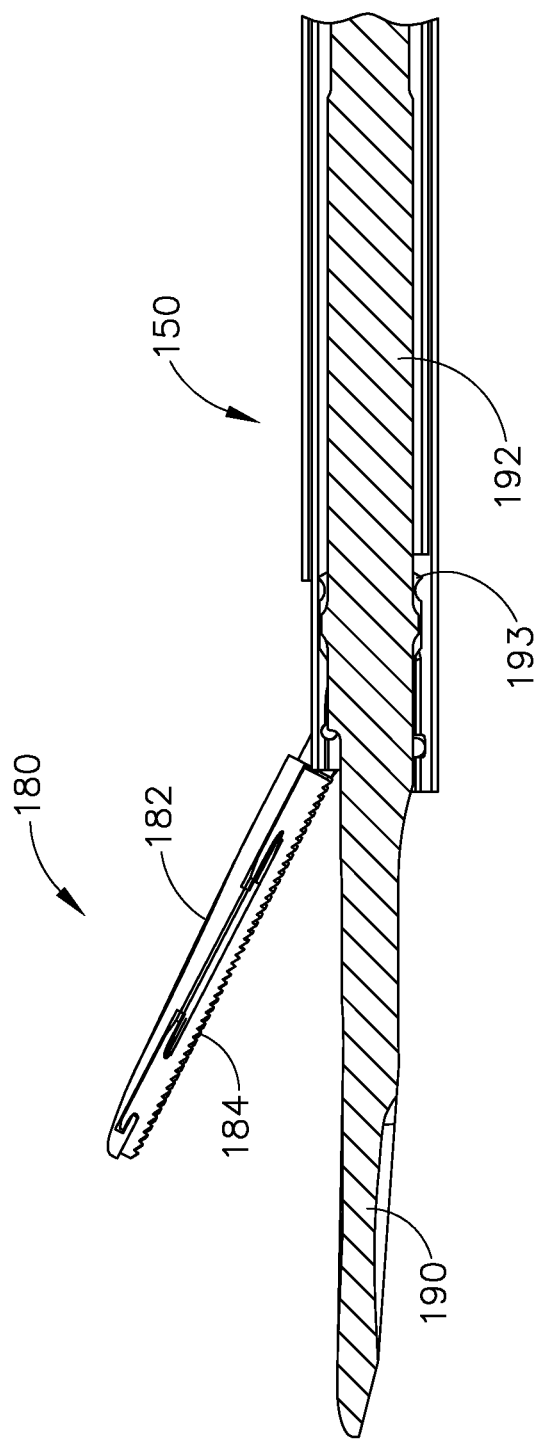
FIG. 37 depicts a side cross-sectional view of the end effector of FIG. 4 in the cleaning mode.

Shaft assembly (150) includes various sealing features whose sealing states change when disposable assembly (100) is transitioned between the cleaning mode and the operational mode. In particular, one sealing feature includes a distal seal (193), which is coaxially interposed between the outer diameter of waveguide (192) and the inner diameter of inner tube (170). In the present example, distal seal (193) comprises an elastomeric material (e.g., rubber, silicone, etc.). Distal seal (193) is located at a position corresponding to a node associated with ultrasonic vibrations that are communicated through waveguide (192). As shown in FIG. 7, when disposable assembly (100) is in normal operating mode, distal seal (193) is positioned to prevent proximal egress of fluid through the gap defined between the outer diameter of waveguide (192) and the inner diameter of inner tube (170). As shown in FIG. 37, when disposable assembly (100) is in cleaning mode, distal seal (193) is positioned past a distal edge of inner tube (170), such that distal seal (193) permits cleaning fluid to be communicated distally through the gap defined between the outer diameter of waveguide (192) and the inner diameter of inner tube (170), with the cleaning fluid ultimately exiting at the distal end of inner tube (170). Thus, when disposable assembly (100) is in cleaning mode, an operator may communicate cleaning fluid through port (153), and such cleaning fluid may advance distally and flush out coagulated blood and/or other surgical debris that may have built up in the gap defined between the outer diameter of waveguide (192) and the inner diameter of inner tube (170).

Figure 40A:
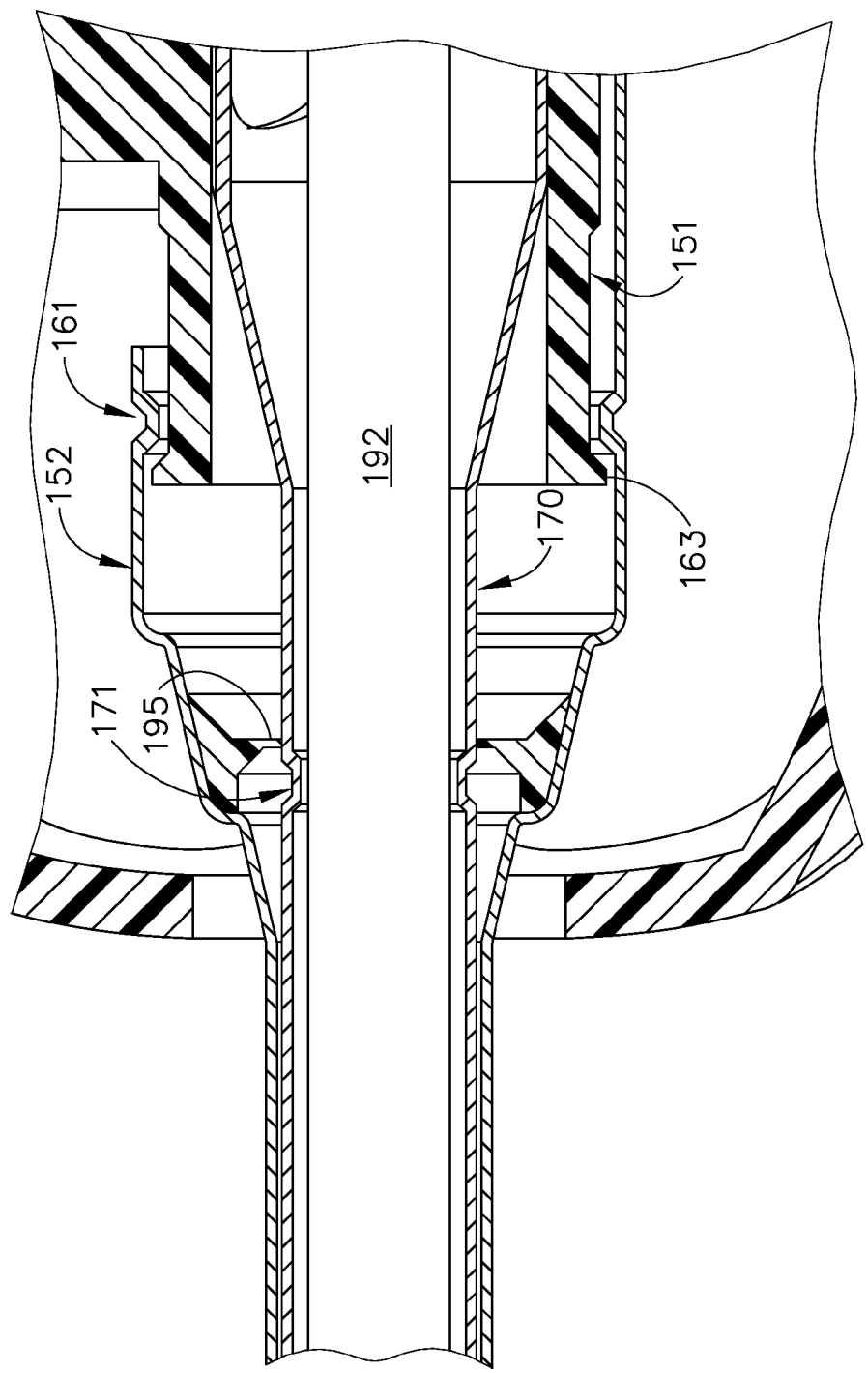
FIG. 40A depicts an enlarged side cross-sectional view of sealing features in the proximal portion of the disposable portion of FIG. 9, in a regular operation mode.
Figure 40B:
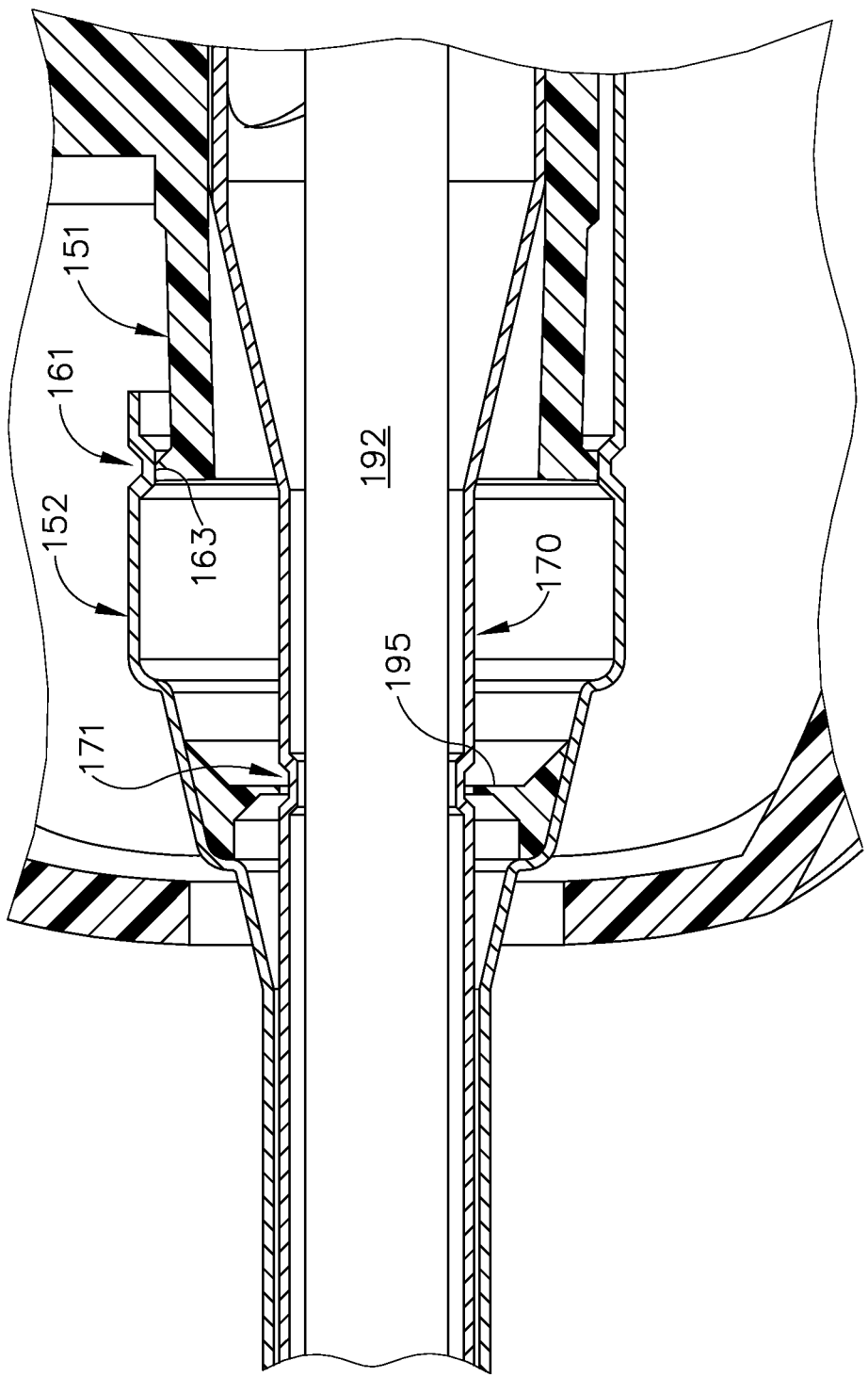
FIG. 40B depicts an enlarged side cross-sectional view of the sealing features of FIG. 40A, in the cleaning mode.

FIGS. 40A-40B show additional sealing features whose sealing states change when disposable assembly (100) is transitioned between the cleaning mode and the operational mode. In particular, a proximal seal (195) is interposed between the inner diameter of outer tube (152) and the outer diameter of inner tube (170). In the present example, proximal seal (195) comprises an elastomeric material (e.g., rubber, silicone, etc.). Proximal seal (195) is secured to the inner diameter of outer tube (152), such that proximal seal (195) translates longitudinally with outer tube (152) relative to inner tube (170). As shown in FIG. 40A, proximal seal (195) seals against the outer diameter of inner tube (170) when disposable assembly (100) is in an operational state. As noted above, instrument (10) may be used in minimally invasive surgical procedures. In some such procedures, instruments are introduced into a patient's abdominal cavity via trocars, and the patient's abdominal cavity is insufflated with pressurized air to improve visualization of and access to organs, etc., within the abdominal cavity. With proximal seal (195) sealing against the outer diameter of inner tube (170) when disposable assembly (100) is in an operational state, and with shaft assembly (150) inserted through a trocar to introduce end effector (180) into a patient's insufflated abdominal cavity, proximal seal (195) may prevent the escape of pressurized air through the gap defined between the inner diameter of outer tube (152) and the outer diameter of inner tube (170). Similarly, distal seal (193) may prevent the escape of pressurized air through the gap defined between the outer diameter of waveguide (192) and the inner diameter of inner tube (170).

When disposable assembly (100) is transitioned to the cleaning mode, as shown in FIG. 40B, proximal seal (195) is positioned in the region corresponding to annular indentation (171) in inner tube (170). Annular indentation (171) provides a gap permitting the communication of cleaning fluid distally through the gap defined between the inner diameter of outer tube (152) and the outer diameter of inner tube (170). As also shown in FIGS. 40A-40B, the distal end of port body (151) includes an annular flange (163) that selectively engages annular indentation (161) of outer tube (152). During the normal operational mode as shown in FIG. 40A, annular flange (163) is disengaged from annular indentation (161). However, during the cleaning mode as shown in FIG. 40B, annular flange (163) engages annular indentation (161), thereby providing a fluid seal. This prevents cleaning fluid from escaping proximally when cleaning fluid is communicated to the gap defined between the inner diameter of outer tube (152) and the outer diameter of inner tube (170). It should be understood from the foregoing that, when disposable assembly (100) is in the cleaning mode, an operator may communicate cleaning fluid through port (155), and such cleaning fluid may advance distally and flush out coagulated blood and/or other surgical debris that may have built up in the gap defined between the inner diameter of outer tube (152) and the outer diameter of inner tube (170).

Figure 41A:
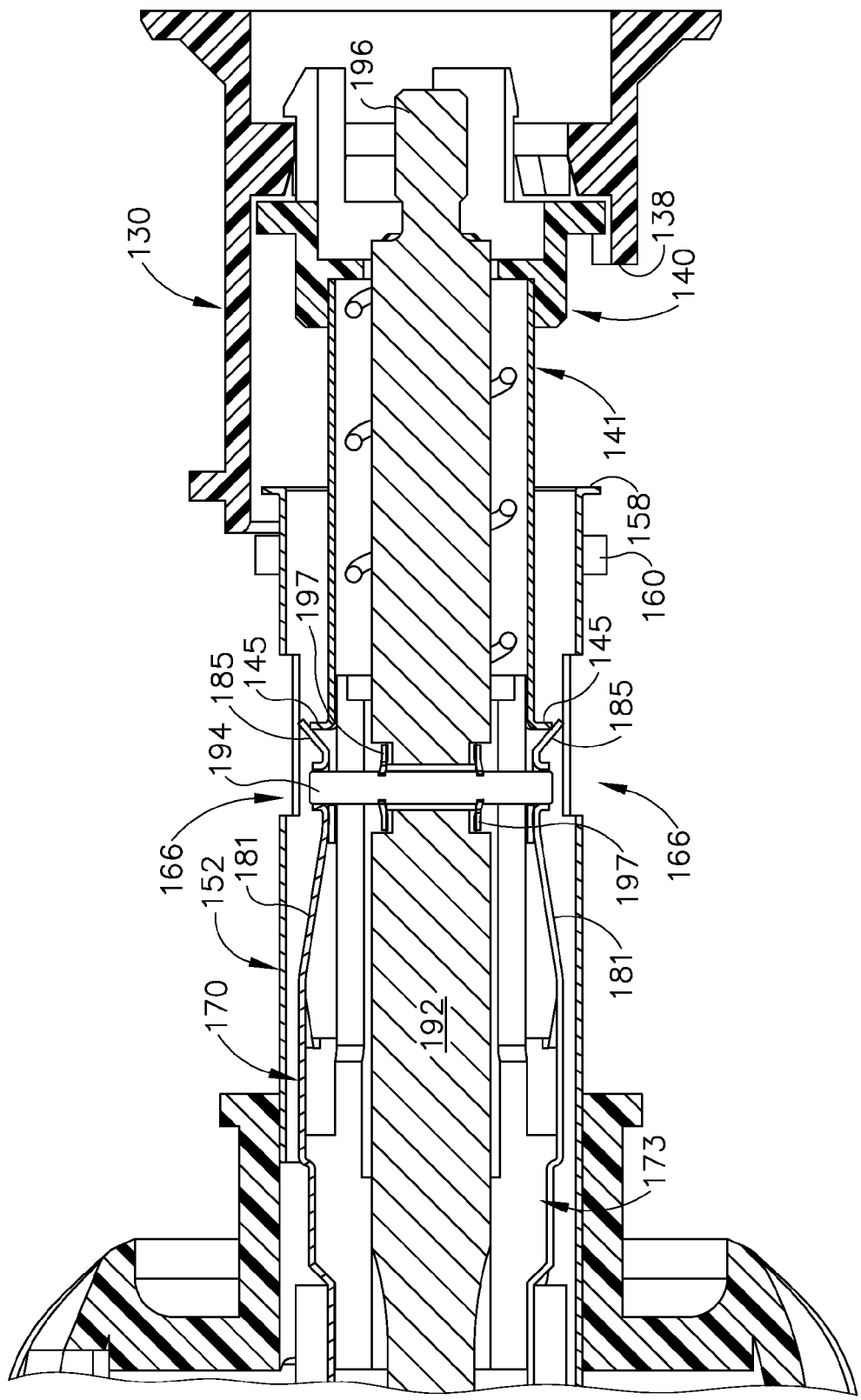
FIG. 41A depicts an enlarged side cross-sectional view of mode selection components in the proximal portion of the disposable portion of FIG. 9, in a regular operation mode.
Figure 41B:
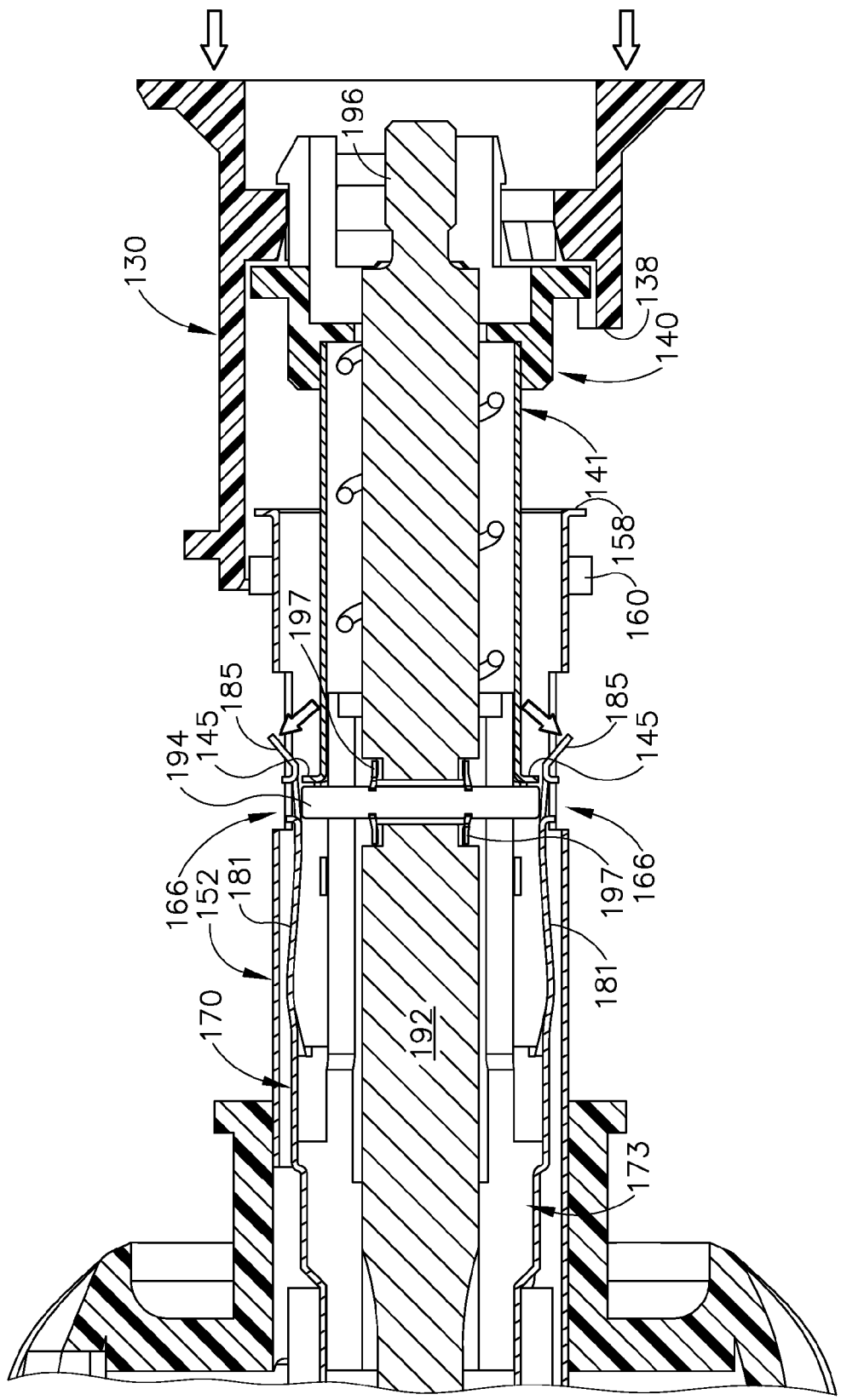
FIG. 41B depicts an enlarged side cross-sectional view of the mode selection components of FIG. 41A, at a first stage during a transition from the regular operation mode to the cleaning mode.

FIGS. 41A-41D show the interactions between various components of shaft assembly (150) during the transition from the normal operating mode to the cleaning mode. In particular, FIG. 41A shows shaft assembly (150) in the normal operating mode. As shown, waveguide (192) is coupled with inner tube (170) via pin (194) and resilient arms (181). FIG. 41B shows mode selection knob (130) at a first state of distal advancement. As noted above, mode selection knob (130) is coupled with mode drive member (141) via coupling member (140). Thus, distal advancement of mode selection knob (130) to a first state of distal advancement has also driven mode drive member (141) to a first state of distal advancement. At this state, upper and lower tabs (145) have engaged the outwardly flared free ends (185) of resilient arms (181) of inner tube (170). In particular, upper and lower tabs (145) have deflected ends (185) of arms (181) outwardly, to a point where arms (181) have disengaged pin (194) of waveguide (192). As also shown in FIG. 41B, upper and lower side openings (166) of outer tube (152) provide clearance for arms (181) to flex outwardly to release pin (194).

Figure 36A:
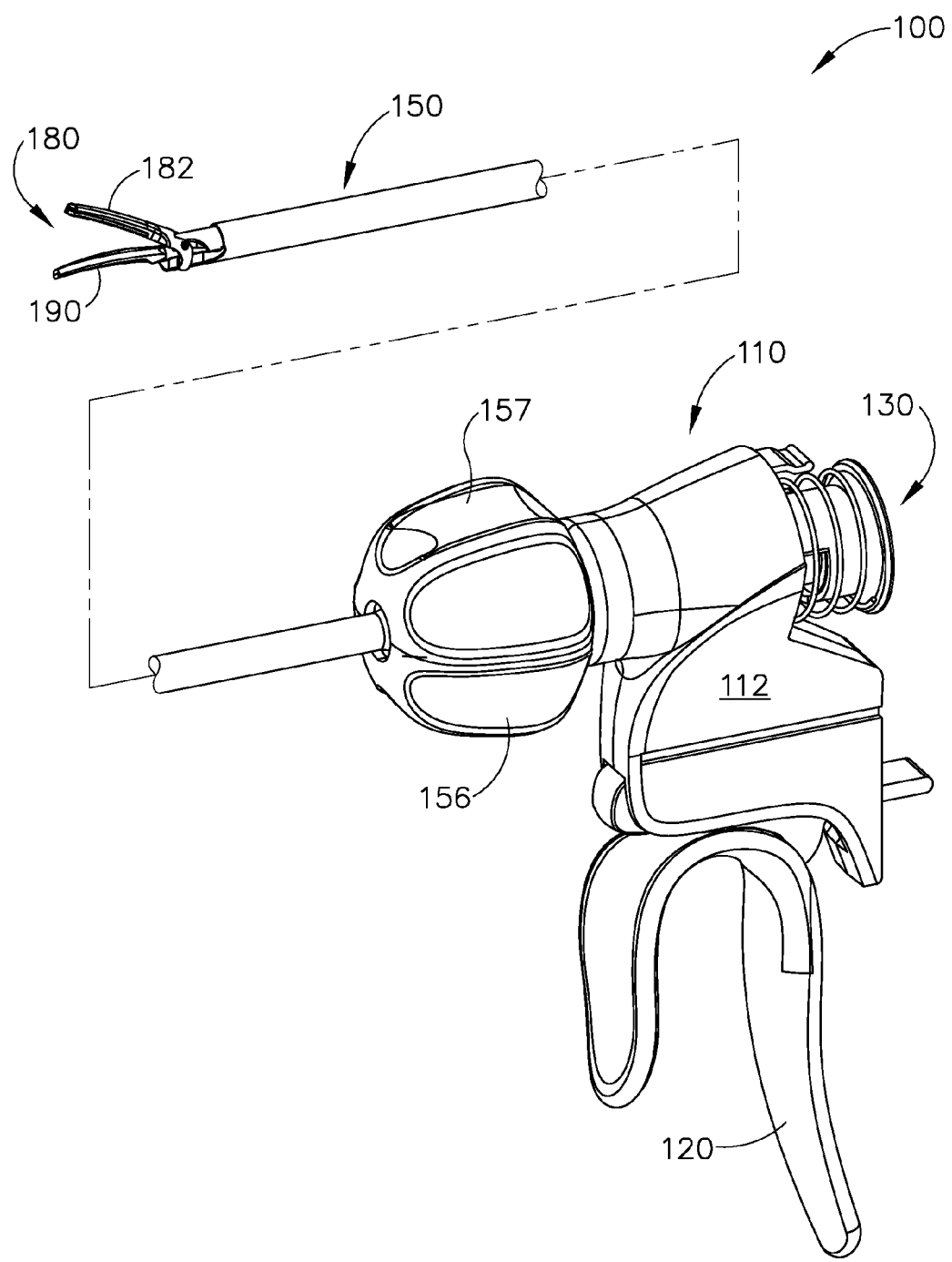
FIG. 36A depicts a partial perspective view of the disposable portion of FIG. 9, with the end effector in the open configuration and the mode selection knob in a non-actuated position.
Figure 36B:
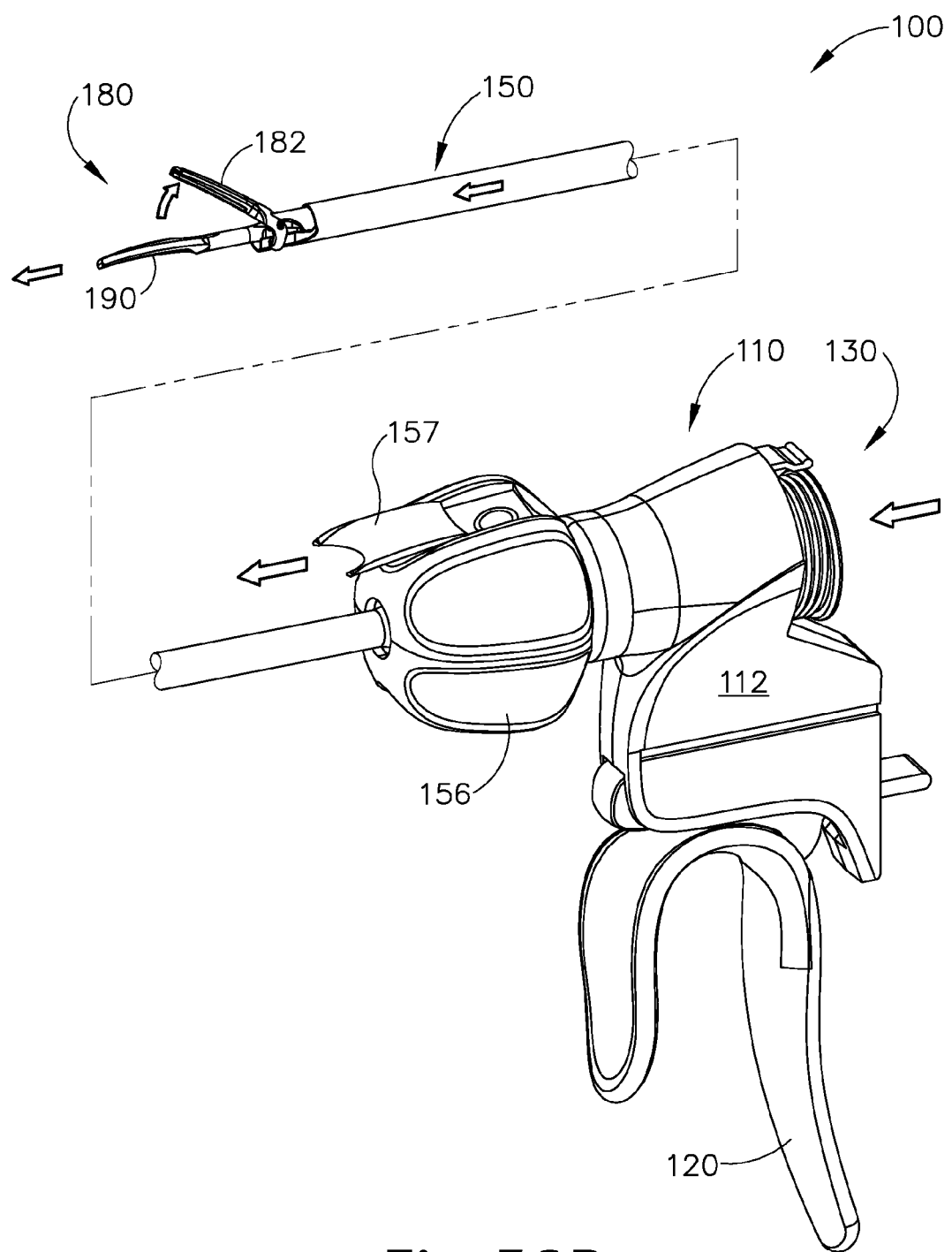
FIG. 36B depicts a partial perspective view of the disposable portion of FIG. 9, with the end effector in a cleaning mode and the mode selection knob in an actuated position.
Figure 41C:
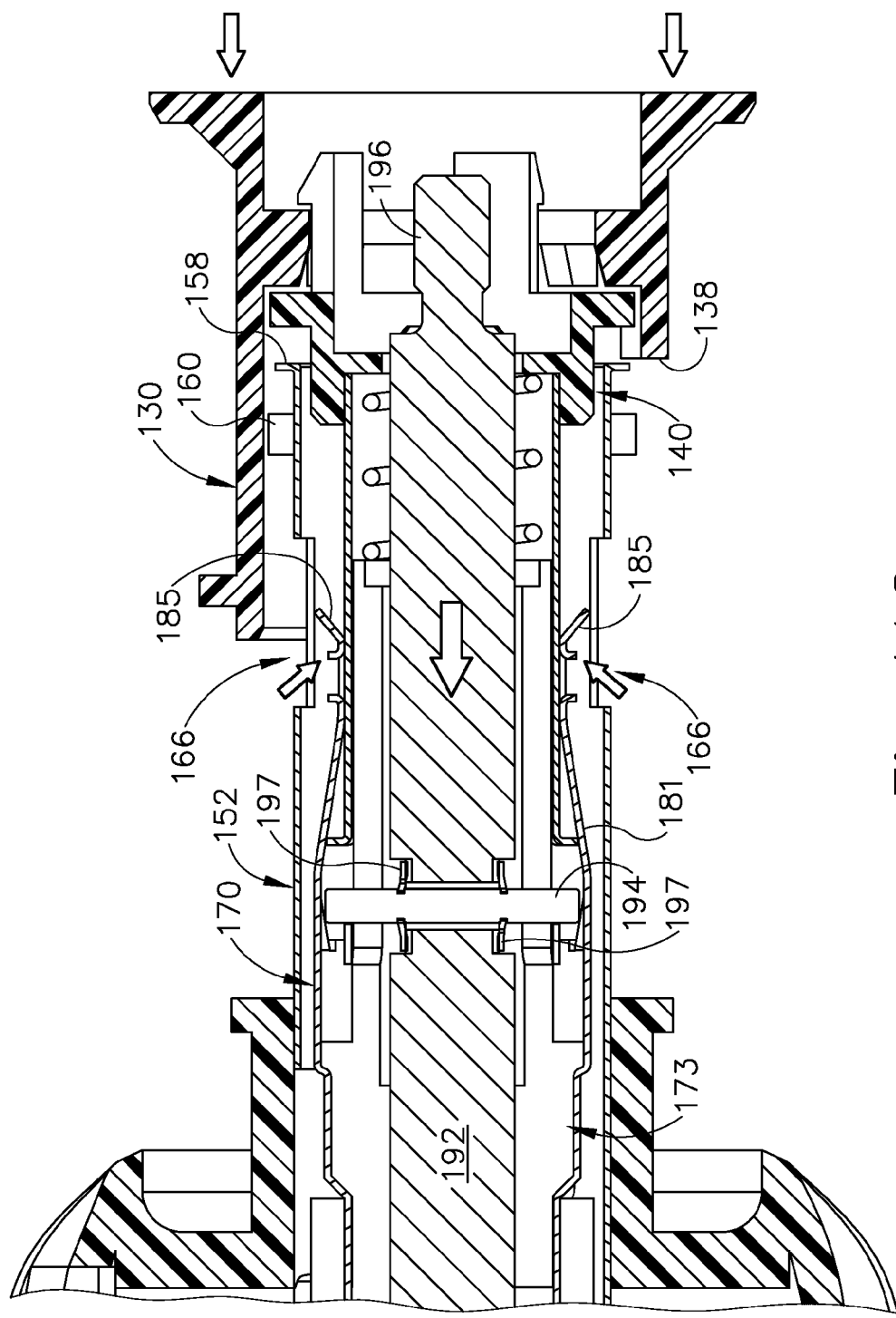
FIG. 41C depicts an enlarged side cross-sectional view of the mode selection components of FIG. 41A, at a second stage during a transition from the regular operation mode to the cleaning mode.
Figure 41D:
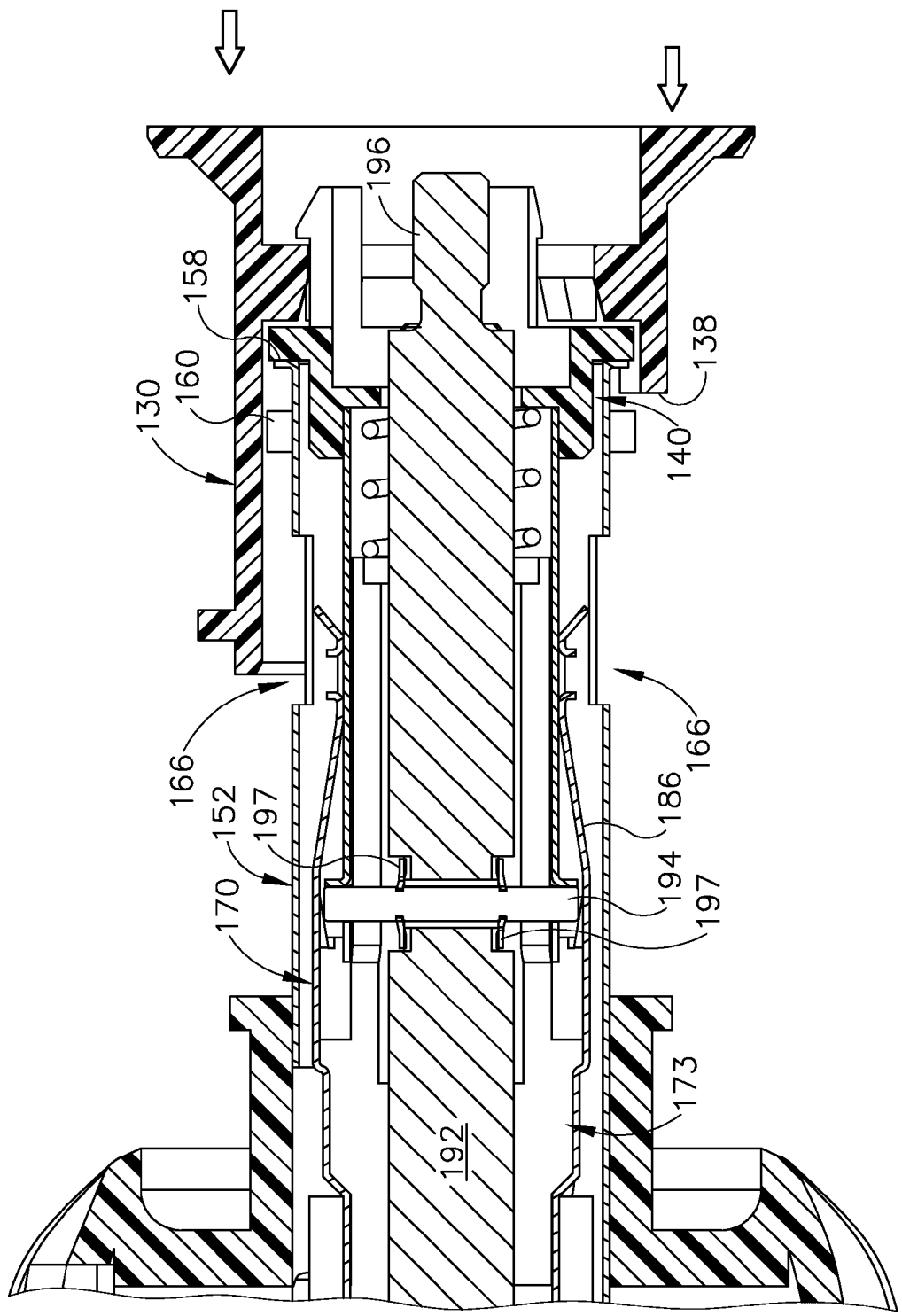
FIG. 41D depicts an enlarged side cross-sectional view of the mode selection components of FIG. 41A, fully transitioned to the cleaning mode.

As the operator continues to advance mode selection knob (130) distally, upper and lower tabs (145) of mode drive member (141) engage pin (194) and thereby drive waveguide (192) distally as shown in FIG. 41C. The resilience of arms (181) drives arms (181) back inwardly once upper and lower tabs (145) clear ends (185) of arms (181). During the range of travel from the state shown in FIG. 41B to the state shown in FIG. 41C, waveguide (192) translates distally relative to inner tube (170) but outer tube (152) does not translate distally relative to inner tube (170). However, upon reaching the state shown in FIG. 41C, distal edge (138) of mode selection knob (130) engages flange (158) of outer tube (152). Thus, as the operator continues to advance mode selection knob (130) distally from the state shown in FIG. 41C to the state shown in FIG. 41D, mode selection knob (130) drives outer tube (152) distally relative to inner tube (170). This distal movement of outer tube (152) relative to inner tube (170) drives clamp arm (182) from the open position shown in FIGS. 6A and 7 to the hyperextended position shown in FIGS. 36B and 37. Having clamp arm (182) in a hyperextended position may facilitate access to blade (190) and an adjacent region of waveguide (192), thereby facilitating the cleaning of blade (190) and the adjacent region of waveguide (192). It should also be understood that blade (190) has transitioned from a proximal position as shown in FIGS. 6A-7 to a distal position as shown in FIGS. 36B and 37; and that this distal positioning of blade (190) may also facilitate access to blade (190) and an adjacent region of waveguide (192), thereby facilitating the cleaning of blade (190) and the adjacent region of waveguide (192).

In some variations, inner tube (170) includes a plurality of annular indentations along its length. Such indentations may be similar to indentation (171). As noted above, a plurality of annular sealing members (e.g., o-rings, etc.) may be positioned at nodal positions along the length of waveguide (192). The annular indentations that are spaced along the length of inner tube (170) may correspond to these annular sealing members that are spaced along the length of waveguide (192). In other words, when disposable assembly (100) is in a normal operating mode, annular indentations of inner tube (170) may encompass the annular sealing members along the length of waveguide (192). In some instances, the sealing members of the waveguide (192) may contact inner tube (170) at the annular indentations. As another merely illustrative alternative, there may be a nominal radial clearance (e.g., approximately 0.002 inches, etc.) between the outer diameter of the sealing members and the inner diameter of the annular indentations. In either case, when disposable assembly (100) is transitioned to the cleaning mode, the distal advancement of waveguide (192) relative to inner tube (170) may cause the sealing members to be substantially spaced from the annular indentations, such that the resulting gaps provide a substantially clear path for cleaning fluid to be flushed distally from port (153) through the space between the outer diameter of waveguide (192) and the inner diameter of inner tube (170).

C. Triggering Features of Disposable Assembly

Figure 42:
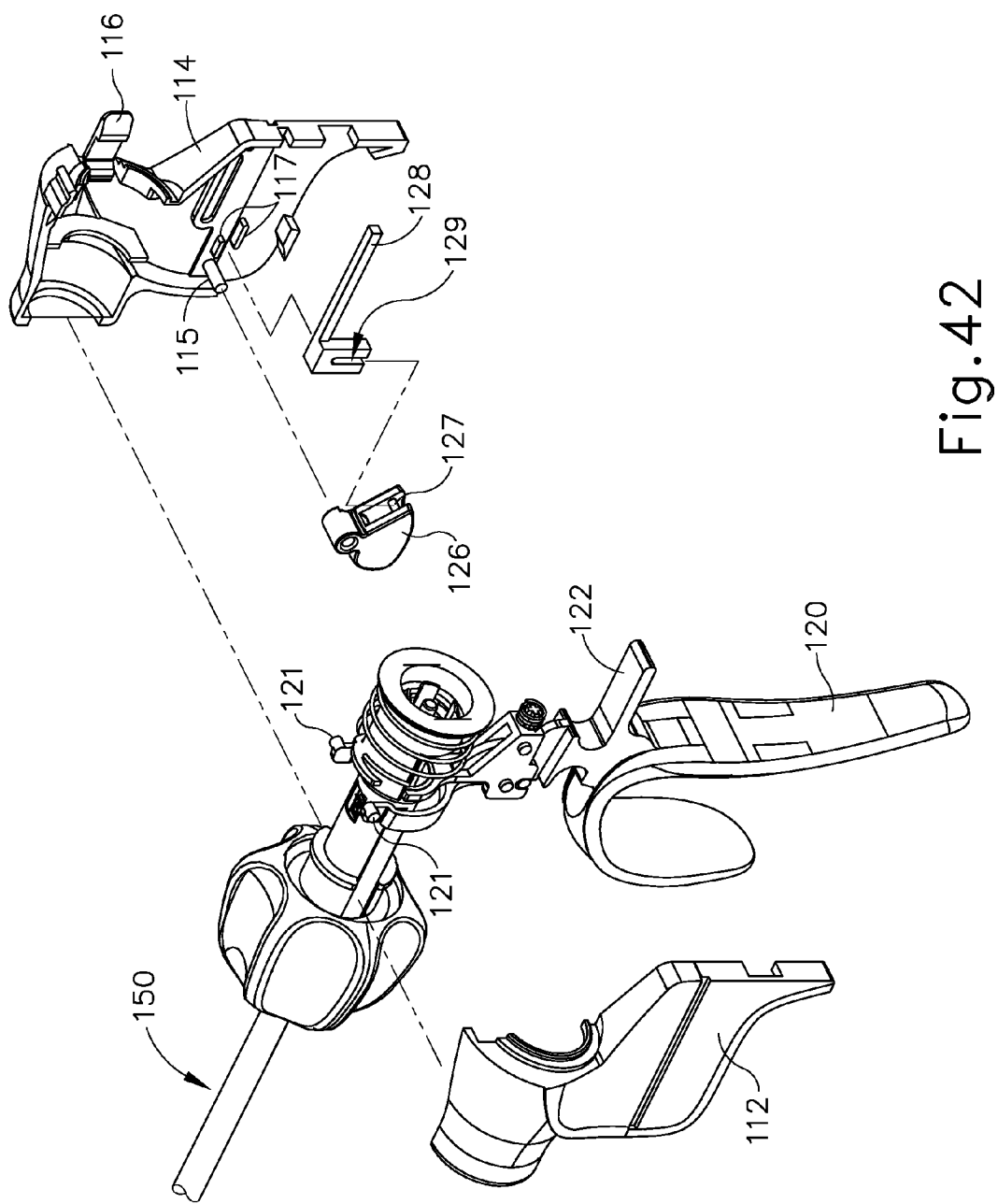
FIG. 42 depicts a partially exploded view of the proximal portion of the disposable portion of FIG. 9, showing trigger components.
Figure 43:
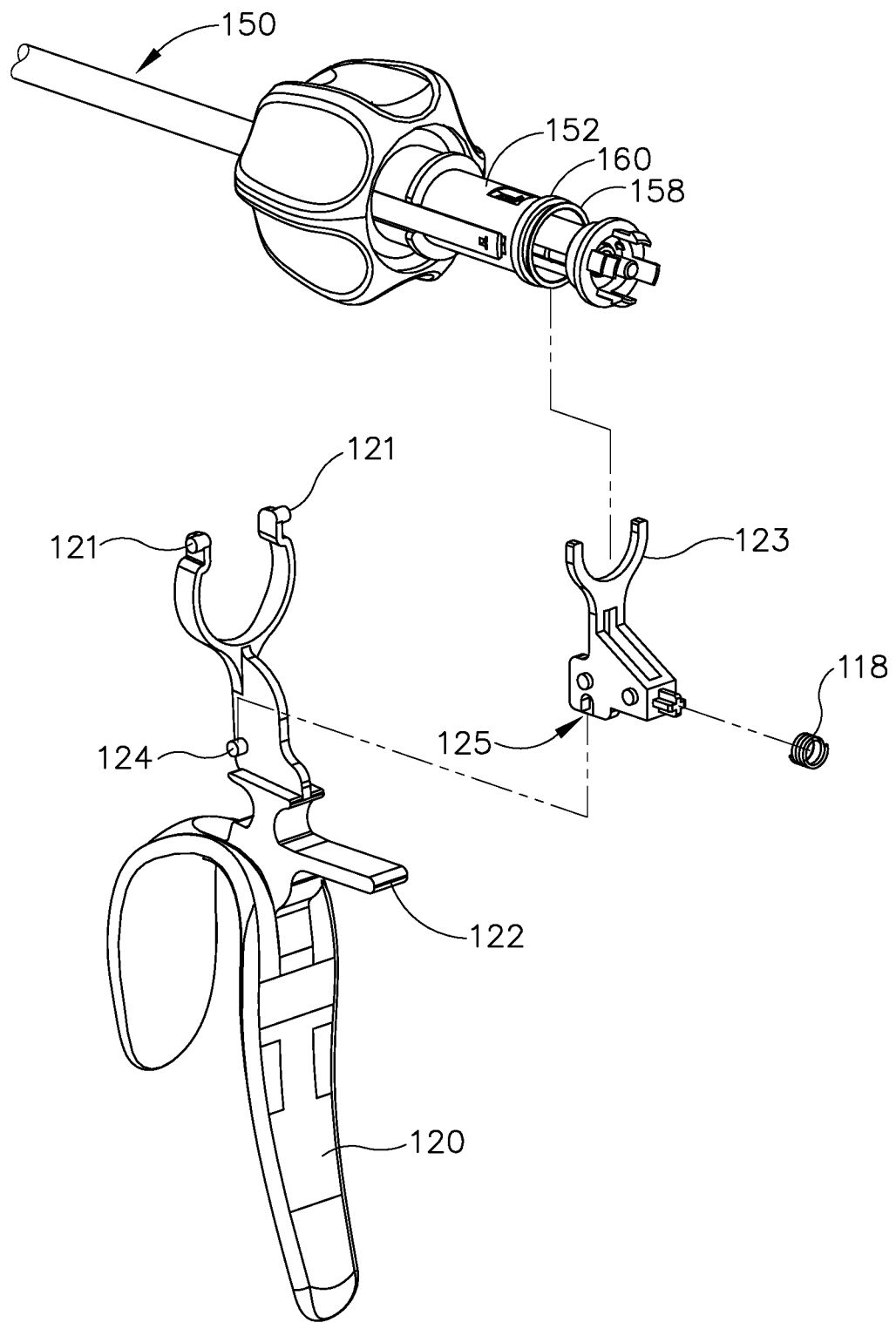
FIG. 43 depicts a partially exploded view of outer tube actuation components of the disposable portion of FIG. 9.

As noted above, body portion (110) of disposable assembly (100) comprises a trigger (120) and a button (126). As shown in FIG. 42, button (126) is pivotally secured to an integral post (115) of housing half (114), such that button (126) is operable to pivot about post (115). Button (126) includes a cross-bar (127), which is received in a slot (129) of arm (128). Arm (128) is slidably positioned in housing half (114) and is guided therein by integral bosses (117) of housing half (114). As button (126) is pressed to pivot button from a non-actuated position (FIG. 44A) to an actuated position (FIG. 44C), cross-bar (127) drives arm (128) proximally. The proximal movement of the proximal end of arm (128) is detected in reusable assembly (200) and thereby activates blade (190) as will be described in greater detail below.

Figure 44A:
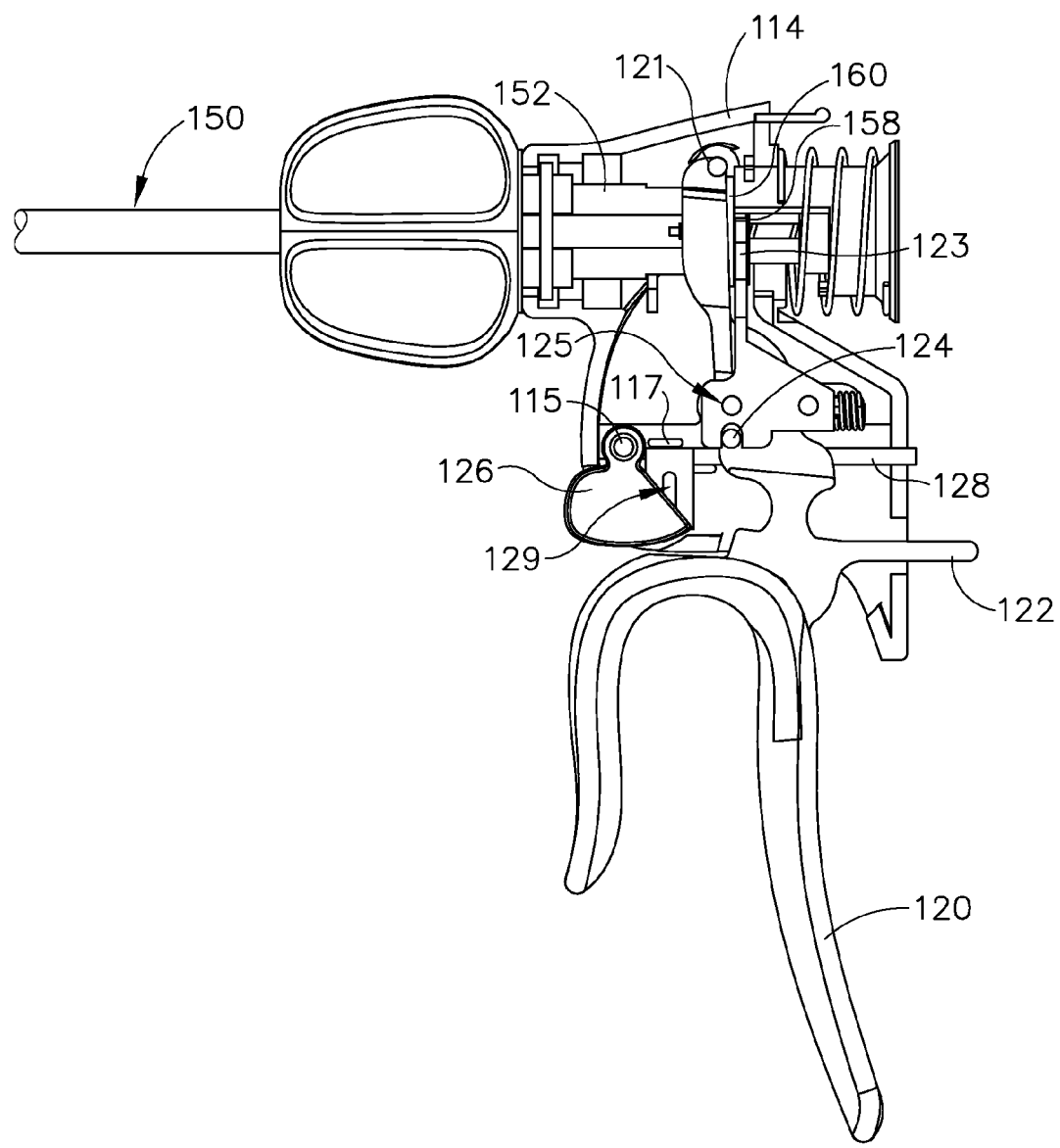
FIG. 44A depicts a side elevational view of the proximal portion of the disposable portion of FIG. 9, with a housing half removed, showing a trigger in a non-actuated position and a button in a non-actuated position.
Figure 44B:
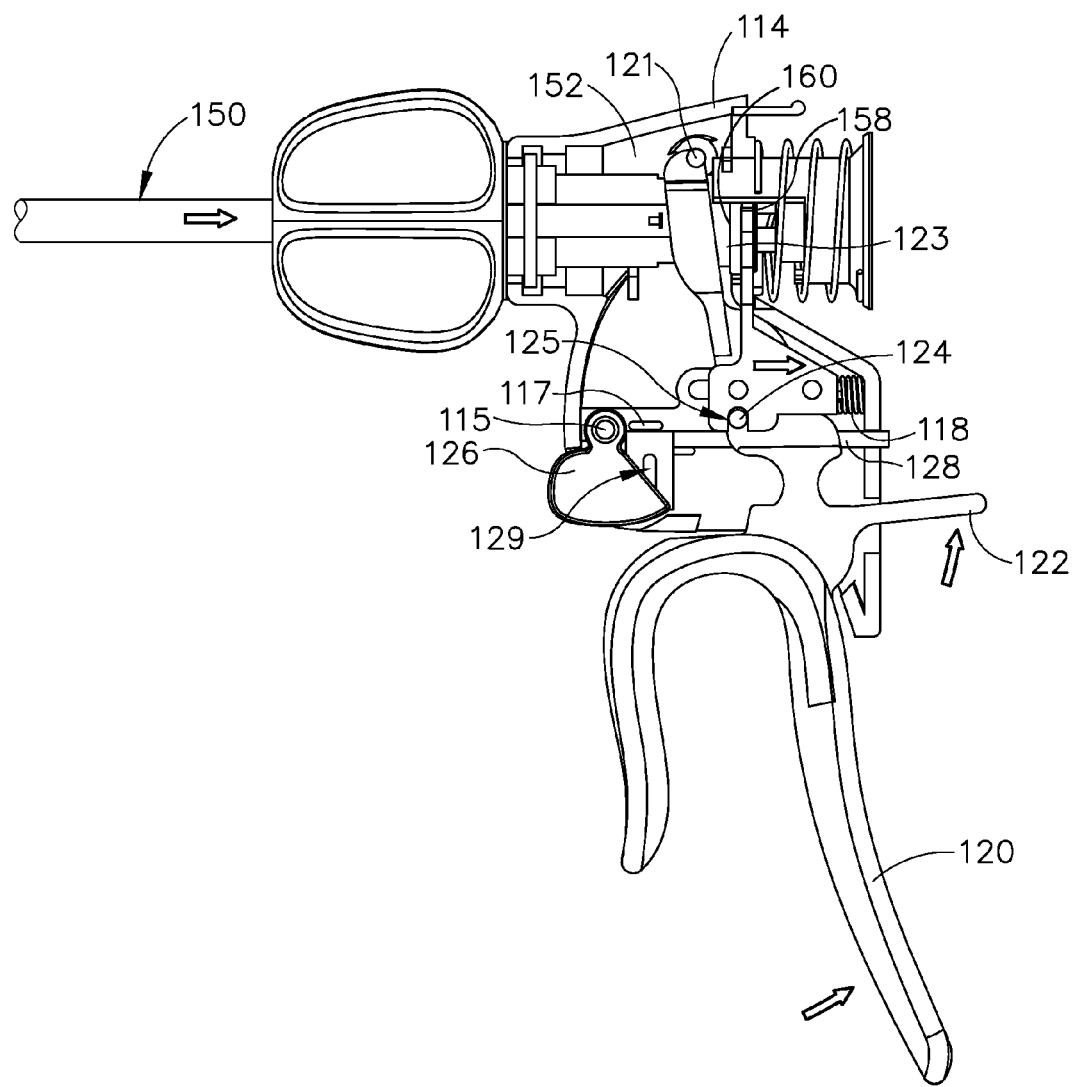
FIG. 44B depicts a side elevational view of the components of FIG. 44A, showing the trigger in an actuated position and the button in the non-actuated position.

As also shown in FIG. 42, trigger (120) is pivotally secured between housing halves (112, 114) via integral pins (121), such that trigger (120) is operable to pivot about pins (121). Trigger (120) is further coupled with a yoke (123). In particular, integral posts (124) are received in corresponding slots (125) of yoke (123). Due to this arrangement, yoke (123) translates longitudinally relative to housing halves (112, 114) when trigger (120) pivots relative to housing halves (112, 114), as shown in FIGS. 44A-44B. Yoke (123) is captured between flange (158) and ring (160) of outer tube (152). Thus, yoke (123) will drive outer tube (152) to translate relative to body (110) when yoke (123) translates relative to housing halves (112, 114). It should therefore be understood that pivoting of trigger (120) relative to housing halves (112, 114) will cause longitudinal movement of outer tube (152) relative to body (110), thereby pivoting clamp arm (182) toward and away from blade (190). A return spring (118) resiliently biases yoke (123) trigger (120), and outer tube (152) distally, thereby resiliently biasing clamp arm (182) to the normal open position shown in FIG. 6A. As noted above, trigger (120) includes an integral tab (122) that protrudes proximally from housing halves (112, 114). As trigger (120) is pivoted, the corresponding movement of tab (122) is detected in reusable assembly (200) as will be described in greater detail below.

III. Reusable Assembly of Exemplary Ultrasonic Surgical Instrument

Figure 45:
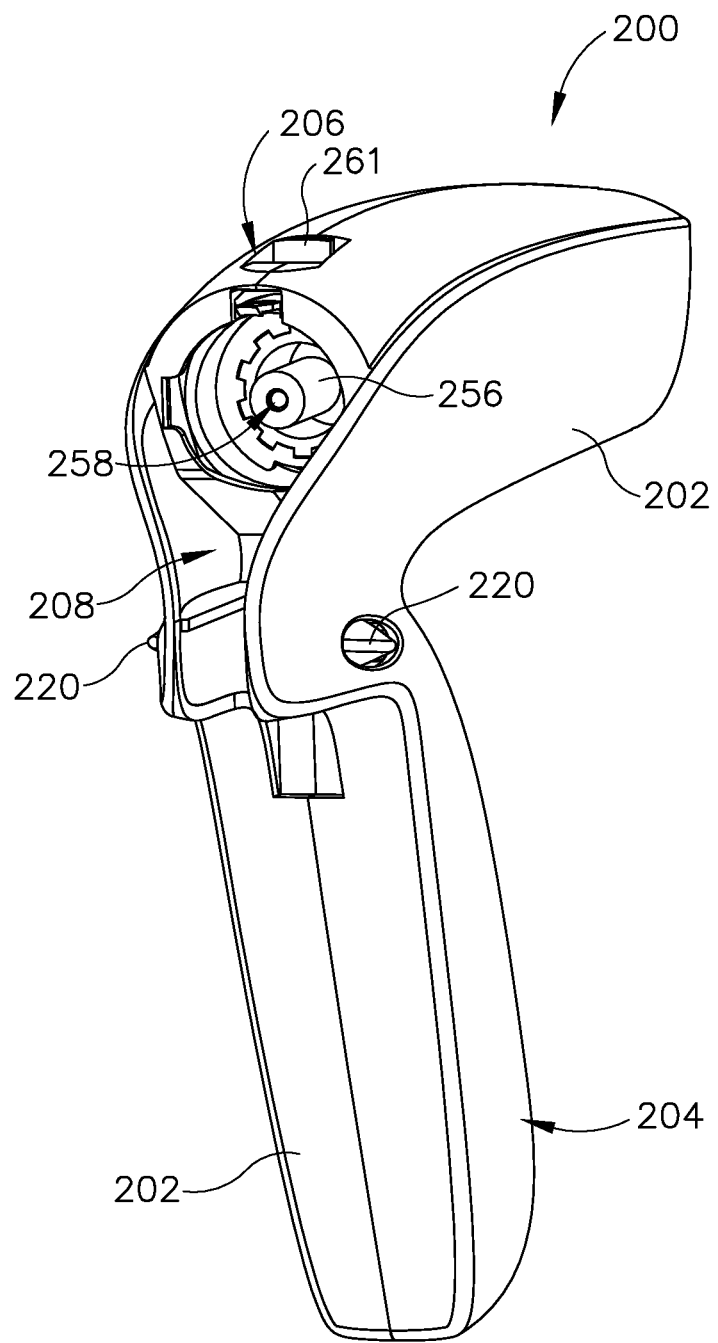
FIG. 45 depicts a perspective view of the reusable portion of the instrument of FIG. 1.
Figure 46:
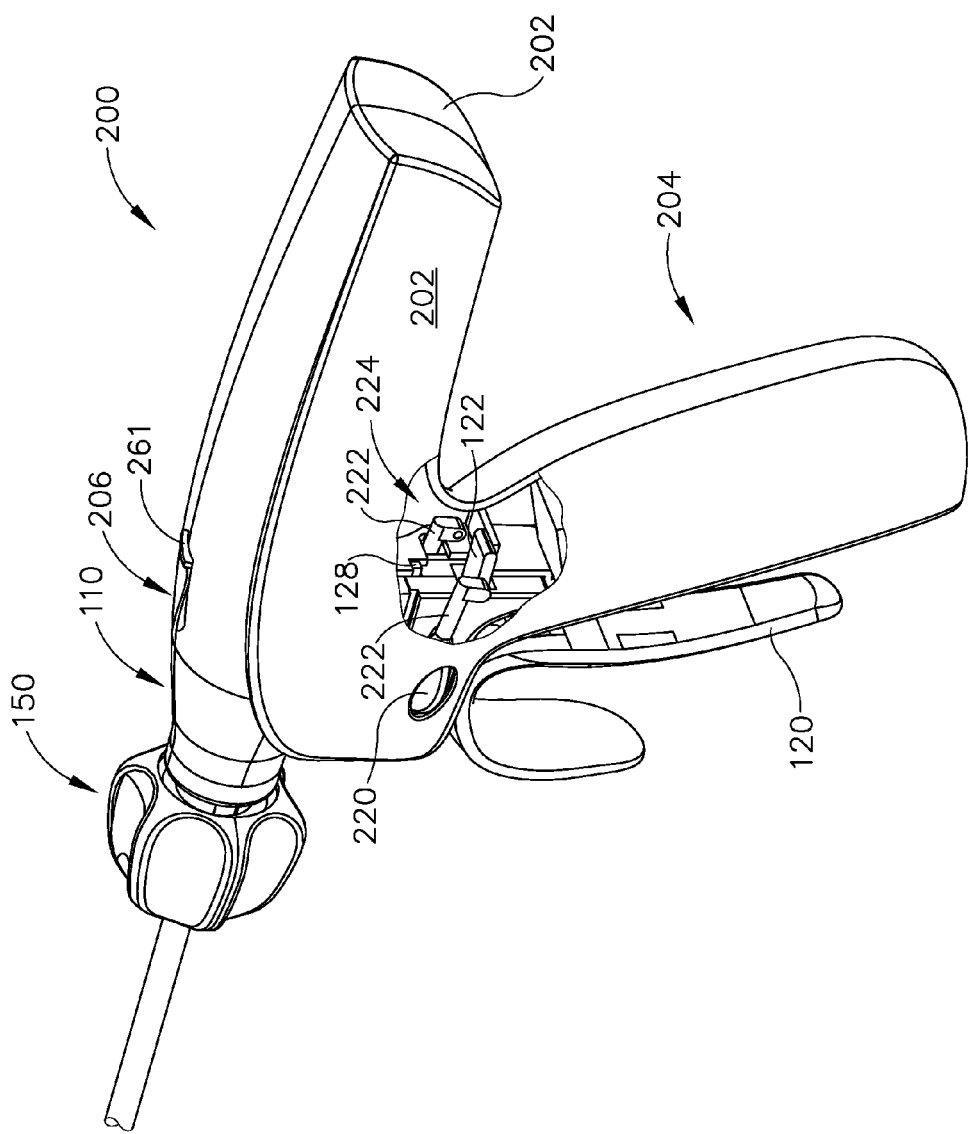
FIG. 46 depicts a perspective view of the instrument of FIG. 1, with a region of the reusable portion of FIG. 45 cut away to reveal positioning of components within the reusable portion.
Figure 47:
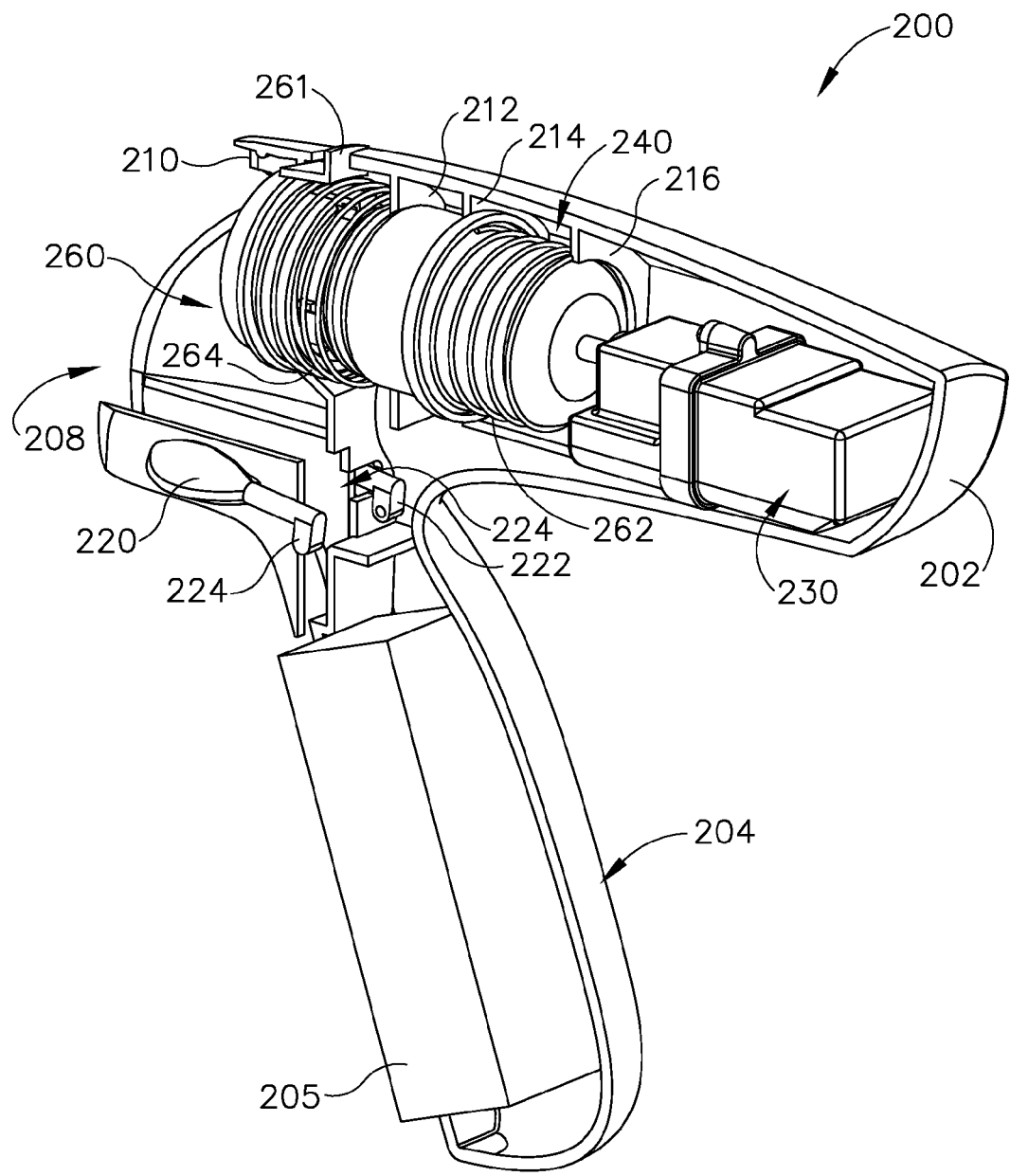
FIG. 47 depicts a perspective view of the reusable portion of FIG. 45 with a housing half removed.

FIGS. 45-47 show reusable assembly (200) in greater detail. As noted above, reusable assembly (200) comprises a pair of complementary handle housings (202). Housings (202) together define a pistol grip (204), an upper window (206), and a distal recess (208). Reusable assembly (200) also includes a pair of side buttons (220). Side buttons (220) include proximally extending stems (222). Side buttons (220) are operable to be actuated inwardly relative to housings (202). The inward actuation of side buttons (220) causes corresponding movement of stems (222). Stems (222) are located within a sensor region (224) of reusable assembly (200). In some versions, stems (222) include integral magnets and hall effect sensors are located in sensor region (224). The hall effect sensors are configured to detect actuation of side buttons (220) by detecting field changes caused by movement of the magnets of stems (222). In some other versions, sensor region (224) includes one or more reed switches that are activated by movement of stems (222) caused by actuation of side buttons (220). Other suitable components and techniques that may be used to detect actuation of side buttons (220) will be apparent to those of ordinary skill in the art in view of the teachings herein. In some variations, side buttons (220) are incorporated into disposable assembly (100) instead of being incorporated into reusable assembly (200).

Figure 44C:
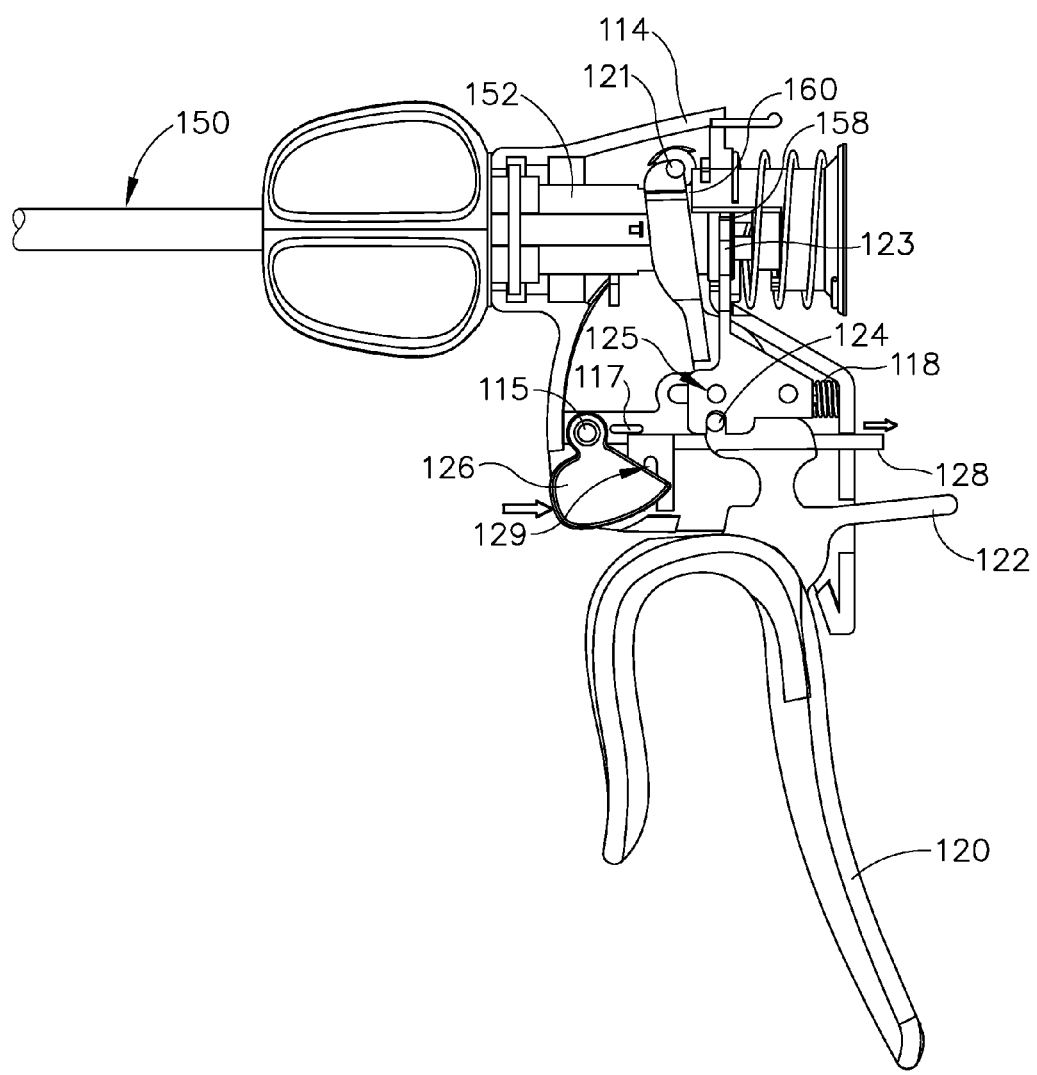
FIG. 44C depicts a side elevational view of the components of FIG. 44A, showing the trigger in the actuated position and the button in an actuated position.

As shown in FIG. 46, when body (110) of disposable assembly (100) is inserted in recess (208), the proximal end of tab (122) and the proximal end of arm (128) are also positioned in sensor region (224) of reusable assembly (200). Thus, when trigger (120) is actuated as shown in FIGS. 44A-44B, one or more sensors in sensor region (224) may detect such actuation of trigger (120). Similarly, when button (126) is actuated as shown in FIGS. 44B-44C, one or more sensors in sensor region (224) may detect such actuation of button (126). Such sensors may include one or more hall effect sensors, one or more reed switches, and/or any other suitable kinds of sensors. Various suitable components and techniques that may be used to detect actuation of trigger (120) and button (126) will be apparent to those of ordinary skill in the art in view of the teachings herein.

When sensors detect actuation of trigger (120), button (126), or buttons (220), such detection may be communicated to generator (230). Generator (230) may include a control logic (e.g., microprocessor, ASIC, and/or other hardware, etc.) that is operable to execute one or more control algorithms in response to actuation of trigger (120), button (126), or buttons (220). Such a control algorithms may also factor in various other conditions, including but not limited to the impedance of tissue engaged by end effector (180). By way of example only, generator (230) may be configured at least partially in accordance a GEN 300 sold by Ethicon Endo-Surgery, Inc. of Cincinnati, Ohio. In addition or in the alternative, generator (230) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (230) may be integrated into a module that is separate from reusable assembly (200). Still other suitable forms that generator (230) may take, as well as various features and operabilities that generator (230) may provide, will be apparent to those of ordinary skill in the art in view of the teachings herein.

An operator may activate buttons (126, 220) to selectively activate transducer assembly (240) to thereby activate ultrasonic blade (190). Buttons (126, 220) of the present example are positioned such that an operator may readily fully operate instrument (10) with a single hand. For instance, the operator may position their thumb about pistol grip (204), position their middle, ring, and/or little finger about trigger (120), and manipulate button (126) using their index finger. The operator may also use their thumb or index finger to manipulate either button (220). Of course, any other suitable techniques may be used to grip and operate instrument (204); and buttons (126, 220) may be located at any other suitable positions. In some versions, button (126) activates ultrasonic blade (190) at a low power and buttons (220) activate ultrasonic blade (190) at a high power. In some other versions, instrument (10) is operable to apply RF energy to tissue via end effector (180), in addition to providing ultrasonic energy at blade (190). In some such versions, buttons (220) are operable to selectively apply such RF energy. By way of example only, buttons (220), button (126), generator (230), and associated components may be operable in accordance with at least some of the teachings of U.S. Pub. No. 2015/0141981, entitled "Ultrasonic Surgical Instrument with Electrosurgical Feature," published May 21, 2015, issued as U.S. Pat. No. 9,949,785 on Apr. 24, 2018, the disclosure of which is incorporated by reference herein.

Battery (205) is fully contained in pistol grip (204) and is configured to provide sufficient power to drive generator (230) in the present example. In some versions, battery (205) is rechargeable. In addition or in the alternative, housings (202) may be configured to permit removability/replacement of battery (205). In addition or in the alternative, reusable portion (200) may include a feature (e.g., cable port, inductive coupling coil, etc.) enabling battery (205) to be recharged. Such recharging may be performed before and/or after instrument (10) is used in a surgical procedure. As yet another merely illustrative example, a recharge port may enable an operator to provide operational power to generator (230) via a cable. Such wired power may be used to recharge battery (205) while also providing operational power to generator (230). By way of example only, instrument (10) may incorporate battery (205) in accordance with at least some of the teachings of U.S. Pub. No. 2014/0207124, entitled "Surgical Instrument with Selectable Integral or External Power Source," published Jul. 24, 2014, now abandoned, the disclosure of which is incorporated by reference herein. In some other variations, battery (205) is omitted altogether, such that generator (230) receives electrical power via cable or in some other fashion.

Figure 48:
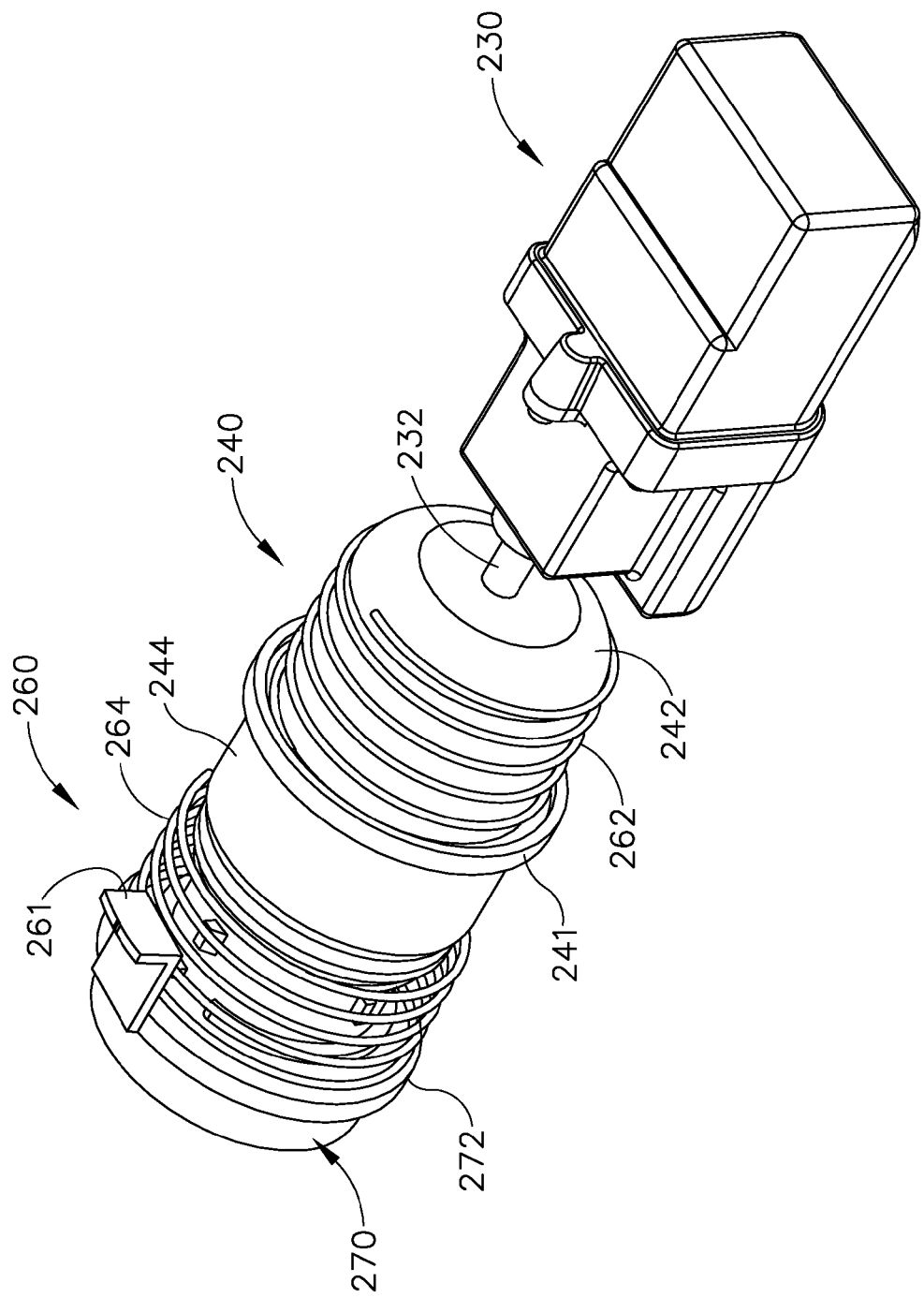
FIG. 48 depicts a perspective view of a generator module and ultrasonic transducer assembly of the reusable portion of FIG. 45.
Figure 49:
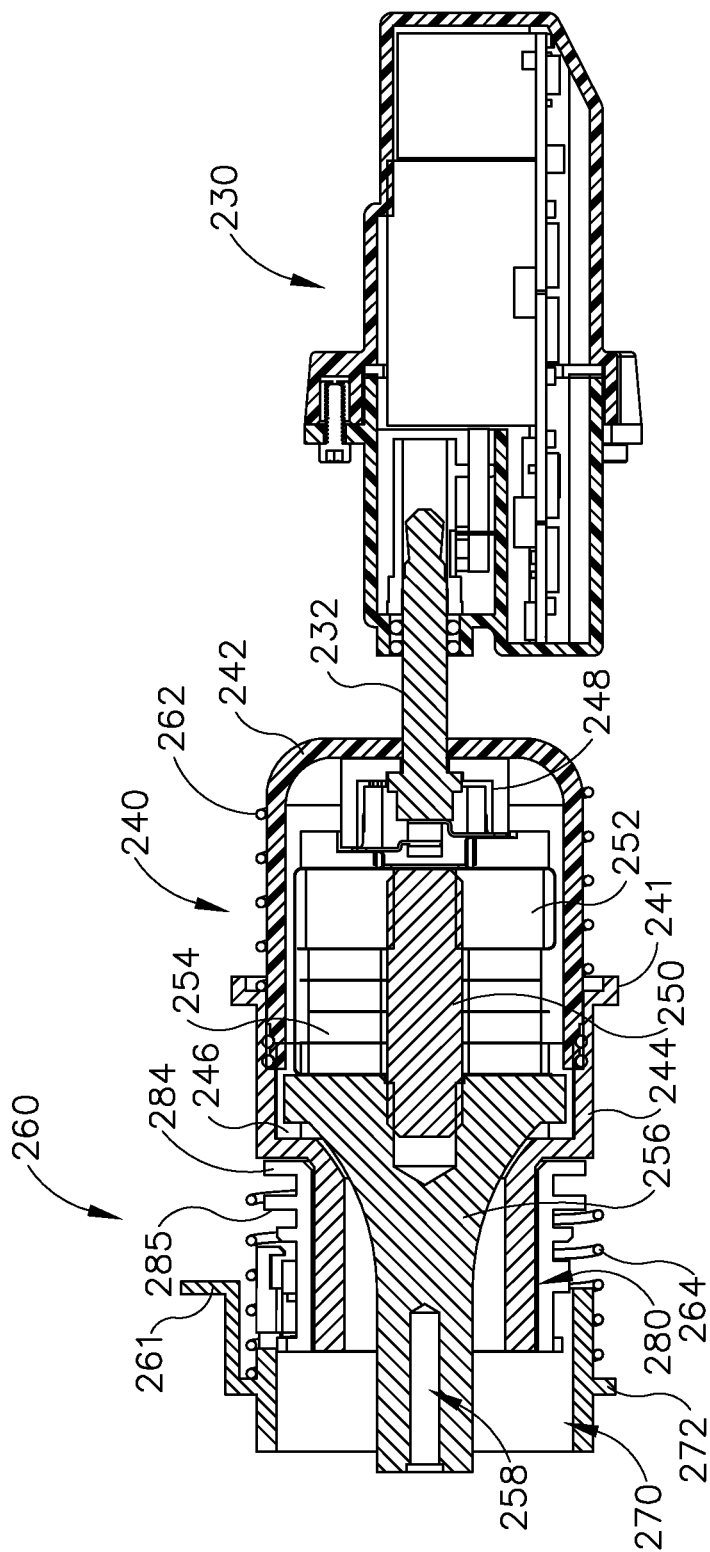
FIG. 49 depicts a side cross-sectional view of the components of FIG. 48.

While generator (230) is fixedly secured within housings (202), transducer assembly (240) is operable to rotate within housings (202). As shown in FIGS. 48-49, generator (230) is coupled with transducer assembly (240) via a spindle (232), such that transducer assembly (240) receives electrical power from generator (230) via spindle (232). Spindle (232) is an integral feature of transducer assembly (240) that is rotatable within generator (230) while maintaining electrical continuity between generator (230) and transducer assembly (240). It should be understood that slip rings and/or other kinds of couplings may be used to maintain electrical continuity between wires, traces, and/or other kinds of electrical conduits in spindle (232) and electrical components in generator (230). Various suitable features and relationships will be apparent to those of ordinary skill in the art in view of the teachings herein.

Figure 50:
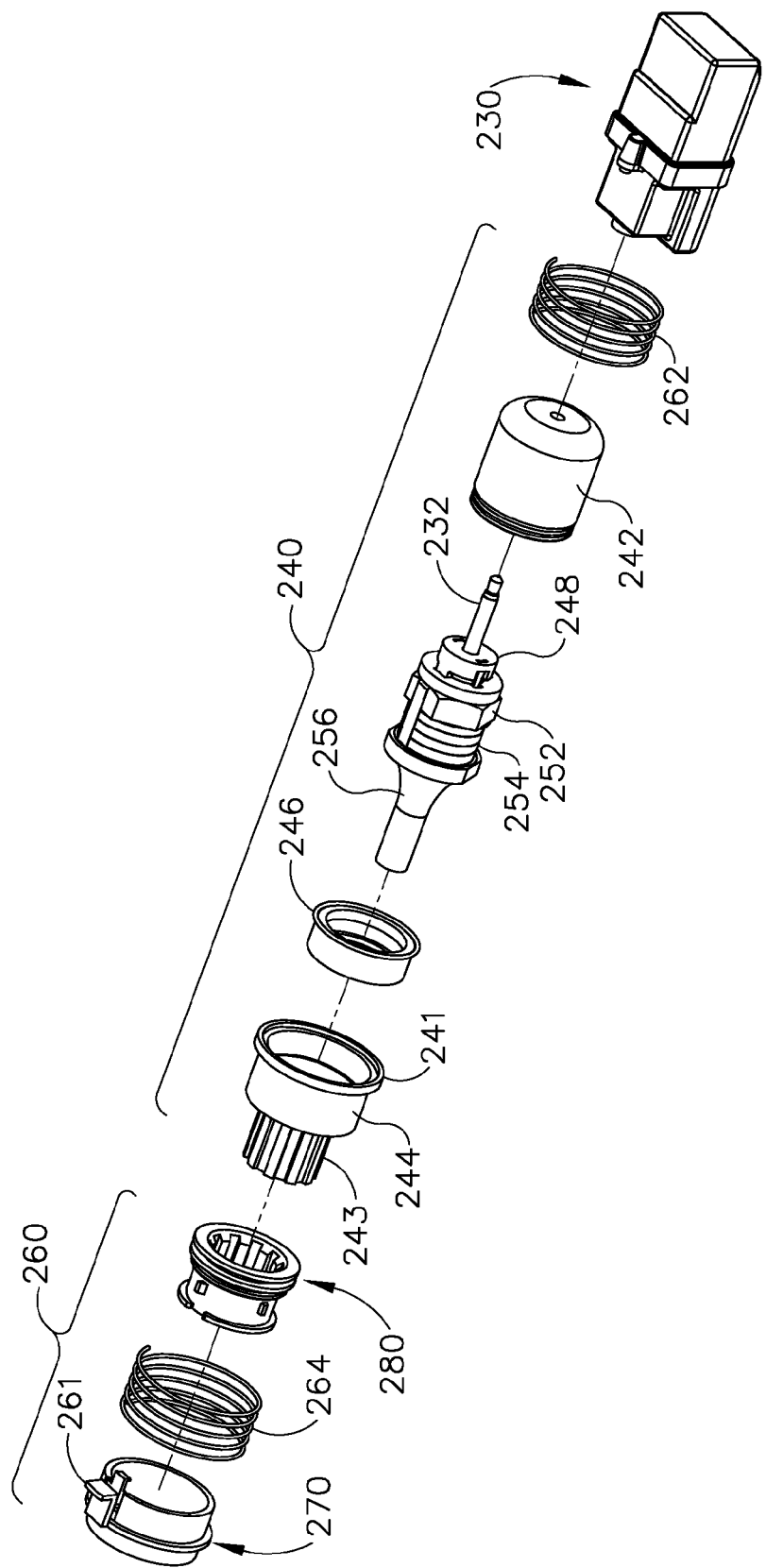
FIG. 50 depicts an exploded view of the components of FIG. 48.

As best seen in FIGS. 49-50, transducer assembly (240) of the present example comprises a proximal casing (242), a distal casing (244), a mount (246), a head (248), a bolt (250), an endmass (252), a set of piezoelectric discs (254), and a horn (256). Casings (242, 244) are threadably coupled together and contain mount (246), head (248), bolt (250), endmass (252) and piezoelectric discs (254). Distal casing (244) includes an annular flange (241) and an angularly spaced array of longitudinally extending splines (243). Mount (246) is interposed between an outer diameter of horn (256) and an inner diameter of distal casing (244). Mount (246) thereby provides structural support for horn (256) in casing (244). Mount (246) is fixedly secured to horn (256) and to casing (244), such that the contents within casings (242, 244) rotate unitarily with casings (242, 244). Mount (246) nevertheless provides acoustic isolation of the contents of within casings (242, 244) relative to casings (242, 244). In the present example, mount (246) is located at a longitudinal position corresponding to a node associated with ultrasonic vibrations that are communicated through horn (256) when ultrasonic transducer assembly (240) is activated.

Bolt (250) compresses piezoelectric discs (254) between horn (256) and endmass (252). Head (248) is configured to provide electrical coupling between piezoelectric discs (254) and spindle (232). When piezoelectric discs (254) receive electrical power from generator (230) via spindle (232) and head (248), piezoelectric discs (254) vibrate ultrasonically. These ultrasonic vibrations are communicated to horn (256). Horn (256) communicates these ultrasonic vibrations to waveguide (192) when disposable assembly (100) is coupled with reusable assembly (200). To provide such communication, the distal end of horn (256) includes a threaded recess (258), which is configured to threadably receive threaded stud (196) of waveguide (192). As will be described as greater detail below, torque wrench assembly (260) is configured to rotatably drive threaded stud (196) into threaded recess (258) with an appropriate amount of torque, avoiding a condition where waveguide (192) is over-torqued relative to horn (256).

Figure 51:
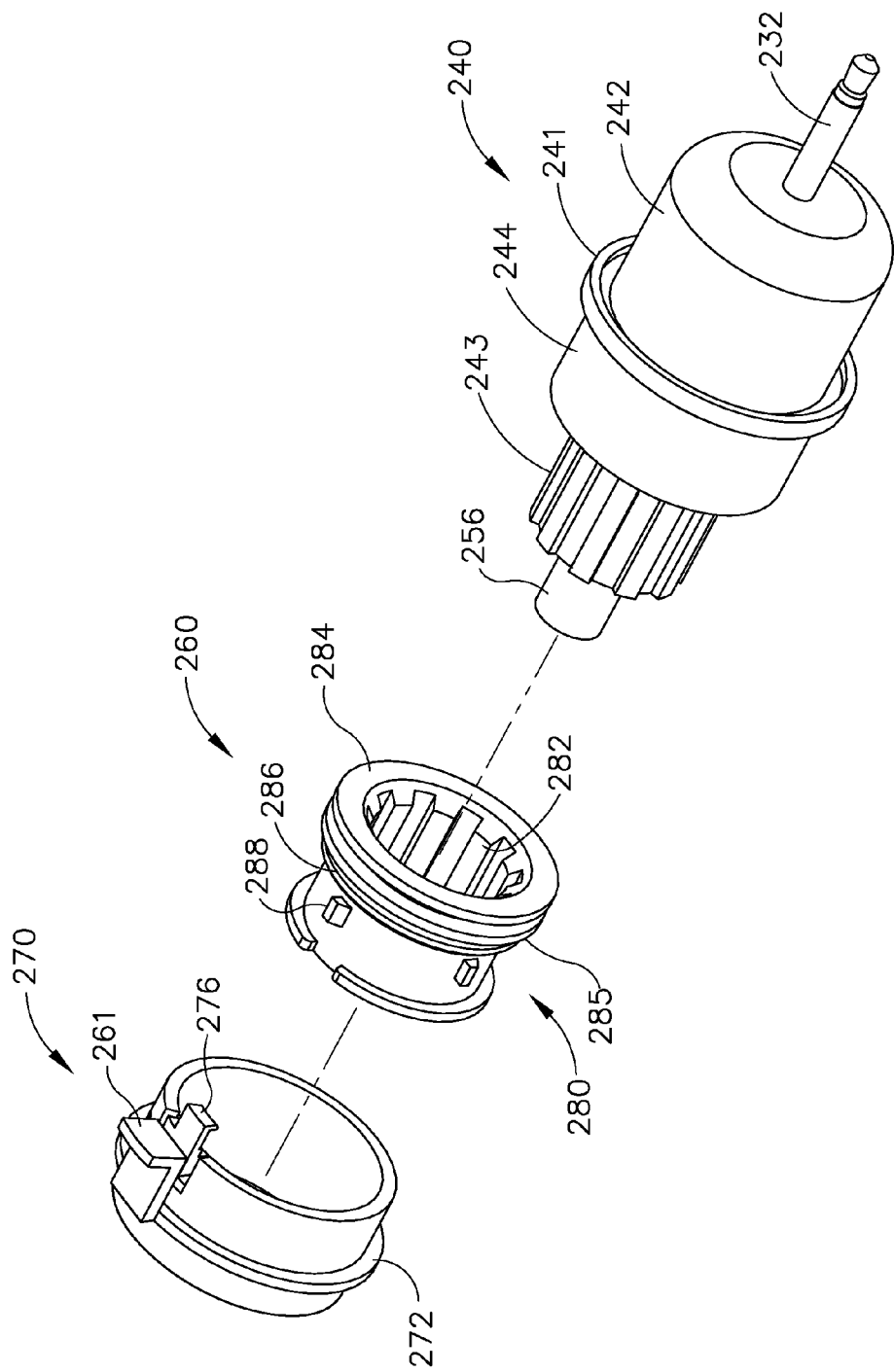
FIG. 51 depicts an exploded view of torque wrench assembly associated with the ultrasonic transducer assembly of FIG. 48.
Figure 52:
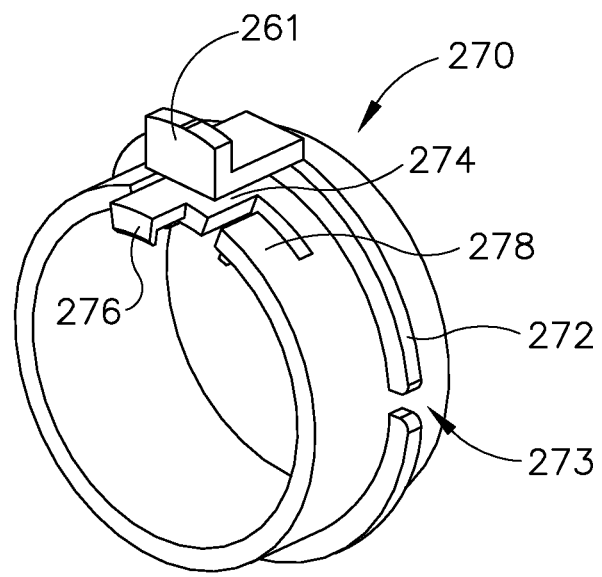
FIG. 52 depicts a perspective view of a pawl ring of the torque wrench assembly of FIG. 51.
Figure 53:
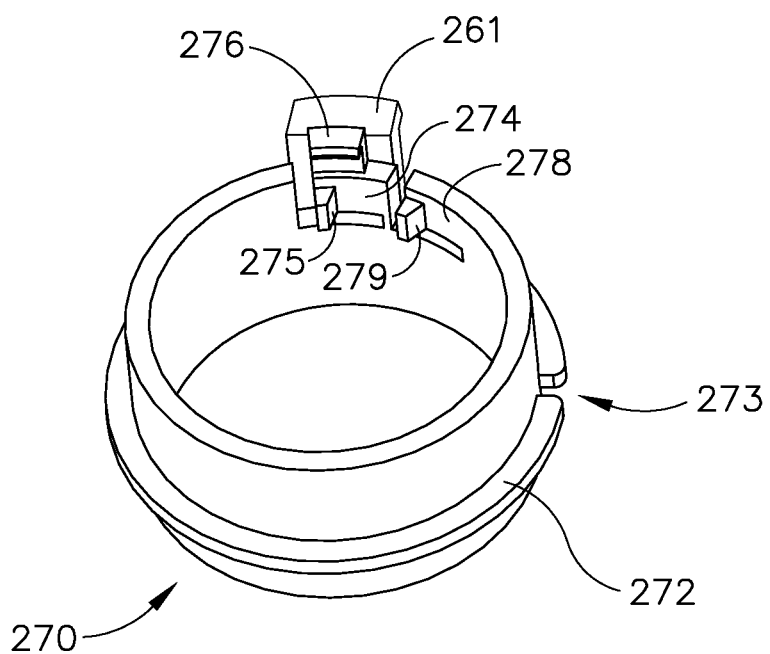
FIG. 53 depicts another perspective view of the pawl ring of FIG. 52.
Figure 54:
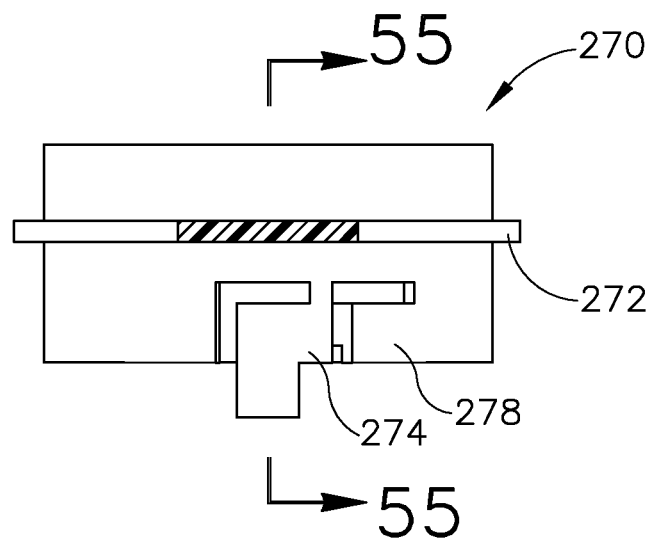
FIG. 54 depicts a cross-sectional view of the pawl ring of FIG. 52, taken along line 54-54 of FIG. 55.
Figure 55:
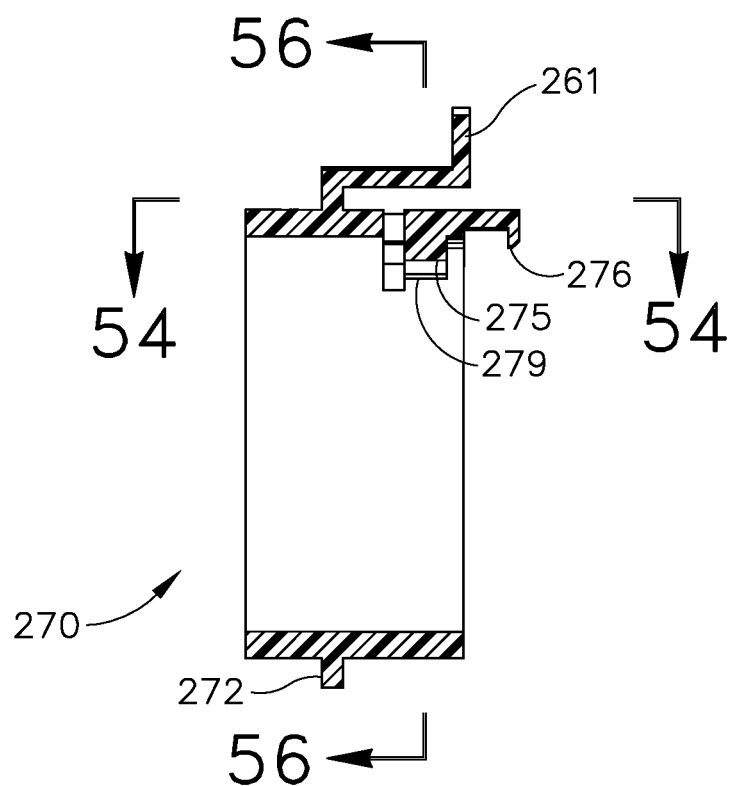
FIG. 55 depicts a cross-sectional view of the pawl ring of FIG. 52, taken along line 55-55 of FIG. 54.
Figure 56:
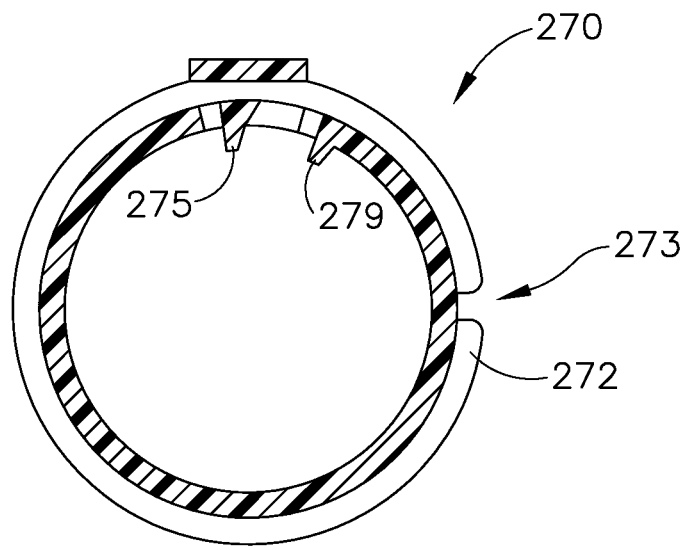
FIG. 56 depicts a cross-sectional view of the pawl ring of FIG. 52, taken along line 56-56 of FIG. 55.

As shown in FIGS. 49-51, torque wrench assembly (260) of the present example comprises a pawl ring (270) and a drive member (280). FIGS. 52-56 show pawl ring (270) in greater detail. Pawl ring (270) of this example comprises an outer annular flange (272). Flange (272) includes a notch (273) that is configured to receive a complementary boss rail (not shown) formed in housing (202). This relationship provides a rotational grounding for pawl ring (270), such that pawl ring (270) is prevented from rotating within housing (202). Nevertheless, the relationship between the boss rail and notch (273) enables pawl ring (270) to translate longitudinally within housing (202). Pawl ring (270) of the present example further comprises a first resilient arm (274) and a second resilient arm (278). Resilient arm (274) includes a pawl (275) and a latch (276). Pawl (275) is directed radially inwardly and extends longitudinally. Latch (276) is directed radially inwardly and extends transversely. Resilient arm (274) is resiliently biased to assume the position shown in FIGS. 52-56. However, resilient arm (274) is operable to flex outwardly as will be described in greater detail below. Second resilient arm (278) also includes a pawl (279), which is directed radially inwardly and extends longitudinally. Resilient arm (278) is resiliently biased to assume the position shown in FIGS. 52-56. However, resilient arm (278) is operable to flex outwardly as will be described in greater detail below. Pawl ring (270) also includes an upwardly extending tab (261). As shown in FIGS. 8, 45-47, 60A-61C, and 63-64, tab (261) is located within upper window (206) of housing (202), such that an operator may engage tab (261) to slide pawl ring (270) longitudinally as will be described in greater detail below.

Figure 57:
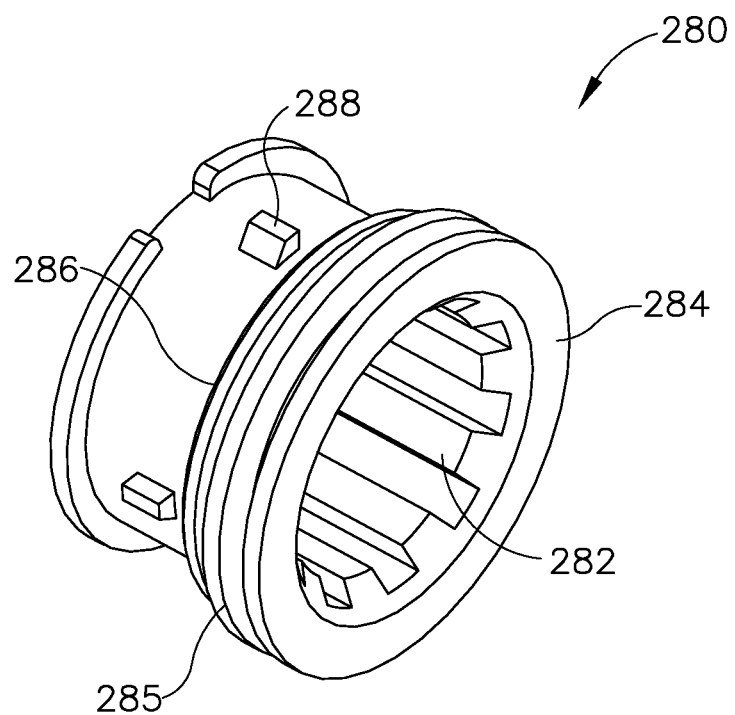
FIG. 57 depicts a perspective view of a sliding rotary drive member of the torque wrench assembly of FIG. 51.
Figure 58:
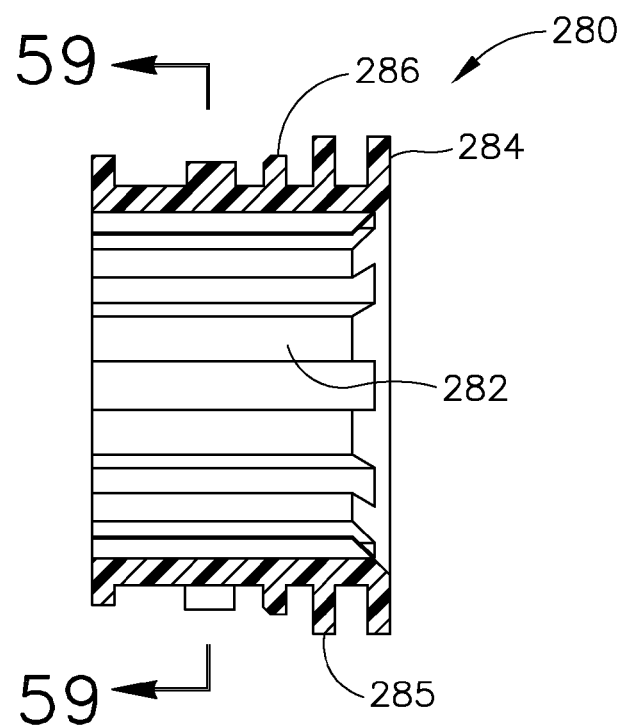
FIG. 58 depicts a cross-sectional view of the drive member of FIG. 57, taken along line 58-58 of FIG. 59.
Figure 59:
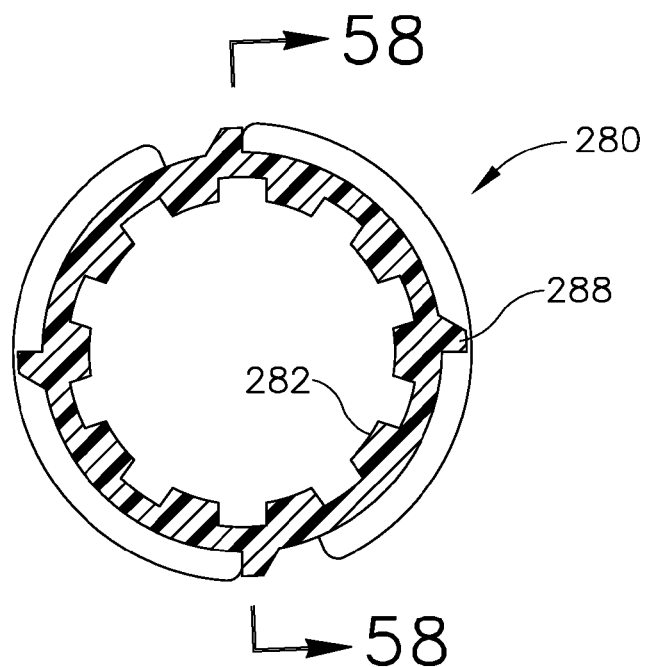
FIG. 59 depicts a cross-sectional view of the drive member of FIG. 57, taken along line 59-59 of FIG. 58.

FIGS. 57-59 show drive member (280) in greater detail. Drive member (280) of this example comprises an angularly spaced array of longitudinally extending splines (282), a proximal outer annular flange (284), an intermediate flange (285), a latching flange (286), and an angularly spaced array of rigid pawls (288). Drive member (280) is positioned in housing (202) such that integral boss (212) is captured between flanges (284, 285). Integral boss (212) thus prevents drive member (280) from translating relative to housing (202). However, integral boss (212) permits drive member (280) to rotate relative to housing (202). Pawls (288) are directed radially outwardly and extend longitudinally. Splines (282) of drive member (280) are configured to mesh with splines (242) of distal casing (244) of transducer assembly (240). Due to this engagement, drive member (280) rotates unitarily with transducer assembly (240). However, this engagement still permits transducer assembly (240) to translate longitudinally relative to drive member (280). Pawls (288) of drive member (280) are configured to interact with pawls (275, 279) of pawl ring (270) during coupling of waveguide (190) with horn (256), as will be described in greater detail below.

As shown in FIGS. 8 and 47, a coil spring (262) is interposed between integral boss (216) of housing (202) and flange (241) of casing (244). Coil spring (262) is resiliently biased to urge transducer assembly (240) distally within housing (202). However, integral boss (214) is configured to engage flange (241) of casing (244) to restrict distal movement of transducer assembly (240) in housing (202). Similarly, as also shown in FIGS. 8 and 47, a coil spring (264) is interposed between integral boss (212) of housing (202) and flange (272) of pawl ring (270). Coil spring (264) thus urges pawl ring (270) distally within housing (202). However, integral boss (210) is configured to engage flange (272) of pawl ring (270) to restrict distal movement of pawl ring (270) in housing (202). It should be understood that one or both of coil springs (262, 264) are intentionally omitted from various drawings of the present disclosure for clarity.

IV. Coupling of Acoustic Drivetrain

Figure 60A:
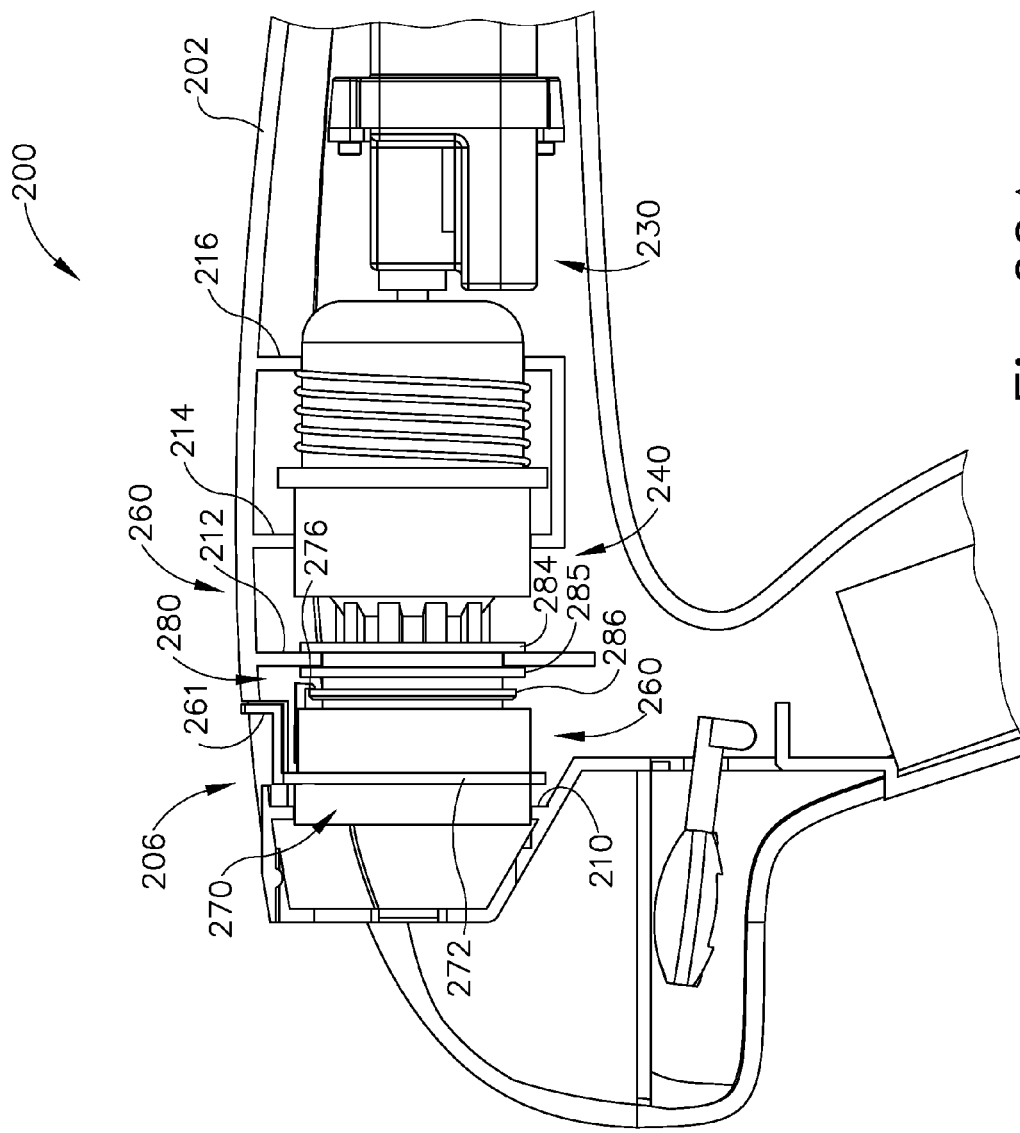
FIG. 60A depicts a partial, side elevational view of the reusable portion of FIG. 45, with a housing half removed.
Figure 60B:
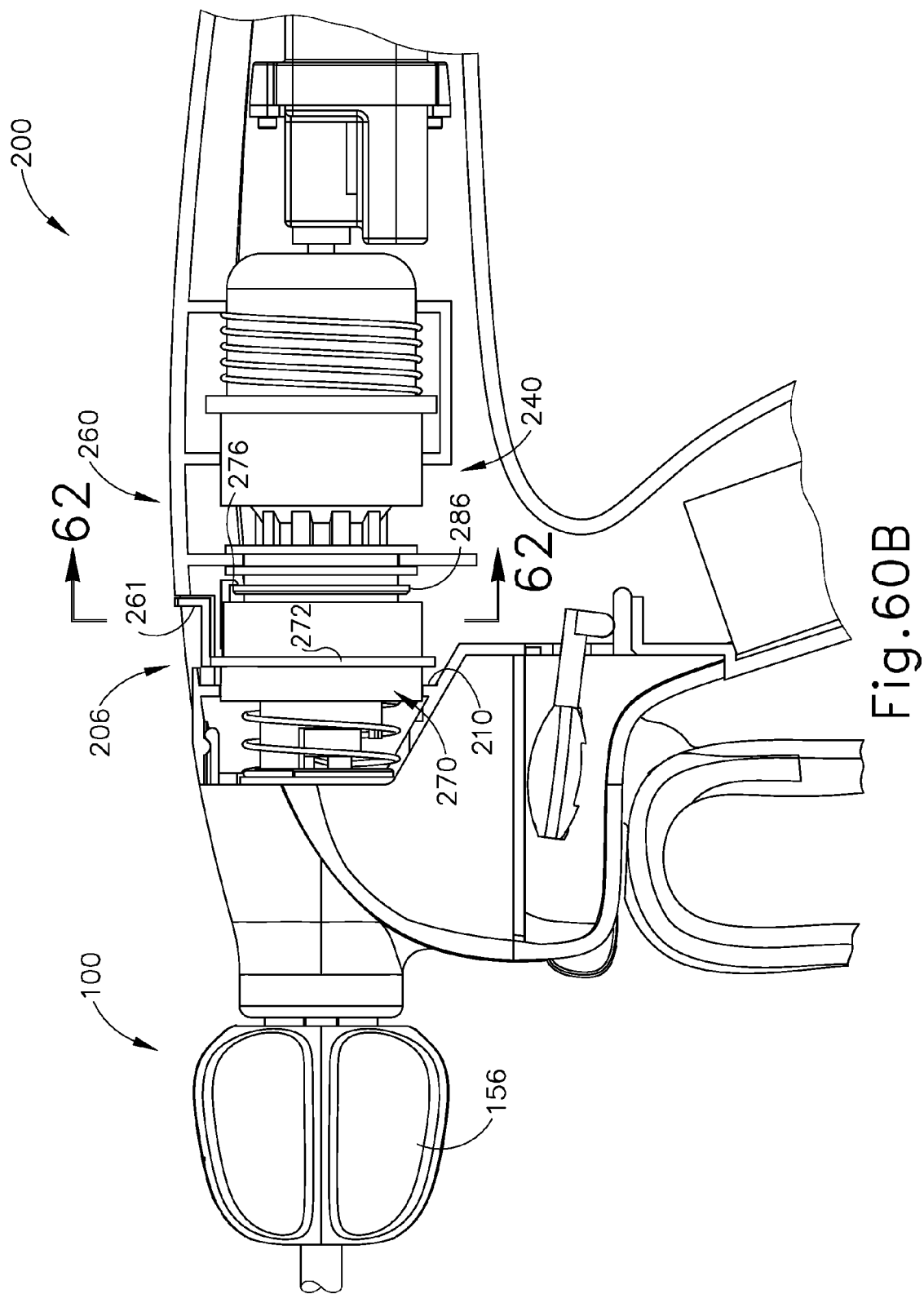
FIG. 60B depicts a partial, side elevational view of the reusable portion of FIG. 45, with a housing half removed, and with the disposable portion of FIG. 9 inserted into a recess of the reusable portion.

FIGS. 60A-64 show how torque wrench assembly (260) operates to mechanically and acoustically couple waveguide (192) with horn (256) in the present example. In particular, FIGS. 60A and 61A show reusable assembly (200) in a mode where reusable assembly (200) is ready to receive disposable assembly (100). In this mode, pawl ring (270) is positioned proximally in housing (202), as indicated by the proximal positioning of tab (261) in upper window (206) of housing (202). When the operator wishes to couple disposable assembly (100) with reusable assembly (200), the operator first inserts the proximal end of body (110) into distal recess (208) of reusable assembly (200), as shown in FIGS. 60B and 61B. At this stage, threaded stud (196) of waveguide (192) is longitudinally aligned with threaded recess (258) of horn (256) and is in contact with the distal end of horn (256). In order to threadably drive stud (196) into recess (258), the operator grasps reusable assembly (200) with one hand and knob (156) with the other hand, then rotates knob (156) relative to reusable assembly (200) to rotate shaft assembly (150) relative to reusable assembly (200), about the longitudinal axis of shaft assembly (150).

Figure 62A:
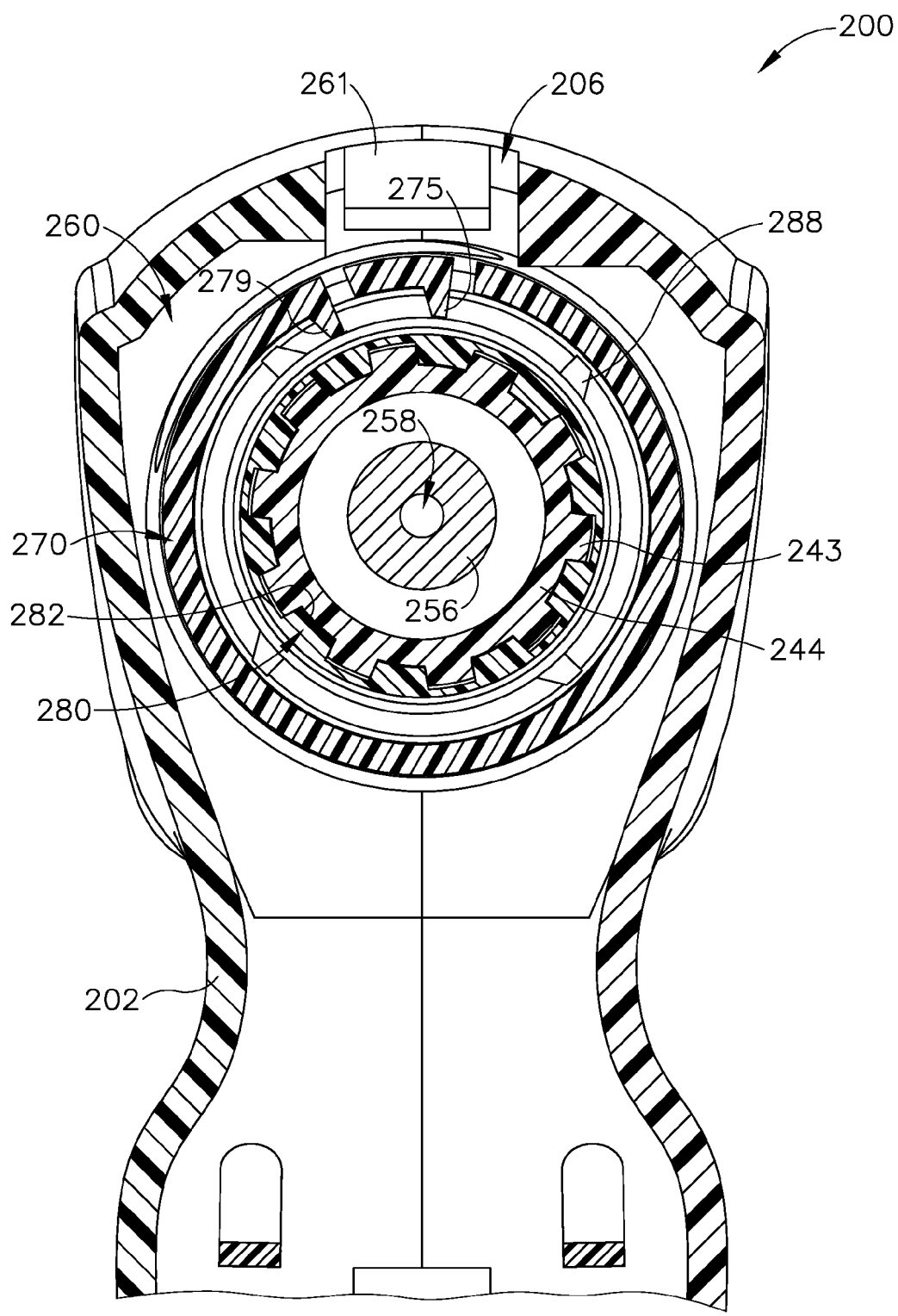
FIG. 62A depicts a cross-sectional view of the assembly of FIG. 60B, taken along line 62-62 of FIG. 60B, with the drive member of FIG. 57 in a first angular position.
Figure 62B:
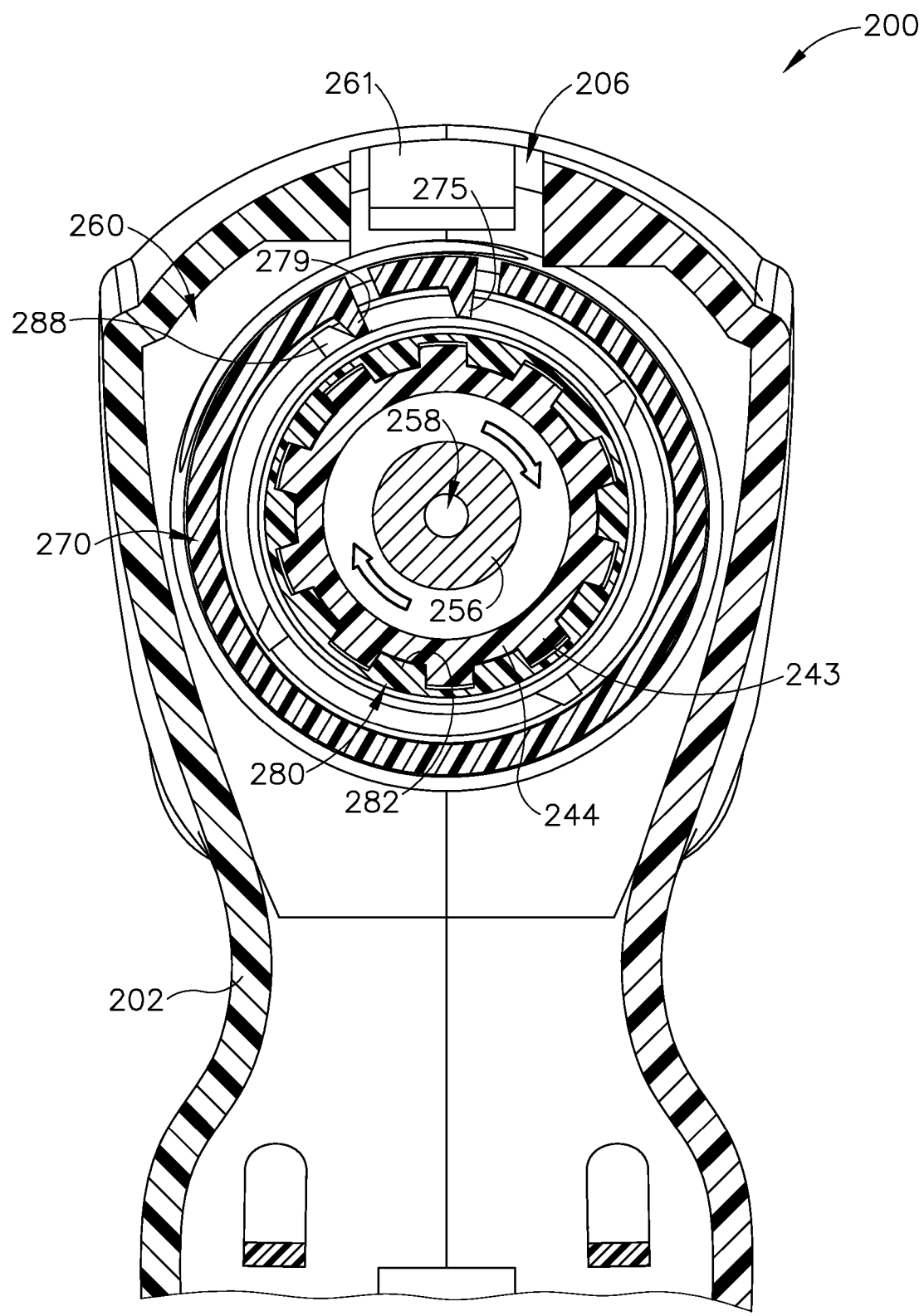
FIG. 62B depicts a cross-sectional view of the assembly of FIG. 60B, taken along line 62-62 of FIG. 60B, with the drive member of FIG. 57 in a second angular position.

FIGS. 62A-62F show key interactions that occur while shaft assembly (150) is being rotated relative to reusable assembly (200) to threadably drive stud (196) into recess (258). As noted above, transducer assembly (240) and drive member (280) are rotatable within housing (202) while pawl ring (270) is not rotatable within housing (202). As also noted above, transducer assembly (240) and pawl ring (270) are translatable within housing (202) while drive member (280) is not translatable within housing (202). FIG. 62A shows torque wrench assembly (260) in a state where no pawls (288) of drive member (280) are in contact with either pawl (275, 279) of pawl ring (270). Thus, as the operator rotates shaft assembly (150) through a first range of motion (e.g., while bearing proximally on disposable assembly (100)), friction may transfer such rotation to transducer assembly (240) and drive member (280). This may cause transducer assembly (240) and drive member (280) to rotate to the position shown in FIG. 62B. In this state, a pawl (288) of drive member (280) is in contact with pawl (279) of pawl ring (270). Pawls (288, 279) thereby cooperate to provide a rotational ground for transducer assembly (240) and drive member (280). In other words, transducer assembly (240) and drive member (280) are rotationally grounded relative to housing (202) at this stage. The rotational grounding of drive member (280) is provided to transducer assembly (240) due to the meshing of splines (243, 282).

As the operator continues to rotate shaft assembly (150) through a second range of motion while pawls (288, 279) cooperate to provide a rotational ground for drive member (280) and transducer assembly (240), stud (196) is threadably driven into recess (258). In particular, while waveguide (192) remains longitudinally stationary relative to housing (202), transducer assembly (240) advances distally within housing (202) to permit driving of stud (196) into recess (258). As noted above, coil spring (262) resiliently biases transducer assembly (240) distally to promote this distal advancement of transducer assembly (240) within housing (202). The configuration of splines (243, 282) further permits transducer assembly (240) to translate longitudinally relative to drive member (280) while maintaining the rotary coupling of transducer assembly (240) with drive member (280).

Figure 62C:
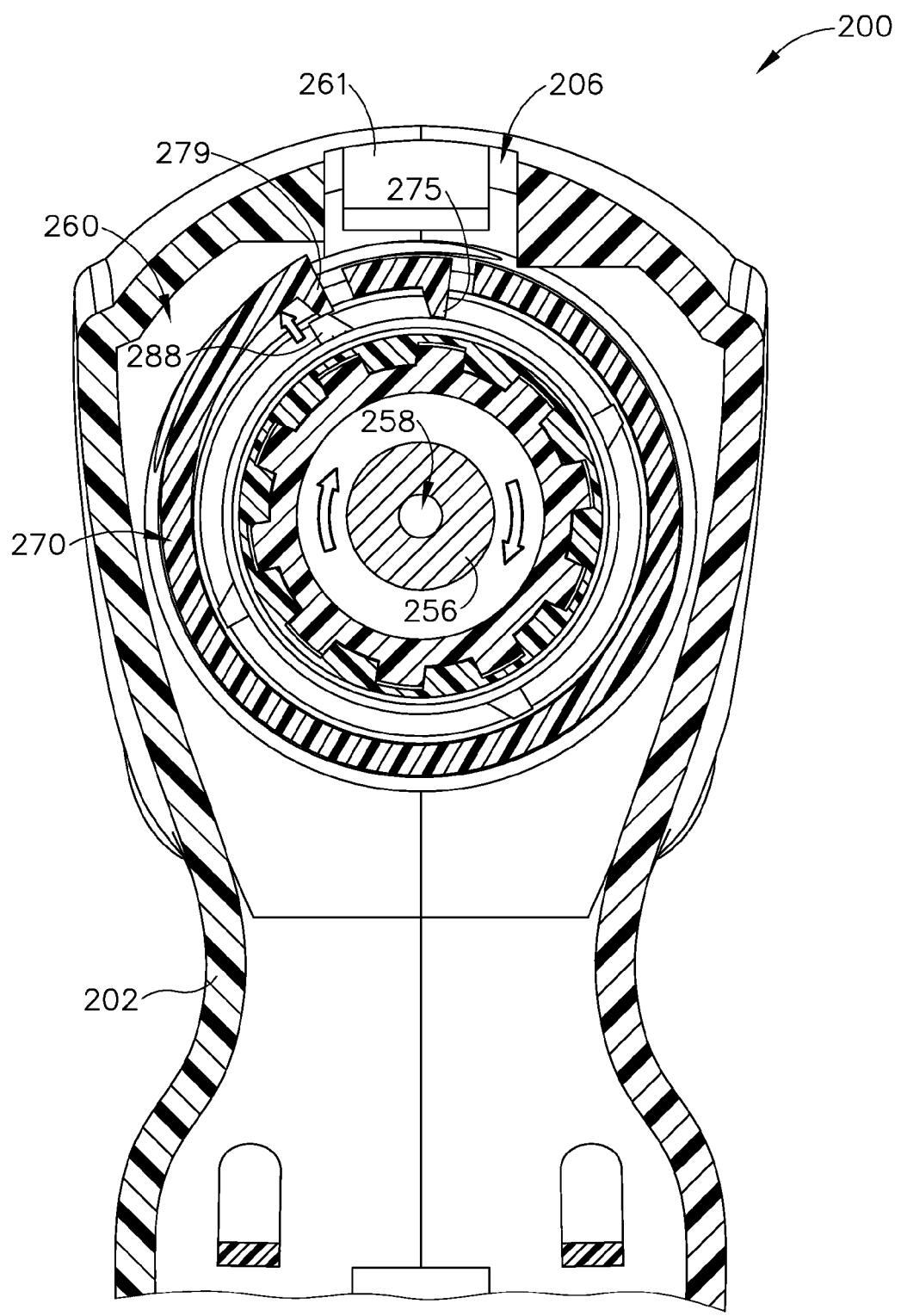
FIG. 62C depicts a cross-sectional view of the assembly of FIG. 60B, taken along line 62-62 of FIG. 60B, with the drive member of FIG. 57 in a third angular position.
Figure 62D:
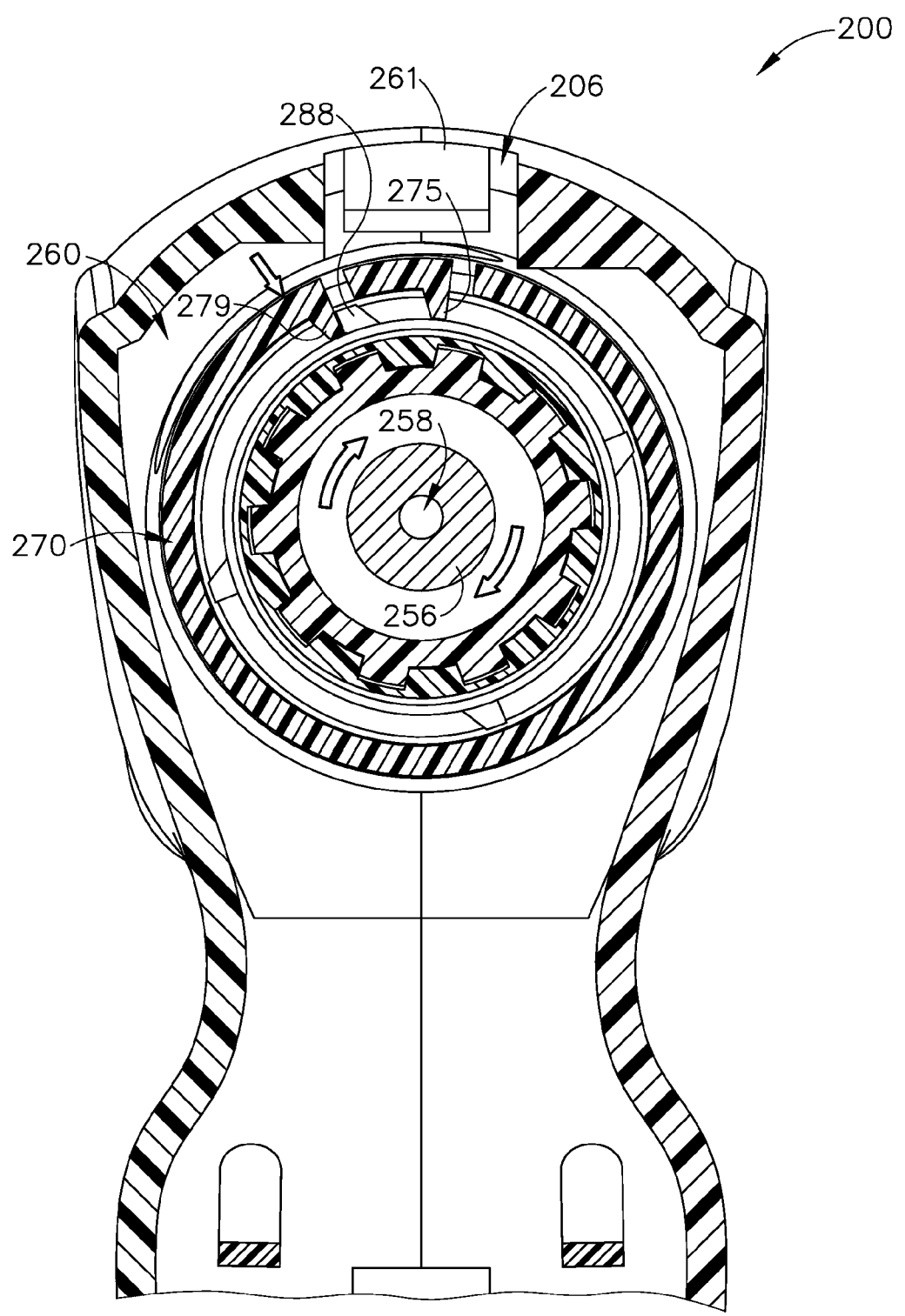
FIG. 62D depicts a cross-sectional view of the assembly of FIG. 60B, taken along line 62-62 of FIG. 60B, with the drive member of FIG. 57 in a fourth angular position.

Once stud (196) reaches a certain degree of insertion into recess (258), the fit between waveguide (192) and horn (256) begins to tighten, resulting in an increase in torque that is applied through the pawl (288) that is engaged with pawl (279). This eventually causes resilient arm (278) to deflect radially outwardly, as shown in FIG. 62C. Pawls (288, 279) include complementary cam surfaces that cooperate to provide such deflection of resilient arm (278) once the coupling between waveguide (192) and horn (256) reaches a certain torque level. As the operator continues to rotate shaft assembly (150), pawl (288) eventually clears pawl (279), at which point the resilience of arm (278) drives pawl (279) back radially inwardly as shown in FIG. 62D. This action of pawl (279) may create a snapping/clicking sound and/or a snapping/clicking tactile sensation that may be felt by the hand grasping reusable assembly (200) and/or the hand grasping knob (156). The operator is thus alerted that the coupling of waveguide (192) and horn (256) is close to reaching a desirable level of torque.

Figure 62E:
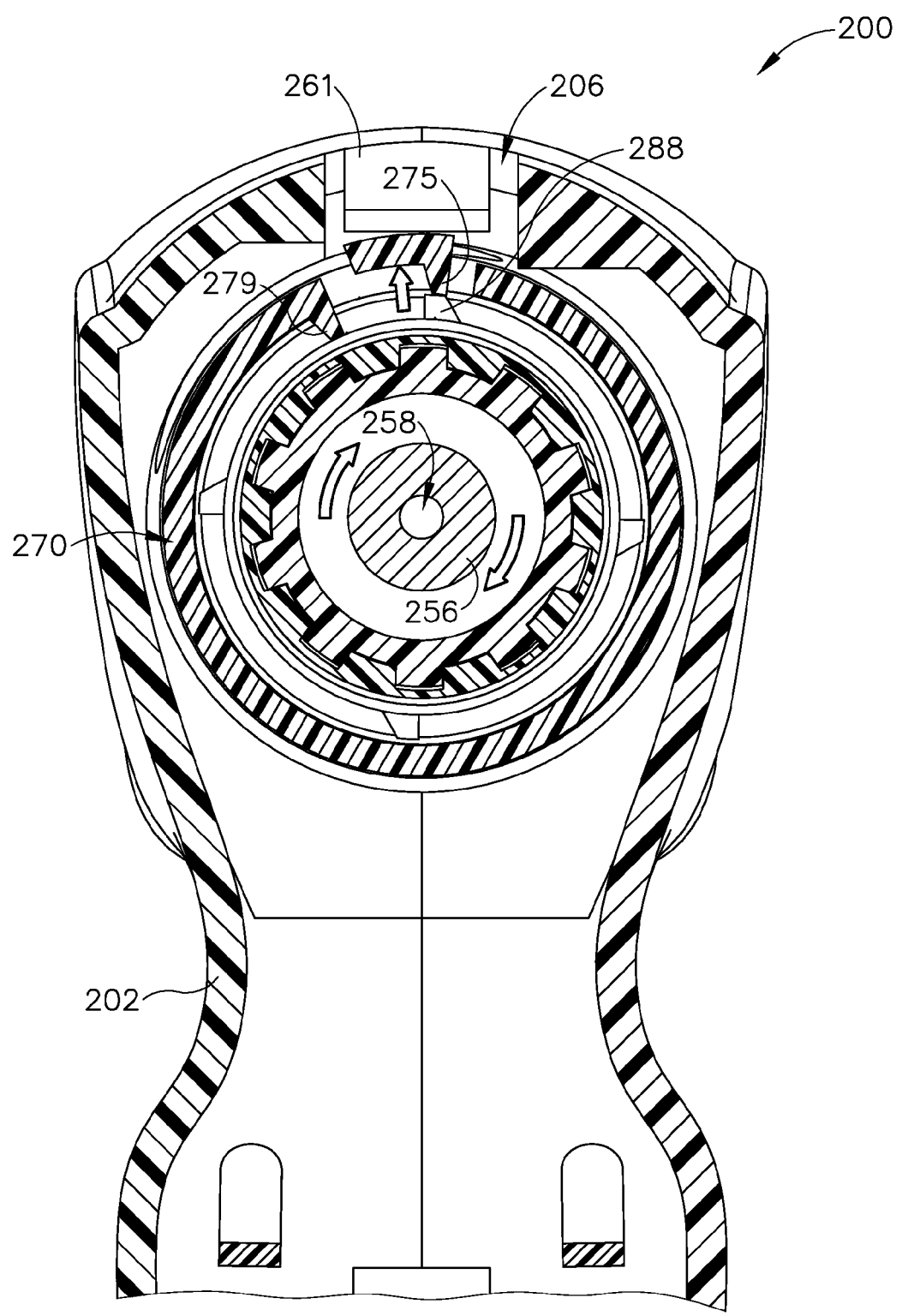
FIG. 62E depicts a cross-sectional view of the assembly of FIG. 60B, taken along line 62-62 of FIG. 60B, with the drive member of FIG. 57 in a fifth angular position.
Figure 62F:
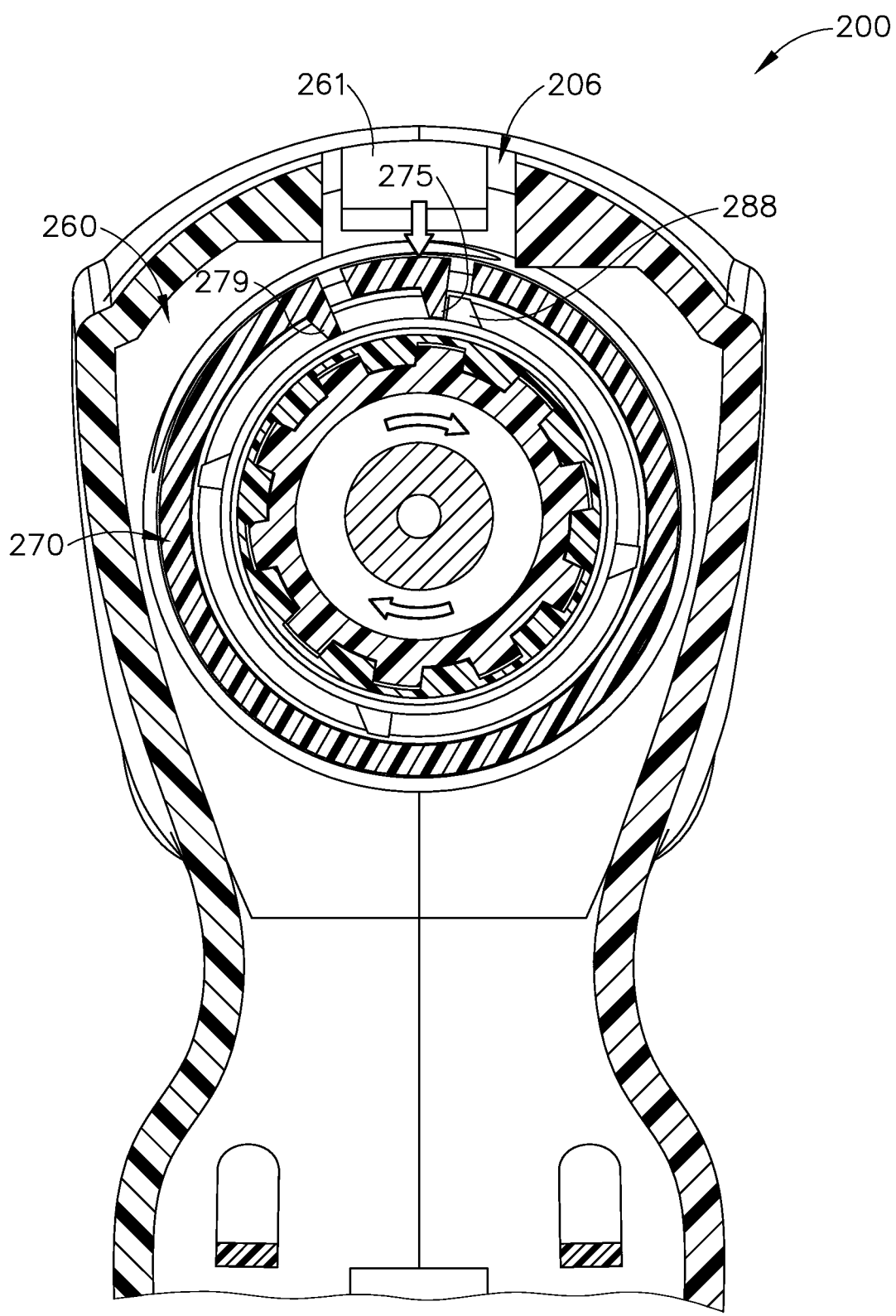
FIG. 62F depicts a cross-sectional view of the assembly of FIG. 60B, taken along line 62-62 of FIG. 60B, with the drive member of FIG. 57 in a sixth angular position.

As the operator continues to rotate shaft assembly (150), that same pawl (288) of drive member (280) encounters pawl (275) of pawl ring (270). Again through a camming action between pawls (288, 275), pawl (288) causes resilient arm (274) to deflect radially outwardly, as shown in FIG. 62E. As the operator continues to rotate shaft assembly (150), pawl (288) eventually clears pawl (275), at which point the resilience of arm (274) drives pawl (275) back radially inwardly as shown in FIG. 62F. This action of pawl (275) may create a snapping/clicking sound and/or a snapping/clicking tactile sensation that may be felt by the hand grasping reusable assembly (200) and/or the hand grasping knob (156). The operator is thus alerted that the coupling of waveguide (192) and horn (256) is has reached a desirable level of torque. In other words, the operator is alerted by a set of two snapping/clicking sounds and/or tactile sensations. Of course, torque wrench assembly (260) may alternatively be configured to provide any other suitable number of snapping/clicking sounds and/or tactile sensations to alert the operator that the coupling of waveguide (192) and horn (256) is has reached a desirable level of torque.

Figure 63:
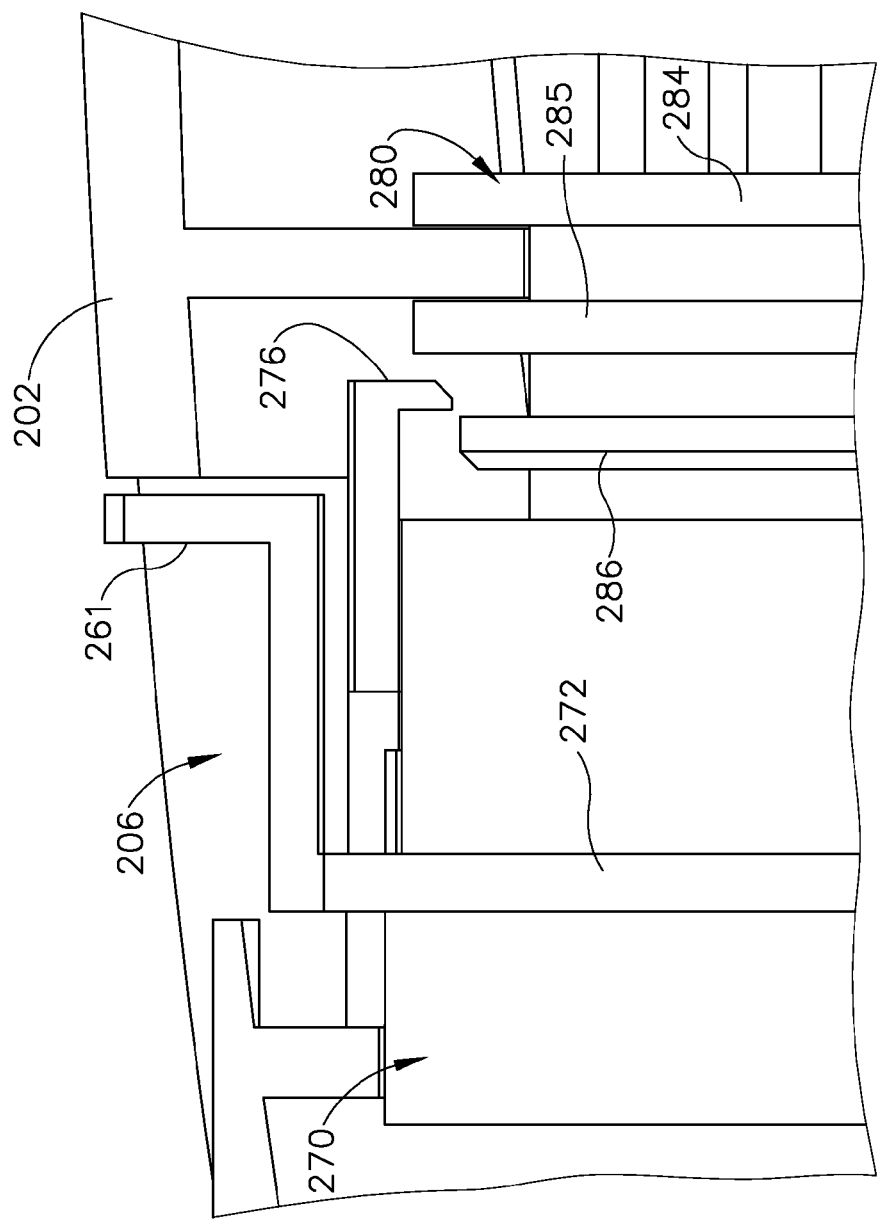
FIG. 63 depicts partial side elevational view of the pawl ring of FIG. 52 and the drive member of FIG. 57, with the drive member of FIG. 57 in the fifth angular position associated with FIG. 62E.

FIG. 63 shows another condition that occurs when the coupling process reaches the stage shown in FIG. 62E. As noted above, resilient arm (274) is deflected radially outwardly at this stage, due to a camming action between pawls (288, 275). As a result of this deflection, and as shown in FIG. 63, latch (276) of pawl ring (270) is positioned to clear latching flange (286) of drive member (280). With latch (276) disengaged from latching flange (286), coil spring (264) drives pawl ring (270) distally, to the position shown in FIGS. 60C and 61C. It should be understood that coil spring (264) is intentionally omitted from FIGS. 60C, 61C, and 63 for clarity. It should also be understood that, during the stages shown in FIGS. 60A-60B, 61A-61B, and 62A-62D, latch (276) and latching flange (286) cooperate to maintain the longitudinal position of pawl ring (270) in housing (202), despite the distal bias provided by coil spring (264).

Figure 61A:
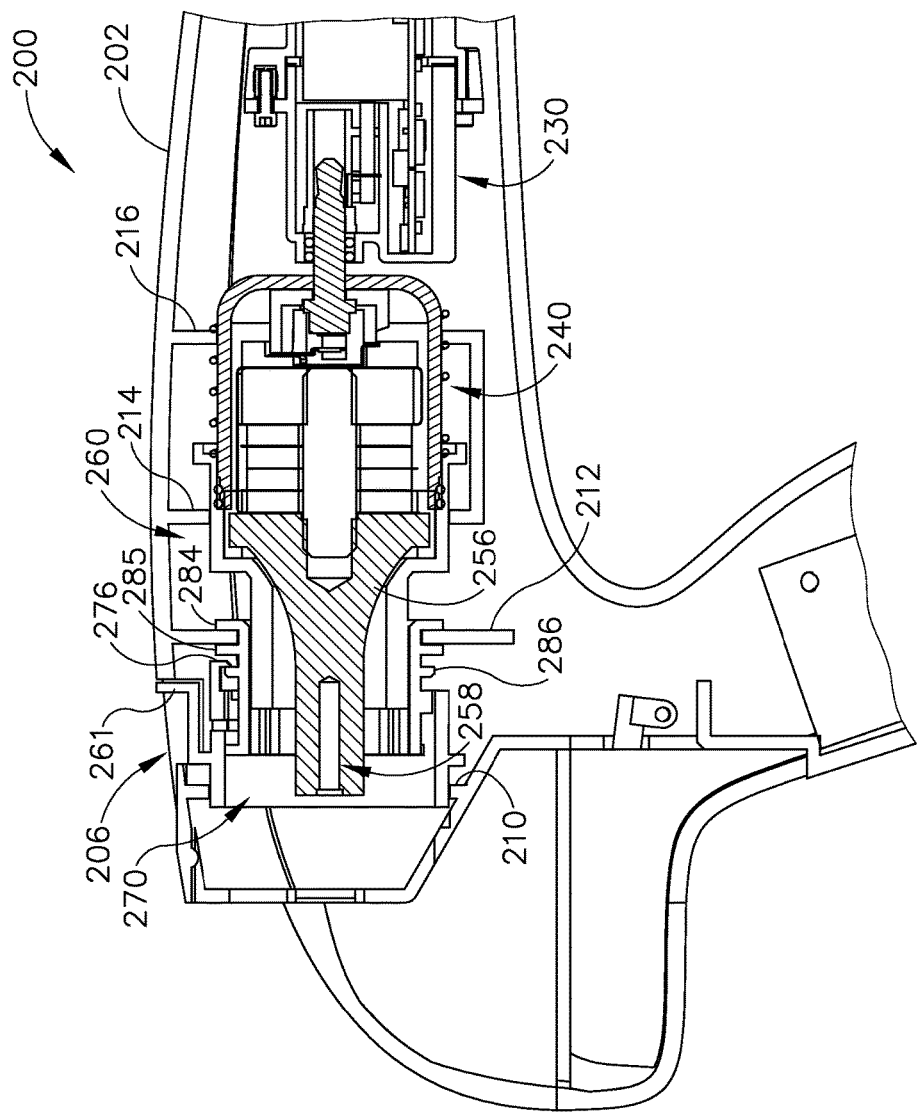
FIG. 61A depicts a partial, side cross-sectional view of the reusable portion of FIG. 45.
Figure 61B:
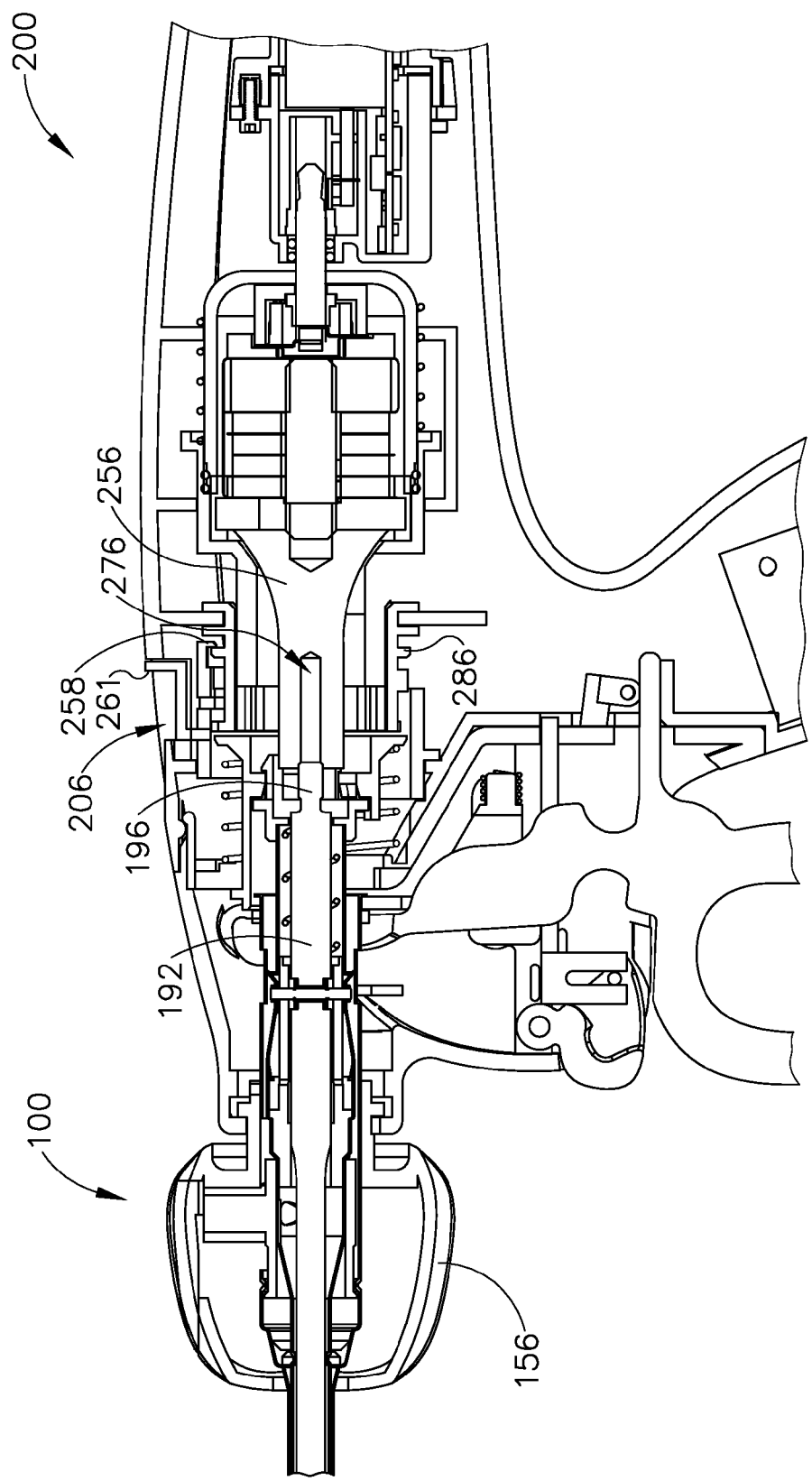
FIG. 61B depicts a partial, side cross-sectional view of the reusable portion of FIG. 45, with the disposable portion of FIG. 9 inserted into a recess of the reusable portion.
Figure 61C:
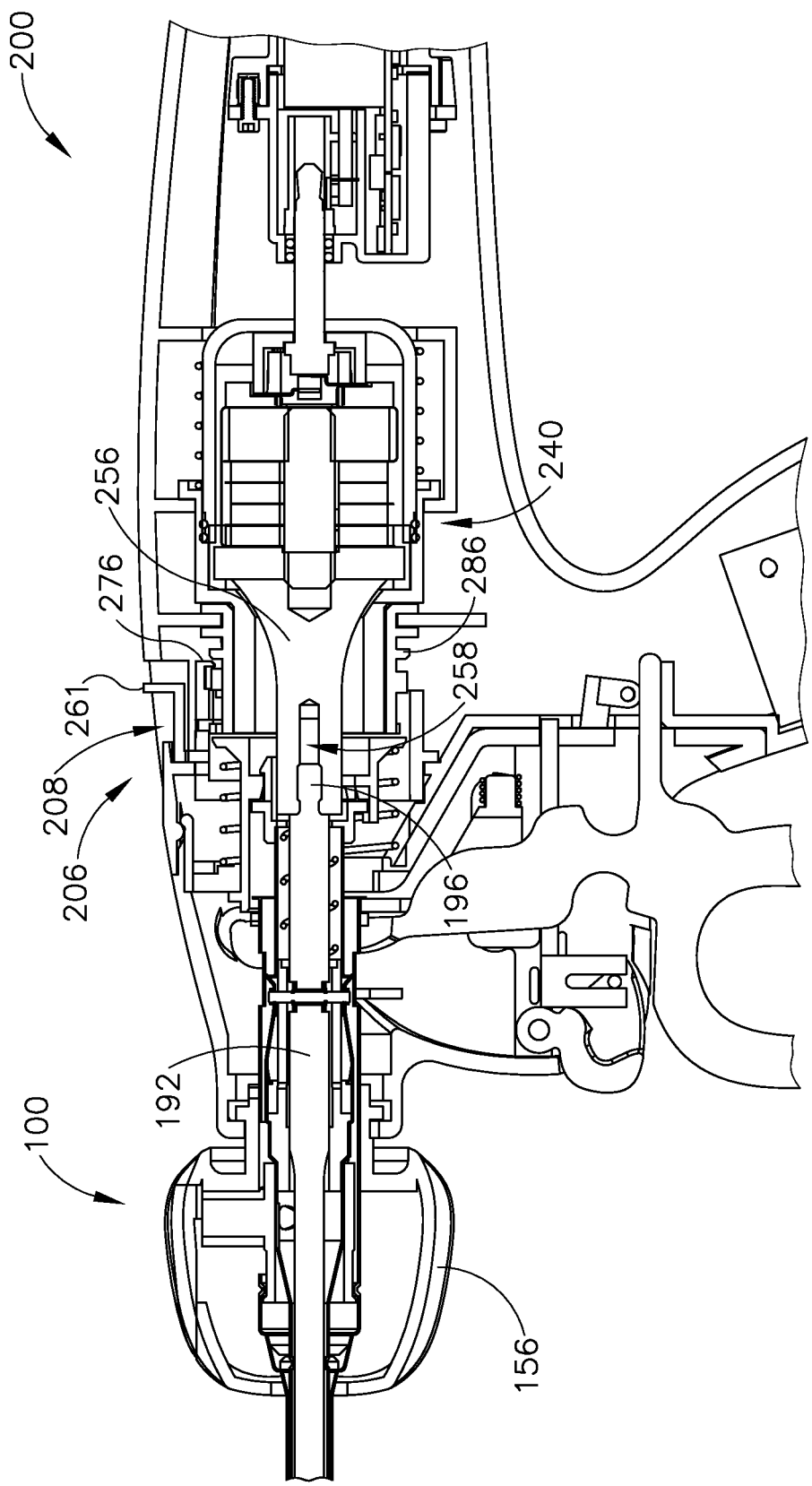
FIG. 61C depicts a partial, side cross-sectional view of the reusable portion of FIG. 45, with the disposable portion of FIG. 9 inserted into the recess of the reusable portion, and with the transducer assembly fully coupled with the waveguide.

When pawl ring (270) is in the distal position as shown in FIGS. 60C and 61C, tab (261) is also in a distal position within upper window (206). Thus, in addition to (or in lieu of) observing audible/tactile clicks/snaps, the operator may observe the longitudinal position of tab (261) in upper window (206) to determine whether waveguide (192) is coupled with horn (256) at a desired level of torque.

Also when pawl ring (270) is in the distal position as shown in FIGS. 60C and 61C, pawls (275, 279) extend along a longitudinal range that is distal to the longitudinal range along which pawls (288) extend. In other words, when the operator rotates shaft assembly (150) after reaching the stage shown in 60C and 61C, pawls (288) will not engage pawls (275, 279). The operator may thus freely use knob (156) to reorient end effector (180) about the longitudinal axis of shaft assembly (150) during a surgical procedure. It should be understood from the foregoing that the same knob (156) that is used to rotate shaft assembly (150) to reorient end effector (180) about the longitudinal axis of shaft assembly (150) may also be used to rotate shaft assembly (150) to threadably couple waveguide (192) with horn (256). It should also be understood from the foregoing that the rotational grounding required to provide threaded coupling of waveguide (192) with horn (256) is fully integrated and contained in housing (202) of reusable assembly (200). In other words, the operator does not need to grasp an otherwise rotatable feature and hold that feature stationary while rotating knob (156) to threadably couple waveguide (192) with horn (256).

Figure 64:
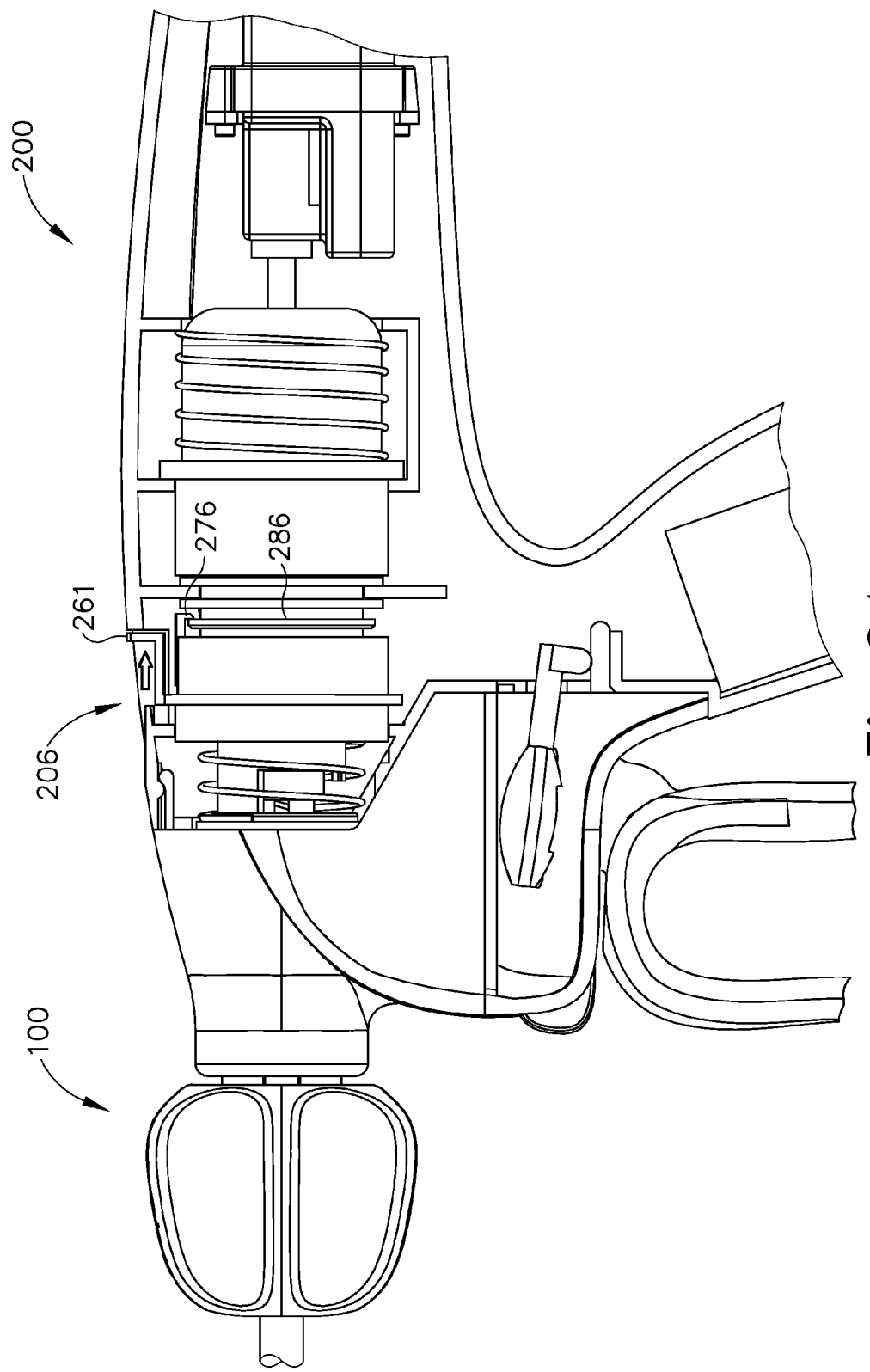
FIG. 64 depicts a partial, side elevational view of the reusable portion of FIG. 45, with a housing half removed, with the disposable portion of FIG. 9 inserted into a recess of the reusable portion, with the transducer assembly fully coupled with the waveguide; and with the pawl ring of FIG. 52 slid to a proximal position to enable decoupling of the waveguide from the transducer assembly.

After a surgical procedure is complete, or even during a surgical procedure (e.g., to clean one or more portions of shaft assembly (150) as described above, etc.), it may be desirable to remove disposable assembly (100) from reusable assembly (200). In order to accomplish this, the operator may slide tab (261) proximally in upper window (206), as shown in FIG. 64. Due to complementary cam features of latch (275) and latching flange (286), the resulting proximal movement of pawl ring (270) causes latch (275) to deflect outwardly and then snap back into place to re-engage flange (286). Pawl ring (270) is thereby retained in the proximal position. With pawl ring (270) back in this proximal position, pawls (288) are again longitudinally positioned to engage pawl (275). In particular, pawl (288) will eventually engage pawl (275) in a manner similar to that shown in FIG. 62F. Thus, when the operator rotates shaft assembly (150) counterclockwise relative to reusable assembly (200), pawl (275) will provide a rotational ground for transducer assembly (240). Moreover, resilient arm (274) will not deflect outwardly as the operator rotates shaft assembly (150) counterclockwise to unscrew stud (196) from recess (258). Once stud (196) is unscrewed from recess (258), the operator may pull disposable assembly (100) from reusable assembly (200). The same disposable assembly (100) or another disposable assembly (100) may then be re-coupled with reusable assembly (200), using the same process described above.

Figure 65:
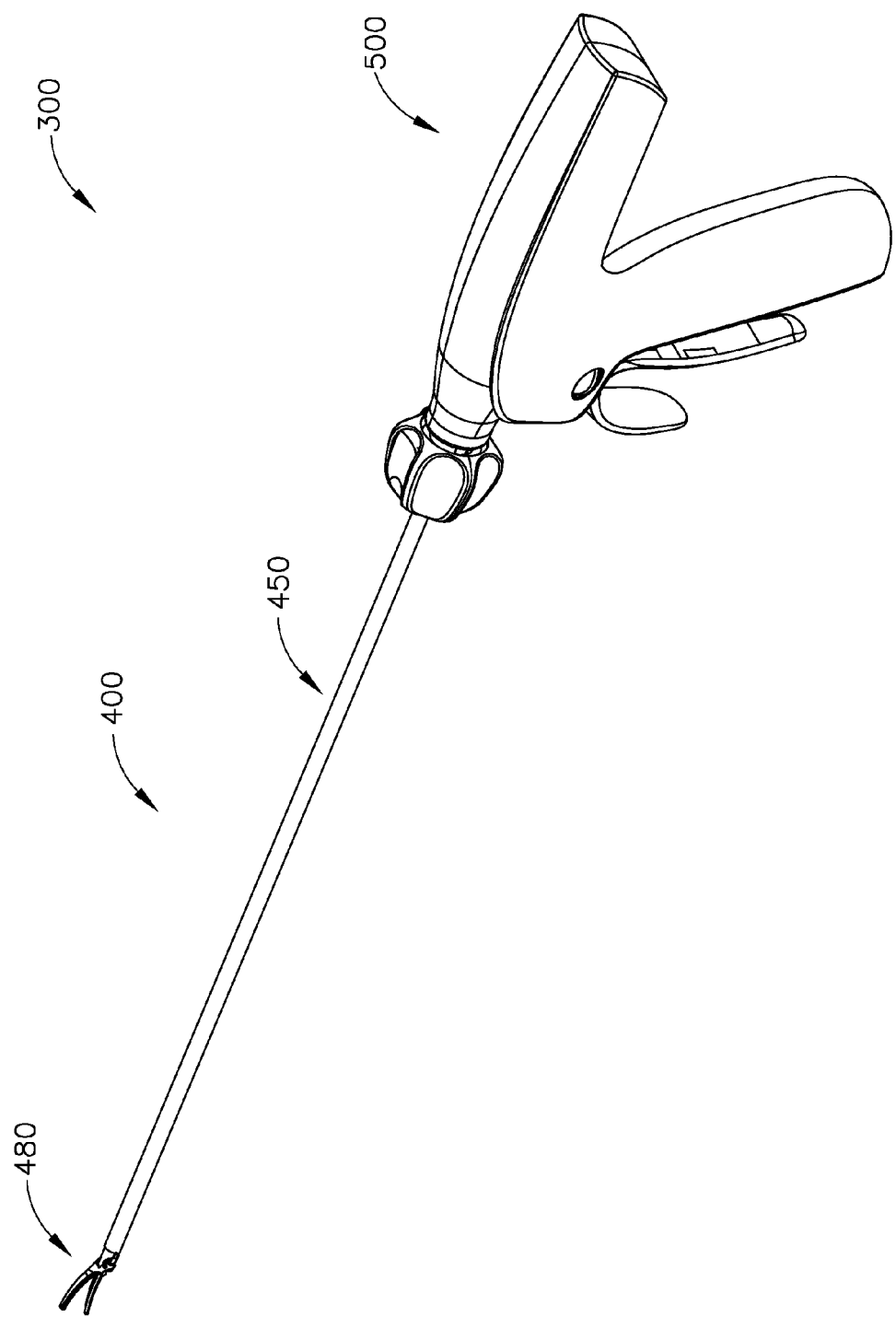
FIG. 65 depicts a perspective view of an exemplary alternative ultrasonic surgical instrument.
Figure 66:
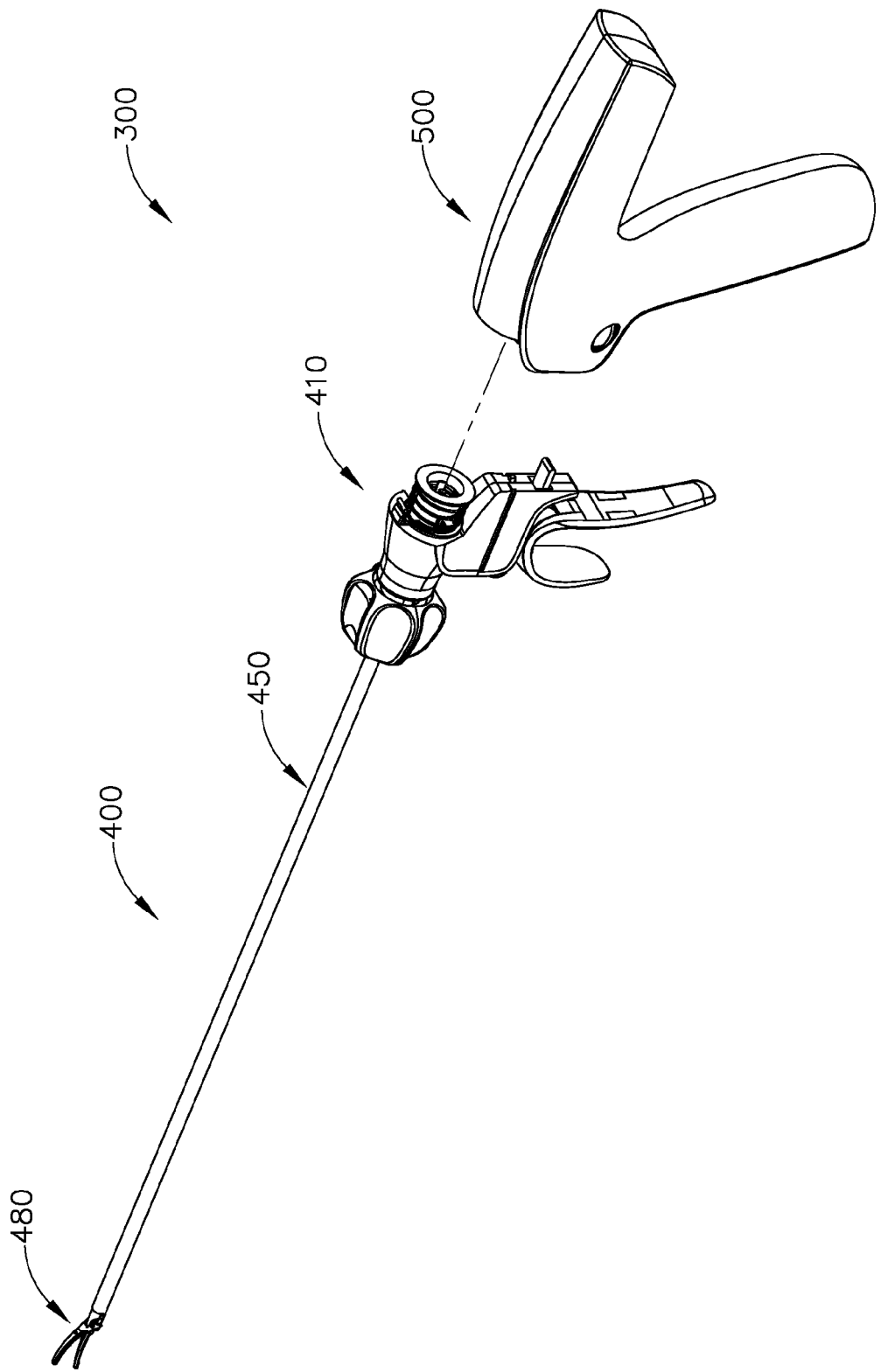
FIG. 66 depicts a perspective view of the instrument of FIG. 65, with a disposable portion separated from a reusable portion.
Figure 67:
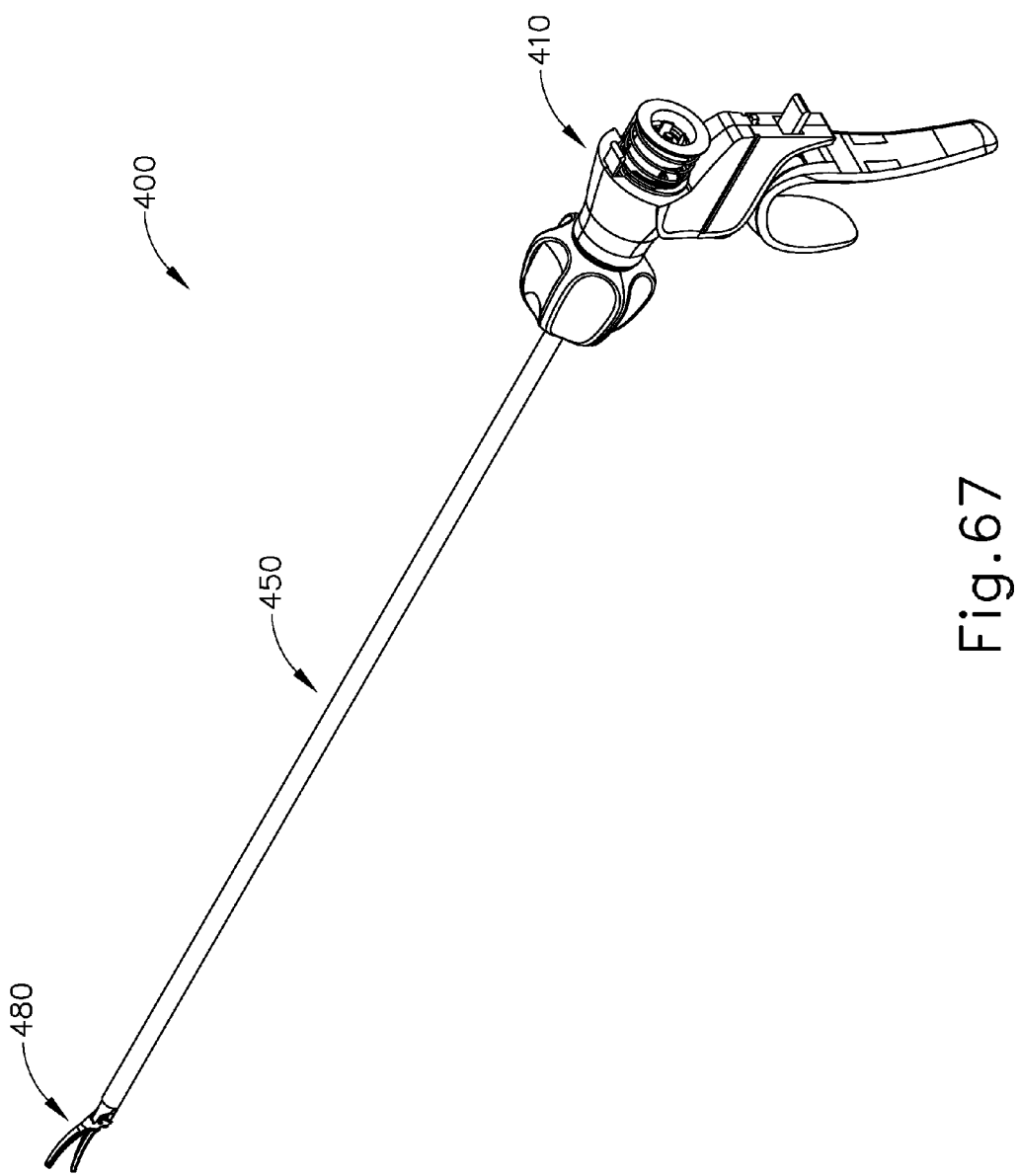
FIG. 67 depicts a perspective view of the disposable portion of the instrument of FIG. 65.

V. Exemplary Alternative Ultrasonic Surgical Instrument with Actuated Port Cover FIGS. 65-66 show an exemplary alternative ultrasonic surgical instrument (300). Instrument (300) of this example is substantially identical to instrument (10) described above, except as otherwise described below. For instance, like instrument (10) described above, instrument (300) of the present example comprises a disposable assembly (400) and a reusable assembly (500). The distal portion of reusable assembly (500) is configured to removably receive the proximal portion of disposable assembly (400), as seen in FIGS. 65-66, to form instrument (300). To the extent that the following discussion omits various details of instrument (300), it should be understood that instrument (300) may incorporate the various details described above with respect to instrument (10). Alternatively, other suitable details will be apparent to those of ordinary skill in the art in view of the teachings herein.

A. Disposable Assembly of Exemplary Alternative Ultrasonic Surgical Instrument

Figure 68:
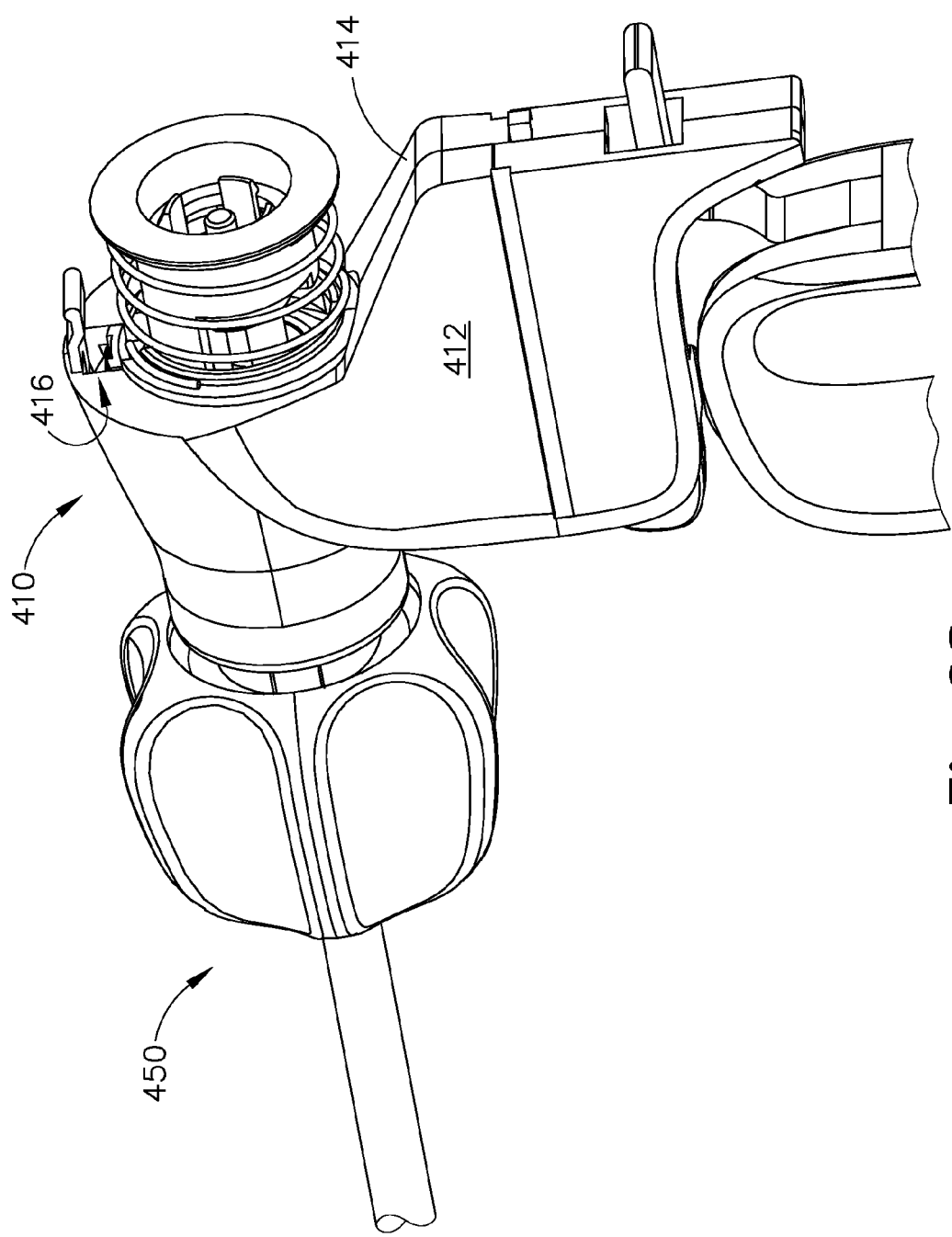
FIG. 68 depicts an enlarged perspective view of a proximal portion of the disposable portion of FIG. 67.
Figure 69:
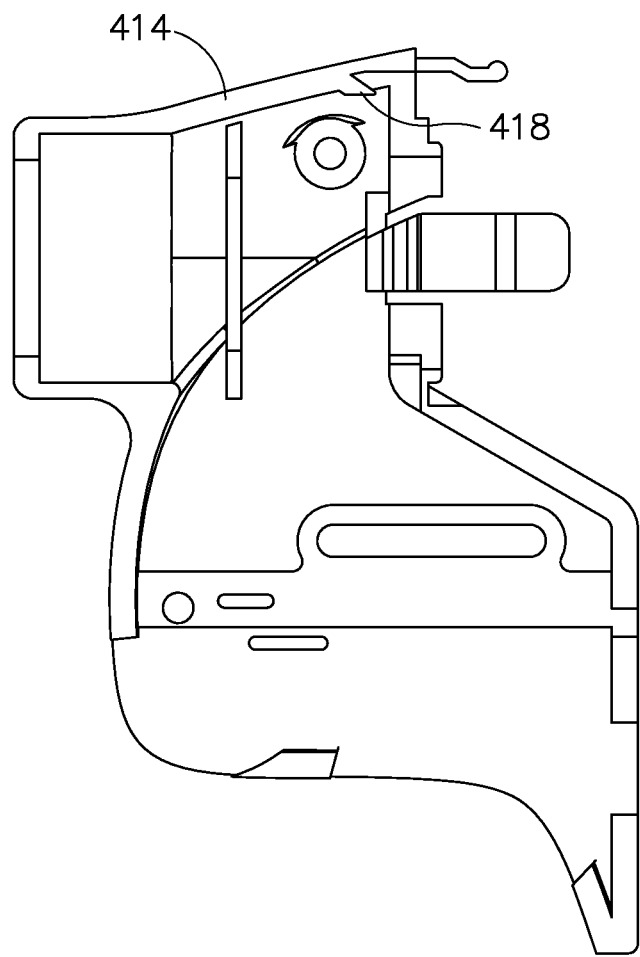
FIG. 69 depicts a side elevational view of a housing half of the disposable portion of FIG. 67.
Figure 70:
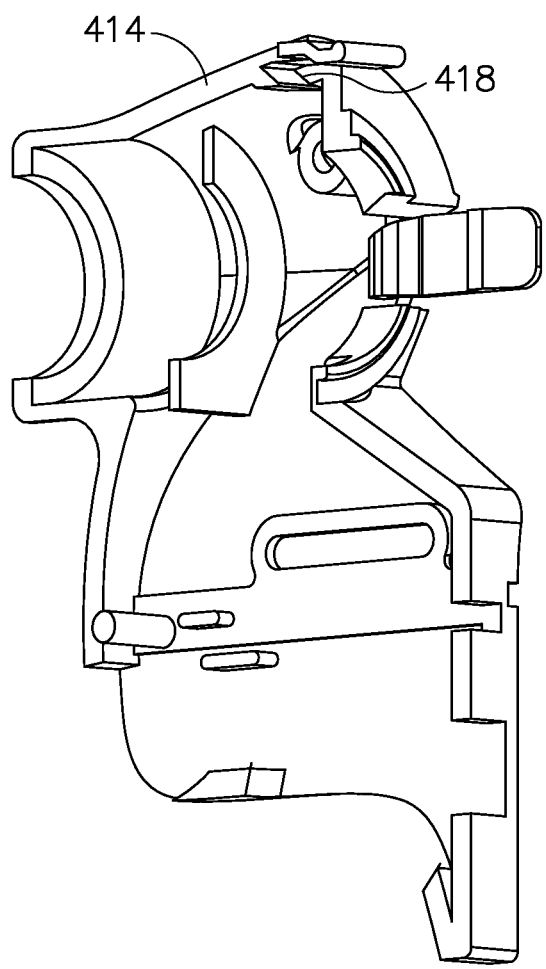
FIG. 70 depicts a perspective view of the housing half of FIG. 69.

FIGS. 67-73 show disposable assembly (400) in greater detail. Disposable assembly (400) of the present example comprises a body portion (410), a shaft assembly (450) extending distally from body portion (410), and an end effector (480) located at the distal end of shaft assembly (450). Body portion (410) comprises a pair of housing halves (412, 414). As best seen in FIG. 68, housing halves (412, 414) together define an upper opening (416), as will be described in greater detail below. As best seen in FIGS. 69-70, housing half (414) also defines a cam ramp (418). It should be understood that housing half (412) may also define a similar cam ramp to correspond with cam ramp (418) of housing half (414). Cam ramp (418) will be described in greater detail below.

Figure 71:
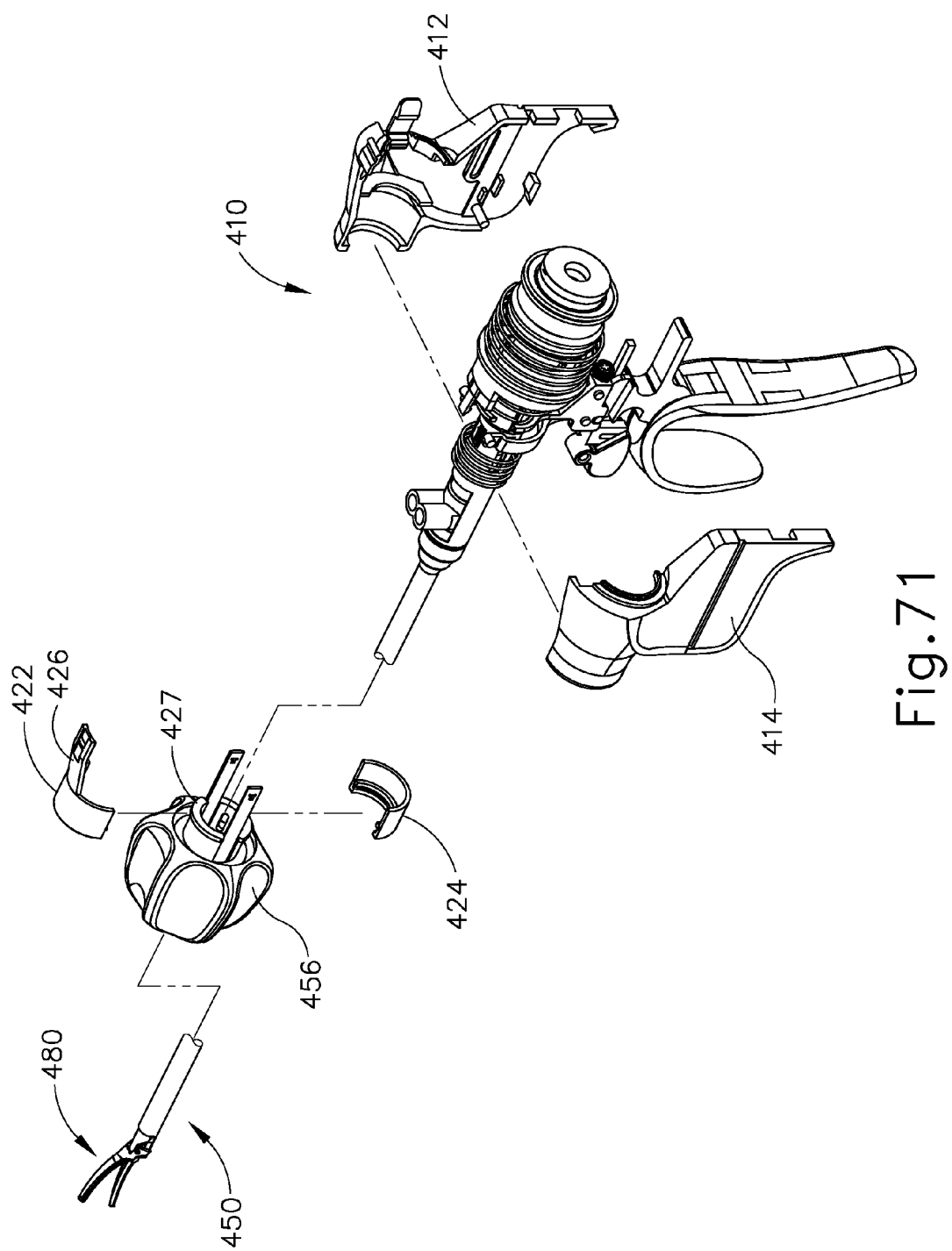
FIG. 71 depicts an exploded view of the disposable portion of FIG. 67.
Figure 72:
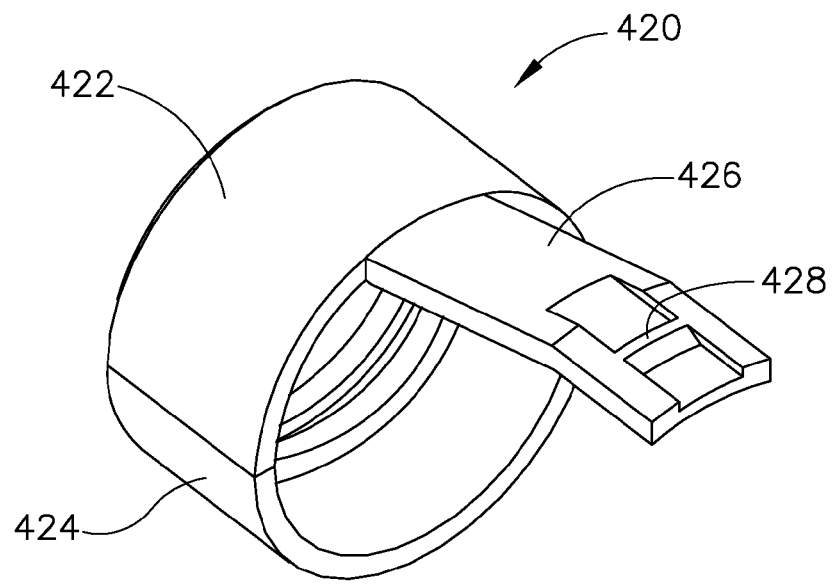
FIG. 72 depicts a perspective view of a selective coupling assembly of the disposable portion of FIG. 67.
Figure 73:
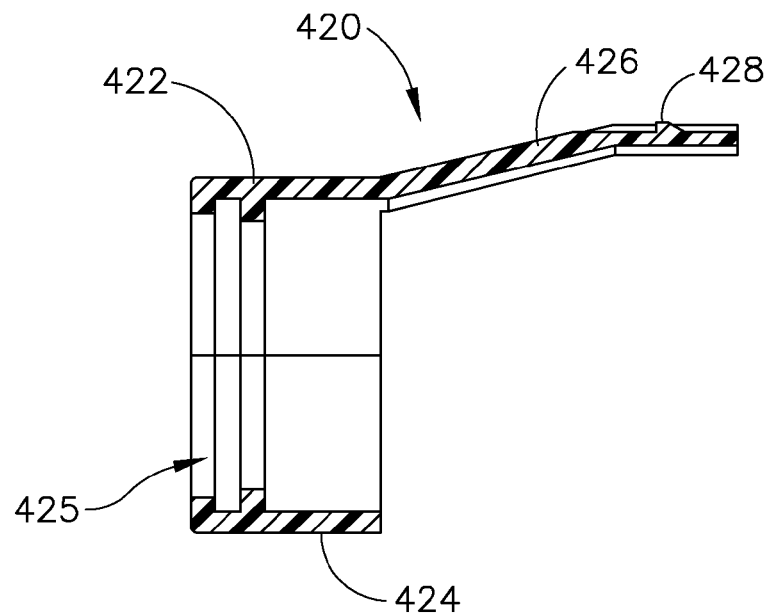
FIG. 73 depicts a side cross-sectional view of the selective coupling assembly of FIG. 72.
Figure 74:
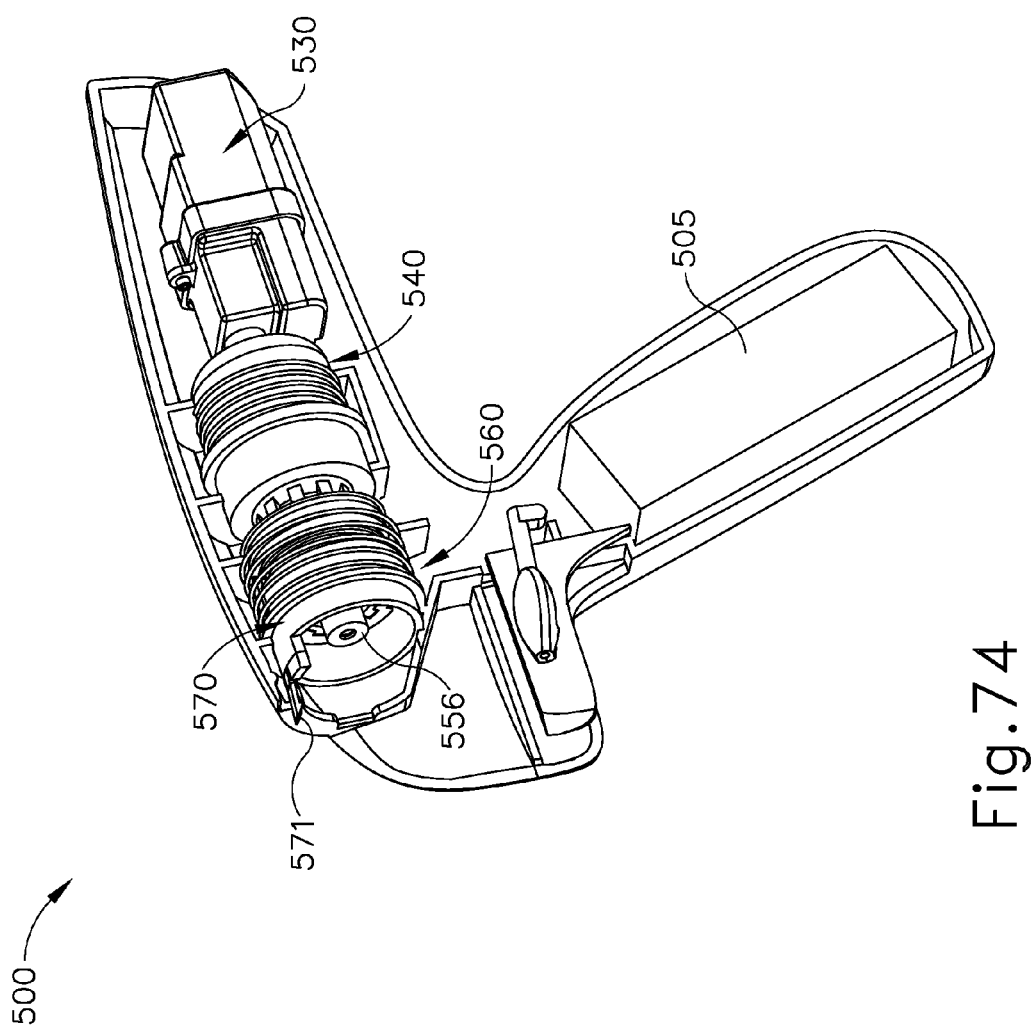
FIG. 74 depicts a perspective view of the reusable portion of the instrument of FIG. 65, with a housing half removed.
Figure 75:
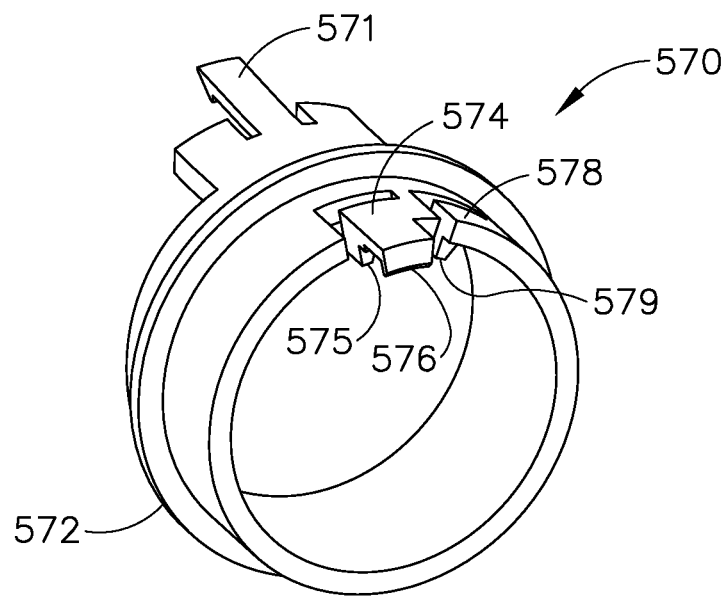
FIG. 75 depicts a perspective view of a pawl ring of the reusable portion of FIG. 74.
Figure 76:
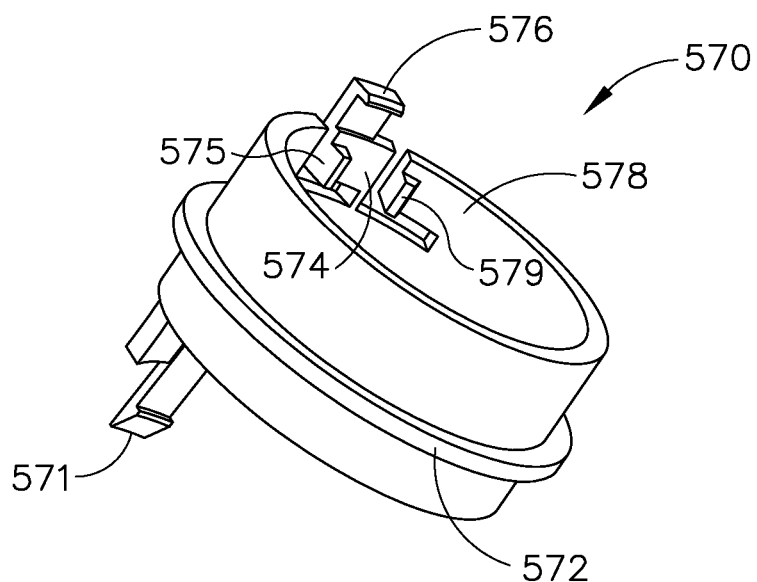
FIG. 76 depicts a perspective view of the pawl ring of FIG. 75.
Figure 77:
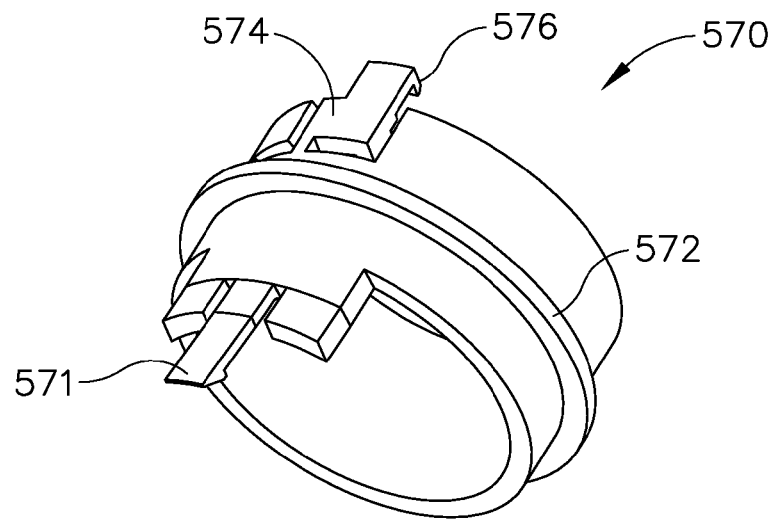
FIG. 77 depicts a perspective view of the pawl ring of FIG. 75.
Figure 78:
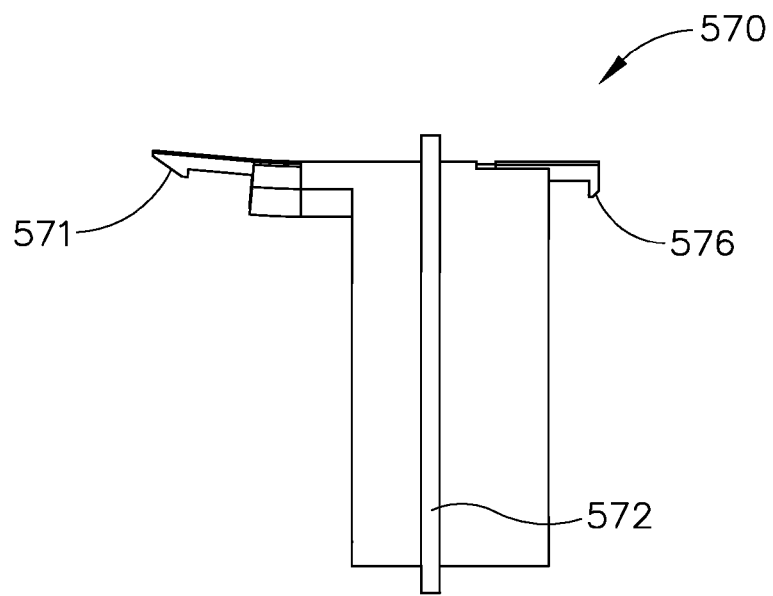
FIG. 78 depicts a side elevational view of the pawl ring of FIG. 75

FIGS. 71-73 show a coupling assembly (420) that is incorporated into shaft assembly (450) in the present example. Coupling assembly (420) includes an upper member (422) and a lower member (424). As best seen in FIG. 73, members (422, 424) together define an annular recess (425). Annular recess (425) is configured to receive a corresponding annular flange (427) of a knob (456) of shaft assembly (456). Thus, coupling assembly (420) translates unitarily with knob (456). However, knob (456) rotates freely relative to coupling assembly (420) in this example. Upper member (422) includes a proximally extending arm (426). Arm (426) has an integral latching feature (428), as will be described in greater detail below. Arm (426) is resiliently biased to assume the upward positioning shown in FIGS. 72-73. However, depending on the longitudinal position of coupling assembly (420) in body (410), cam ramp (418) may bear downwardly on arm (426) to deflect arm (426) downwardly from its natural position. Longitudinal movement of coupling assembly (420) in body (410) will be described in greater detail below.

The other components of disposable assembly (400) are substantially identical to corresponding components of disposable assembly (100) described above.

B. Reusable Assembly of Exemplary Alternative Ultrasonic Surgical Instrument

FIGS. 74-78 show reusable assembly (500) in greater detail. Reusable assembly (500) of this example comprises a battery (505), a generator (530), an ultrasonic transducer assembly (540), and a torque wrench assembly (560). Torque wrench assembly (560) is operable to couple a waveguide of shaft assembly (450) with an ultrasonic transducer horn (556) of transducer assembly (540). Torque wrench assembly (560) of the present example comprises a pawl ring (570), among other components. Those other components, including a drive member (580), are substantially identical to corresponding components of torque wrench assembly (260) described above.

FIGS. 75-78 show pawl ring (570) in greater detail. Pawl ring (570) of the present example comprises an annular flange (572), a first resilient arm (574) and a second resilient arm (578). Resilient arm (574) includes a pawl (575) and a latch (576). Pawl (575) is directed radially inwardly and extends longitudinally. Latch (576) is directed radially inwardly and extends transversely. Resilient arm (574) is resiliently biased to assume the position shown in FIGS. 75-78. However, resilient arm (574) is operable to flex outwardly as will be described in greater detail below. Second resilient arm (578) also includes a pawl (579), which is directed radially inwardly and extends longitudinally. Resilient arm (578) is resiliently biased to assume the position shown in FIGS. 75-78. However, resilient arm (578) is operable to flex outwardly as will be described in greater detail below. Pawl ring (570) also includes a distally projecting latch (571).

Figure 79A:
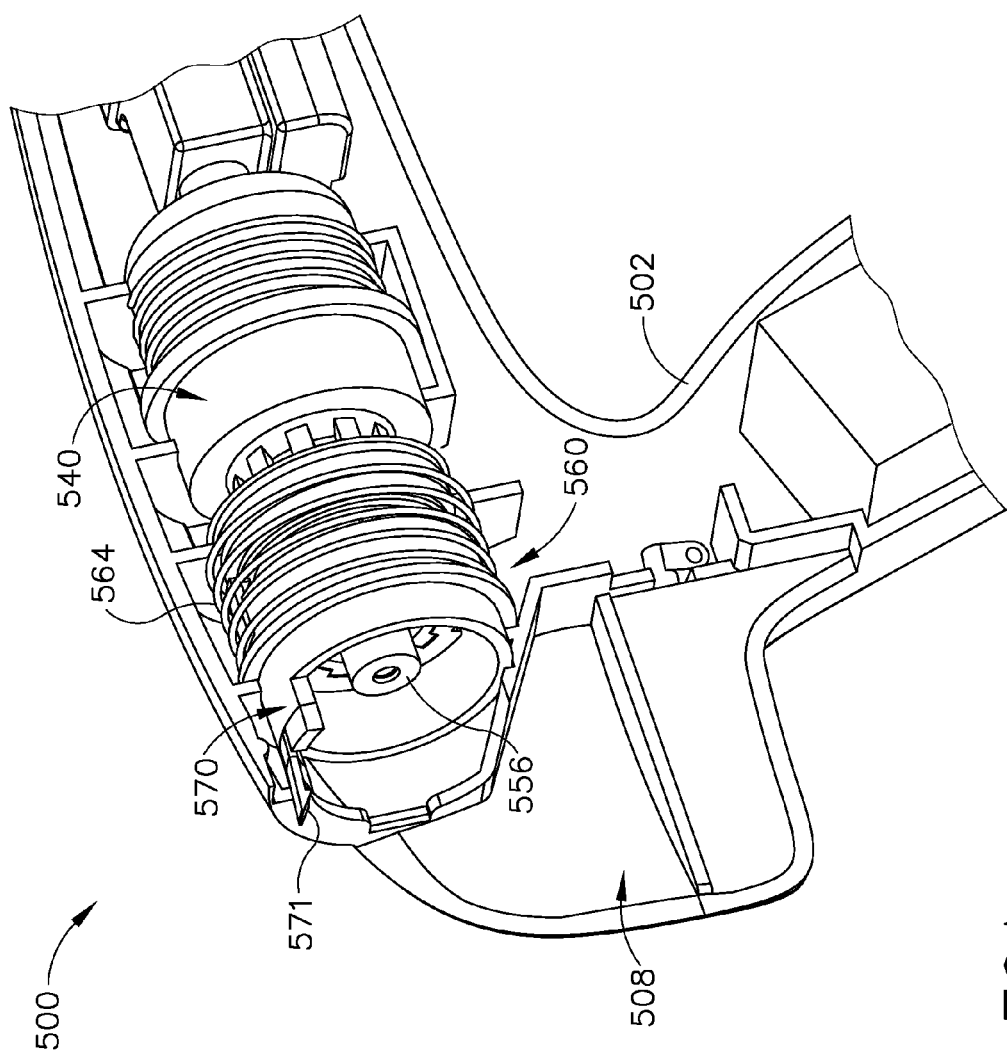
FIG. 79A depicts a partial perspective view of the reusable portion of FIG. 65, with a housing half removed.
Figure 79B:
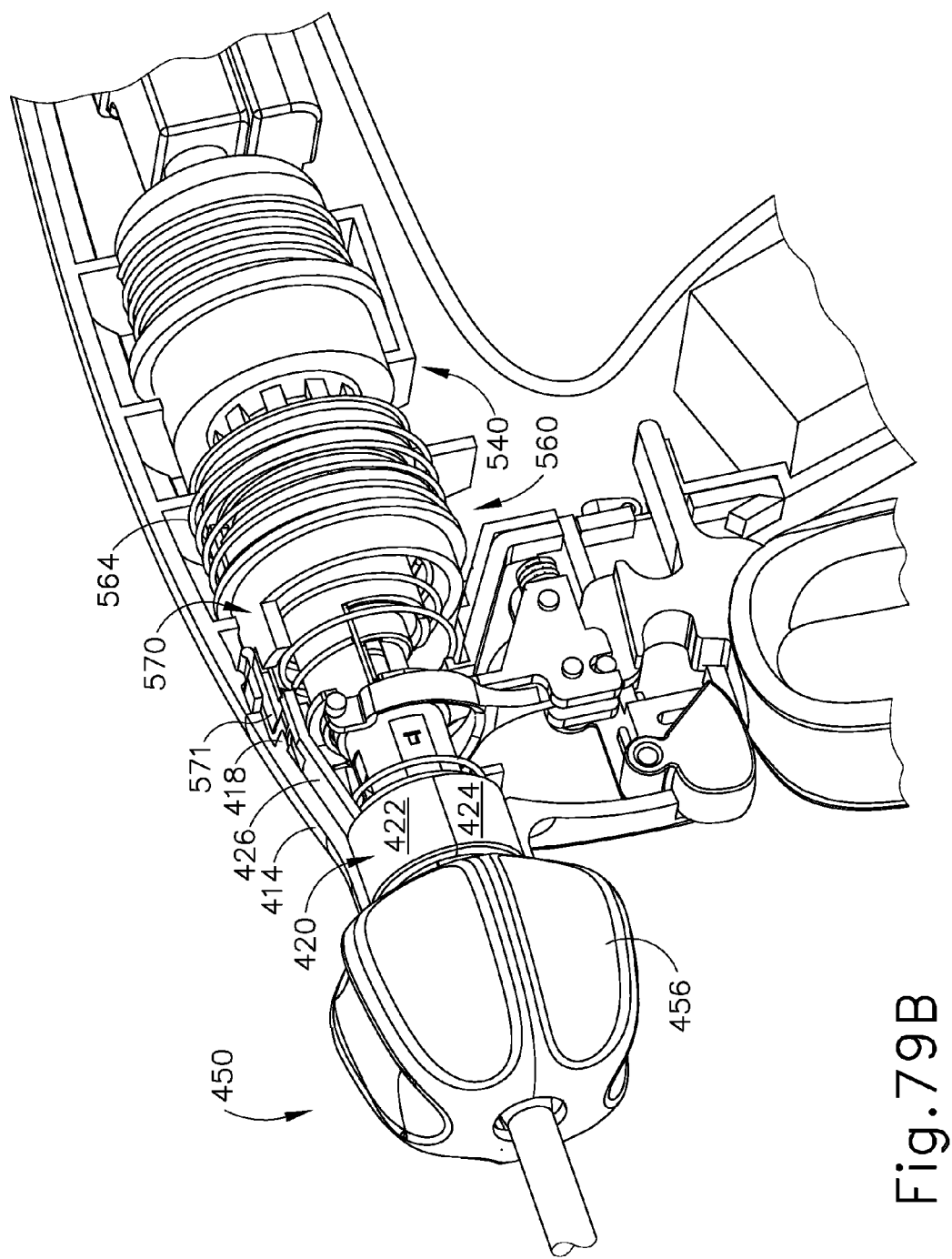
FIG. 79B depicts a partial perspective view of the reusable portion of FIG. 65, with a housing half removed, and with the disposable portion of FIG. 67 inserted into a recess of the reusable portion.

C. Coupling of Alternative Disposable Assembly with Alternative Reusable Assembly FIGS. 79A-80D show how torque wrench assembly (560) operates to mechanically and acoustically couple a waveguide of shaft assembly (450) with horn (556) in the present example. In particular, FIGS. 79A and 80A show reusable assembly (500) in a mode where reusable assembly (500) is ready to receive disposable assembly (400). In this mode, pawl ring (570) is positioned proximally in housing (502). When the operator wishes to couple disposable assembly (400) with reusable assembly (500), the operator first inserts the proximal end of body (410) into distal recess (508) of reusable assembly (500), as shown in FIGS. 79B and 80B. At this stage, a threaded stud of the waveguide of shaft assembly (450) is longitudinally aligned with a threaded recess of horn (556) and is in contact with the distal end of horn (556). As the operator inserts the proximal end of body (410) into distal recess (508) of reusable assembly (500), latch (571) of pawl ring (570) enters upper opening (416) of body (410).

Figure 79C:
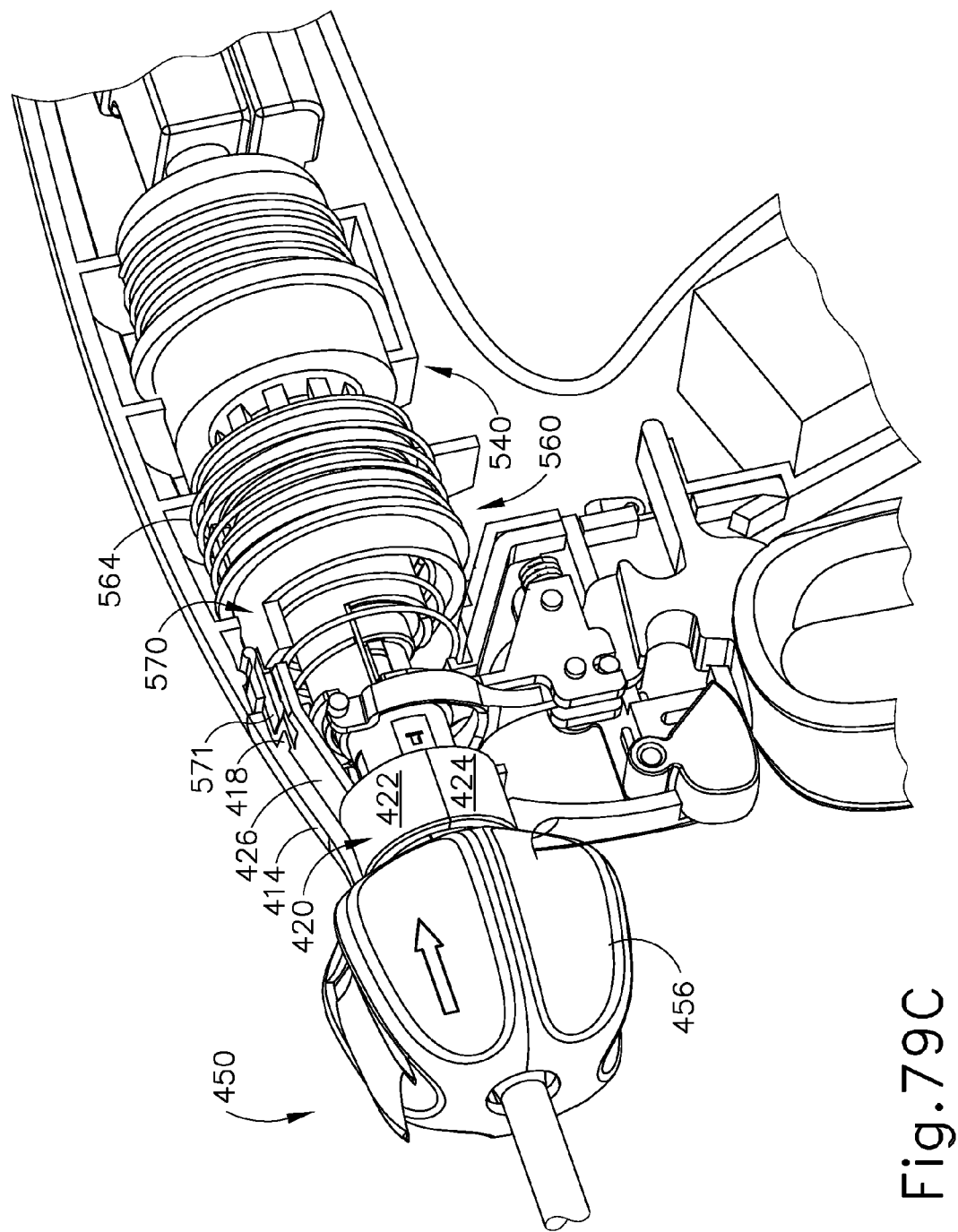
FIG. 79C depicts a partial perspective view of the reusable portion of FIG. 65, with a housing half removed, with the disposable portion of FIG. 67 inserted into the recess of the reusable portion, and with the selective coupling assembly of FIG. 72 slid to a proximal position to engage the pawl ring of FIG. 75.
Figure 79D:
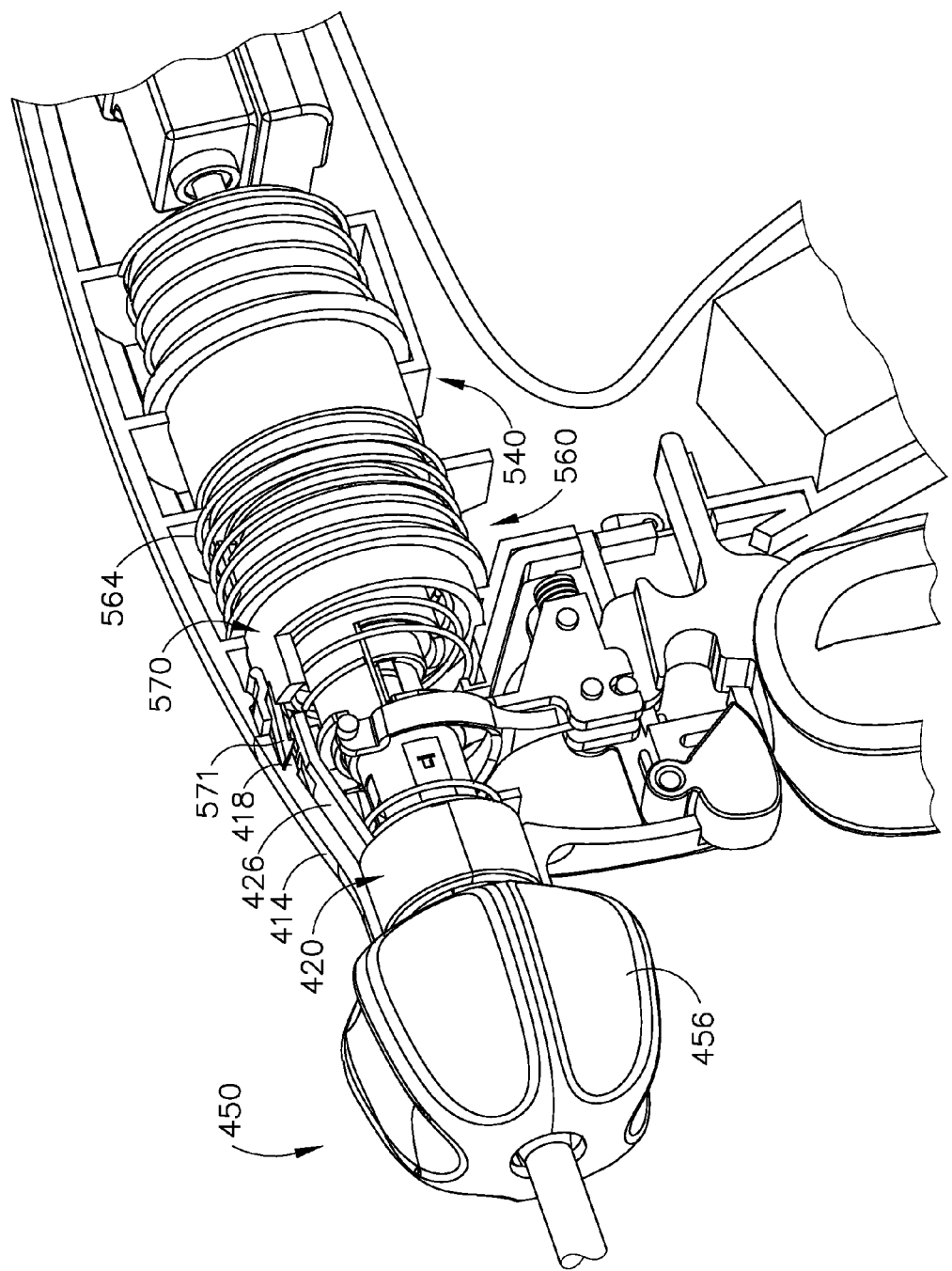
FIG. 79D depicts a partial perspective view of the reusable portion of FIG. 65, with a housing half removed, with the disposable portion of FIG. 67 inserted into the recess of the reusable portion, and with the transducer assembly fully coupled with the waveguide.
Figure 80C:
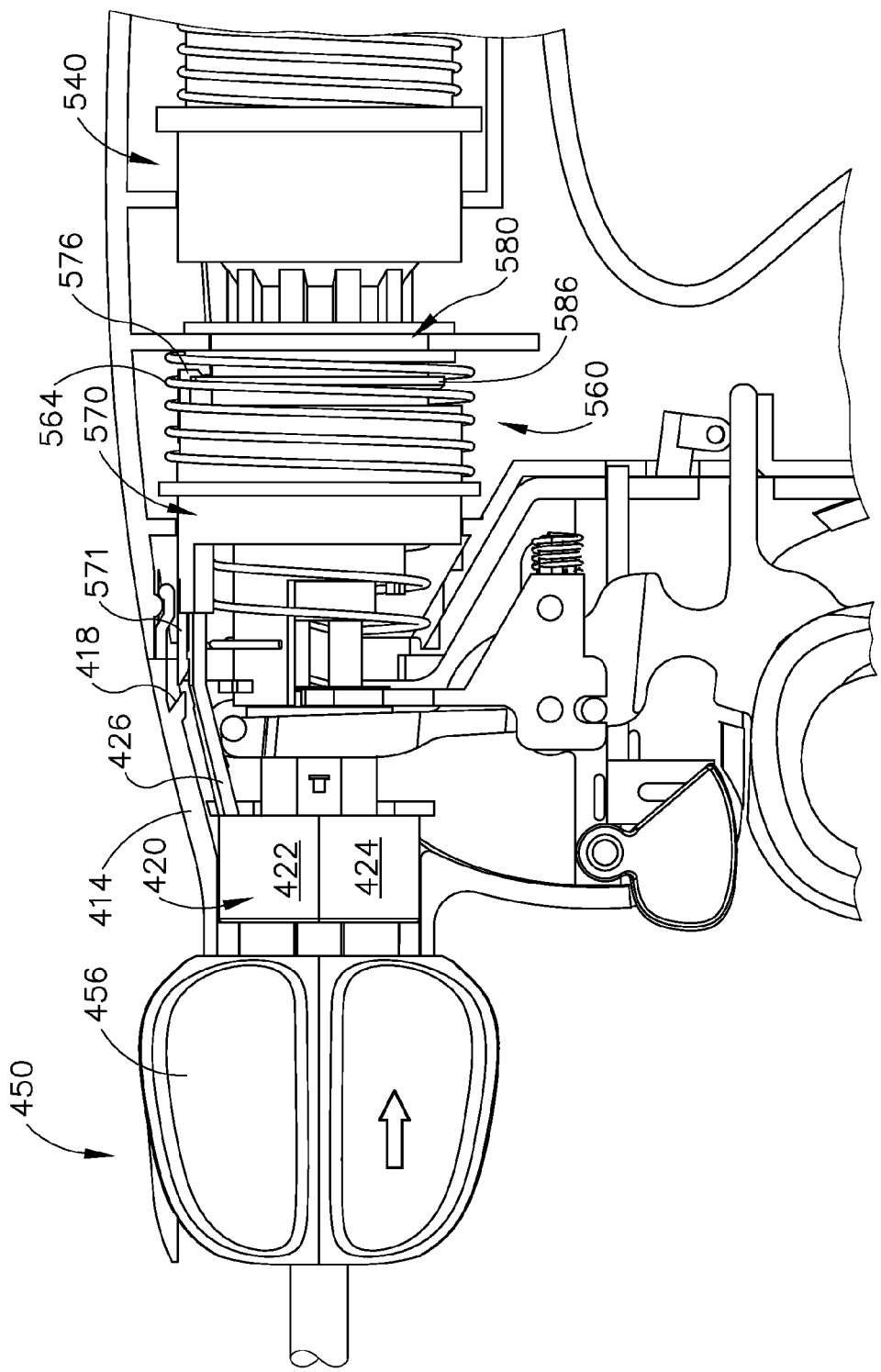
FIG. 80C depicts a partial, side elevational view of the reusable portion of FIG. 65, with a housing half removed, with the disposable portion of FIG. 67 inserted into the recess of the reusable portion, and with the selective coupling assembly of FIG. 72 slid to a proximal position to engage the pawl ring of FIG. 75.

The operator then pulls knob (456) proximally, as shown in FIGS. 79C and 80C. This drives knob (456) and coupling assembly (420) proximally relative to other components of shaft assembly (450). As a result of this proximal movement of coupling assembly (420), latching feature (428) of arm (426) engages latch (571) of pawl ring (570). The upward bias of arm (426) maintains engagement between latching feature (428) and latch (571) when knob (456) and coupling assembly (420) are in the proximal position relative to housing (502). Thereafter, in order to threadably couple the waveguide with horn (556), the operator grasps reusable assembly (500) with one hand and knob (456) with the other hand, then rotates knob (456) relative to reusable assembly (500) to rotate shaft assembly (450) relative to reusable assembly (500), about the longitudinal axis of shaft assembly (550). As described above with respect to torque wrench assembly (260), torque wrench assembly (560) of this example provides a rotational ground for transducer assembly (540) as shaft assembly (450) is rotated. During this process, a pawl of drive member (580) eventually engages pawl (579) of pawl ring (570), then pawl (575) of pawl ring (570), to provide the two snaps/clicks associated with a proper level of torque between the waveguide and horn (556). This interaction may be substantially identical to that described above with reference to FIGS. 62A-F. It should therefore be understood that latch (576) of pawl ring (570) will eventually be driven out of engagement with latch flange (586) of drive member (580). When latch (576) has disengaged latch flange (586), a coil spring (564) will drive pawl ring (570) distally in housing (502), as shown in FIGS. 79D and 80D.

Figure 80D:
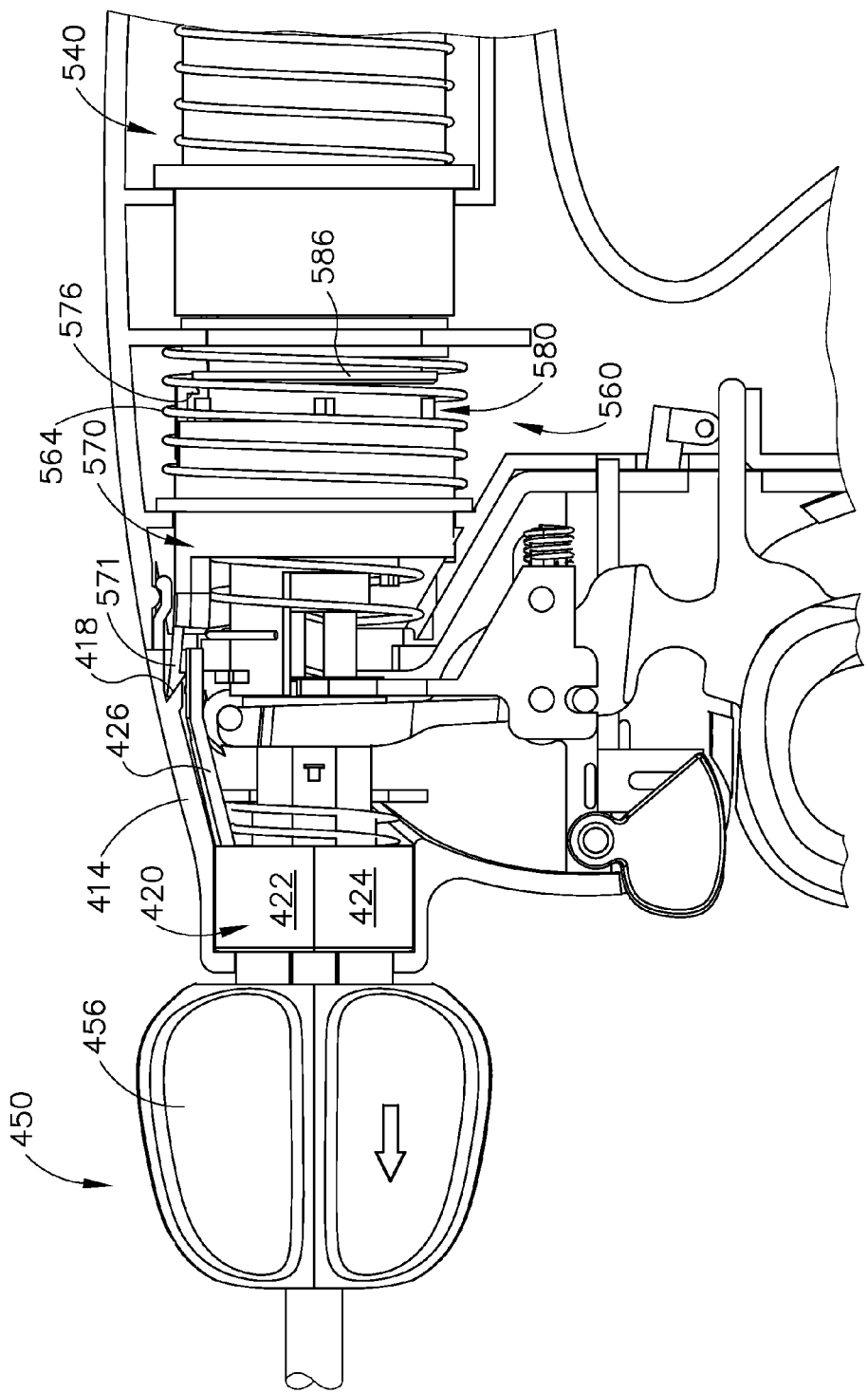
FIG. 80D depicts a partial, side elevational view of the reusable portion of FIG. 65, with a housing half removed, with the disposable portion of FIG. 67 inserted into the recess of the reusable portion, and with the transducer assembly fully coupled with the waveguide.

With pawl ring (570) in the distal position as shown in FIGS. 79D and 80D, pawls (575, 579) are longitudinally positioned such that they will not engage pawls of drive member (580). The combination of shaft assembly (450) and transducer assembly (540) is thus free to rotate as a unit relative to housing (502). As can also be seen in FIGS. 79A and 80D, when pawl ring (570) travels distally, latch (571) engages cam ramp (418) and is urged upwardly. In particular, cam ramp (418) disengages latch (571) from latching feature (428) of arm (426). This enables knob (450) to be advanced distally relative to housing (502), without also advancing pawl ring (570) distally any further. It should be understood that instrument (300) is ready for use in a surgical procedure after reaching the stage shown in FIGS. 79D and 80D. The operator may thus freely use knob (456) to reorient end effector (480) about the longitudinal axis of shaft assembly (450) during a surgical procedure.

It should be understood from the foregoing that the same knob (456) that is used to rotate shaft assembly (450) to reorient end effector (480) about the longitudinal axis of shaft assembly (450) may also be used to rotate shaft assembly (450) to threadably couple the waveguide with horn (556). It should also be understood from the foregoing that the rotational grounding required to provide threaded coupling of the waveguide with horn (556) is fully integrated and contained in housing (502) of reusable assembly (500). In other words, the operator does not need to grasp an otherwise rotatable feature and hold that feature stationary while rotating knob (456) to threadably couple the waveguide with horn (556).

After a surgical procedure is complete, or even during a surgical procedure (e.g., to clean one or more portions of shaft assembly (450) as described above, etc.), it may be desirable to remove disposable assembly (400) from reusable assembly (500). In order to accomplish this, the operator may slide knob (456) proximally again relative to housing (502). Sliding knob (456) proximally relative to housing (502) causes coupling assembly (420) to slide proximally relative to housing (502). As coupling assembly (420) slides proximally relative to housing (502), arm (426) engages pawl ring (570) and drives pawl ring proximally relative to housing (502). Due to complementary cam features of latch (576) and latching flange (586), the proximal movement of pawl ring (570) causes latch (576) to deflect outwardly and then snap back into place to re-engage flange (586). Pawl ring (570) is thereby retained in the proximal position. With pawl ring (570) back in this proximal position, the pawls of drive member (280) are again longitudinally positioned to engage pawl (575). In particular, a pawl of drive member (280) will eventually engage pawl (575) in a manner similar to that shown in FIG. 62F. Thus, when the operator rotates shaft assembly (450) counterclockwise relative to reusable assembly (500), pawl (575) will provide a rotational ground for transducer assembly (540). Moreover, resilient arm (574) will not deflect outwardly as the operator rotates shaft assembly (450) counterclockwise to unscrew the waveguide from horn (556). Once the waveguide is unscrewed from horn (556), the operator may pull disposable assembly (400) from reusable assembly (500). The same disposable assembly (400) or another disposable assembly (400) may then be re-coupled with reusable assembly (500), using the same process described above.

VI. Exemplary Disposable Assembly with Usage Indicator

In some instances, it may be desirable to provide some form of visual indication that shows whether and/or how many times a disposable assembly (100, 400) has been used. Such indication may be observed by the operator to determine that the disposable assembly (100, 400) should no longer be used, such that the disposable assembly (100, 400) should be replaced. By way of example only, a usage indicator may be configured to indicate the number of uses that have occurred, the number of uses remaining, and/or the end of the life of the disposable assembly (100, 400). A usage indicator may be temporary or permanent.

Figure 81:
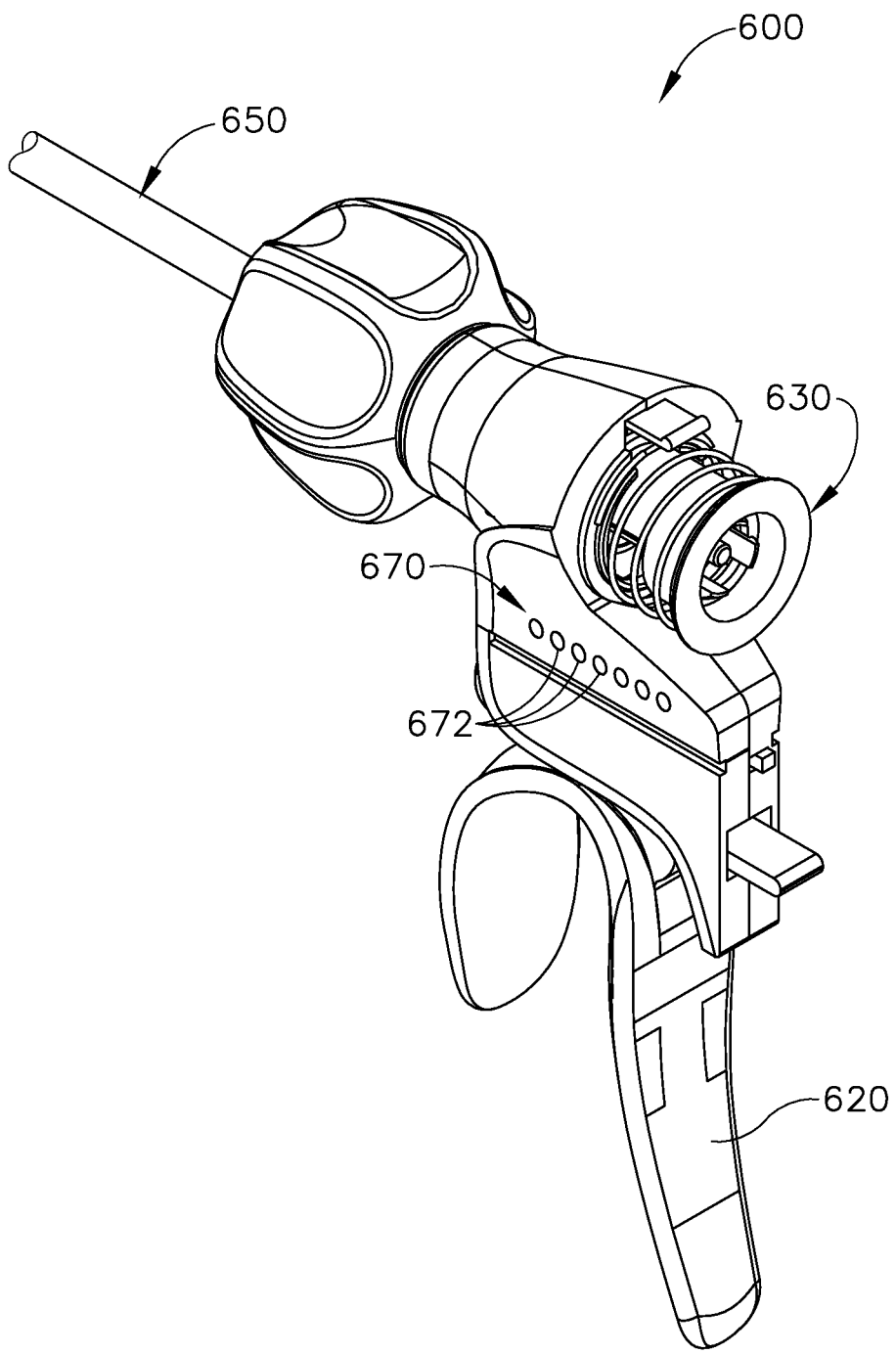
FIG. 81 depicts a perspective view of the proximal end of an exemplary alternative disposable portion of the instrument of FIG. 1.

FIG. 81 shows an exemplary alternative disposable assembly (600) that may readily incorporated into instrument (10) in place of disposable assembly (100). Disposable assembly (600) of this example is substantially identical to disposable assembly (100) described above. For instance, disposable assembly (600) includes a pivotable trigger (620), a mode selection knob (630), and a shaft assembly (650), which are identical to trigger (120), mode selection knob (130), and shaft assembly (150), respectively. However, unlike disposable assembly (100), disposable assembly (600) of this example further includes a usage indicator (670). Usage indicator (670) of this example comprises a linearly arranged array of discrete visual indicators (672). By way of example only, usage indicator (670) may be configured such that the first visual indicator (672) activates the first time disposable assembly (600) is used, the second visual indicator (672) activates the second time disposable assembly (600) is used, and so on. The non-activated visual indicators (672) thus indicate the remaining number of uses available. When all visual indicators (672) are activated, this will indicate that disposable assembly (600) has reached the end of its life, such that disposable assembly (600) should be disposed of (and replaced with a new disposable assembly (600), if the operator wishes to continue using instrument (10)).

Visual indicators (672) may be energized by a battery (e.g., coin cell or button cell, etc.) located in disposable assembly (600), an energized capacitor located in disposable assembly (600), an electrical connector between disposable assembly (600) and reusable assembly (200, 500), and/or using any other suitable power source in any other suitable location. In versions where an electrical connector is provided between disposable assembly (600) and reusable assembly (200, 500), the electrical connector may transmit voltage and current from reusable assembly (200, 500) to disposable assembly (600) while the instrument is assembled, based on meeting the appropriate usage criteria. Visual indicators (672) may be located on a surface that is only visible when disposable assembly (600) is removed from reusable assembly (200, 500), as noted below. Various suitable electrical components that may be incorporated into usage indicator (670) in order to successively illuminate Visual indicators (672) in response to usage of instrument (10) will be apparent to those of ordinary skill in the art in view of the teachings herein.

While visual indicators (672) are shown as being arranged in a linear array, it should be understood that any other suitable arrangement may be used. Similarly, while visual indicators (672) are shown as being positioned on the lateral side of disposable assembly (600), visual indicators (672) may instead be positioned at any other suitable location(s) on disposable assembly (600). In some versions, visual indicators (672) are visible when disposable assembly (600) is coupled with reusable assembly (200). In some other versions, visual indicators (672) are obscured when disposable assembly (600) is coupled with reusable assembly (200), such that visual indicators (672) are only visible when disposable assembly (600) is decoupled from reusable assembly (200).

Figure 82:
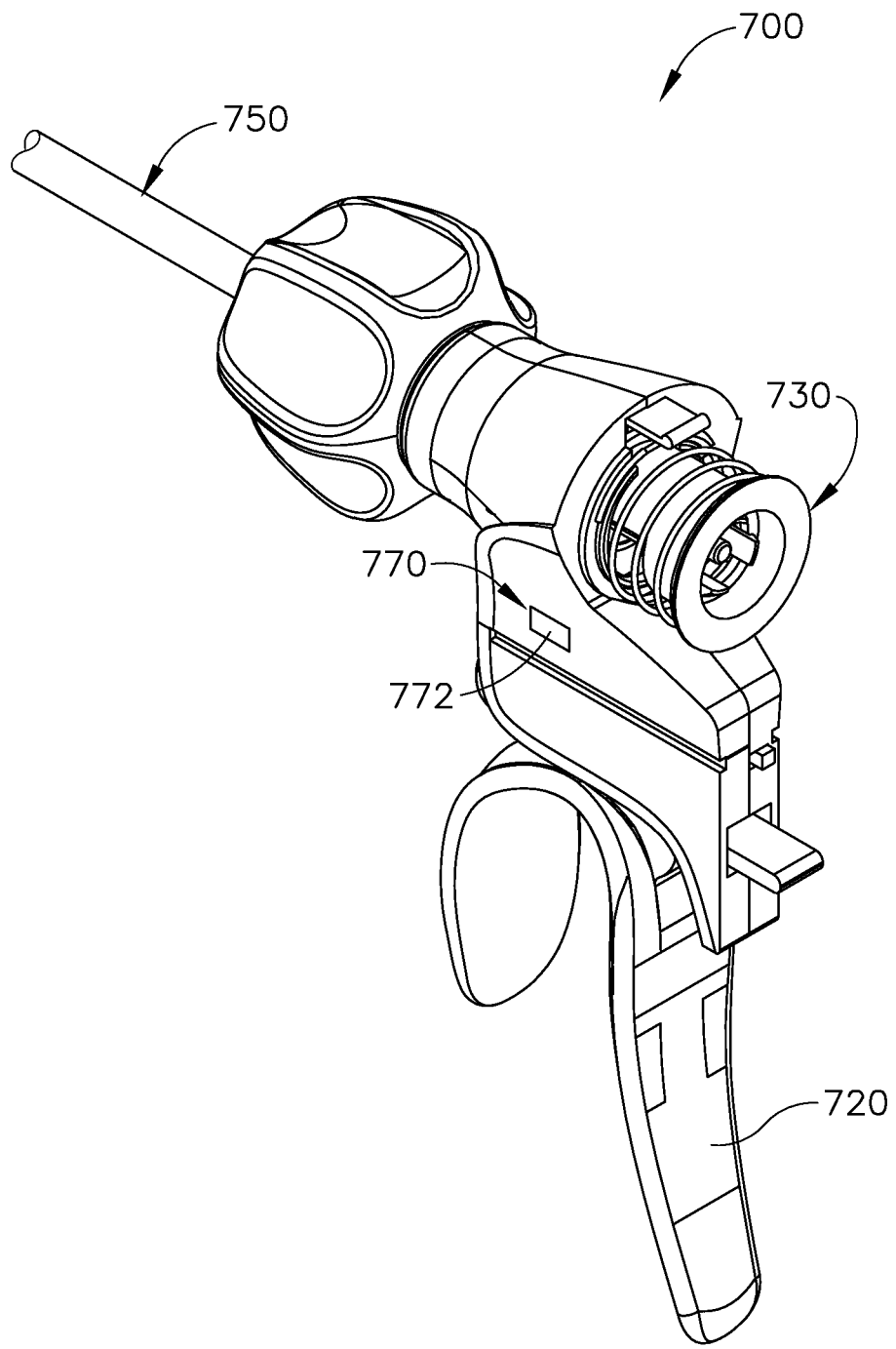
FIG. 82 depicts a perspective view of the proximal end of another exemplary alternative disposable portion of the instrument of FIG. 1.

FIG. 82 shows another exemplary alternative disposable assembly (700) that may readily incorporated into instrument (10) in place of disposable assembly (100). Disposable assembly (700) of this example is substantially identical to disposable assembly (100) described above. For instance, disposable assembly (700) includes a pivotable trigger (720), a mode selection knob (730), and a shaft assembly (750), which are identical to trigger (120), mode selection knob (130), and shaft assembly (150), respectively. However, unlike disposable assembly (100), disposable assembly (700) of this example further includes a usage indicator (770). Usage indicator (770) of this example comprises a single indicator that is activated when the end of life of disposable assembly (700) has been reached. In some versions, usage indicator (770) comprises an LED or other light source. In the present example, usage indicator (770) comprises one or more thermochromic materials (772). Thermochromic material (772) is configured to change in visual appearance in response to an increase in temperature. For instance, before disposable assembly (700) is used, thermochromic material (772) may be black; and then turn red or some other color after disposable assembly (700) is used. Various suitable kinds of materials and combinations of materials that may be used to form thermochromic material (772) will be apparent to those of ordinary skill in the art in view of the teachings herein. It should also be understood that visual indicator (672) described above may comprise a thermochromic material.

In some versions, thermochromic material (772) is coupled with one or more features of disposable assembly (700) that are electrically activated during use of an instrument (10) incorporating disposable assembly (700). For instance, a resistor may be used to generate heat in response to electrical activation of components in disposable assembly (700) during use of an instrument (10) incorporating disposable assembly (700). Other suitable ways in which thermochromic material (772) may be heated due to use of an instrument (10) incorporating disposable assembly (700) will be apparent to those of ordinary skill in the art in view of the teachings herein. It should also be understood that some versions of thermochromic material (772) may be configured to maintain a changed color even after the temperature falls back to a level where it was before disposable assembly (700) was used. For instance, before disposable assembly (700) is used, thermochromic material (772) may be black. When thermochromic material (772) is heated in response to use of disposable assembly (700), thermochromic material (772) changes red (or some other color). After disposable assembly (700) is used and thermochromic material (772) cools back down to the same temperature it was at before disposable assembly (700) was used, the color of thermochromic material (772) may remain red (or some other color indicating use).

By way of example only, thermochromic material (772) may comprise a thermochromic material by LCR Hallcrest of Glenview, Ill. Other suitable forms that thermochromic material (772) may take, as well as various other ways in which thermochromic material (772) may be incorporated into disposable assembly (700), will be apparent to those of ordinary skill in the art in view of the teachings herein.

In addition to or in lieu of using thermochromic material (772), usage indicator (770) may incorporate an exposed section of electrochromic material. Such electrochromic material may change color in response to an applied voltage and/or current. Such electrochromic material may be coupled with one or more features of disposable assembly (700) that are electrically activated during use of an instrument (10) incorporating disposable assembly (700). Various suitable ways in which an electrochromic material may be incorporated into disposable assembly (700) to visually indicate use of disposable assembly (700) will be apparent to those of ordinary skill in the art in view of the teachings herein. By way of example only, the electrochromic material may comprise an electrochromic ink by Chameleon Optics, Inc. of Bethlehem, Pa. Other suitable forms that electrochromic material may take, as well as various other ways in which electrochromic material may be incorporated into disposable assembly (700), will be apparent to those of ordinary skill in the art in view of the teachings herein.

In addition to or in lieu of using thermochromic material (772) and/or electrochromic material, usage indicator (770) may incorporate a UV activated ink, a fuse assembly, and/or various other kinds of features that may provide visual indication that disposable assembly (700) has been used.

While disposable assemblies (600, 700) are both described as substitutes for disposable assembly (100), it should be understood that disposable assembly (400) may also be modified in accordance with disposable assemblies (600, 700). In other words, disposable assemblies (600, 700) may each be configured to couple with reusable assembly (500). Furthermore, usage indicators (670, 770) as described herein may be readily incorporated into various other kinds of surgical instruments, including but not limited to electrosurgical instrument, other ultrasonic surgical instruments, surgical stapling and cutting devices (e.g., endocutters, etc.), robotic surgical instruments, etc. Various suitable kinds of instruments in which usage indicators (670, 770) may be incorporated will be apparent to those of ordinary skill in the art in view of the teachings herein.

Figure 83:
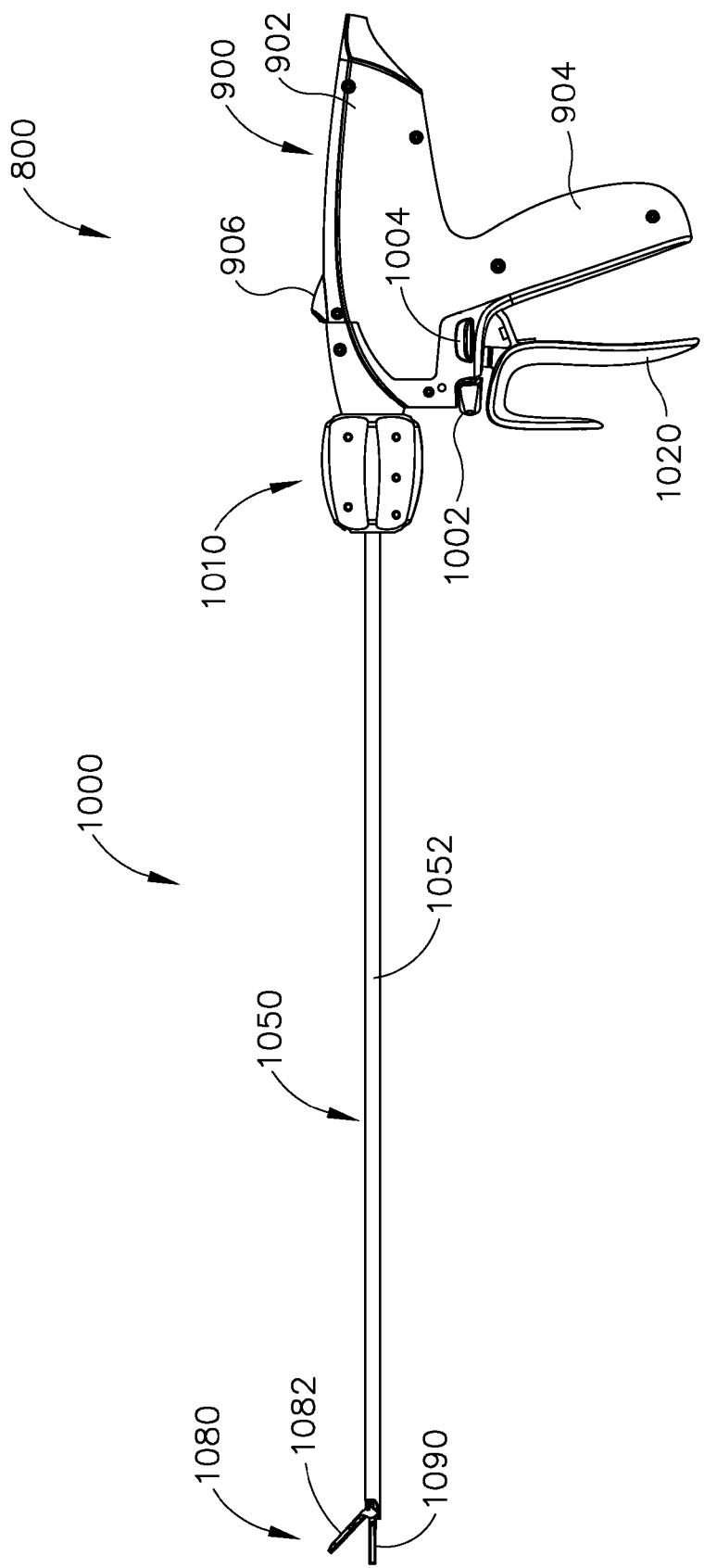
FIG. 83 depicts a side elevational view of an exemplary alternative ultrasonic surgical instrument.

VII. Exemplary Alternative Ultrasonic Surgical Instrument with Removable Acoustic Waveguide FIG. 83 shows an exemplary alternative ultrasonic surgical instrument (800). Instrument (800) of this example is substantially identical to instrument (10) described above, except as otherwise described below. For instance, like instrument (10) described above, instrument (800) of the present example comprises a disposable assembly (1000) and a reusable assembly (900). The distal portion of reusable assembly (900) is configured to removably receive the proximal portion of disposable assembly (1000). To the extent that the following discussion omits various details of instrument (800), it should be understood that instrument (800) may incorporate the various details described above with respect to instrument (10). Alternatively, other suitable details will be apparent to those of ordinary skill in the art in view of the teachings herein.

In an exemplary use, assemblies (900, 1000) are coupled together to form instrument (800) before a surgical procedure, the assembled instrument (800) is used to perform the surgical procedure, and then assemblies (900, 1000) are decoupled from each other for further processing. In some instances, after the surgical procedure is complete, disposable assembly (1000) is immediately disposed of while reusable assembly (900) is sterilized and otherwise processed for re-use. By way of example only, reusable assembly (900) may be sterilized in a conventional relatively low temperature, relatively low pressure, hydrogen peroxide sterilization process. Alternatively, reusable assembly (900) may be sterilized using any other suitable systems and techniques (e.g., autoclave, etc.). In some versions, reusable assembly (900) may be sterilized and reused approximately 100 times. Alternatively, reusable assembly (900) may be subject to any other suitable life cycle. For instance, reusable assembly (900) may be disposed of after a single use, if desired. While disposable assembly (1000) is referred to herein as being "disposable," it should be understood that, in some instances, disposable assembly (1000) may also be sterilized and otherwise processed for re-use. By way of example only, disposable assembly (1000) may be sterilized and reused approximately 2-30 times, using any suitable systems and techniques. Alternatively, disposable assembly (1000) may be subject to any other suitable life cycle. It should also be understood that, as described above, disposable assembly (1000) and/or reusable assembly (900) includes one or more features that are operable to track usage of the corresponding assembly (900, 1000), and selectively restrict operability of the corresponding assembly (900, 1000) based on use.

A. Reusable Assembly of Exemplary Alternative Ultrasonic Surgical Instrument

Figure 85:
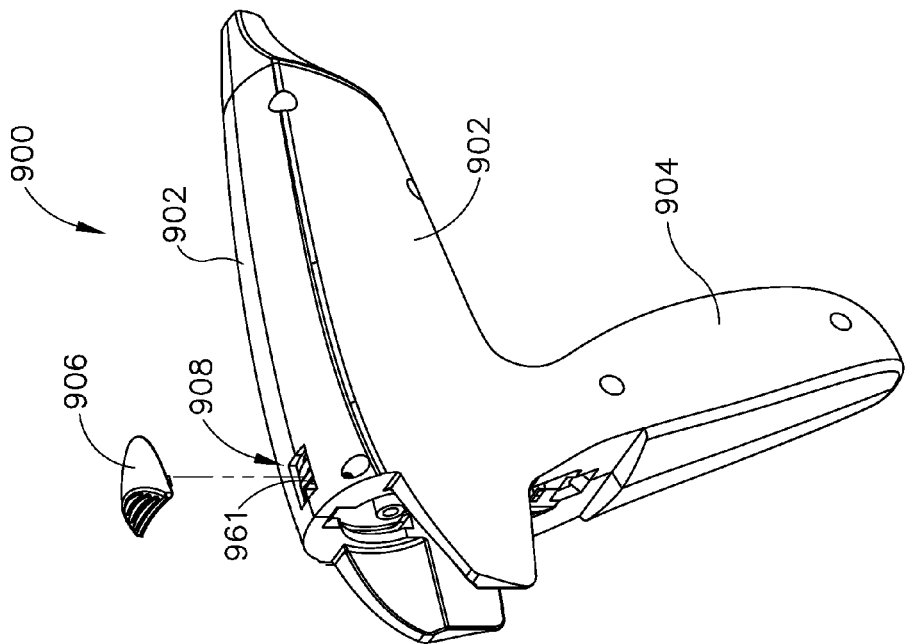
FIG. 85 depicts another perspective view of the reusable portion of FIG. 84, with a slider exploded away from the rest of the reusable portion.
Figure 84:
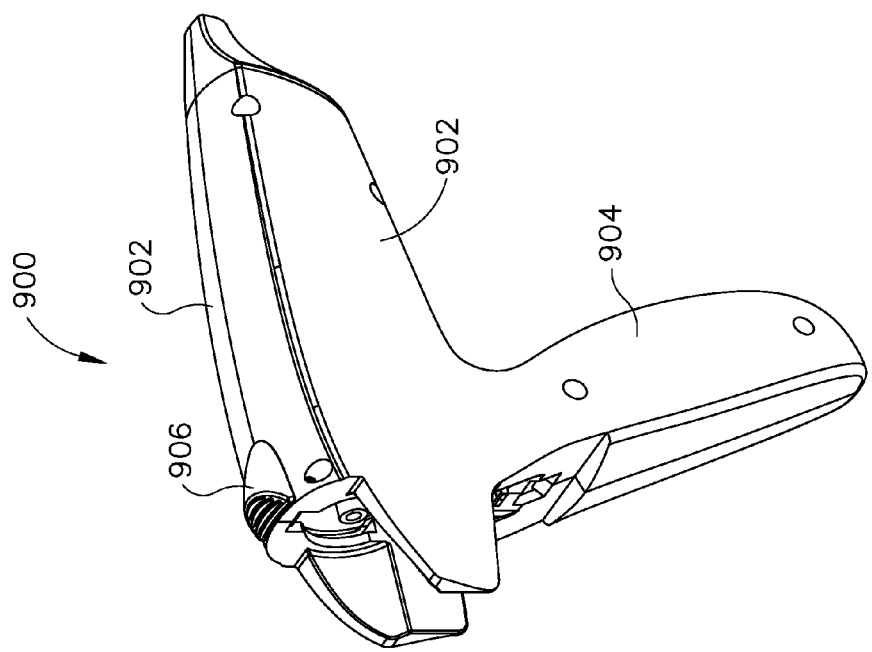
FIG. 84 depicts a perspective view of a reusable portion of the instrument of FIG. 83.
Figure 86:
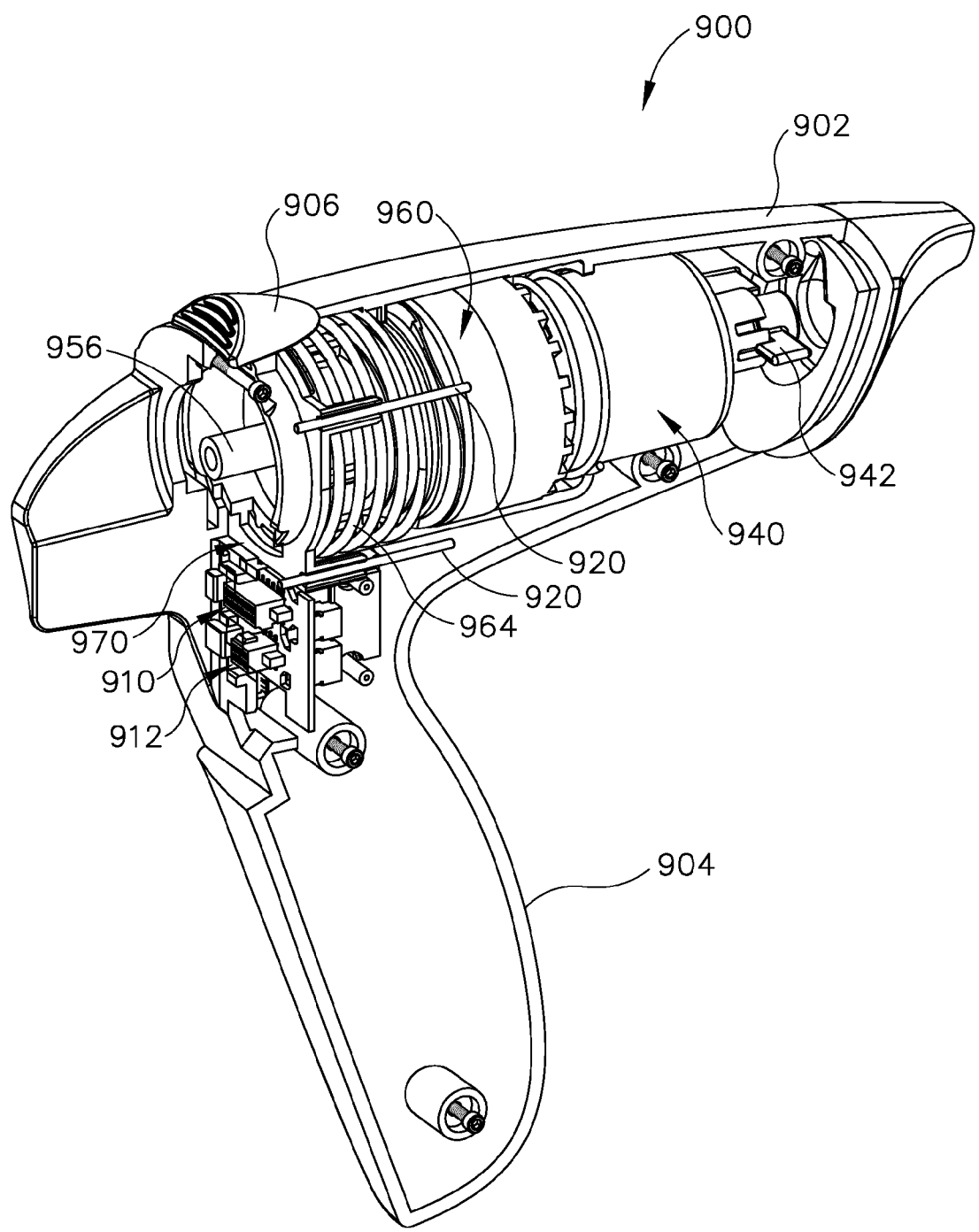
FIG. 86 depicts another perspective view of the reusable portion of FIG. 84, with a housing half removed.

FIGS. 84-86 show reusable assembly (900) in greater detail. Reusable assembly (900) of this example is substantially identical to reusable assembly (200) except for the differences noted below. Reusable assembly (900) comprises a pair of housings (902) that together define a pistol grip (904). As shown in FIG. 86, reusable assembly (900) comprises a transducer assembly (940) and a torque wrench assembly (960). Transducer assembly (940) is configured and operable just like transducer assembly (240). However, unlike transducer assembly (240), transducer assembly (940) of this example comprises a port (942) that is configured to couple with a power cable (not shown) that is received through the proximal end of housing (902). Transducer assembly (940) thus receives power from a source external to instrument (800), such that reusable assembly (900) lacks a generator (230) and battery (205). In some alternative versions, however, reusable assembly (900) may include an integral generator (230) and battery (205).

Another difference between reusable assembly (900) and reusable assembly (200) is that reusable assembly (900) of this example lacks buttons (220). Instead, buttons (1004) are incorporated into disposable assembly (1000) as described below. However, reusable assembly (900) includes mating features (910, 912) that are configured to mate with corresponding mating features (1012, 1014) associated with buttons (1002, 1004) of disposable assembly (1000). Mating features (910, 912) thus provide a route for processing user inputs received through buttons (1002, 1004) to activate transducer assembly (940) at an appropriate power level based on the user inputs. Various suitable ways in which user input signals received through mating features (910, 912) may be routed and processed will be apparent to those of ordinary skill in the art in view of the teachings herein.

Figure 87:
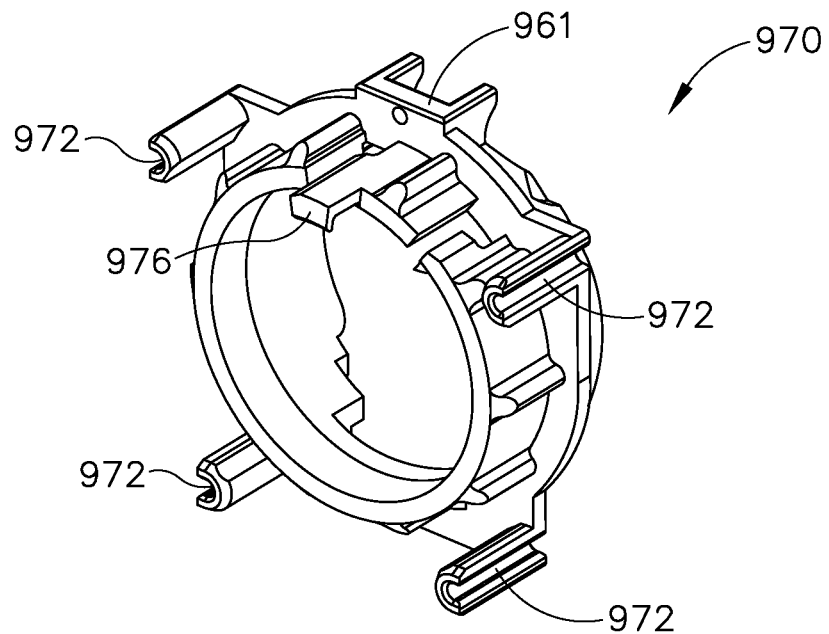
FIG. 87 depicts a perspective view of a pawl ring of the reusable portion of FIG. 84.
Figure 88:
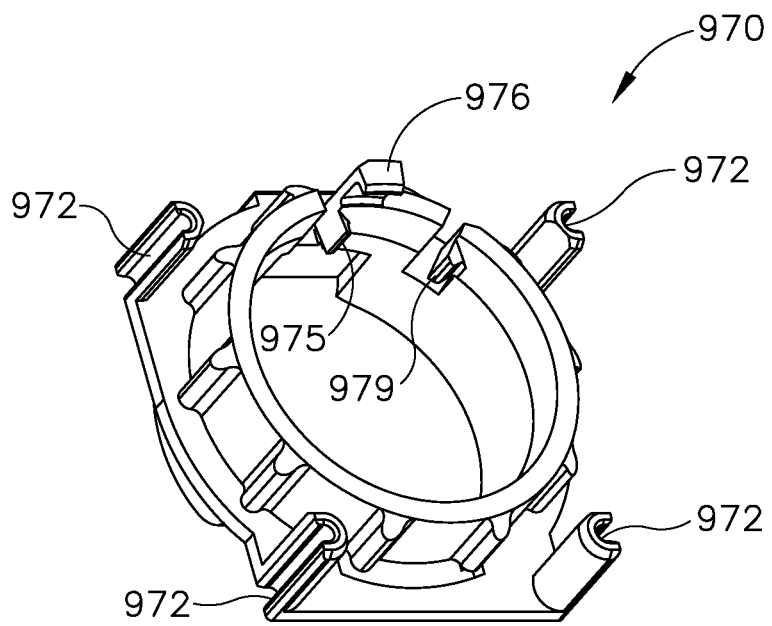
FIG. 88 depicts another perspective view of the pawl ring of FIG. 87.

Torque wrench assembly (960) is configured and operable just like torque wrench assembly (260). In particular, torque wrench assembly (960) is configured to ensure that a horn (956) of transducer assembly (940) is coupled with a threaded stud (1096) of an acoustic waveguide (1092) at an appropriate level of torque. However, torque wrench assembly (960) of this example has a pawl ring (970) that is configured slightly differently from pawl ring (270) of torque wrench assembly (260). As best seen in FIGS. 87-88, pawl ring (970) of this example includes a set of pawls (975, 979) that are configured and operable just like pawls (275, 279) of pawl ring (270). Pawl ring (970) of this example also includes a latch (976) that is configured and operable just like latch (276).

In addition, pawl ring (970) includes a tab (961) that is similar to tab (261). As shown in FIG. 85, tab (961) is accessible through a window (908) defined by housings (902). Tab (961) is coupled with a slider (906), which is configured to be easily manipulated by the operator to manually slide pawl ring (970) longitudinally via tab (961) as described above with reference to FIG. 64. In particular, when the operator wishes to decouple disposable assembly (1000) from reusable assembly (900), the operator may slide pawl ring (970) proximally by moving slider (906) proximally along housings (902). This may rotationally fix transducer assembly (940) relative to housings (902), allowing the operator to unscrew threaded stud (1096) of waveguide (1092) from horn (956) of transducer assembly (940).

The main structural difference between pawl ring (970) of this example and pawl ring (270) described above is that pawl ring (970) includes a set of rod channels (972) for rotational stability instead of having a notch (273) in a flange (272) for rotational stability. In the present example, pawl ring (970) has four rod channels (972), though it should be understood that pawl ring (970) may instead have any other suitable number of rod channels (972). As shown in FIG. 86, rod channels (972) are configured to slidably receive rods (920). Rods (920) are fixedly secured within housings (902). Rods (920) and rod channels (972) are configured to enable pawl ring (970) to slide longitudinally within housings (902) yet prevent pawl ring (970) from rotating within housings (902). Various other suitable structural features that may be used to provide such functionality will be apparent to those of ordinary skill in the art in view of the teachings herein.

B. Disposable Assembly of Exemplary Alternative Ultrasonic Surgical Instrument

FIGS. 89-90B show disposable assembly (1000) in greater detail. Disposable assembly (100) of this example comprises a set of buttons (1002, 1004) as noted above, a pair of housings (1006), a knob assembly (1010), a trigger (1020), a shaft assembly (1050), and an end effector (1080). Buttons (1002, 1004) are operable to selectively activate transducer assembly (940) as noted above. While only one side button (1004) is shown, it should be understood that another side button (1004) may be included on the obscured side of disposable assembly (1000). Housings (1006) are configured to mate with housings (902) of reusable assembly (1000) to form the full assembly of instrument (800) as shown in FIG. 83. Knob assembly (1010) is configured to rotate shaft assembly (1050) and end effector (1080) about the longitudinal axis of shaft assembly (1050). Trigger (1020) is operable to actuate a clamp arm (1082) of end effector (1080) as will be described in greater detail below. Shaft assembly (1050) comprises a plurality of coaxially arranged components that are operable to communicate ultrasonic vibrations and longitudinal clamp arm (1082) driving forces as will also be described in greater detail below.

End effector (1080) comprises clamp arm (1082) and an ultrasonic blade (1090). Clamp arm (1082) is operable to pivot from an open position (FIG. 90A) to a closed position (FIG. 90B). Such pivotal movement is accomplished through relative longitudinal movement of an inner tube (1070) of shaft assembly (1050) and an outer tube (1052) of shaft assembly (1050). In particular, one portion of clamp arm (1082) is pivotably coupled with the distal end of inner tube (1070). Another portion of clamp arm (1082) is pivotably coupled with the distal end of outer tube (1052). Such coupling may be identical to the coupling between clamp arm (182), inner tube (1070), and outer tube (152) as described above and as shown in FIGS. 4-7. Thus, when outer tube (1052) is translated longitudinally while inner tube (1070) remains stationary, clamp arm (1082) pivots toward and away from blade (1090). End effector (1080) may thus receive tissue between clamp arm (1082) and blade (1090) when clamp arm (1082) is in the open position; and clamp the tissue between clamp arm (1082) and blade (1090) when clamp arm (1082) is driven to the closed position. Blade (1090) of this example is configured and operable just like blade (1090) described above, such that blade (1090) is operable to oscillate at ultrasonic frequencies and thereby sever tissue that is clamped between clamp arm (1082) and blade (1090) as described above. Exemplary features that may be used to actuate clamp arm (1082) will be described in greater detail below.

1. Actuation Components of Disposable Assembly

Figure 91A:
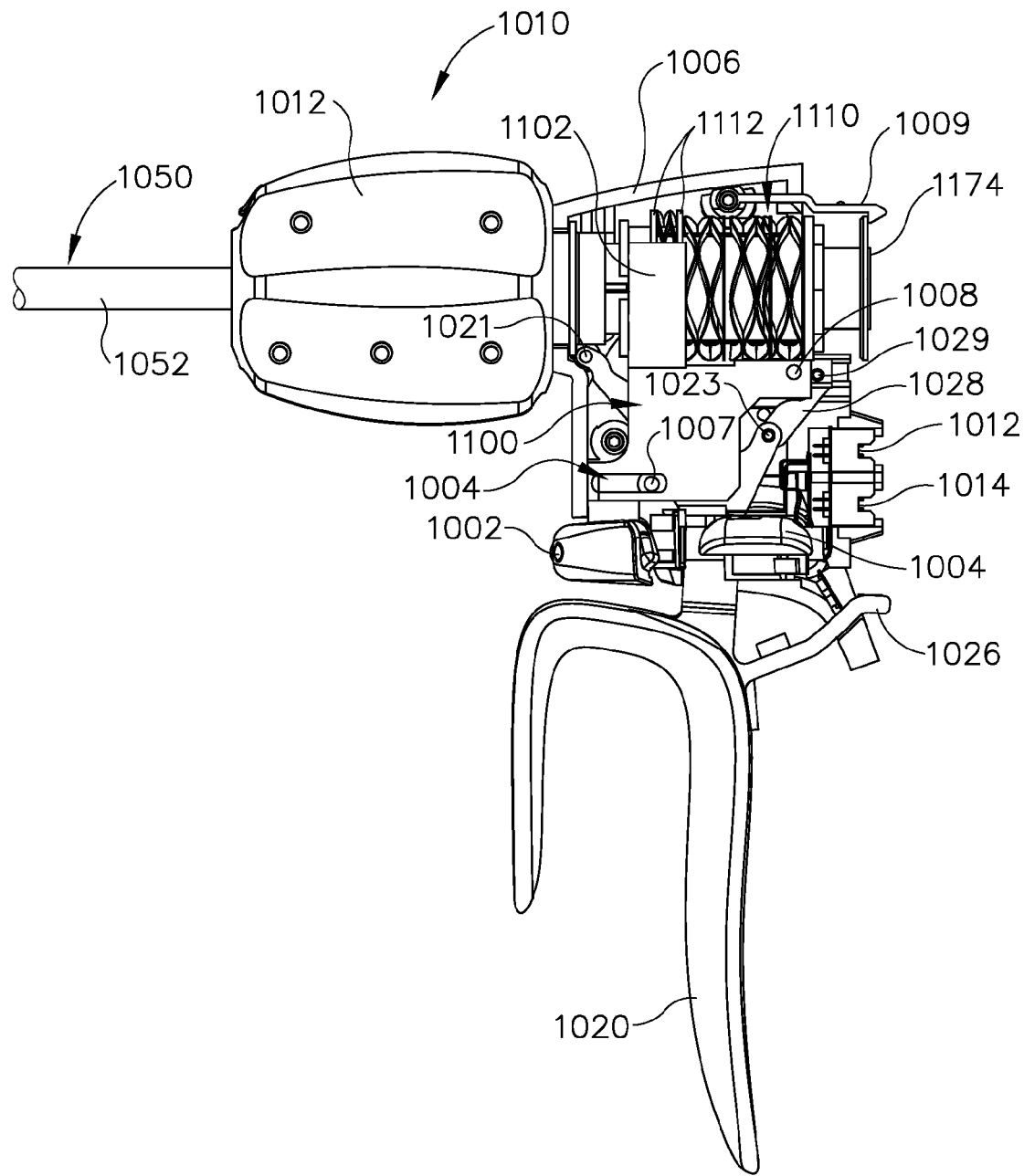
FIG. 91A depicts a side elevational view of the proximal end of the disposable portion of FIG. 89, with a housing half removed, and with a trigger in a non-actuated position.
Figure 91B:
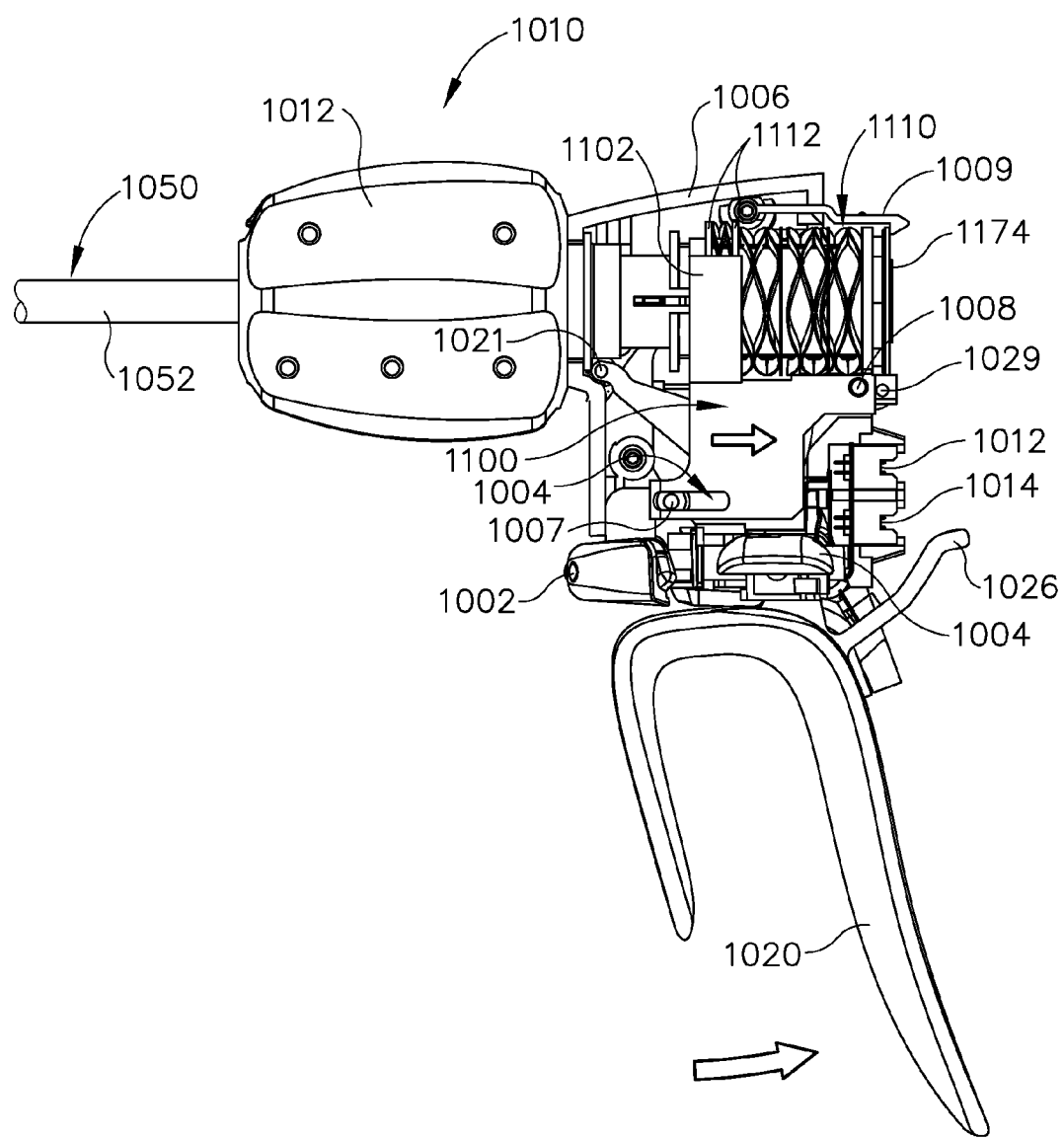
FIG. 91B depicts a side elevational view of the proximal end of the disposable portion of FIG. 89, with a housing half removed, and with the trigger in an actuated position.

In the present example, trigger (1020) is operable to actuate clamp arm (1082) by pivoting trigger (1020) toward and away from pistol grip (904). In particular, trigger (1020) is pivotable between a first position (FIGS. 91A and 93A) and a second position (FIGS. 91B and 93B). When trigger (1020) is in the first position, clamp arm (1082) is in the open position (FIG. 90A). When trigger (1020) is in the second position, clamp arm (1082) is in the closed position (FIG. 90B). FIGS. 91A-93B depict actuation components that couple trigger (1020) with clamp arm (1082). In particular, trigger (1020) is coupled with clamp arm (1082) via a yoke (1100), a coupling assembly (1110), and outer tube (1052). As best seen in FIGS. 93A-93B, trigger (1020) comprises a first arm (1022), a second arm (1024), and a third arm (1026). First arm (1022) is pivotably coupled with housings (1006) via a pin (1021). Trigger (1020) thus pivots about an axis defined by pin (1021). Second arm (1024) is pivotably coupled with a link (1028) via a pin (1023). Third arm (1026) protrudes proximally from disposable assembly (1000). As described above with respect to tab (122) of trigger (120), reusable assembly (900) may include a sensor and/or other feature(s) that is/are operable to detect movement of third arm (1026) to thereby detect actuation of trigger (1020).

Figure 92:
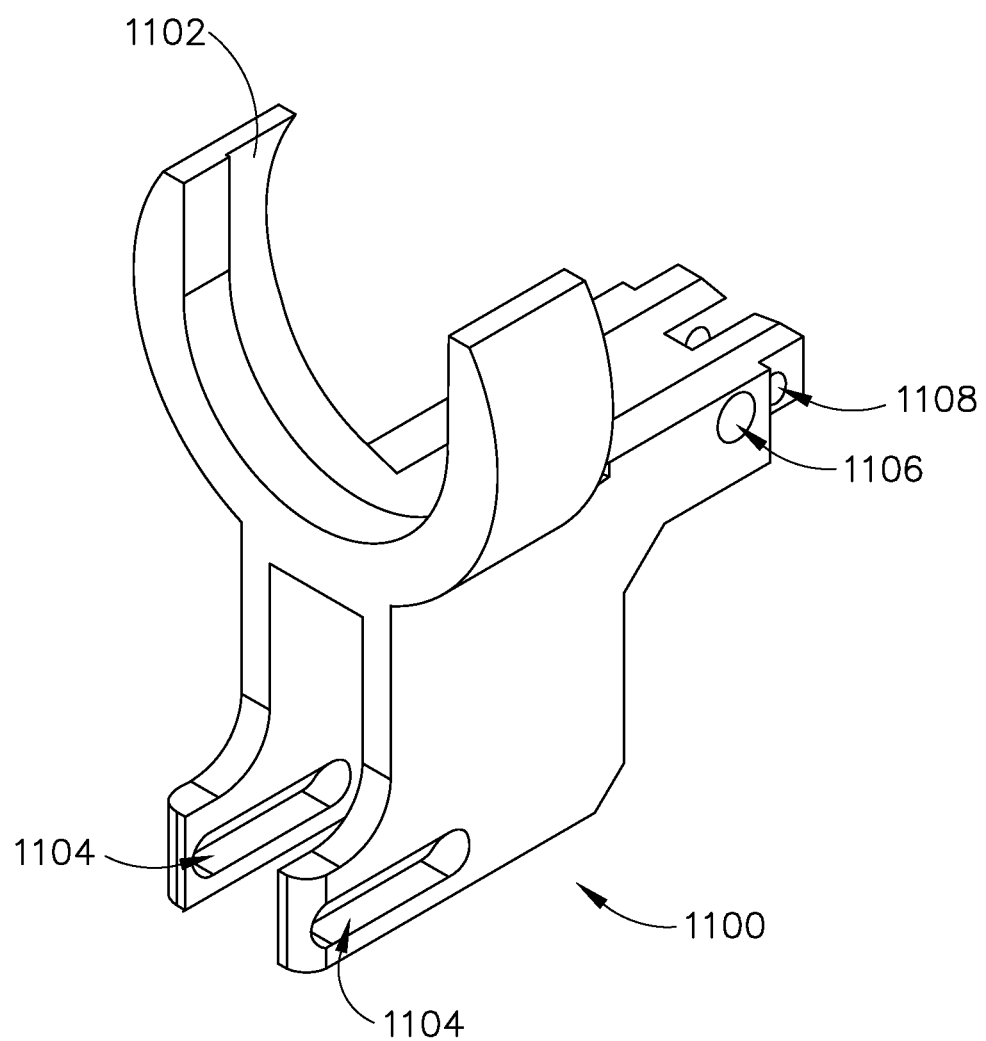
Figure 93A:
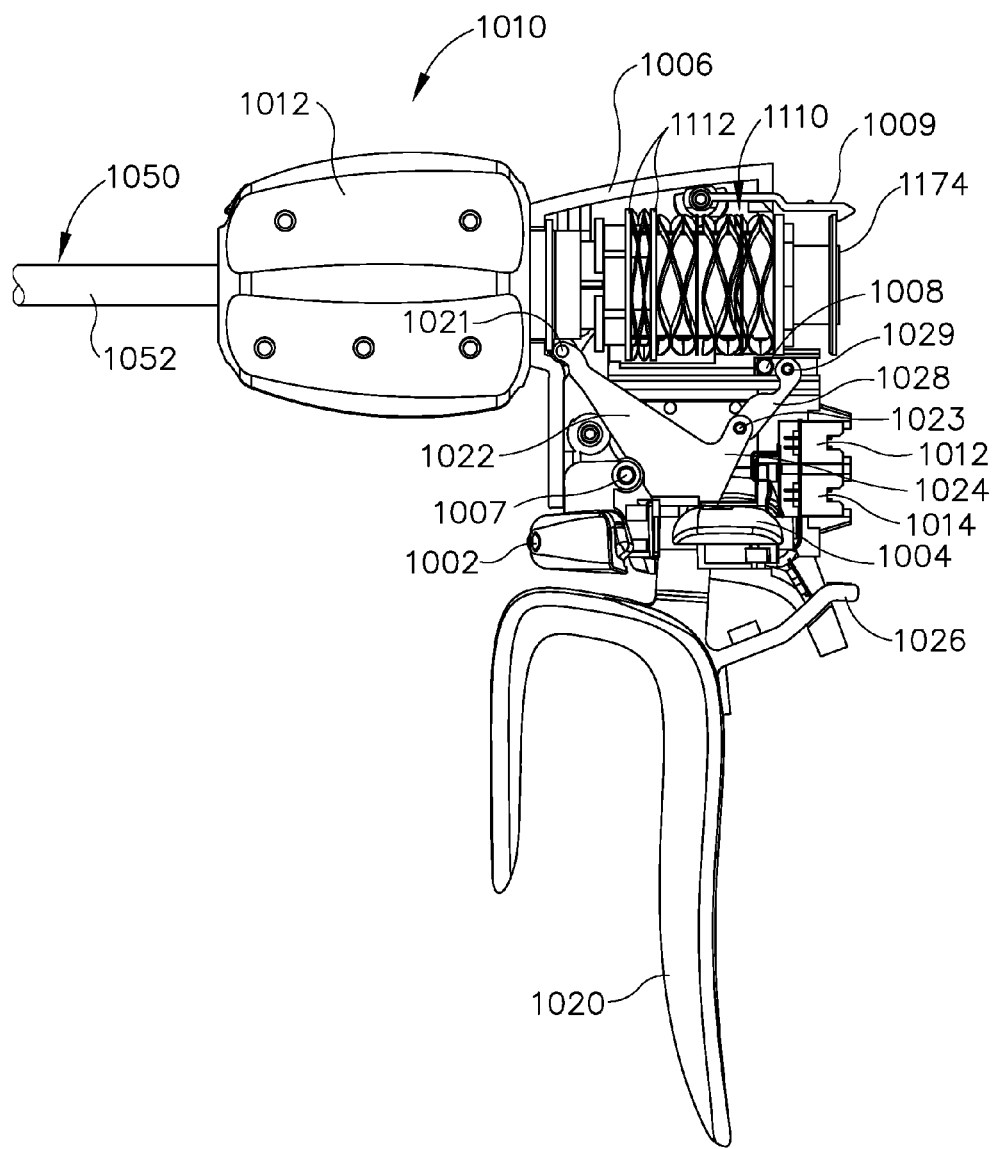
Figure 93B:
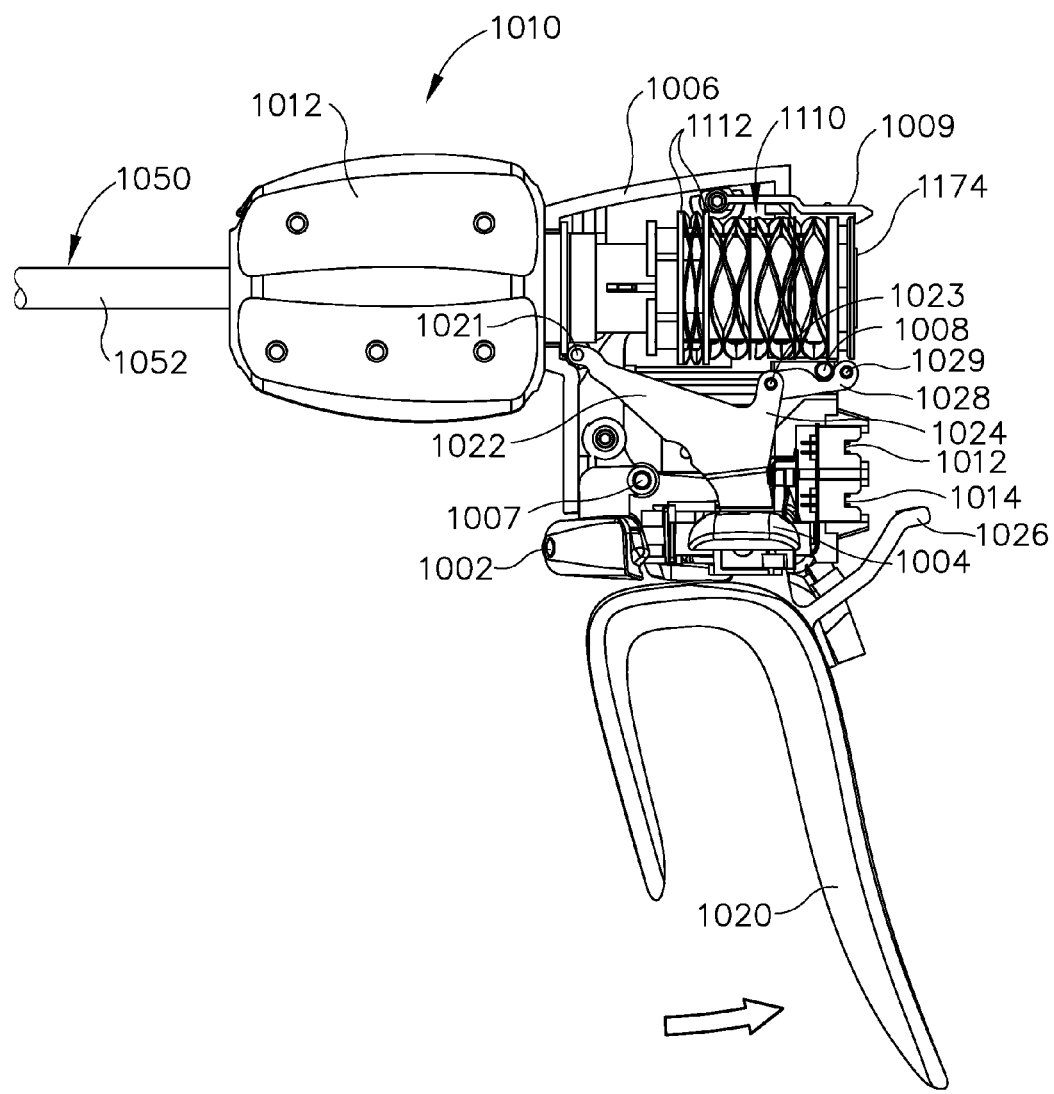

As best seen in FIG. 92, yoke (1100) comprises a fork member (1102). Fork member (1102) is configured to couple with a set of flanges (1112) of coupling assembly (1110), such that longitudinal translation of yoke (1100) provides longitudinal translation of coupling assembly (1110). Coupling assembly (1110) is secured to the proximal end of outer tube (1052) as described in greater detail below, such that longitudinal translation of coupling assembly (1110) provides longitudinal translation of outer tube (1052) to actuate clamp arm (1082). Yoke (1100) defines an elongate slot (1104), a first pin opening (1106) and a set of second pin openings (1108). As best seen in FIGS. 91A-91B, a pin (1007) is slidably disposed in elongate slot (1104). Pin (1007) is fixedly secured within housings (1006) such that pin (1007) slidably supports yoke (1100). A pin (1008) is secured in pin opening (1106). Pin (1008) is slidably received in elongate channels that are formed in housings (1006), such that pin (1008) also slidably supports yoke (1100). Yoke (1100) is coupled with link (1028) via a pin (1029), which is disposed in second pin openings (1108). Link (1028) is pivotable relative to yoke (1100) about the axis of pin (1029).

As best seen in the transition from FIG. 93A to FIG. 93B, as trigger (1020) is pivoted proximally, second arm (1024) drives pin (1023) upwardly. This upward movement of pin (1023) causes link (1028) to pivot about both pins (1023, 1029) and also causes link (1028) to drive pin (1029) proximally. As best seen in the transition from FIG. 91A to FIG. 91B, this proximal movement of pin (1029) pulls yoke (1100) proximally. The proximal movement of yoke (1100) moves coupling assembly (1110) proximally. The proximal movement of coupling assembly (1110) moves outer tube (1052) proximally. With inner tube (1070) remaining stationary as outer tube (1052) moves proximally, the proximal movement of outer tube (1052) drives clamp arm (1082) from the open position to the closed position. To return clamp arm (1082) to the open position, trigger (1020) is simply pivoted distally back to the position shown in FIGS. 91A and 93A, which will reverse the above motions. Of course, any other suitable components and operational sequences may be used to actuate clamp arm (1082).

2. Shaft Assembly Components of Disposable Assembly

Figure 95:
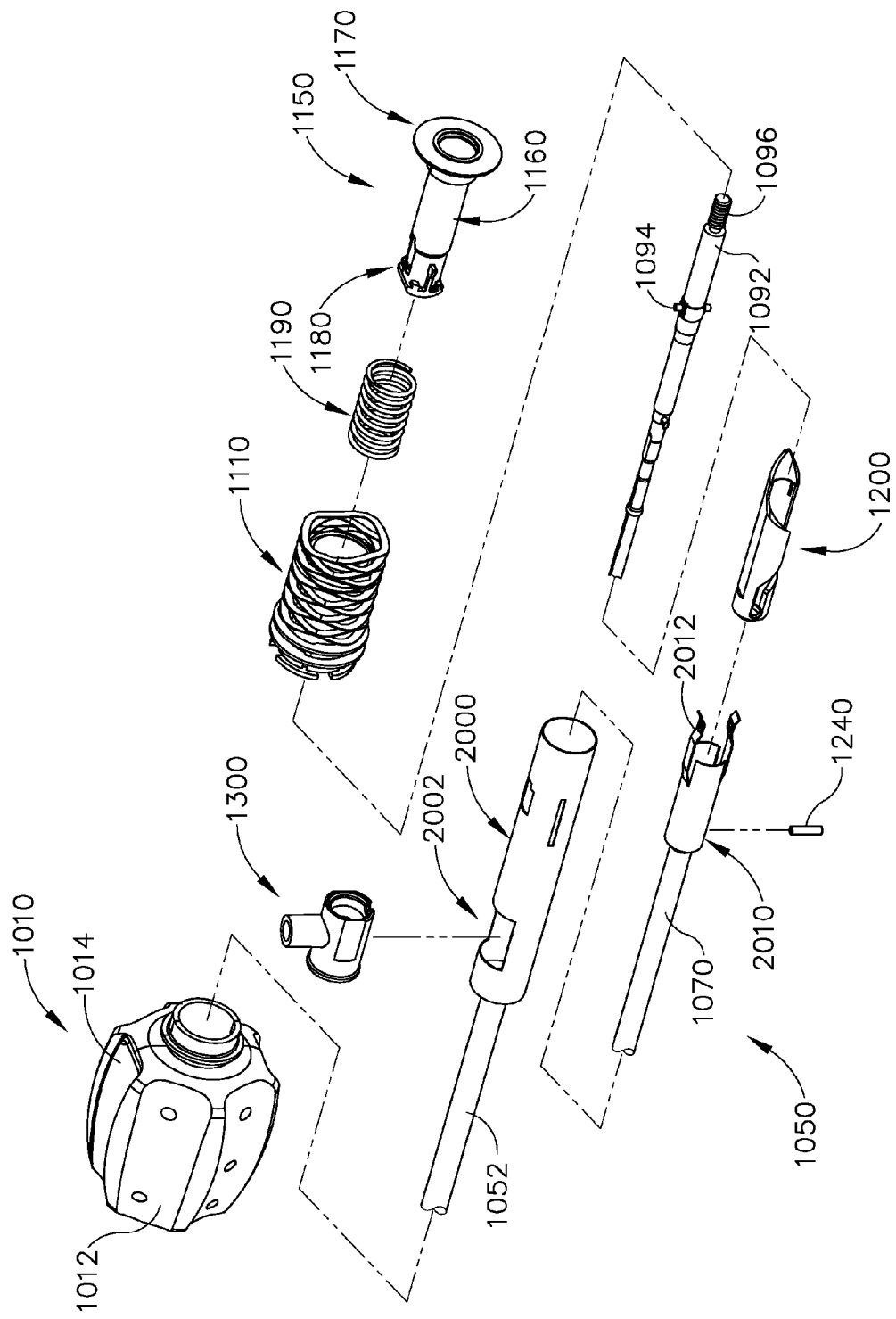

FIGS. 94-108 depict various components of shaft assembly (1050). In particular, FIGS. 94-95 show how shaft assembly (1050) comprises outer tube (1052), inner tube (1070), acoustic waveguide (1092), a waveguide guiding member (1200), yoke coupling assembly (1110), an inner tube coupling member assembly (1150), a coil spring (1190), a cleaning port body (1300), and knob assembly (1010). These components are all coaxially aligned with each other. Each of these components will be described in greater detail below.

Figure 96:
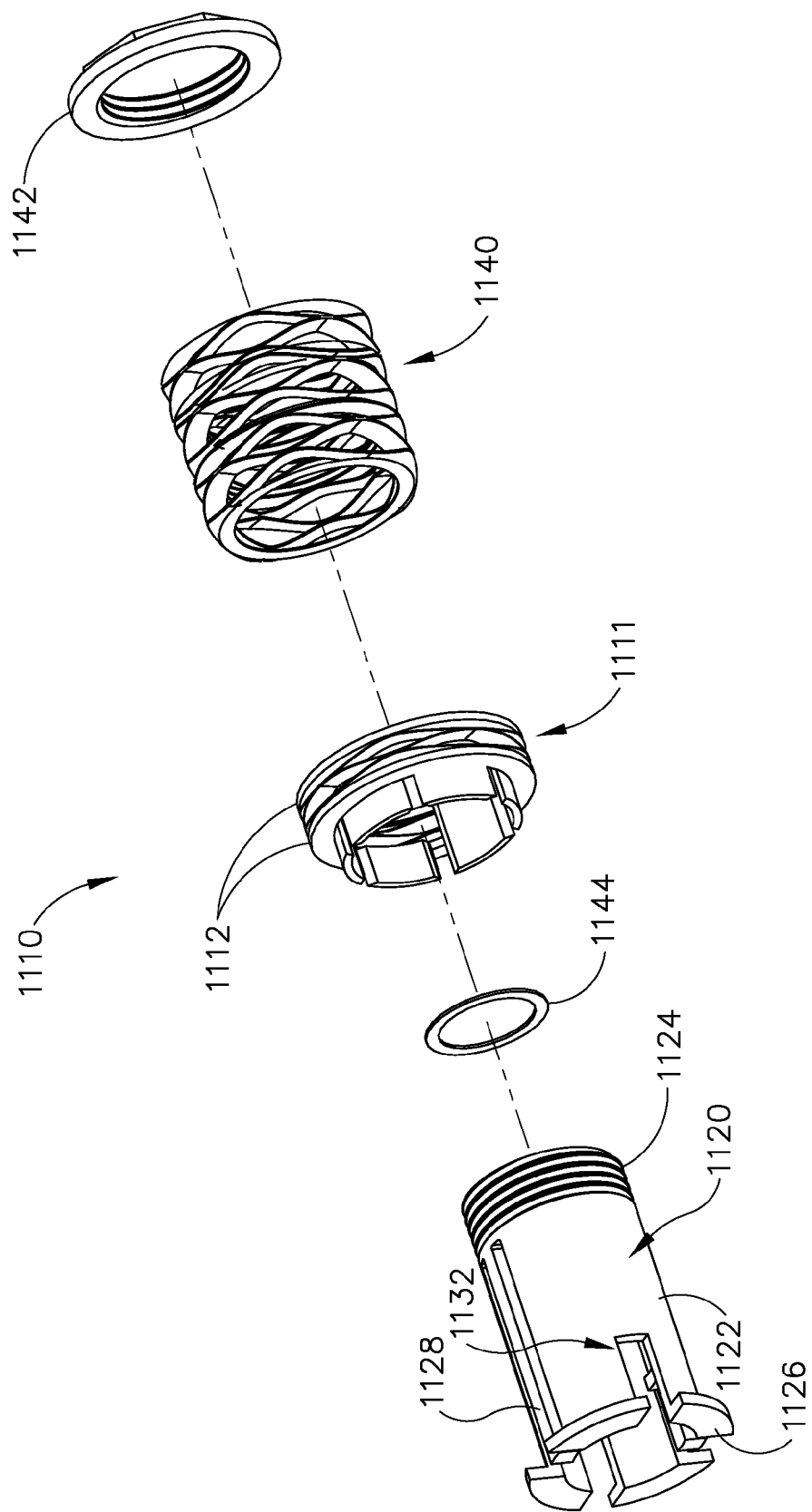
Figure 97:
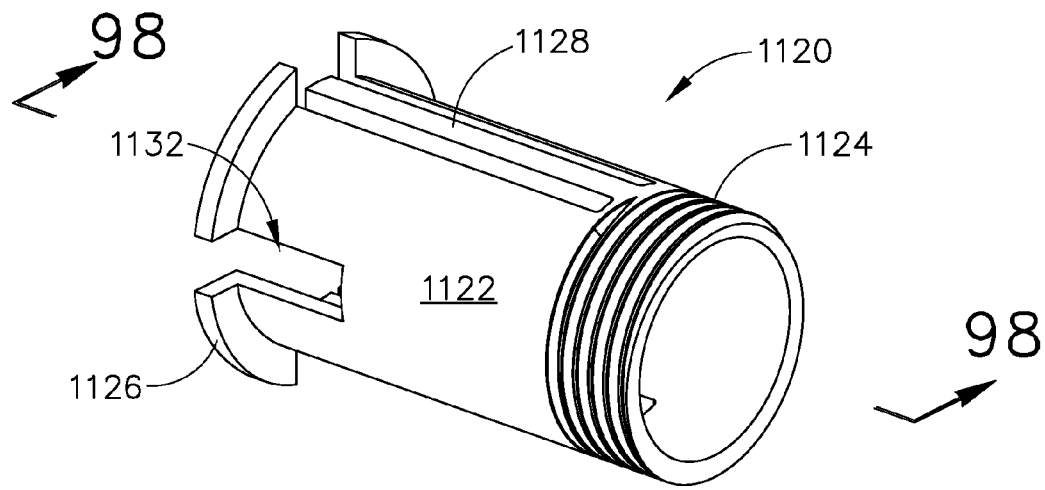
Figure 98:
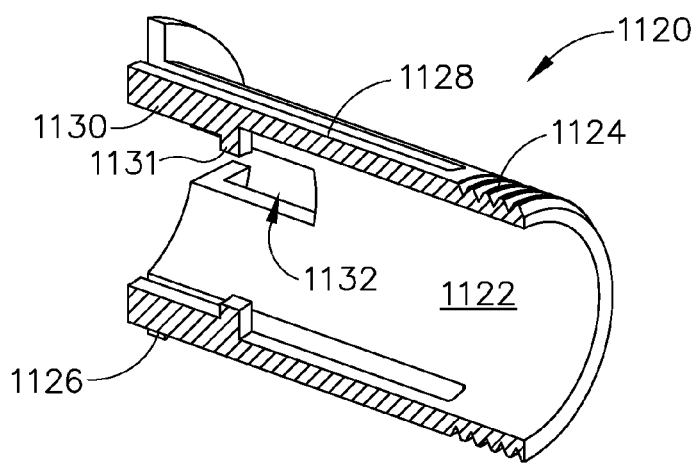

FIG. 96 shows yoke coupling assembly (1110) in greater detail. Yoke coupling assembly (1110) of this example comprise a flange assembly (1111), a tube coupling member (1120), a set of wave springs (1140), a nut (1142), and a washer (1144). Flange assembly (1111) comprises a set of flanges (1112) that couple with fork member (1102) of yoke (1100) as described above. As shown in FIGS. 96-98, tube coupling member (1120) comprises an elongate cylindraceous body (1122) having a flange portion (1126) at the distal end and a threaded portion (1124) at the proximal end. Body (1122) also defines a pair of elongate, resilient arms (1128). The distal end of each resilient arm (1128) includes an elongate tab (1130). A protrusion (1131) extends inwardly from the proximal end of each elongate tab (1130). The distal end of body (1122) further includes a pair of elongate notches (1132). Notches (1132) are angularly offset from arms (1128) by 90°.

Figure 99:
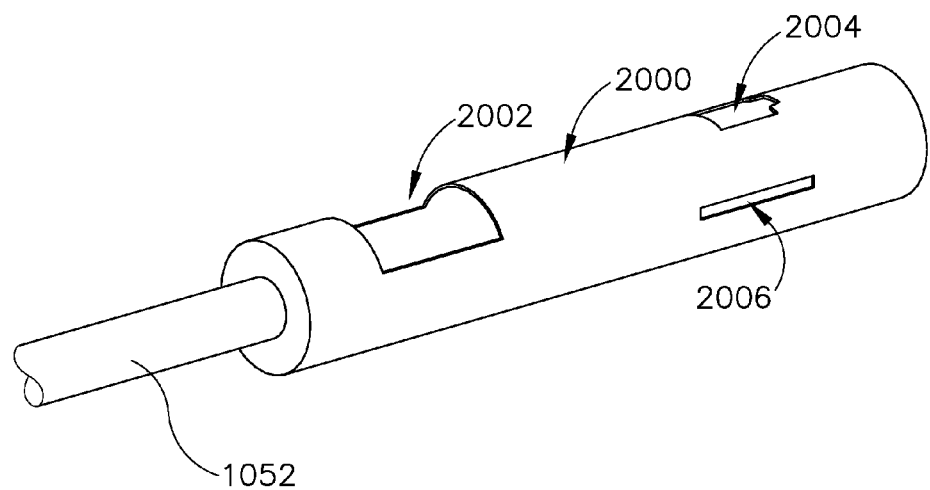
Figure 100:
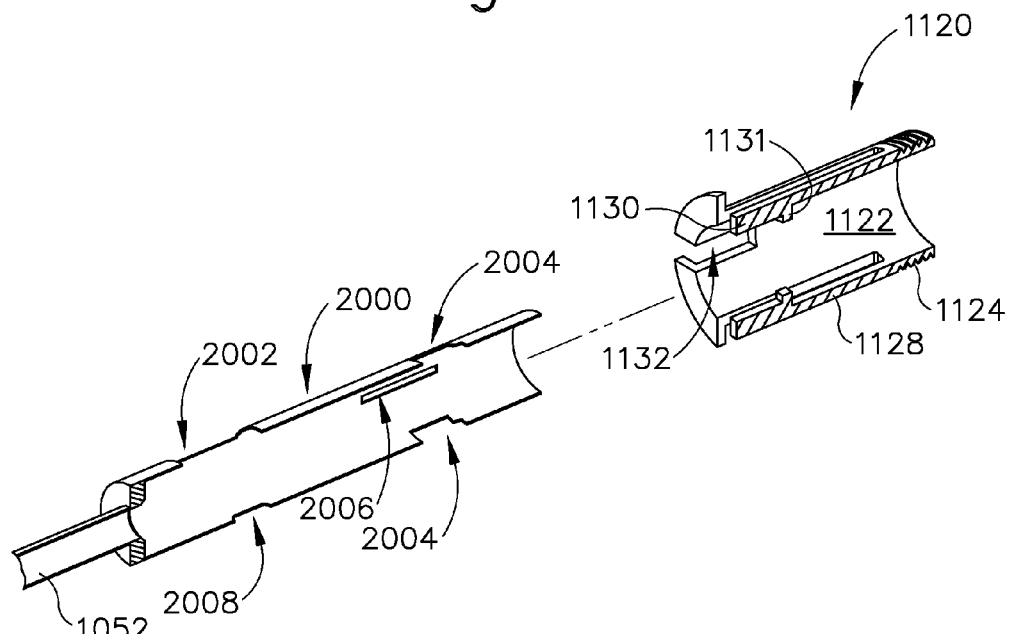
Figure 101:
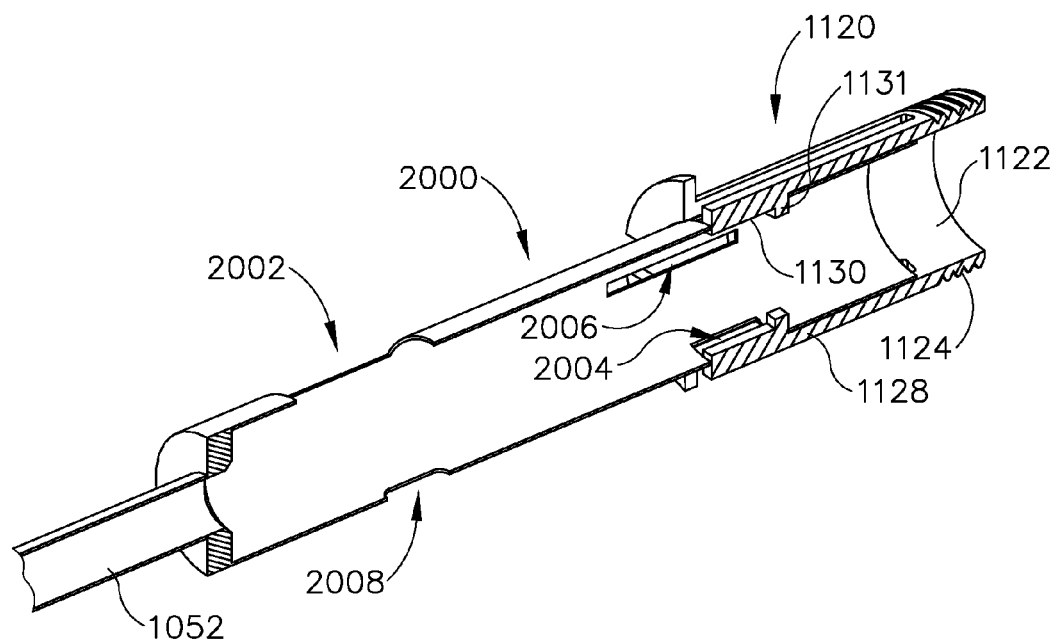

As best seen in FIGS. 99-101, tube coupling member (1120) is configured to couple with a proximal mounting portion (2000) of outer tube (1052). Proximal mounting portion (2000) includes a distal lateral opening (2002), a first pair of proximal lateral openings (2004), a second pair of proximal lateral openings (2006), and an elongate lateral pin opening (2008). Openings (2006) are angularly offset from openings (2004) by 90°. Opening (2008) is offset from opening (2002) by 180°. Tube coupling member (1120) may be coupled with proximal mounting portion (2000) by sliding tube coupling member (1120) distally over the proximal end of proximal mounting portion (2000). When this is done, arms (1128) will initially deform outwardly and then snap back into place once elongate tabs (1130) reach openings (2004). Openings (2004) are sized to receive the full length of elongate tabs (1130) such that tube coupling member (1120) and proximal mounting portion (2000) are longitudinally and rotationally fixed together. With tube coupling member (1120) secured to proximal mounting portion (2000), openings (2002, 2006, 2008) are left exposed; and notches (1132) are angularly and longitudinally aligned with openings (2006).

Once tube coupling member (1120) is secured to proximal mounting portion (2000), flange assembly (1111) and wave springs (1140) are slid over body (1122), and then nut (1142) is secured to threaded portion (1124) to capture flange assembly (1111) and wave springs (1140) between nut (1142) and flange portion (1126). Washer (1144) is inserted into the interior of body (1122) until washer (1144) abuts protrusions (1131). This assembled yoke coupling assembly (1110) is sized to receive inner tube (1070) and inner tube coupling member assembly (1150). Before inner tube (1070) and inner tube coupling member assembly (1150) are inserted into yoke coupling assembly (1110), coil spring (1190) is inserted into the interior of body (1122). Washer (1144) is sized to provide a distal bearing surface for the distal end of coil spring (1190), and protrusions (1131) provide a distal bearing surface for washer (1144). The proximal end of coil spring (1190) is configured to engage inner tube coupling member assembly (1150) as will be described in greater detail below, such that coil spring (1190) provides engagement between yoke coupling assembly (1110) and inner tube coupling member assembly (1150).

FIGS. 102-103 show inner tube coupling member assembly (1150) in greater detail. Inner tube coupling member assembly (1150) is engaged with a proximal mounting portion (2010) of inner tube (1070). Proximal mounting portion (2010) includes a set of proximally projecting resilient arms (2012). Arms (2012) are configured identically to arms (181) described above, such that their structural details will not be repeated here. Arms (2012) are configured to engage a pin (1094) of waveguide (1092) as will be described in greater detail below.

Inner tube coupling member assembly (1150) comprises a cylindraceous body (1160), a proximal flange member (1170), and a distal deflector member (1180). Cylindraceous body (1160) defines a first pair of lateral openings (1162) and a second pair of lateral openings (1164). Openings (1164) are angularly offset from openings (1162) by 90°. Openings (1162) are configured to correspond with pin (1094) of waveguide (1092) and arms (2012) of proximal mounting portion (2010) of inner tube (1070). Openings (1164) are positioned to angularly and longitudinally correspond with openings (2006) of proximal mounting portion (2000) of outer tube (1052). Openings (1164) are also sized to receive latch tabs (1188) of distal deflector member (1180) as will be described in greater detail below.

Flange member (1170) is secured to the proximal end of body (1160) through a snap fit in the present example, though it should be understood that any suitable structures and techniques may be used to secure flange member (1170) to body (1160). Flange member (1170) comprises a cylindraceous portion (1172) and a flange portion (1174). As shown in FIGS. 91A-91B, 93A-93B, and 94, flange portion (1174) is engaged with a resilient latch (1009). Latch (1009) is secured to housings (1006) and is configured to provide a proximal ground for flange portion (1174) when disposable assembly (1000) is in an operational mode. However, when disposable assembly (1000) is converted to a cleaning mode as described in greater detail below, latch (1009) disengages flange portion (1174), allowing flange member (1170) and the rest of inner tube coupling member assembly (1150) to travel proximally. As best seen in FIG. 94, the distal edge of cylindraceous portion (1172) is configured to engage the proximal end of coil spring (1190). It should be understood that, when trigger (1020) is actuated to close clamp arm (1082), yoke coupling assembly (1110) will travel proximally, and this proximal travel will compress coil spring (1190) against the distal edge of cylindraceous portion (1172). Flange member (1170) thus provides a proximal mechanical ground; and coil spring (1190) thereby imparts a distal bias to yoke coupling assembly (1110). In other words, coil spring (1190) and flange member (1170) cooperate to bias clamp arm (1082) to the open position.

FIG. 104 shows deflector member (1180) in greater detail. Deflector member (1180) comprises upper and lower ridges (1182) and a pair of resilient arms (1184). The proximal end of each resilient arm (1184) includes an inwardly directed latch tab (1188) and an outwardly directed guide tab (1186). As noted above, latch tabs (1188) are disposed in openings (1164) of body (1160) to secure deflector member (1180) to body (1160) in a snap fit manner. Guide tabs (1186) are sized and positioned for slidable receipt in openings (2006) of proximal mounting portion (2000) of outer tube (1052). Guide tabs (1186) and openings (2006) are sized and configured to enable inner tube coupling member assembly (1150) to slide longitudinally relative to proximal mounting portion (2000) of outer tube (1052). However, the positioning of guide tabs (1186) in openings (2006) provides concomitant rotation of proximal mounting portion (2000) with inner tube coupling member assembly (1150). In other words, tubes (1052, 1070) rotate together due in part to the positioning of guide tabs (1186) in openings (2006); yet outer tube (1052) may still translate longitudinally relative to inner tube (1070) despite the positioning of guide tabs (1186) in openings (2006). It should also be noted that, when disposable assembly (1000) is in an operational mode, arms (2012) are configured to effectively reach over ridges (1182) to engage pin (1094) of waveguide (1092).

As best seen in FIGS. 105-107, waveguide guiding member (1200) of the present example comprises a hollow elongate body (1202) having a plurality of cam surfaces (1212, 1214, 1216, 1218, 1220, 1222) on one side of a channel (1204) and another plurality of cam surfaces (1242, 1244, 1246, 1248) on the other side of channel (1204). Body (1202) also defines a lateral opening (1270) near the distal end of body (1202). Cam surfaces (1212, 1242) converge at a point (1250) at the proximal end of body (1202). Cam surfaces (1222, 1248) converge at an end surface (1260) at the distal end of body (1202).

Cam surface (1212) extends along a helical path in a first angular direction and leads to cam surface (1214). Cam surface (1214) extends along a straight longitudinal path and leads to cam surface (1216). Cam surface (1216) extends along a helical path in the first angular direction and leads to cam surface (1218). Cam surface (1218) extends along a straight longitudinal path and leads to cam surface (1220). Cam surface (1220) extends along a helical path in a second angular direction and leads to cam surface (1222). Cam surface (1222) extends along a straight longitudinal path and leads to end surface (1260).

Cam surface (1242) extends along a helical path in the second angular direction and leads to cam surface (1244). Cam surface (1244) extends along a straight longitudinal path and leads to cam surface (1246). Cam surface (1246) extends along a helical path in the second angular direction and leads to cam surface (1248). Cam surface (1248) extends along a straight longitudinal path and leads to end surface (1260). As will be described in greater detail below, cam surfaces (1212, 1214, 1216, 1218, 1220, 1222, 1242, 1244, 1246, 1248) cooperate to guide and thereby orient waveguide (1092) at an appropriate angular orientation as waveguide (1092) is inserted through body (1202).

As best seen in FIG. 108, waveguide (1092) of the present example comprises an elastomeric fender (1093), pin (1094), threaded stud (1096), and a laterally extending guide post (1099). Blade (1090) is located at the distal end of waveguide (1092). As shown in FIG. 94, fender (1093) is coaxially interposed between the outer diameter of waveguide (1092) and the inner diameter of inner tube (1070). In the present example, fender (1093) comprises an elastomeric material (e.g., rubber, silicone, etc.) and is located at a position corresponding to a node associated with ultrasonic vibrations that are communicated through waveguide (1092). It should be understood that a plurality of fenders (1093) may be located at nodal positions along the length of waveguide (1092). Such fenders (1093) may provide lateral support and/or spacing for waveguide (1092).

Referring back to FIG. 108, pin (1094) is secured to waveguide (1092) by a set of clips (1097). Clips (1097) are configured to ensure that pin (1094) is centered within the corresponding transverse bore formed through waveguide (1092), to secure and support pin (1094) in that bore, and to provide acoustic isolation between waveguide (1092) and pin (1094). Of course, any other suitable structures or features may be used in addition to or in lieu of clips (1097). In some versions, an elastomeric outer sleeve is positioned about sleeve (1094) and/or elastomeric members positioned about clips (1097). Such an elastomeric sleeve and/or members may provide further acoustic isolation of pin (1094) and/or clips (1097) relative to waveguide (1092).

As noted above, stud (1096) is configured to mechanically and acoustically couple waveguide (1092) with horn (956) of transducer assembly (940). As will be described in greater detail below, guide post (1099) is configured to interact with cam surfaces (1212, 1214, 1216, 1218, 1220, 1222, 1242, 1244, 1246, 1248) of waveguide guiding member (1200) to guide and thereby orient waveguide (1092) at an appropriate angular orientation as waveguide (1092) is inserted through body (1202).

Referring back to FIGS. 94-95, knob assembly (1010) of the present example comprises a pair of housings (1012) and a lid (1014), which is pivotably coupled with housings (1012). Housings (1012) are secured together and thereby encompass a proximal portion of shaft assembly (1050) and a cleaning port body (1300), which will be described in greater detail below. Housings (1012) also define recesses (1018) that are configured to receive a pin (1240). As shown in FIGS. 94-95, a pin (1240) is incorporated into shaft assembly (1050) in order to couple components of shaft assembly (1050) that rotate together concomitantly. In particular, pin (1240) is secured within opening (1270) of waveguide guiding member (1200), a corresponding lateral opening (not shown) of proximal mounting portion (2010) of inner tube (1070), opening (2008) of proximal mounting portion (2000) of outer tube (1052), and recesses (1018) of housings (1012). Pin (1240) does not contact waveguide (1092) at all.

Pin (1240), opening (1270), the corresponding lateral opening of proximal mounting portion (2010), and the combination of recesses (1018) all have a circular cross-section, such that pin (1240) provides longitudinal fixation between waveguide guiding member (1200), inner tube (1070), and housings (1012). However, opening (2008) is elongate, such that pin (1240) does not prevent outer tube (1052) from translating longitudinally relative to the components that are longitudinally fixed together by pin (1240). Nevertheless, pin (1240) provides concomitant rotation of waveguide guiding member (1200), inner tube (1070), outer tube (1052), and knob assembly (1010). Waveguide (1092) will rotate concomitantly with these components due to post (199) being engaged with waveguide guiding member (1200) as described below; and due to pin (1094) being engaged with arms (2012) as described above. An operator may thus grasp and rotate knob assembly (1010) relative to housings (1006) to thereby rotate shaft assembly (1050) and end effector (1080) relative to housings (1006).

3. Exemplary Cleaning Mode of Disposable Assembly

As noted above, it may be desirable to clean disposable assembly (1000) from time to time, particularly in interior portions of shaft assembly (1050). As part of this process, it may be desirable to remove waveguide (1092) from disposable assembly (1000). Removal of waveguide (1092) may facilitate cleaning of waveguide (1092) and cleaning of the interior of inner tube (1070). FIGS. 109-114 depict disposable assembly (1000) in a cleaning mode that includes removal of waveguide (1092). As shown, when disposable assembly (1000) is in the cleaning mode, lid (1014) is in an open position, flange portion (1174) is disengaged from latch (1009) such that inner tube coupling member assembly (1150) is in a proximal position, and waveguide (1092) is removed from shaft assembly (1052). It should be understood that an operator may wish to transition disposable assembly (1000) to the cleaning mode after instrument (800) has been used in a surgical procedure. It should also be understood that, before transitioning disposable assembly (1000) to the cleaning mode, the operator may first decouple waveguide (1092) from transducer assembly (940) as taught above; then decouple disposable assembly (1000) from reusable assembly (900).

By way of example, the operator may simply lift lid (1014) manually in order to place lid (1014) in the open position. The operator may need to simply overcome friction that is otherwise holding lid (1014) in the closed position. Alternatively, features of instrument (800) may automatically open lid (1014), such as when the operator decouples disposable assembly (1000) from reusable assembly (900). The operator may also manually lift latch (1009) to deform latch (1009) and thereby release flange portion (1174) from latch (1009). Alternatively, features of instrument (800) may automatically disengage flange portion (1174) from latch (1009), such as when the operator decouples disposable assembly (1000) from reusable assembly (900). Various suitable ways in which lid (1014) may be opened automatically, as well as various suitable ways in which flange portion (1174) may be disengaged from latch (1009) automatically, will be apparent to those of ordinary skill in the art in view of the teachings herein.

As best seen in FIG. 113, when flange portion (1174) is disengaged from latch (1009), and inner tube coupling member assembly (1150) is moved to the proximal position, ridges (1182) of deflector member (1180) bear against arms (2012) of proximal mounting portion (2010) of inner tube (1070), thereby deflecting arms (2012) outwardly. This outward deflection of arms (2012) disengages arms (2012) from pin (1094) of waveguide (1092), allowing waveguide (1092) to be withdrawn proximally from inner tube (1070). It should therefore be understood that ridges (1182) of deflector member (1180) operate similar to tabs (145) of mode drive member (141) against arms (181) as described above. In some versions, a separate instrument may be coupled with waveguide (1092) to facilitate removal of waveguide (1092) from inner tube (1070) after inner tube coupling member assembly (1150) has been moved to the proximal position. For instance, a waveguide removal instrument may include a handle with a shaft that is sized to fit within the inner bore of inner tube coupling member assembly (1150). The shaft of the waveguide removal instrument may have a threaded feature that may be threaded onto stud (1096) of waveguide (1092) to couple the waveguide removal instrument with waveguide (1092). Other suitable ways in which waveguide (1092) may be removed from shaft assembly (1050) will be apparent to those of ordinary skill in the art in view of the teachings herein. It should also be understood that the interior of inner tube (1070) may be cleaned in any suitable fashion after waveguide (1092) has been removed.

As shown in FIGS. 113-114, cleaning port body (1300) is disposed within proximal mounting portion (2000) of outer tube (1052). Cleaning port body (1300) comprises an elastomeric material (e.g., silicone, etc.) in the present example. As best seen in FIGS. 115-116, cleaning port body (1300) includes a longitudinally extending portion (1310) and a transversely extending portion (1320). Transversely extending portion (1320) extends through lateral opening (2002) of proximal mounting portion (2000) and defines a port opening (1322). Lid (1014) includes a stopper (1016) that is configured to fit in port opening (1322) when lid (1014) is in a closed position (as shown in FIG. 94) and thereby provide a fluid and air tight seal of port opening (1322). However, when lid (1014) is in an open position (as shown in FIGS. 109-114), stopper (1016) is fully disengaged from port opening (1322).

Longitudinally extending portion (1310) of port body (1300) includes a distal sealing flange (1312) and defines a lower lumen region (1314) and an upper lumen region (1316). As best seen in FIG. 114, distal sealing flange (1312) is sized and configured to provide a fluid and air tight seal against the inner surface of proximal mounting portion (2000) of outer tube (1052). The proximal end of lower lumen region (1314) is sized and configured to provide a fluid and air tight seal against the outer surface of the distal portion of proximal mounting portion (2010) of inner tube (1070) when inner tube (1070) is fully inserted in lower lumen region (1314). The portion of lower lumen region (1314) that is coincident with upper lumen region (1316) is defined by a radius of curvature that is less than the radius of curvature defining upper lumen region (1316). When inner tube (1070) is inserted through lower lumen region (1314), upper lumen region (1316) remains open to communicate with port opening (1322) and a gap (1071) that is defined between the outer diameter of inner tube (1070) and the inner diameter of outer tube (1052). In other words, port opening (1322) and upper lumen region (1316) together provide a path for communication of fluid to the gap (1071) that is defined between the outer diameter of inner tube (1070) and the inner diameter of outer tube (1052). An operator may thus couple port opening (1322) with a source of cleaning fluid as described above with respect to ports (153, 155).

However, it should also be understood that when lid (1014) is in a closed position, and when waveguide (1092) is disposed in inner tube (1070), the fluid and air tight seal provided by stopper (1016) against port opening (1322), the fluid and air tight seal provided by sealing flange (1312) against the inner diameter of the inner surface of proximal mounting portion (2000), the fluid and air tight seal provided by the proximal end of lower lumen region (1314) against the outer surface of the distal portion of proximal mounting portion (2010), and the fluid tight seal provided by fenders (1093) against the inner surface of inner tube (1070) will all provide a proximal seal for shaft assembly (1050). In other words, fenders (1093), port body (1300), and stopper (1016) will together permit shaft assembly (1050) to be inserted into an insufflated body cavity (e.g., an insufflated abdomen) without fear of losing insufflation pressure through interior features of shaft assembly (1050).

4. Exemplary Waveguide Guiding Feature of Disposable Assembly

As described above, an operator may remove waveguide (1092) from shaft assembly (1050) to place disposable portion (1000) in a cleaning mode. After disposable portion (1000) has been suitably cleaned and disposable portion (1000) is otherwise ready for re-use, it may be desirable to re-insert waveguide (1092) into shaft assembly (1050) to prepare disposable portion (1000) for another use in a surgical procedure. This may be done with a waveguide (1092) that had been previously used and then cleaned; or with a new waveguide (1092). In either case, it may be desirable to ensure that waveguide (1092) is ultimately positioned at a particular, predetermined angular orientation before disposable portion (1000) is used again. This may be desirable in settings where blade (1090) has a non-circular cross-section. In such settings, the effects on tissue when clamp arm (1082) compresses tissue against an ultrasonically activated blade (1090) may vary based on the geometric configuration of the region of blade (1090) that is facing arm. Thus, providing predictability and consistency in the angular orientation of blade (1090) may provide predictable and consistent performance of end effector (1080). Providing consistency in the angular orientation of blade (1090) will also provide consistent angular alignment of pin (1094) with arms (2012) when blade (1090) reaches a fully inserted position.

FIGS. 117A-118F show how waveguide guiding member (1200) will consistently guide waveguide (1092) into a specific, predetermined angular orientation when waveguide (1092) is fully inserted into waveguide guiding member (1200), regardless of the angular orientation at which waveguide (1092) is initially inserted into waveguide guiding member (1200). Before waveguide (1092) is inserted into waveguide guiding member (1200) as described below, the operator can push inner tube coupling member assembly (1150) from the proximal position shown in FIG. 113 to the distal position shown in FIG. 94, with latch (1009) re-engaging flange (1174). This will disengage ridges (1182) of deflector member (1180) from arms (2012), enabling arms (2012) to resiliently to resiliently return to the position shown in FIGS. 94 and 102. With inner tube coupling member assembly (1150) in the distal position and arms (2012) returned to the shown in FIGS. 94 and 102, arms (2012) will again reach over ridges (1182) of deflector member (1180) to engage pin (1094) of waveguide (1092) when waveguide (1092) is fully inserted into waveguide guiding member (1200) as described below. Alternatively, waveguide (1092) and inner tube coupling member assembly (1150) can be simultaneously inserted into waveguide guiding member (1200). As waveguide (1092) and inner tube coupling member assembly (1150) are simultaneously inserted into waveguide guiding member (1200), ridges (1182) of deflector member (1180) will disengage from arms (2012), enabling arms (2012) to resiliently return to the position shown in FIGS. 94 and 102.

FIG. 117A shows waveguide (1092) being initially inserted into waveguide guiding member (1200) at an orientation where post (1099) is angularly misaligned by approximately 45° clockwise (viewing distally from threaded stud (1096)). As the operator inserts waveguide (1092) further distally as shown in FIG. 117B, post (1099) first engages cam surface (1214), passing cam surface (1212) without engaging cam surface (1212). If waveguide (1092) were initially misaligned to a greater angle clockwise, post (1099) would have engaged cam surface (1212) first. As the operator inserts waveguide further distally (1092) as shown in FIG. 117C, post (1099) engages cam surface (1216). Due to the helical orientation of cam surface (1216), cam surface (1216) acts against post (1099) to rotate waveguide (1092) counterclockwise. This counterclockwise rotation continues as waveguide (1092) is inserted further distally as shown in FIG. 117D, until post (1099) eventually encounters the gap defined between cam surfaces (1218, 1244). As waveguide (1092) is inserted further distally as shown in FIG. 117E, cam surfaces (1218, 1244) cooperate to guide waveguide (1092) through a certain range of longitudinal motion without rotating waveguide (1092). Post (1099) eventually encounters cam surface (1246), as shown in FIG. 117F. At this point, the complementary helical orientations of guide surfaces (1220, 1246) cooperate against post (1099) to guide waveguide (1092) distally while rotating waveguide (1092) clockwise as waveguide (1092) is inserted further distally as shown in FIG. 117G. Post (1099) eventually encounters cam surface (1222) as shown in FIG. 117H. As waveguide (1092) is inserted further distally as shown in FIG. 117I, cam surfaces (1222, 1248) cooperate against post (1099) to guide waveguide (1092) without rotating waveguide (1092) until post (1099) nears end surface (1260). In the present example, post (1099) does not actually contact end surface (1260) or cam surfaces (1222, 1248) when waveguide (1092) is fully disposed in waveguide guiding member (1200). Instead, engagement between pin (1094) and arms (2012) of inner tube coupling member assembly (1150) arrests longitudinal advancement of waveguide (1092) and maintains the position of waveguide (1092) relative to waveguide guiding member (1200) such that post (1099) is slightly spaced away from end surface (1260) and cam surfaces (1222, 1248).

At the stage shown in FIG. 117I, waveguide (1092) is fully inserted, with end cam surfaces (1222, 1248) and post (1099) cooperating to provide waveguide (1092) at a proper angular and longitudinal position within waveguide guiding member (1200). Since waveguide guiding member (1200) is already rotationally and longitudinally fixed within shaft assembly (1050) via pin (1240), waveguide (1092) will be at a proper angular and longitudinal position within shaft assembly (1050) upon reaching the position shown in FIG. 117I. It should be noted that, in the present example, pin (1094) of waveguide (1092) is positioned adjacent to cam surface (1214) and the proximal portion of cam surface (1244) when waveguide (1092) reaches full insertion in waveguide guiding member (1200). In other words, cam surfaces (1214, 1244) are positioned to accommodate pin (1094) waveguide (1092) reaches full insertion in waveguide guiding member (1200). In addition, waveguide (1092) is positioned longitudinally via pin (1094) engaging with arms (2012) of inner tube coupling member assembly (1150).

FIG. 118A shows waveguide (1092) being initially inserted into waveguide guiding member (1200) at an orientation where post (1099) is angularly misaligned by approximately 45° counterclockwise (viewing distally from threaded stud (1096)). As the operator inserts waveguide further distally (1092) as shown in FIG. 118B, post (1099) first engages cam surface (1242). Due to the helical orientation of cam surface (1242), cam surface (1242) acts against post (1099) to rotate waveguide (1092) clockwise until post (1099) reaches cam surface (1244) as shown in FIG. 118C. As the operator inserts waveguide (1092) further distally, cam surfaces (1218, 1244) cooperate to guide waveguide (1092) through a certain range of longitudinal motion without rotating waveguide (1092). Post (1099) eventually encounters cam surface (1246), as shown in FIG. 118D. At this point, the complementary helical orientations of guide surfaces (1220, 1246) cooperate against post (1099) to guide waveguide (1092) distally while rotating waveguide (1092) clockwise until post (1099) encounters cam surface (1222) as shown in FIG. 118E. As waveguide (1092) is inserted further distally as shown in FIG. 118F, cam surfaces (1222, 1248) cooperate against post (1099) to guide waveguide (1092) without rotating waveguide (1092) until post (1099) nears end surface (1260). At this stage, waveguide (1092) is fully inserted. Again, post (1099) does not actually contact end surface (1260) or cam surfaces (1222, 1248) when waveguide (1092) is fully disposed in waveguide guiding member (1200). Instead, engagement between pin (1094) and arms (2012) of inner tube coupling member assembly (1150) arrests longitudinal advancement of waveguide (1092) and maintains the position of waveguide (1092)

relative to waveguide guiding member (1200) such that post (1099) is slightly spaced away from end surface (1260) and cam surfaces (1222, 1248).

It should be understood that, regardless of the angle at which waveguide (1092) is misaligned when waveguide (1092) is being initially inserted into waveguide guiding member (1200), cam surfaces (1212, 1214, 1216, 1218, 1220, 1222, 1242, 1244, 1246, 1248) will cooperate to guide and thereby orient waveguide (1092) at an appropriate angular orientation as waveguide (1092) is fully inserted through body (1202). The configuration of point (1250) will deflect post (1099) to either cam surface (1212) or cam surface (1242) in the event that waveguide is (1092) initially inserted into waveguide guiding member (1200) at a misalignment angle of 180°.

After the components of shaft assembly (1050) have been cleaned as described above, inner tube coupling member assembly (1150) has been pushed back to the distal position as described above, and waveguide (1092) has been inserted back into shaft assembly (1050) as described above, the operator may then close lid (1014) if the operator has not been closed already. At this stage, disposable assembly (1000) may be re-coupled with reusable assembly (900) to re-assemble instrument (800). This re-assembly would include re-coupling of threaded stud (1096) of waveguide (1092) with horn (956) of transducer assembly (940) as described above. Re-assembled instrument (800) may then be used in a surgical procedure as described above.

VIII. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An instrument comprising: (a) a body; (b) a shaft assembly extending distally from the body, wherein the shaft assembly defines a longitudinal axis; (c) a waveguide guiding member coaxially aligned with the longitudinal axis, wherein the waveguide guiding member has a plurality of cam surfaces; and (d) an ultrasonic waveguide, wherein the ultrasonic waveguide comprises an outwardly extending post, wherein the ultrasonic waveguide is insertable into the waveguide guiding member along the longitudinal axis, wherein the cam surfaces of the waveguide guiding member are configured to bear against the post to angularly orient the waveguide about the longitudinal axis.

Example 2

The instrument of Example 1, wherein the post extends outwardly from the waveguide at only one angular position about a circumference of the waveguide.

Example 3

The instrument of any one or more of Examples 1 through 2, wherein the waveguide further comprises a pin, wherein the pin extends outwardly from the waveguide at two opposing angular positions about a circumference of the waveguide.

Example 4

The instrument of Example 3, wherein the pin is proximal to the post.

Example 5

The instrument of any one or more of Examples 3 through 4, wherein the pin is located at a position along the length of the waveguide corresponding to a node associated with ultrasonic vibrations communicated through the waveguide.

Example 6

The instrument of any one or more of Examples 1 through 5, wherein at least one of the cam surfaces extends along a helically oriented path.

Example 7

The instrument of Example 6, wherein a first cam surface of the plurality of cam surfaces extends along a helical path at a first orientation, wherein a second cam surface of the plurality of cam surfaces extends along a helical path at a second orientation.

Example 8

The instrument of any one or more of Examples 1 through 7, wherein at least one of the cam surfaces extends along a path that is parallel to the longitudinal axis.

Example 9

The instrument of any one or more of Examples 1 through 8, wherein the shaft assembly comprises an inner tube and an outer tube, wherein the waveguide guiding member is coaxially disposed within a proximal portion of the inner tube.

Example 10

The instrument of Example 9, wherein the inner tube is longitudinally secured relative to the body.

Example 11

The instrument of Example 10, wherein the outer tube is operable to translate relative to the body and relative to the inner tube.

Example 12

The instrument of Example 11, further comprising a clamp arm, wherein a first portion of the clamp arm is pivotably coupled with the inner tube, wherein a second portion of the clamp arm is pivotably coupled with the outer tube, wherein the clamp arm is configured to pivot toward and away from the longitudinal axis in response to longitudinal motion of the outer tube along the longitudinal axis.

Example 13

The instrument of Example 9, wherein the inner tube, the outer tube, the waveguide guiding member, and the waveguide are all rotatable together relative to the body.

Example 14

The instrument of any one or more of Examples 1 through 13, further comprising a grip assembly, wherein the body is configured to removably couple with the grip assembly.

Example 15

The instrument of Example 14, wherein the grip assembly comprises an ultrasonic transducer, wherein the ultrasonic transducer is configured to couple with the waveguide.

Example 16

An apparatus, comprising: (a) a body; (b) a shaft assembly configured to couple with the body such that the shaft assembly extends distally relative to the body, wherein the shaft assembly comprises: (i) a tubular member, (ii) an acoustic waveguide, wherein the acoustic waveguide is operable to selectively couple with an ultrasonic transducer assembly, wherein the tubular member is configured to insertingly receive the acoustic waveguide, wherein the acoustic waveguide comprises a guide feature, and (iii) a guiding member, wherein the guiding member is configured to engage the guide feature of the acoustic waveguide and thereby orient the acoustic waveguide in relation to the tubular member.

Example 17

The apparatus of Example 16, wherein the tubular member defines a longitudinal axis, wherein the acoustic waveguide defines a longitudinal axis, wherein the acoustic waveguide is configured to fit in the tubular member such that the longitudinal axes are coaxially aligned with each other.

Example 18

The apparatus of any one or more of Examples 16 through 17, wherein the tubular member defines a longitudinal axis, wherein the guiding member is configured to engage the guide feature of the acoustic waveguide and thereby orient the acoustic waveguide about the longitudinal axis in relation to the tubular member.

Example 19

The apparatus of Example 18, wherein the guiding member comprises a first guide surface, wherein the first guide surface is configured to engage the guide feature of the acoustic waveguide and thereby orient the acoustic waveguide about the longitudinal axis in relation to the tubular member by rotating the acoustic waveguide in a first direction about the longitudinal axis in response to advancement of the acoustic waveguide along the longitudinal axis.

Example 20

The apparatus of Example 19, wherein the guiding member further comprises a second guide surface, wherein the second guide surface is configured to engage the guide feature of the acoustic waveguide and thereby orient the acoustic waveguide about the longitudinal axis in relation to the tubular member by rotating the acoustic waveguide in a second direction about the longitudinal axis in response to advancement of the acoustic waveguide along the longitudinal axis.

Example 21

The apparatus of Example 20, wherein the first and second guide surfaces converge together at a point.

Example 22

The apparatus of Example 21, wherein the guiding member has a proximal end and a distal end, wherein the point is located at the proximal end.

Example 23

The apparatus of any one or more of Examples 19 through 22, wherein the second guide surface is distal to the first guide surface.

Example 24

The apparatus of any one or more of Examples 16 through 23, wherein the tubular member defines a longitudinal axis, wherein the guiding member comprises a pair of longitudinally extending cam surfaces, wherein the longitudinally extending cam surfaces are configured to engage the guide feature of the acoustic waveguide and thereby maintain an angular orientation of the acoustic waveguide as the acoustic waveguide is inserted along the longitudinal axis.

Example 25

The apparatus of Example 24, wherein the guiding member has a proximal end and a distal end, wherein the longitudinally extending cam surfaces converge at the distal end.

Example 26

The apparatus of any one or more of Examples 16 through 25, wherein the tubular member defines a longitudinal axis, wherein the guiding member defines a guide channel, wherein the engage the guide feature of the acoustic waveguide is configured to traverse the guide channel as the acoustic waveguide is inserted along the longitudinal axis.

Example 27

The apparatus of Example 26, wherein the guide channel is configured to rotate the acoustic waveguide in a first direction as the acoustic waveguide is inserted along the longitudinal axis through a first range of longitudinal motion.

Example 28

The apparatus of Example 27, wherein the guide channel is configured to rotate the acoustic waveguide in a second direction as the acoustic waveguide is inserted along the longitudinal axis through a second range of longitudinal motion.

Example 29

The apparatus of any one or more of Examples 16 through 28, wherein the shaft assembly further comprises a fluid port, wherein the fluid port is configured to provide communication of fluid along at least a portion of the length of the shaft assembly.

Example 30

The apparatus of Example 29, wherein the fluid port is located distal to the guiding member.

Example 31

The apparatus of any one or more of Examples 16 through 30, wherein the guide feature of the acoustic waveguide comprises a post extending transversely relative to a longitudinal axis of the acoustic waveguide.

Example 32

The apparatus of any one or more of Examples 16 through 31, wherein the guiding member is fixedly secured relative to the tubular member.

Example 33

The apparatus of any one or more of Examples 16 through 32, wherein the shaft assembly further comprises: (i) an ultrasonic blade located at a distal end of the acoustic waveguide, and (ii) a clamp arm pivotably coupled with the tubular member, wherein the clamp arm is operable to pivot toward and away from the ultrasonic blade.

Example 34

An apparatus, comprising: (a) a body; (b) a shaft assembly configured to couple with the body such that the shaft assembly extends distally relative to the body, wherein the shaft assembly comprises: (i) a tubular member, wherein the tubular member defines a longitudinal axis, (ii) an acoustic waveguide, wherein the acoustic waveguide is sized for insertion into the tubular member along the longitudinal axis, and (iii) a guiding member, wherein the guiding member is configured rotate the acoustic waveguide and thereby orient the acoustic waveguide in relation to the tubular member in response to insertion of the acoustic waveguide into the tubular member along the longitudinal axis.

Example 35

A method of assembling a surgical instrument, the method comprising: (a) positioning a distal end of an acoustic waveguide proximal to a proximal end of a tubular member, wherein the tubular member defines a longitudinal axis; (b) inserting the distal end of the acoustic waveguide into the proximal end of the tubular member; (c) advancing the acoustic waveguide through a first range of motion into the tubular member and along the longitudinal axis; (d) engaging a first cam surface with the acoustic waveguide while advancing the acoustic waveguide through the first range of motion, wherein the first cam surface causes the acoustic waveguide to rotate in a first direction as the acoustic waveguide is advanced through the first range of motion; (e) advancing the acoustic waveguide through a second range of motion into the tubular member and along the longitudinal axis; and (f) engaging a second cam surface with the acoustic waveguide while advancing the acoustic waveguide through the second range of motion, wherein the second cam surface causes the acoustic waveguide to rotate in a second direction as the acoustic waveguide is advanced through the second range of motion.

IX. Miscellaneous

It should be understood from the foregoing that each instrument (10, 300) permits a disposable assembly (100, 400) to be removably coupled with a reusable assembly (200, 500). As noted above, it may be desirable to decouple a disposable assembly (100, 400) from a reusable assembly (200, 500) in order to clean disposable assembly (100, 400) and re-couple disposable assembly (100, 400) with reusable assembly (200, 500); or in order to replace a used disposable assembly (100, 400) with a new disposable assembly (100, 400). It should also be understood that reusable assemblies (200, 500) may be coupled with different kinds of disposable assemblies (100, 400). For instance, an operator may be presented with a selection of disposable assemblies (100, 400) having various lengths of shaft assemblies (150, 450), such that the operator may choose a disposable assembly (100, 400) having a shaft assembly (150, 450) length that is particularly suited for the task at hand. As another merely illustrative example, an operator may be presented with a selection of disposable assemblies (100, 400) having various kinds of end effectors (180, 480) (e.g., those with and without clamp arms (182), those with different configurations of blades (190), etc.). The operator may thus choose a disposable assembly (100, 400) having an end effector (180, 480) that is particularly suited for the task at hand. Various suitable ways in which operators may be provided with kits and other vehicles for modularity of disposable assemblies (100, 400) will be apparent to those of ordinary skill in the art in view of the teachings herein.

It should be understood that any of the versions of instruments described herein may include various other features in addition to or in lieu of those described above. By way of example only, in addition to the teachings above, it should be understood that at least part of instrument (10, 300) may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pub. No. 2009/0105750, issued as U.S. Pat. No. 8,623,027 on Jan. 7, 2014; U.S. Pub. No. 2010/0069940, issued as U.S. Pat. No. 9,023,071 on May 5, 2015; U.S. Pub. No. 2011/0015660, issued as U.S. Pat. No. 8,461,744 on Jun. 11, 2013; U.S. Pub. No. 2012/0112687, issued as U.S. Pat. No. 9,381,058 on Jul. 5, 2016; U.S. Pub. No. 2012/0116265, now abandoned; U.S. Pub. No. 2014/0005701, issued as U.S. Pat. No. 9,393,037 on Jul. 19, 2016; U.S. Pub. No. 2015/0080924, issued as U.S. Pat. No. 10,172,636 on Jan. 8, 2019; and/or U.S. Pat. App. No. 61/410,603. The disclosures of each of the foregoing patents, publications, and applications are incorporated by reference herein. It should also be understood that instrument (10, 300) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to instrument (10, 300), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus, comprising:
   a shaft assembly, wherein the shaft assembly comprises:
   (i) a tubular member, wherein the tubular member defines a longitudinal axis,
   (ii) an acoustic waveguide, wherein the acoustic waveguide is operable to selectively couple with an ultrasonic transducer assembly, wherein the tubular member is configured to insertingly receive the acoustic waveguide, wherein the acoustic waveguide comprises a guide feature, and
   (iii) a guiding member, wherein the guiding member defines a guide channel, wherein the guide feature of the acoustic waveguide is configured to traverse the guide channel as the acoustic waveguide is inserted along the longitudinal axis, wherein the guiding member is configured to engage the guide feature of the acoustic waveguide and thereby orient the acoustic waveguide in relation to the tubular member.

2. The apparatus of claim 1, wherein the tubular member defines a longitudinal axis, wherein the acoustic waveguide defines a longitudinal axis, wherein the acoustic waveguide is configured to fit in the tubular member such that the longitudinal axes are coaxially aligned with each other.

3. The apparatus of claim 1, wherein the tubular member defines a longitudinal axis, wherein the guiding member is configured to engage the guide feature of the acoustic waveguide and thereby orient the acoustic waveguide about the longitudinal axis in relation to the tubular member.

4. The apparatus of claim 3, wherein the guiding member comprises a first guide surface, wherein the first guide surface is configured to engage the guide feature of the acoustic waveguide and thereby orient the acoustic waveguide about the longitudinal axis in relation to the tubular member by rotating the acoustic waveguide in a first direction about the longitudinal axis in response to advancement of the acoustic waveguide along the longitudinal axis.

5. The apparatus of claim 4, wherein the guiding member further comprises a second guide surface, wherein the second guide surface is configured to engage the guide feature of the acoustic waveguide and thereby orient the acoustic waveguide about the longitudinal axis in relation to the tubular member by rotating the acoustic waveguide in a second direction about the longitudinal axis in response to advancement of the acoustic waveguide along the longitudinal axis.

6. The apparatus of claim 5, wherein the first and second guide surfaces converge together at a point.

7. The apparatus of claim 6, wherein the guiding member has a proximal end and a distal end, wherein the point is located at the proximal end.

8. The apparatus of claim 5, wherein the second guide surface is distal to the first guide surface.

9. The apparatus of claim 1, wherein the tubular member defines a longitudinal axis, wherein the guiding member comprises a pair of longitudinally extending cam surfaces, wherein the longitudinally extending cam surfaces are configured to engage the guide feature of the acoustic waveguide and thereby maintain an angular orientation of the acoustic waveguide as the acoustic waveguide is inserted along the longitudinal axis.

10. The apparatus of claim 9, wherein the guiding member has a proximal end and a distal end, wherein the longitudinally extending cam surfaces converge at the distal end.

11. The apparatus of claim 1, wherein the guide channel is configured to rotate the acoustic waveguide in a first direction as the acoustic waveguide is inserted along the longitudinal axis through a first range of longitudinal motion.

12. The apparatus of claim 11, wherein the guide channel is configured to rotate the acoustic waveguide in a second direction as the acoustic waveguide is inserted along the longitudinal axis through a second range of longitudinal motion.

13. The apparatus of claim 1, wherein the shaft assembly further comprises a fluid port, wherein the fluid port is configured to provide communication of fluid along at least a portion of the length of the shaft assembly.

14. The apparatus of claim 13, wherein the fluid port is located distal to the guiding member.

15. The apparatus of claim 1, wherein the guide feature of the acoustic waveguide comprises a post extending transversely relative to a longitudinal axis of the acoustic waveguide.

16. The apparatus of claim 1, wherein the guiding member is fixedly secured relative to the tubular member.

17. The apparatus of claim 1, wherein the shaft assembly further comprises:
(i) an ultrasonic blade located at a distal end of the acoustic waveguide, and
(ii) a clamp arm pivotably coupled with the tubular member, wherein the clamp arm is operable to pivot toward and away from the ultrasonic blade.

18. An apparatus, comprising:
a shaft assembly, wherein the shaft assembly comprises:
(i) a tubular member, wherein the tubular member defines a longitudinal axis,
(ii) an acoustic waveguide, wherein the acoustic waveguide is operable to selectively couple with an ultrasonic transducer assembly, wherein the tubular member is configured to insertingly receive the acoustic waveguide, wherein the acoustic waveguide comprises a guide feature, and
(iii) a guiding member, wherein the guiding member comprises a pair of longitudinally extending cam surfaces, wherein the guiding member is configured to engage the guide feature of the acoustic waveguide and thereby orient the acoustic waveguide in relation to the tubular member, wherein the longitudinally extending cam surfaces are configured to engage the guide feature of the acoustic waveguide and thereby maintain an angular orientation of the acoustic waveguide as the acoustic waveguide is inserted along the longitudinal axis.

19. An apparatus, comprising:
a shaft assembly, wherein the shaft assembly comprises:
(i) a tubular member,
(ii) an acoustic waveguide, wherein the acoustic waveguide is operable to selectively couple with an ultrasonic transducer assembly, wherein the tubular member is configured to insertingly receive the acoustic waveguide, wherein the acoustic waveguide comprises a guide feature, wherein the guide feature of the acoustic waveguide comprises a post extending transversely relative to a longitudinal axis of the acoustic waveguide, and
(iii) a guiding member, wherein the guiding member is configured to engage the guide feature of the acoustic waveguide and thereby orient the acoustic waveguide in relation to the tubular member.

* * * * *